(12) United States Patent
Smith et al.

(10) Patent No.: US 10,654,833 B2
(45) Date of Patent: May 19, 2020

(54) ASK1 ISOINDOLIN-1-ONE INHIBITORS AND METHODS OF USE THEREOF

(71) Applicant: Hepatikos Therapeutics, LLC, Dover, DE (US)

(72) Inventors: Christopher Ronald Smith, San Diego, CA (US); Justin Chapman, San Diego, CA (US)

(73) Assignee: Hepatikos Therapeutics, LLC, Dover, DE (US)

( * ) Notice: Subject to any disclaimer, the term of this patent is extended or adjusted under 35 U.S.C. 154(b) by 0 days.

(21) Appl. No.: 16/457,101

(22) Filed: Jun. 28, 2019

(65) Prior Publication Data

US 2020/0002312 A1 Jan. 2, 2020

Related U.S. Application Data

(60) Provisional application No. 62/793,076, filed on Jan. 16, 2019, provisional application No. 62/691,161, filed on Jun. 28, 2018.

(51) Int. Cl.

| | | |
|---|---|---|
| *C07D 401/14* | (2006.01) | |
| *C07D 409/14* | (2006.01) | |
| *C07D 487/04* | (2006.01) | |
| *C07D 471/04* | (2006.01) | |
| *C07D 417/14* | (2006.01) | |
| *A61K 31/44* | (2006.01) | |

(52) U.S. Cl.
CPC ......... *C07D 401/14* (2013.01); *C07D 409/14* (2013.01); *C07D 417/14* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | |
|---|---|---|
| 4,164,559 A | 8/1979 | Miyata |
| 4,474,752 A | 10/1984 | Haslam |
| 6,080,546 A | 6/2000 | Monia |
| 6,120,484 A | 9/2000 | Silverstein |
| 6,194,187 B1 | 2/2001 | Miyazono |
| 6,377,849 B1 | 4/2002 | Lenarz |
| 6,440,102 B1 | 8/2002 | Arenberg |
| 6,648,873 B2 | 11/2003 | Arenberg |
| 6,911,211 B2 | 6/2005 | Eini |
| 2006/0264897 A1 | 11/2006 | Lobl |

FOREIGN PATENT DOCUMENTS

| | | |
|---|---|---|
| WO | WO 1987/005297 | 9/1987 |
| WO | WO 2011/008709 | 1/2011 |
| WO | WO 2013/112741 | 8/2013 |
| WO | WO 2018/133865 | 7/2018 |
| WO | WO 2018/187506 | 10/2018 |

OTHER PUBLICATIONS

Mansoori et al, Polymers for Advanced Technologies, 26(6), pp. 658-664 (Year: 2015).*
Roulton et al., "ERKs: A family of protein-serine/threonine kinases that are activated and tyrosine phosphorylated in response to insulin and NGF," Cell, 65(4): 663-675, 1991.
Chou and Talalay, "Quantitative analysis of dose-effect relationships: the combined effects of multiple drugs or enzyme inhibitors," Advances in Enzyme Regulation, 22: 27-55, 1984.
Dérijard et al., "JNK1: a protein kinase stimulated by UV light and Ha-Ras that binds and phosphorylates the c-Jun activation domain," Cell, 76(6): 1025-1037, 1994.
Egan and Weinberg, "The pathway to signal achievement," Nature, 365: 781-783, 1993.
Errede and Levin, "A conserved kinase cascade for MAP kinase activation in yeast," Curr. Opin. Cell Biol., 5(2): 254-260, 1993.
Galcheva-Gargova et al., "An osmosensing signal transduction pathway in mammalian cells," Science, 265(5173): 806-808, 1994.
Graham et al., "Theoretical studies applied to drug design: ab initio electronic distributions in bioisosteres," J. Mol. Structure: Theochem, 343: 105-109, 1995.
Harper and LoGrasso. "Signalling for survival and death in neurones: the role of stress-activated kinases, JNK and p38," Cell. Signal., 13(5): 299-310, 2001.
Hatai et al., "Execution of Apoptosis signal-regulating kinase 1 (ASK1)-induced apoptosis by the mitochondria-dependent caspase activation," J. Biol. Chem., 275(34): 26576-26581, 2000.
Hayakawa et al.. "The ASK1-MAP kinase pathways in immune and stress responses," Microbes and Infection, 8(4): 1098-1107, 2006.
Ichijo "From receptors to stress-activated MAP kinases," Oncogene. 18: 6087-6093, 1999.
Ichijo et al., "Induction of Apoptosis by ASK1, a mammalian MAPKKK that activates SAPK/JNK and p38 signaling pathways," Science, 275(5296): 90-94, 1997.
Imoto et al., "Impact of mitochondrial reactive oxygen species and apoptosis signal-regulating kinase 1 on insulin signaling," Diabetes, 55: 1197-1204, 2006.
International Search Report and Written Opinion in Application No. PCT/US2019/039857, dated Aug. 29, 2019.
Kanamoto et al., "Role of apoptosis signal-regulating kinase in regulation of the c-Jun N-Terminal kinase pathway and apoptosis in sympathetic neurons," Mol. Cell Biol., 20(1): 196-204, 2000.
Kawasaki et al., "Activation and involvement of p38 mitogen-activated protein kinase in glutamate-induced apoptosis in rat cerebellar granule cells," J. Biol. Chem., 272(30): 18518-18521, 1997.
Kim et al., "A conserved p38 MAP kinase pathway in Caenorhabclitis elegans innate immunity," Science, 297(5581): 623-626, 2002.
Kuan et al., "The Jnk1 and Jnk2 protein kinases are required for regional specific apoptosis during early brain development," Neuron, 22(4): 667-676, 1999.

(Continued)

*Primary Examiner* — Zinna Northington Davis
(74) *Attorney, Agent, or Firm* — Fish & Richardson P.C.

(57) ABSTRACT

Isoindolin-1-one compounds for treating various diseases and pathologies are disclosed. More particularly, the present disclosure concerns the use of an isoindolin-1-one compound or analogs thereof, in the treatment of disorders characterized by the activation of ASK1 (e.g., cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes).

18 Claims, 1 Drawing Sheet

(56) References Cited

OTHER PUBLICATIONS

Kyriakis and Avruch, "Mammalian mitogen-activated protein kinase signal transduction pathways activated by stress and inflammation," J. Physiol. Rev., 81(2): 807-869, 2001.
Lanier et al., "Structure Based Design of ASK1 Inhibitors as Potential Agents for Heart Failure,", ACS Medicinal Chemistry Letters, vol. 8, No. 3,pp. 316-320, 2017.
Lee et al., "A MAP kinase targeted by endotoxin and hyperosmolarity in mammalian cells," Science, 265(5173): 808-811, 1994.
Lipinski, "Bioisosterisni in drug design," Annual Reports in Medicinal Chemistry, Chapter 27, 21: 283-291, 1986.
Los et al , "The role of caspases in development, immunity, and apoptotic signal transduction: lessons from knockout mice," Immunity, 10: 629-639, 1999.
Marshall, "MAP kinase kinase kinase, MAP kinase kinase and MAP kinase," Curr. Opin. Genet. Dev., 82-89, 1994.
Matsukawa et al., "The ASK1-MAP kinase cascades in mammalian stress response," J. Biochem. (Tokyo), 136: 261-265, 2004.
Matsuzawa et al., "ROS-dependent activation of the TRAF6-ASK1-p38 pathway is selectively required for TLR4-mediated innate immunity." Nat. Immunol., 6(6): 587-592, 2005.
Minden et al., "c-Jun N-terminal phosphorylation correlates with activation of the JNK subgroup but not the ERK subgroup of mitogen-activated protein kinases," Mol. Cell. Biol., 1994. 14: 6683-6688, 1994.
Nishida and Gotoh, "The MAP kinase cascade is essential for diverse signal transduction pathways," Trends Biochem. Sci., 18: 128-131, 1993.
Nishitoh et al , "ASK1 is essential for endoplasmic reticulum stress-induced neuronal cell death triggered by expanded polyglutamine repeats," Genes Dev., 16: 1345-1355, 2002.
Nishitoh et a "ASK1 is essential for JNK/SAPK activation by TRAF2 " Mol. Cell 2: 389-395, 1998.
Sabapathy et al., "JNK2 is required for efficient T-cell activation and apoptosis but not for normal lymphocyte development," Curr. Biol., 199. 9(3): 116-125, 1999.
Sagasti et al., "The CaMKII UNC-43 activates the MAPKKK NSY-1 to execute a lateral signaling signaling required for asymmetric olfactory neuron fates," Cell, 105(2): 221-232, 2001.
Saitoh et al., "Mammalian thioredoxin is a direct inhibitor of apoptosis signal-regulating kinase (ASK) 1," EMBO J., 17: 2596-2606, 1998.
Sayama et al., "Apoptosis signal-regulating kinase 1 (ASK1) is an intracellular inducer of keratinocvte differentiation." J. Biol. Chem., 276: 999-1004, 2000.
Sturgill and Wu, "Recent progress in characterization of protein kinase cascades for phosphorylation of ribosomal protein S6," Biochim. Biophys. Acta, 1092(3): 350-357, 1993.
Takeda et al., "Apoptosis signal-regulating kinase I (ASK1) induces neuronal differentiation and survival of PC12 cells," J. Biol. Chem., 275(13): 9805-9813, 2000.
Takeda et al., "Involvement of ASK1 in CA2+-induced p38 MAP kinase activation," EMBO Rep., 5: 161-166, 2004.
Thompson, "Apoptosis in the pathogenesis and treatment of disease," Science. 267(5203): 1456-1462, 1995.
Tibbles and Woodgett, "The stress-activated protein kinase pathways," Cell Mol. Life Sci., 55(10): 1230-1254, 1999.
Tobiume et al., "ASK1 is required for sustained activations of JNK/p38 MAP kinases and apoptosis," EMBO Rep., 2: 222-228, 2001.
Tobiume et al., "Molecular cloning and characterization of the mouse apoptosis signal-regulating kinase," Biochem. Biophys. Res. Commun., 239(3): 905-910, 1997.
Widmann et al- b "Mitouen-activated protein kinase: conservation of a three-kinase module from yeast to human," Physiol. Rev. 79, 143-180, 1999.
Xia et al., "Opposing Efkcts of ERK and JNK-p38 MAP kinases on apoptosis," Science, 270(5240): 1326-1331, 1995.
Xuhong et al., "Molecular cloning and characterization of a novel protein kinase with a catalytic domain homologous to mitogen-activated protein kinase kinase kinase," J. Biol. Chem. 271(49): 31607-31611, 1996.
Yang et al., "Absence of excitotoxicity-induced apoptosis in the hippocampus of mice lacking the Jnk3 gene," Nature, 389: 865-870, 1997.
Yuan and Yankner. "Apoptosis in the nervous system," Nature, 407: 802-809, 2000.
Zhou et al., "Components of a new human protein kinase signal transduction pathway," J. Biol. Chem., 270(21): 12665-12669, 1995.

* cited by examiner

ASK1 ISOINDOLIN-1-ONE INHIBITORS AND METHODS OF USE THEREOF

RELATED APPLICATIONS

This application claims the benefit of U.S. Provisional Application Nos. 62/691,161, filed Jun. 28, 2018, and 62/793,076, filed Jan. 16, 2019, which are incorporated herein by reference in their entirety.

BACKGROUND

Technical Field

This disclosure relates to inhibitors of apoptosis signal-regulating kinase 1 (ASK1), and compositions comprising the same. More particularly, it concerns the use of an isoindolin-1-one compound or salts or analogs thereof, in the treatment of disorders characterized by the over activation or overexpression of ASK1 (e.g., cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes).

Background

Apoptosis signal-regulating kinase 1 (ASK1), is a member of the mitogen-activated protein kinases (MAPKs) family, which are members of the serine/threonine kinase family. Wang et al. *J. Biol. Chem.* 1996, 271, 31607-31611, Ichijo et al. *Science* 1997, 275, 90-94. ASK1 is also known as mitogen activated protein kinase kinase 5 (MAPKKK5, MAP3K5), MAP/ERK kinase kinase 5 (MEKK5), MEK kinase 5, MEKK5, MAP/ERK kinase kinase 5. The protein kinase composes of 1375 amino acids encompassing 11 kinase subdomains; particularly a serine/threonine kinase domain in the middle part of the molecule with long NH- and COOH-terminal flanking regions. Wang et al. *J. Biol. Chem.* 1996, 271, 31607-31611, Ichijo et al. *Science* 1997, 275, 90-94; Tobiume et al. Biochem. *Biophys. Res. Commun.* 1997, 239, 905-910; U.S. Pat. Nos. 6,080,546 and 6,194,187. The nucleotide sequence of ASK1 is accessible in the NCBI Reference Sequence database by the accession number NM_005923. ASK1 is ubiquitously expressed with the high expression in the heart, pancreas, testis, liver and ovaries.

The MAP kinases mediate signal transduction from the cell surface to the nucleus via phosphorylation cascades. Egan and Weinbery *Nature* 1993, 365, 781-783.

The MAPK cascades are multifunctional intracellular signaling pathways that are evolutionarily conserved in all eukaryotic cells. Widmann et al. *Physiol Rev* 1999, 79, 143 180; Kyriakis and Avruch, *J. Physiol Rev* 2001, 81, 807-869; Ichijo Oncogene 1999, 18:6087-6093. All eukaryotic cells possess multiple MAPK pathways. In mammalian cells, three MAPK cascades that converge on ERKs, c-Jun N-terminal kinases (JNKs), and p38 MAP kinases have been extensively characterized. Egan and Weinbery *Nature* 1993, 365, 781 783; Boulton et al. *Cell* 1994, 65, 663-675; and Zhou et al. *J. Biol. Chem.* 1995, 270, 12665-12669 (the MAPK/ERK pathway); Derujard et al. *Cell* 1994, 76, 1025-1037; Galcheva Gargova et al. *Science* 1994, 265, 806-808; Minden et al. Mol. *Cell. Biol.* 1994, 14, 6683-6688 (the c-Jun N-terminal kinase (JNK) pathway; and Lee et al. *Science* 1994, 265, 808-811, (the p38 MAPK pathways). ERK pathway is activated by various growth factors and closely linked to the regulation of cell cycle. The JNK and p38 pathways are preferentially activated by various cytotoxic stress such as UV radiation, X-ray, heat shock, osmotic shock, oxidative stress and proinflammatory cytokines such as tumor necrosis factor (TNF) and interleukin-1. Tibbles and Woodgett, *Cell Mol, Life Sci.* 1999, 55:1230-1254. JNK and p38 are thus also called stress activated protein kinases (SAPKs).

Each MAPK cascade involves three classes of serine/threonine kinases, MAPK, MAPK kinase (MAP2K) and MAP2K kinase (MAP3K). In the MAPK signaling cascades, MAP3K phosphorylates and thereby activates MAP2K which in turn phosphorylates and activates MAPK. Activated MAPK may translocate to the cell nucleus and regulate the activities of transcription factors and thereby control gene expression. Sturgill and Wu, *Biochim. Biophys. Acta* 1993, 1092, 350; Nishida and Gotoh, *Trends Biochem. Sci.* 1993, 18, 128; Errede and Levin *Curr Opin. Cell Biol.* 1993, 5, 254; Marshall *Curr. Opin. Genet. Dev.* 1994, 82.

MAP3Ks play pivotal roles in sensing and signaling of cellular and environmental stress. The MAP3Ks in the JNK and p38 pathways are highly divergent in number and structure. At least eleven MAP3Ks have been identified upstream of JNK, each of which activates single or multiple downstream MAPK cascades. This diversity and complexity are consistent with the variety of stimuli that activate MAPK pathways. Kyriakis and Avruch *Physiol. Rev.* 2001, 81, 807-869.

One of the important biological responses mediated through these stress-activated MAP kinase pathways appears to be the decision of cell fate by regulating apoptosis. The possible roles of the JNK pathway in pro-apoptosis signaling have been demonstrated by knockout mouse studies. Yang et al. *Nature* 1997, 389:865-870; Sabapathy et al. *Curr. Biol.* 1999, 9:116-125; Kuan et al. *Neuron* 1999, 22:667-676. Several lines of evidence have also suggested the pro-apoptotic roles of the p38 pathway. Xia et al. *Science* 1995, 270: 1326-1331; Kawaski et al. *J. Biol. Chem.* 1997, 272:18518-18521; Harper and LoGrasso et al. *Cell Signal.* 2001, 13:299-310.

ASK1 was originally identified as an apoptosis-inducing MAP3K. ASK1 regulates the p38 and JNK pathways by directly phosphorylating and thereby activating their respective MAPKKs, MKK4(SEK1)/MKK7 and MKK3/MKK6. Wang et al. *J. Biol. Chem.* 1996, 271, 31607-31611; Ichijo et al. *Science* 1997, 275, 90-94. The activity of ASK1 is tightly regulated; a ubiquitously expressed reduction/oxidation protein thioredoxin (Trx) binds to the N-terminal and inhibits its activity. ASK1 is activated by various cytotoxic stresses including oxidative stress, endoplasmic reticulum (ER) stress, and calcium overload, and by receptor-mediated inflammatory signals such as tumor necrosis factor (TNF) and endotoxic lipopolysaccharide (LPS). Hayakaw et al. *Microbes and Infection* 2006, 8, 1098-1107; Saitoh et al *EMBO J.* 1998, 17:2596-2606; Nishitoh et al. *Genes Dev.* 2002, 16:1345-1355; Takeda et al. *EMBO Rep.* 2004, 5, 161-166; Nishitoh et al. *Mol Cell* 1998, 2, 389-395; Matsukawa et al. *Nat Immunol* 2005, 6, 587-592. It has been shown that ASK1 is required for apoptosis induced by oxidative stress, TNF and ER stresses. Nishitoh et al. *Genes Dev.* 2002, 16:1345-1355; Matsukawa et al. *Nat Immunol* 2005, 6, 587-592; Tobiume et al. *EMBO Rep.* 2001, 2:222-228. Overexpression of wild-type or constitutively active ASK1 induces apoptosis in various cells through mitochondria-dependent caspase activation. Saitoh et al *EMBO J.*

1998, 17:2596-2606; Kanamoto et al. *Mol. Cell Biol.* 2000, 20, 196-204; Hatai et al. *J. Biol. Chem.* 2000, 275, 26576-26588.

Recent studies revealed that ASK1 contributes not only to regulation of cell death but also has diverse functions in the decision of cell fate such as cytokine responses, cell differentiation, and innate immune responses. Matsukawa et al. *J. Biochem.* (Tokyo) 2004, 136, 261-265. Sayama et al. *J. Biol. Chem.* 2000, 276:999-1004; Takeda et al. *J. Biol. Chem.* 2000, 27519805-9813; Sagasti et al. *Cell* 2001, 105:221-232; Kim et al. *Science* 2002, 297:623-626; Nishitoh et al. *Genes Dev.* 2002, 16:1345-1355; Matsukawa et al. *Nat Immunol* 2005, 6, 587-592; Tobiume et al. *EMBO Rep.* 2001, 2:222-228; Imoto, et al. *Diabetes* 2006, 55:1197-1204. Constitutively active ASK1 induces neurite outgrowth in PC12 cells. ASK1 is activated by CaMKII, which activates ASK1-p38 pathway in neurons, suggesting that ASK1 might play critical roles in synaptic plasticity. Moreover, TRAF6-ASK1-p38 pathway plays an essential role in inflammatory and innate immune responses. Hayakawa et al. *Microbes and Infection* 2006, 8, 1098-1 107. It has also been demonstrated that ASK1 has a role in the pathogenesis of TNF-alpha-induced insulin resistance. Overexpression of wild-type ASK1 increases serine phosphorylation of insulin receptor substrate (IRS)-1, and decreases insulin-stimulated tyrosine phosphorylation of IRS-1, leading to impaired insulin signaling. Imoto, et al. *Diabetes* 2006, 55: 1197-1204.

ASK1 is thus a pivotal component not only in stress-induced cell death but also in a broad range of biological activities in order for cells to adapt to or oppose various stresses. Modulating the activities of ASK1 potentially have beneficial effect in treating or preventing a wide range of diseases and conditions including, but not limited to, cardiovascular diseases, inflammatory disorders (acute or chronic), autoimmune diseases, destructive bone disorders, neurodegenerative disorders, and metabolic diseases such as diabetes. Thompson, *Science* 1995, 267, 1456-1462; Yuan and Yanker, *Nature* 2000, 407, 802-809; Los et al. *Immunity* 1999, 10, 629-639.

SUMMARY

The present disclosure provides methods and reagents, involving contacting a cell with an agent, such as an isoindolin-1-one compound, in a sufficient amount to antagonize ASK1 activity, e.g., to control the decision of a cell's fate such as in cytokine responses, cell differentiation, and innate immune responses.

Some embodiments disclosed herein include ASK1 inhibitors containing an isoindolin-1-one core. Other embodiments disclosed herein include pharmaceutical compositions and methods of treatment using these compounds.

One embodiment disclosed herein includes a compound having the structure of Formula I:

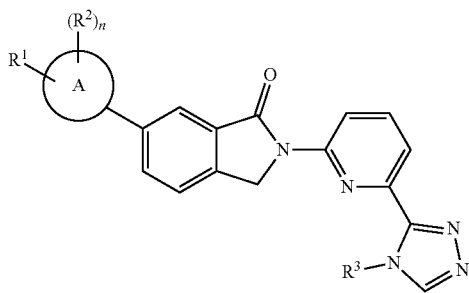

as well as prodrugs and pharmaceutically acceptable salts thereof.

In some embodiments of Formula (I):

Ring A is selected from the group consisting of -aryl, heteroaryl, 5-6-membered heterocyclyl, and 5-6-membered carbocyclyl;

$R^1$ is selected from the group consisting of H, —$(C_{1-6}$ alkylene$)_p CO_2 H$, an acid bioisostere as define herein, unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-6}$ alkylene$)_p$carbocyclyl optionally substituted with 1-10 $R^4$, —$(C_{1-6}$ alkylene$)_p$heterocyclyl optionally substituted with 1-10 $R^5$, —$(C_{1-6}$ alkylene$)_p$aryl optionally substituted with 1-5 $R^6$, —$(C_{1-6}$ alkylene$)_p$heteroaryl optionally substituted with 1-5 $R^7$, —$(C_{1-6}$ alkylene$)_p OR^8$, —$(C_{1-6}$ alkylene$)_p SR^8$, —$(C_{1-6}$ alkylene$)_p S(=O)R^9$, —$(C_{1-6}$ alkylene$)_p SO_2 R^{10}$, —$(C_{1-6}$ alkylene$)_p N(R^{11})SO_2 R^{12}$, —$(C_{1-6}$ alkylene$)_p SO_2 N(R^{13})_2$, —$(C_{1-6}$ alkylene$)_p N(R^4)_2$, —$(C_{1-6}$ alkylene$)_p N(R^{11})C(=O)N(R^5)_2$, —$(C_{1-6}$ alkylene$)_p NRC(=O)OR^{16}$, —$(C_{1-6}$ alkylene$)_p C(=O)N(R^{17})_2$, —$(C_{1-6}$ alkylene$)_p N(R^{11})C(=O)R^{18}$, —$(C_{1-6}$ alkylene$)_p OC(=O)N(R^{19})_2$, and —$(C_{1-6}$ alkylene$)_p CO_2 R^{20}$; wherein each —$(C_{1-4}$ alkylene) is, independently, optionally substituted with one or more substituents as defined anywhere herein;

$R^2$ is selected from the group consisting of halide, Me, OMe, CN, —NHMe, —$(C_{1-4}$ alkylene)OH; wherein —$(C_{1-4}$ alkylene) of —$(C_{1-4}$ alkylene)OH is optionally substituted with one or more OH;

alternatively, an adjacent $R^1$ and $R^2$ are taken together with the atoms to which they are attached to form a ring which is selected from the group consisting of,

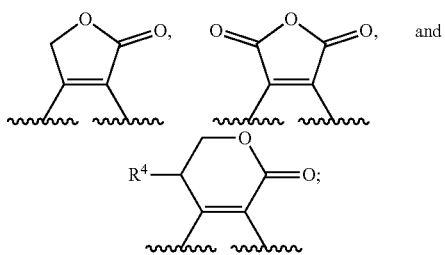

$R^3$ is selected from the group consisting of unsubstituted —$(C_{1-9}$ alkyl), unsubstituted —$(C_{2-9}$ alkenyl), unsubstituted —$(C_{2-9}$ alkynyl), unsubstituted —$(C_{1-9}$ haloalkyl), —$(C_{1-4}$ alkylene)$OR^{21}$, and —$(C_{1-4}$ alkylene$)_p$carbocyclyl optionally substituted with one or more halides; wherein each —$(C_{1-4}$ alkylene) is, independently, optionally substituted with one or more halides;

each $R^4$ is selected from the group consisting of halide, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —OH, —$N(R^{23})_2$, —CN, and —OMe;

each $R^5$ is selected from the group consisting of halide, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —OH, —$N(R^{23})_2$, —CN, and —OMe;

each $R^6$ is selected from the group consisting of halide, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —OH, —$N(R^{23})_2$, —CN, and —OMe;

each $R^7$ is selected from the group consisting of halide, unsubstituted —$(C_{1-6}$ alkyl), unsubstituted —$(C_{2-6}$ alkenyl), unsubstituted —($C_{2-6}$ alkynyl), unsubstituted —($C_{1-6}$ haloalkyl), —OH, —N($R^{23}$)$_2$, —CN, and —OMe;

$R^8$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^9$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{10}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{11}$ is selected from the group consisting of H, unsubstituted —($C_{1-6}$ alkyl), unsubstituted —($C_{2-6}$ alkenyl), unsubstituted —($C_{2-6}$ alkynyl), and unsubstituted —($C_{1-6}$ haloalkyl);

$R^{12}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{13}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{14}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{15}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{16}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{17}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{18}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{19}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{20}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{21}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each n is independently 0 to 5; and each p is independently 0 or 1.

In other embodiments of Formula (I):

Ring A is selected from the group consisting of -aryl, heteroaryl, 5-6-membered heterocyclyl, and 5-6-membered carbocyclyl;

$R^1$ is selected from the group consisting of H, —($C_{1-6}$ alkylene)$_p$CO$_2$H or an acid bioisostere thereof, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-6}$ alkylene)$_p$carbocyclyl optionally substituted with 1-10 $R^4$, —($C_{1-6}$ alkylene)$_p$heterocyclyl optionally substituted with 1-10 $R^5$, —($C_{1-6}$ alkylene)$_p$aryl optionally substituted with 1-5 $R^6$, —($C_{1-6}$ alkylene)$_p$heteroaryl optionally substituted with 1-5 $R^7$, —($C_{1-6}$ alkylene)$_p$OR$^8$, —($C_{1-6}$ alkylene)$_p$SR$^9$, —($C_{1-6}$ alkylene)$_p$S(=O)R$^9$, —($C_{1-6}$ alkylene)$_p$SO$_2$R$^{10}$, —($C_{1-6}$ alkylene)$_p$N(R$^{11}$)SO$_2$R$^{12}$, —($C_{1-6}$ alkylene)$_p$SO$_2$N(R$^{13}$)$_2$, —($C_{1-6}$ alkylene)$_p$N(R$^4$)$_2$, —($C_{1-6}$ alkylene)$_p$N(R$^{11}$)C(=O)N(R$^5$)$_2$, —($C_{1-6}$ alkylene)$_p$NRC(=O)OR$^{16}$, —($C_{1-6}$ alkylene)$_p$C(=O)N(R$^{17}$)$_2$, —($C_{1-6}$ alkylene)$_p$N(R$^{11}$)C(=O)R$^{18}$, —($C_{1-6}$ alkylene)$_p$OC(=O)N(R$^{19}$)$_2$, and —($C_{1-6}$ alkylene)$_p$CO$_2$R$^{20}$; wherein each —($C_{1-4}$ alkylene) is, independently, optionally substituted with one or more substituents as defined anywhere herein;

$R^2$ is selected from the group consisting of halide, Me, OMe, CN, —NHMe —($C_{1-4}$ alkylene)OH; wherein —($C_{1-4}$ alkylene) of —($C_{1-4}$ alkylene)OH is optionally substituted with one or more OH;

alternatively, an adjacent $R^1$ and $R^2$ are taken together with the atoms to which they are attached to form a ring which is selected from the group consisting of,

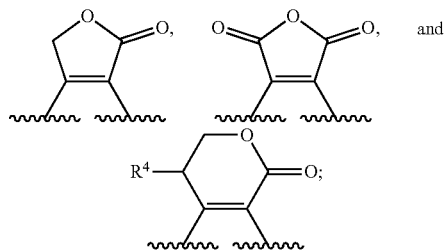

$R^3$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)OR$^{21}$, and —($C_{1-4}$ alkylene)$_p$carbocyclyl optionally substituted with one or more halides; wherein each —($C_{1-4}$ alkylene) is, independently, optionally substituted with one or more halides;

each $R^4$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —N(R$^{23}$)$_2$, —CN, and —OMe;

each $R^5$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —N(R$^{23}$)$_2$, —CN, and —OMe;

each $R^6$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —N(R$^{23}$)$_2$, —CN, and —OMe;

each $R^7$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —N(R$^{23}$)$_2$, —CN, and —OMe;

$R^8$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^9$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one or more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{10}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one or more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{11}$ is selected from the group consisting of H, unsubstituted —($C_{1-6}$ alkyl), unsubstituted —($C_{2-6}$ alkenyl), unsubstituted —($C_{2-6}$ alkynyl), and unsubstituted —($C_{1-6}$ haloalkyl);

$R^{12}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{13}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{14}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{15}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{16}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{17}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{18}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{19}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{20}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene)$_p$carbocyclyl optionally substituted with one of more halides and/or unsubstituted —($C_{1-6}$ alkyl), —($C_{1-3}$ alkylene)$_p$heterocyclyl optionally substituted with one of more halides and/or unsubstituted —($C_{1-6}$ alkyl), —($C_{1-3}$ alkylene)$_p$aryl optionally substituted with one of more halides and/or unsubstituted —($C_{1-6}$ alkyl), and —($C_{1-3}$ alkylene)$_p$heteroaryl optionally substituted with one of more halides and/or unsubstituted —($C_{1-6}$ alkyl); wherein each —($C_{1-4}$ alkylene) is, independently, optionally substituted with one or more halides;

$R^{21}$ is selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl);

each n is independently 0 to 5; and
each p is independently 0 or 1.

In other embodiments of Formula (I):

Ring A is selected from the group consisting of -aryl, heteroaryl, 5-6-membered heterocyclyl, and 4-6-membered carbocyclyl;

$R^1$ is selected from the group consisting of —$(C_{1-6}$ alkylene$)_p CO_2 R^{20}$, —O($C_{1-6}$ alkylene$)_p CO_2 R^{20}$, —($C_{1-6}$ alkylene$)_p$(carbocyclylene)$CO_2 R^{20}$, —O($C_{1-6}$ alkylene$)_p$(carbocyclylene)$CO_2 R^{20}$, unsubstituted —($C_{2-9}$ alkenyl), unsubstituted —($C_{2-9}$ alkynyl), unsubstituted —($C_{1-9}$ haloalkyl), —($C_{1-6}$ alkylene)carbocyclyl optionally substituted with 1-10 $R^4$, —($C_{1-6}$ alkylene$)_p$heterocyclyl optionally substituted with 1-10 $R^5$, —($C_{1-6}$ alkylene$)_p$aryl optionally substituted with 1-5 $R^6$, —($C_{1-6}$ alkylene$)_p$heteroaryl optionally substituted with 1-5 $R^7$, —($C_{1-6}$ alkylene$)_p OR^8$, —($C_{1-6}$ alkylene$)_p SR^8$, —($C_{1-6}$ alkylene$)_p S(=O)R^9$, —($C_{1-6}$ alkylene$)_p SO_2 R^{10}$, —($C_{1-6}$ alkylene$)_p N(R^{11})SO_2 R^{12}$, —($C_{1-6}$ alkylene$)_p SO_2 N(R^{13})_2$, —($C_{1-6}$ alkylene$)_p N(R^4)_2$, —($C_{1-6}$ alkylene$)_p N(R^{11})C(=O)N(R^{15})_2$, —($C_{1-6}$ alkylene$)_p NRC(=O)OR^{16}$, —($C_{1-6}$ alkylene$)_p C(=O)N(R^{17})_2$, —($C_{1-6}$ alkylene$)_p N(R^{11})C(=O)R^{18}$, and —($C_{1-6}$ alkylene$)_p OC(=O)N(R^{19})_2$; wherein each —($C_{1-4}$ alkylene) is, independently, optionally substituted with one or more substituents as defined anywhere herein; wherein each (carbocyclylene) is, independently, optionally substituted with one or more substituents as defined anywhere herein; wherein each $CO_2 R^{20}$ can be replaced with a carbocyclic acid bioisostere thereof;

$R^2$ is selected from the group consisting of halide, Me, OMe, CN, —$SO_2 R^{10}$, —$N(R^4)_2$, —($C_{1-4}$ alkylene$)_p OH$; wherein —($C_{1-4}$ alkylene) of —($C_{1-4}$ alkylene$)_p OH$ is optionally substituted with one or more OH;

alternatively, an adjacent $R^1$ and $R^2$ are taken together with the atoms to which they are attached to form a ring which is selected from the group consisting of

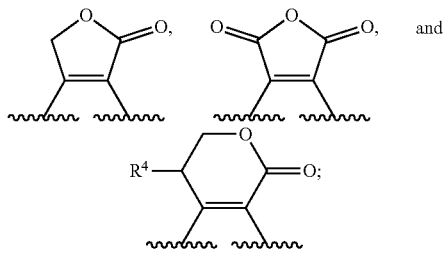

$R^3$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-4}$ alkylene)$OR^{21}$, and —($C_{1-4}$ alkylene$)_p$carbocyclyl optionally substituted with one or more halides; wherein each —($C_{1-4}$ alkylene) is, independently, optionally substituted with one or more halides;

each $R^4$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —$N(R^{23})_2$, —CN, and —OMe;

each $R^5$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —$N(R^{23})_2$, —CN, and —OMe;

each $R^6$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —$N(R^{23})_2$, —CN, and —OMe;

each $R^7$ is selected from the group consisting of halide, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —OH, —$N(R^{23})_2$, —CN, and —OMe;

$R^8$ is selected from the group consisting of H, unsubstituted —($C_{3-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene$)_p$carbocyclyl optionally substituted with one of more halides and/or unsubstituted —($C_{1-6}$ alkyl), —($C_{1-3}$ alkylene$)_p$heterocyclyl optionally substituted with one of more halides and/or unsubstituted —($C_{1-6}$ alkyl), —($C_{1-3}$ alkylene$)_p$aryl optionally substituted with one of more halides and/or unsubstituted —($C_{1-6}$ alkyl), and —($C_{1-3}$ alkylene$)_p$heteroaryl optionally substituted with one of more halides and/or unsubstituted —($C_{1-6}$ alkyl); wherein each —($C_{1-4}$ alkylene) is, independently, optionally substituted with one or more halides;

$R^9$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene$)_p$carbocyclyl optionally substituted with one of more halides and/or unsubstituted —($C_{1-6}$ alkyl), —($C_{1-3}$ alkylene$)_p$heterocyclyl optionally substituted with one of more halides and/or unsubstituted —($C_{1-6}$ alkyl), —($C_{1-3}$ alkylene$)_p$aryl optionally substituted with one of more halides and/or unsubstituted —($C_{1-6}$ alkyl), and —($C_{1-3}$ alkylene$)_p$heteroaryl optionally substituted with one of more halides and/or unsubstituted —($C_{1-6}$ alkyl); wherein each —($C_{1-4}$ alkylene) is, independently, optionally substituted with one or more halides;

$R^{10}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene$)_p$carbocyclyl optionally substituted with one of more halides and/or unsubstituted —($C_{1-6}$ alkyl), —($C_{1-3}$ alkylene$)_p$heterocyclyl optionally substituted with one of more halides and/or unsubstituted —($C_{1-6}$ alkyl), —($C_{1-3}$ alkylene$)_p$aryl optionally substituted with one of more halides and/or unsubstituted —($C_{1-6}$ alkyl), and —($C_{1-3}$ alkylene$)_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{11}$ is selected from the group consisting of H, unsubstituted —($C_{1-6}$ alkyl), unsubstituted —($C_{2-6}$ alkenyl), unsubstituted —($C_{2-6}$ alkynyl), and unsubstituted —($C_{1-6}$ haloalkyl);

$R^{12}$ is selected from the group consisting of unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene$)_p$carbocyclyl optionally substituted with one of more halides and/or unsubstituted —($C_{1-6}$ alkyl), —($C_{1-3}$ alkylene$)_p$heterocyclyl optionally substituted with one of more halides and/or unsubstituted —($C_{1-6}$ alkyl), —($C_{1-3}$ alkylene$)_p$aryl optionally substituted with one of more halides and/or unsubstituted —($C_{1-6}$ alkyl), and —($C_{1-3}$ alkylene$)_p$heteroaryl optionally substituted with one of more halides and/or unsubstituted —($C_{1-6}$ alkyl); wherein each —($C_{1-4}$ alkylene) is, independently, optionally substituted with one or more halides;

each $R^{13}$ is selected from the group consisting of H, unsubstituted —($C_{1-6}$ alkyl), unsubstituted —($C_{2-6}$ alkenyl), unsubstituted —($C_{2-6}$ alkynyl), unsubstituted —($C_{1-6}$ haloalkyl), —($C_{1-3}$ alkylene$)_p$carbocyclyl optionally substituted with one of more halides and/or unsubstituted —($C_{1-6}$ alkyl), —($C_{1-3}$ alkylene$)_p$heterocyclyl optionally substituted with one of more halides and/or unsubstituted —($C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

each $R^{14}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

each $R^{15}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{16}$ is selected from the group consisting of unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

each $R^{17}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{18}$ is selected from the group consisting of unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

each $R^{19}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{20}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{21}$ is selected from the group consisting of H, unsubstituted —$(C_{15}$ alkyl), unsubstituted —$(C_{2-5}$ alkenyl), unsubstituted —$(C_{2-5}$ alkynyl), and unsubstituted —$(C_{1-5}$ haloalkyl);

each n is independently 0 to 5; and each p is independently 0 or 1.

In other embodiments of Formula (I):

Ring A is -aryl;

$R^1$ is selected from the group consisting of —$(C_{1-6}$ alkylene)$_p$CO$_2$H, —O$(C_{1-6}$ alkylene)$_p$CO$_2$H, —$(C_{1-6}$ alkylene)$_p$(carbocyclylene)CO$_2$H, —O$(C_{1-6}$ alkylene)$_p$(carbocyclylene)CO$_2$H, and tetrazole; wherein each —$(C_{1-4}$ alkylene) is, independently, optionally substituted with one or more substituents as defined anywhere herein; wherein each (carbocyclylene) is, independently, optionally substituted with one or more substituents as defined anywhere herein;

$R^2$ is selected from the group consisting of halide, Me, OMe, CN, —SO$_2$R$^{10}$, —N(R$^4$)$_2$, —$(C_{1-4}$ alkylene)$_p$OH; wherein —$(C_{1-4}$ alkylene) of —$(C_{1-4}$ alkylene)$_p$OH is optionally substituted with one or more OH;

$R^3$ is selected from the group consisting of unsubstituted —$(C_{1-9}$ alkyl), unsubstituted —$(C_{1-9}$ haloalkyl), and -carbocyclyl optionally substituted with one or more halides;

$R^{10}$ is unsubstituted —$(C_{1-3}$ alkyl);

each $R^{14}$ is selected from the group consisting of H and unsubstituted —$(C_{1-3}$ alkyl);

each n is independently 0 to 5; and each p is independently 0 or 1.

Some embodiments include stereoisomers and pharmaceutically acceptable salts of a compound of Formula (I). Some embodiments include pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting apoptosis signal-regulating kinase 1 (ASK1) by administering to a patient affected by a disorder or disease in which over activation or overexpression of ASK1 is implicated, such as diseases associated with cytokine responses, cell differentiation, and innate immune responses, a compound according to Formula (I). Accordingly, the compounds and compositions provided herein can be used to treat cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes.

Non-limiting examples of diseases which can be treated with the compounds and compositions provided herein include cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes.

Some embodiments of the present disclosure include methods to prepare compounds of Formula (I).

It is to be understood that both the foregoing general description and the following detailed description are exemplary and explanatory only and are not restrictive of the disclosure, as claimed.

DETAILED DESCRIPTION

Figure 1:
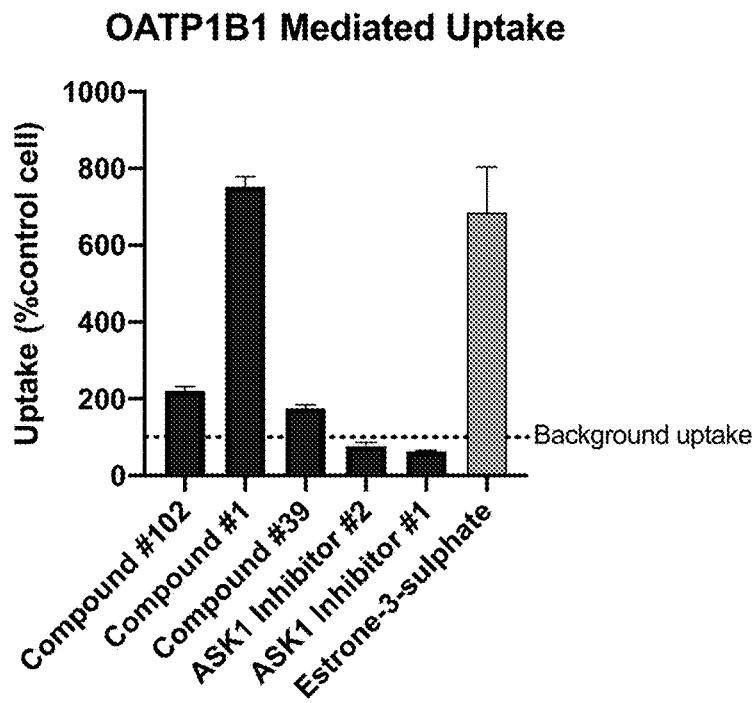
FIG. 1 is a graph showing OATP1B1 mediated uptake of compounds 1, 39 and 102 as a % of control cell.
Figure 2:
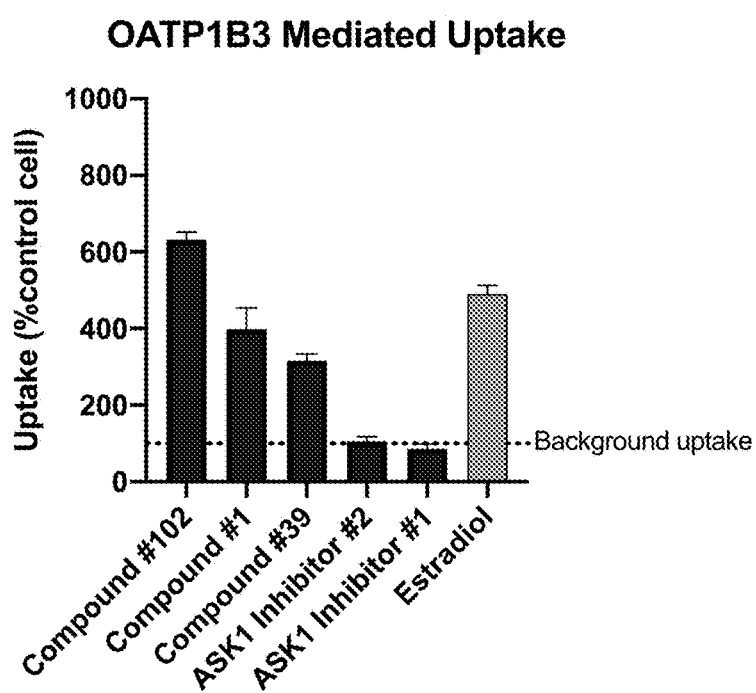
FIG. 2 is a graph showing OATP1B3 mediated uptake of compounds 1, 39 and 102 as a % of control cell.

Provided herein are compositions and methods for inhibiting apoptosis signal-regulating kinase 1 (ASK1).

Some embodiments provided herein relate to a method for treating a disease including, but not limited to, cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes.

In some embodiments, non-limiting examples of a neurological disease or disorder associated with tau protein, amyloid or alpha-synuclein pathology which can be treated with the compounds and compositions provided herein include, but are not limited to, Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, non-limiting examples of diseases in which inflammation is involved which can be treated with the compounds and compositions provided herein include eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

In some embodiments, pharmaceutical compositions are provided that are effective for treatment of a disease of an animal, e.g., a mammal, caused by either the pathological activation or overexpression of ASK1. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that none of the rings in the ring system are aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "carbocyclylene" means a bivalent cyclic ring system containing only carbon atoms in the ring system backbone, such as cyclopropylene, cyclobutylene, cyclopentylene, cyclohexylene, and cyclohexenylene. Carbocyclylenes may include multiple fused rings. Carbocyclylenes may have any degree of saturation provided that none of the rings in the ring system are aromatic. Carbocyclylene groups can either be unsubstituted or substituted with one or more substituents. In some embodiments, carbocyclylene groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 3-11 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N or S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N or S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

As used herein, "carboxylic acid bioisostere" means a group which has chemical and physical similarities producing broadly similar biological properties to a carboxylic acid (see Lipinski, Annual Reports in Medicinal Chemistry, 1986, 21, p 283 "Bioisosterism In Drug Design"; Yun, Hwahak Sekye, 1993, 33, pages 576-579 "Application Of Bioisosterism To New Drug Design"; Zhao, Huaxue Tongbao, 1995, pages 34-38 25 "Bioisosteric Replacement And Development Of Lead Compounds In Drug Design"; Graham, Theochem, 1995, 343, pages 105-109 "Theoretical Studies Applied To Drug Design:ab initio Electronic Distributions In Bioisosteres"). Examples of suitable carboxylic acid bioisostere include: sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl. For example, a carboxylic acid bioisostere can be selected from the group consisting of —C(=O)NHOH, —C(=O)CH$_2$OH, —C(=O)CH$_2$SH, —C(=O)NH—CN,

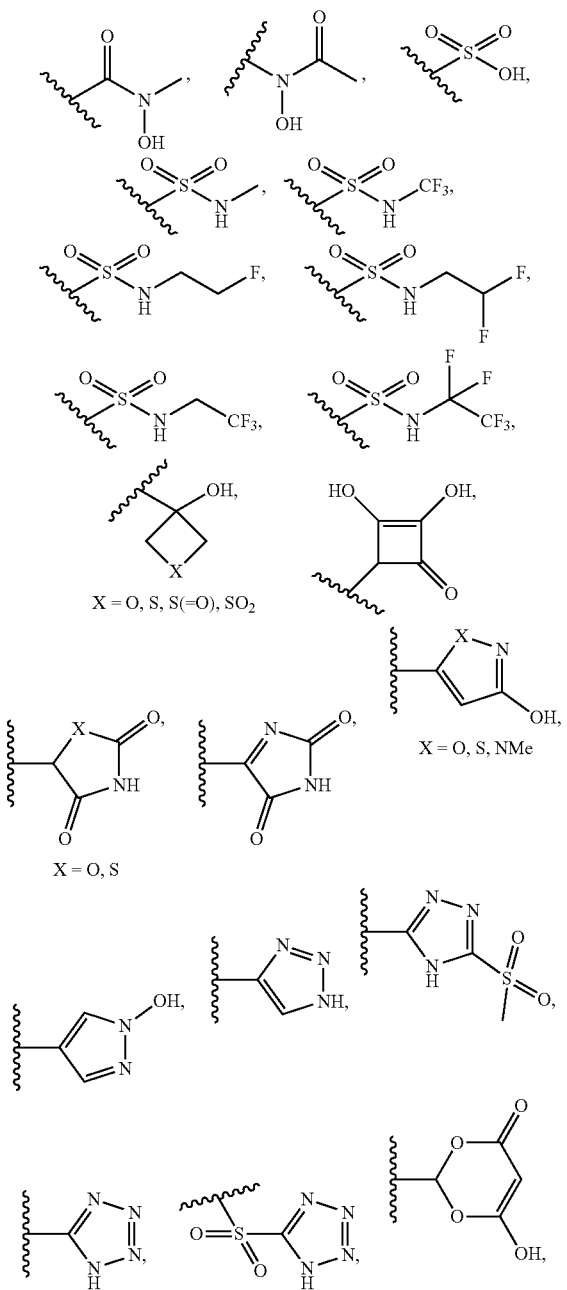

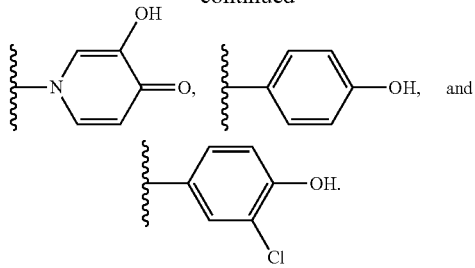

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —(C$_{1-9}$ alkyl) optionally substituted with one or more of hydroxyl, —NH$_2$, —NH(C$_{1-3}$ alkyl), and —N(C$_{1-3}$ alkyl)$_2$; —(C$_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —(C$_{1-9}$ alkoxy) optionally substituted with one or more of halide, hydroxyl, —NH$_2$, —NH(C$_{1-3}$ alkyl), and —N(C$_{1-3}$ alkyl)$_2$; —OPO(OH)$_2$; a phosphonate [such as —PO(OH)$_2$ and —PO(OR')$_2$]; —OPO(OR')R''; —NRR'; —C(O)NRR'; —C(NR)NR'R''; —C(NR')R''; a cyano; a nitro; an azido; —SH; —S—R; —OSO$_2$(OR)]; a sulfonate [such as —SO$_2$(OH) and —SO$_2$(OR)]; —SO$_2$NR'R''; and —SO$_2$R; in which each occurrence of R, R' and R'' are independently selected from H; —(C$_{1-9}$ alkyl); C$_{6-10}$ aryl optionally substituted with from 1-3R'''; 5-10 membered heteroaryl having from 1-4 heteroatoms independently selected from N, O, and S and optionally substituted with from 1-3 R'''; C$_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —(C$_{1-6}$ alkyl), —(C$_{1-6}$ haloalkyl), a halide (e.g., F), a hydroxyl, —C(O)OR, —C(O)R, —(C$_{1-6}$ alkoxyl), —NRR', —C(O)NRR', and a cyano, in which each occurrence of R and R' is independently selected from H and —(C$_{1-6}$ alkyl). In some embodiments, the substituent is selected from —(C$_{1-6}$ alkyl), —(C$_{1-6}$ haloalkyl), a halide (e.g., F), a hydroxyl, —C(O)OR, —C(O)R, —(C$_{1-6}$ alkoxyl), —NRR', —C(O)NRR', and a cyano, in which each occurrence of R and R' is independently selected from H and —(C$_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formula I wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^2$H (deuterium) and $^3$H (tritium), carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracysticaliy, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Brunton et al. (Eds.) (2017); *Goodman and Gilman's: The Pharmacological Basis of Therapeutics,* 13th Ed., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

Compounds

The compounds and compositions provided herein can be used as inhibitors and/or modulators of ASK1, and thus can be used to treat a variety of disorders and diseases in which aberrant ASK1 activity is implicated, such as in cytokine responses, cell differentiation, and inflammatory and innate immune responses. Accordingly, the compounds and compositions provided herein can be used to treat cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes.

Some embodiments of the present disclosure include compounds of Formula I:

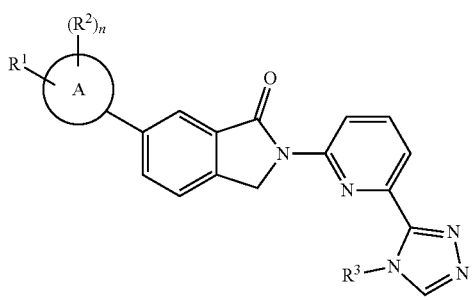

I or enantiomers, diastereomers, tautomers, prodrugs, and pharmaceutically acceptable salts thereof.

Some embodiments of the present disclosure include compounds of Formula Ia:

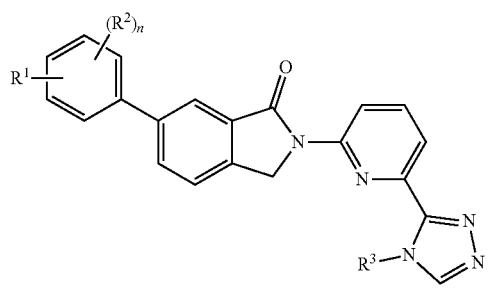

Ia or enantiomers, diastereomers, tautomers, prodrugs, and pharmaceutically acceptable salts thereof.

In some embodiments of Formula I, Ring A is selected from the group consisting of -aryl, heteroaryl, 5-6-membered heterocyclyl, and 5-6-membered carbocyclyl.

In some embodiments of Formulas I or Ia, $R^1$ is selected from the group consisting of H, —($C_{1-6}$ alkylene)$_p$$CO_2$H or an acid bioisostere thereof, unsubstituted —($C_{1-9}$ alkyl) (e.g., $C_{1-8}$, $C_{1-7}$, $C_{1-6}$, $C_{1-5}$, $C_{1-4}$, $C_{1-3}$, $C_{1-2}$, $C_1$), unsubstituted —($C_{2-9}$ alkenyl) (e.g., $C_{2-8}$, $C_{2-7}$, $C_{2-6}$, $C_{2-5}$, $C_{2-4}$, $C_{2-3}$, $C_2$), unsubstituted —($C_{2-9}$ alkynyl) (e.g., $C_{2-8}$, $C_{2-7}$, $C_{2-6}$, $C_{2-5}$, $C_{2-4}$, $C_{2-3}$, $C_2$), unsubstituted —($C_{1-9}$ haloalkyl) (e.g., $C_{1-8}$, $C_{1-7}$, $C_{1-6}$, $C_{1-5}$, $C_{1-4}$, $C_{1-3}$, $C_{1-2}$, $C_1$), —($C_{1-6}$ alkylene)$_p$carbocyclyl optionally substituted with 1-10 (e.g., 1-9, 1-8, 1-7, 1-6, 1-5, 1-4, 1-3. 1-2. 1) $R^4$, —($C_{1-6}$ alkylene)$_p$heterocyclyl optionally substituted with 1-10 (e.g., 1-9, 1-8, 1-7, 1-6, 1-5, 1-4, 1-3. 1-2. 1) $R^5$, —($C_{1-6}$ alkylene)$_p$aryl optionally substituted with 1-5 (e.g., 1-4, 1-3. 1-2. 1) $R^6$, —($C_{1-6}$ alkylene)$_p$heteroaryl optionally substituted with 1-5 (e.g., 1-4, 1-3. 1-2. 1) $R^7$, —($C_{1-6}$ alkylene)$_p$$OR^8$, —($C_{1-6}$ alkylene)$_p$$SR^8$, —($C_{1-6}$ alkylene)$_p$S(=O)$R^9$, —($C_{1-6}$ alkylene)$_p$$SO_2R^{10}$, —($C_{1-6}$ alkylene)$_p$N($R^{11}$)$SO_2R^{12}$, —($C_{1-6}$ alkylene)$_p$$SO_2N(R^{13})_2$, —($C_{1-6}$ alkylene)$_p$N($R^4$)$_2$, —($C_{1-6}$ alkylene)$_p$N($R^{11}$)C(=O)N($R^5$)$_2$, —($C_{1-6}$ alkylene)$_p$NRC(=O)$OR^{16}$, —($C_{1-6}$ alkylene)$_p$C(=O)N($R^{17}$)$_2$, —($C_{1-6}$ alkylene)$_p$N($R^{11}$)C(=O)$R^{18}$, —($C_{1-6}$ alkylene)$_p$OC(=O)N($R^{19}$)$_2$, and —($C_{1-6}$ alkylene)$_p$$CO_2R^{20}$; wherein each —($C_{1-4}$ alkylene) is, independently, optionally substituted with one or more substituents as defined anywhere herein.

In some embodiments of Formulas I or Ia, $R^1$ is selected from the group consisting of —($C_{1-6}$ alkylene)$_p$$CO_2R^{20}$, —O($C_{1-6}$ alkylene)$_p$$CO_2R^{20}$, —($C_{1-6}$ alkylene)$_p$(carbocyclylene)$CO_2R^{20}$, —O($C_{1-6}$ alkylene)$_p$(carbocyclylene)$CO_2R^{20}$, unsubstituted —($C_{2}$-9 alkenyl) (e.g., $C_{2-8}$, $C_{2-7}$, $C_{2-6}$, $C_{2-5}$, $C_{2-4}$, $C_{2-3}$, $C_2$), unsubstituted —($C_{2-9}$ alkynyl) (e.g., $C_{2-8}$, $C_{2-7}$, $C_{2-6}$, $C_{2-5}$, $C_{2-4}$, $C_{2-3}$, $C_2$), unsubstituted —($C_{1-9}$ haloalkyl) (e.g., $C_{1-8}$, $C_{1-7}$, $C_{1-6}$, $C_{1-5}$, $C_{1-4}$, $C_{1-3}$, $C_{1-2}$, $C_1$), —($C_{1-6}$ alkylene)$_p$carbocyclyl optionally substituted with 1-10 (e.g., 1-9, 1-8, 1-7, 1-6, 1-5, 1-4, 1-3. 1-2. 1) $R^4$, —($C_{1-6}$ alkylene)$_p$heterocyclyl optionally substituted with 1-10 (e.g., 1-9, 1-8, 1-7, 1-6, 1-5, 1-4, 1-3. 1-2. 1) $R^5$, —($C_{1-6}$ alkylene)$_p$aryl optionally substituted with 1-5 (e.g., 1-4, 1-3. 1-2. 1) $R^6$, —($C_{1-6}$ alkylene)$_p$heteroaryl optionally substituted with 1-5 (e.g., 1-4, 1-3. 1-2. 1) $R^7$, —($C_{1-6}$ alkylene)$_p$$OR^8$, —($C_{1-6}$ alkylene)$_p$SR, —($C_{1-6}$ alkylene)$_p$S(=O)$R^9$, —($C_{1-6}$ alkylene)$_p$$SO_2R^{10}$, —($C_{1-6}$ alkylene)$_p$N($R^{11}$)$SO_2R^{12}$, —($C_{1-6}$ alkylene)$_p$$SO_2N(R^{13})_2$, —($C_{1-6}$ alkylene)$_p$N($R^4$)$_2$, —($C_{1-6}$ alkylene)$_p$N($R^{11}$)C(=O)N($R^5$)$_2$, —($C_{1-6}$ alkylene)$_p$NRC(=O)$OR^{16}$, —($C_{1-6}$ alkylene)$_p$C(=O)N($R^{17}$)$_2$, —($C_{1-6}$ alkylene)$_p$N($R^{11}$)C(=O)$R^{18}$, and —($C_{1-6}$ alkylene)$_p$OC(=O)N($R^{19}$)$_2$; wherein each —($C_{1-4}$ alkylene) is, independently, optionally substituted with one or more substituents as defined anywhere herein; wherein each (carbocyclylene) is, independently, optionally substituted with one or more substituents as defined anywhere herein; wherein each $CO_2R^{20}$ can be replaced with a carbocyclic acid bioisostere thereof.

In some embodiments of Formulas I or Ia, $R^1$ is selected from the group consisting of —($C_{1-6}$ alkylene)$_p$$R^{22}$, wherein $R^{22}$ is selected from the group consisting of —$CO_2H$, —C(=O)NHOH, —C(=O)$CH_2OH$, —C(=O)$CH_2SH$, —C(=O)NH—CN,

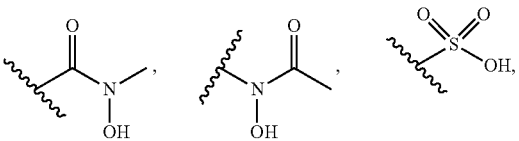

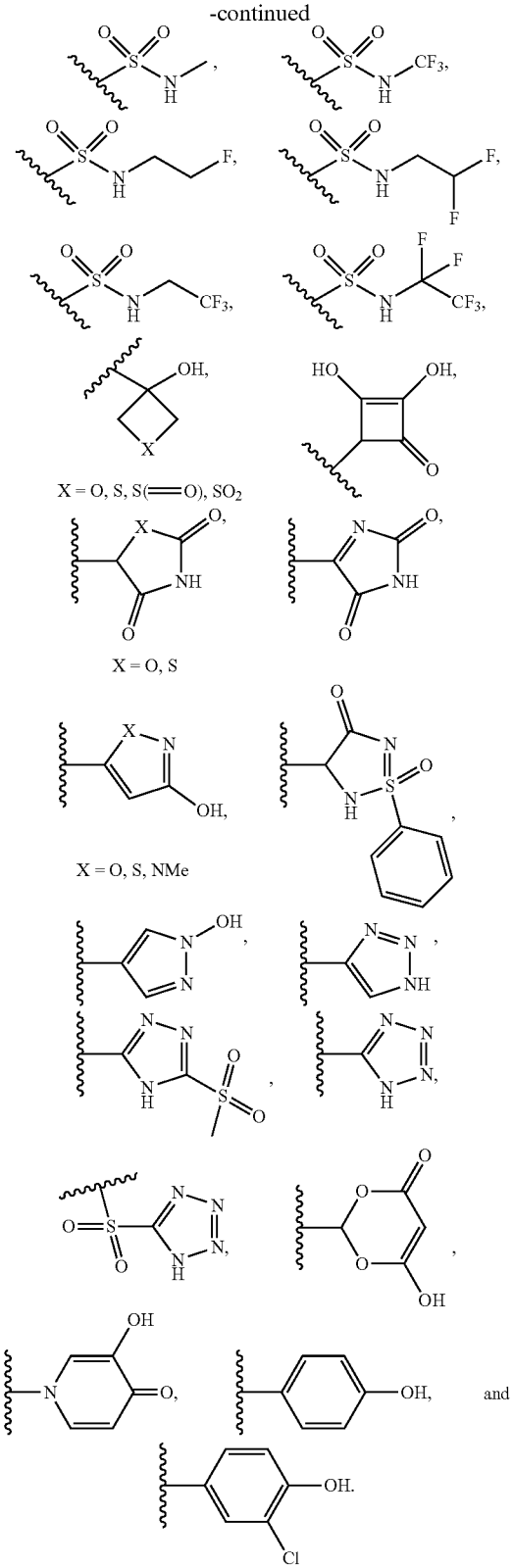
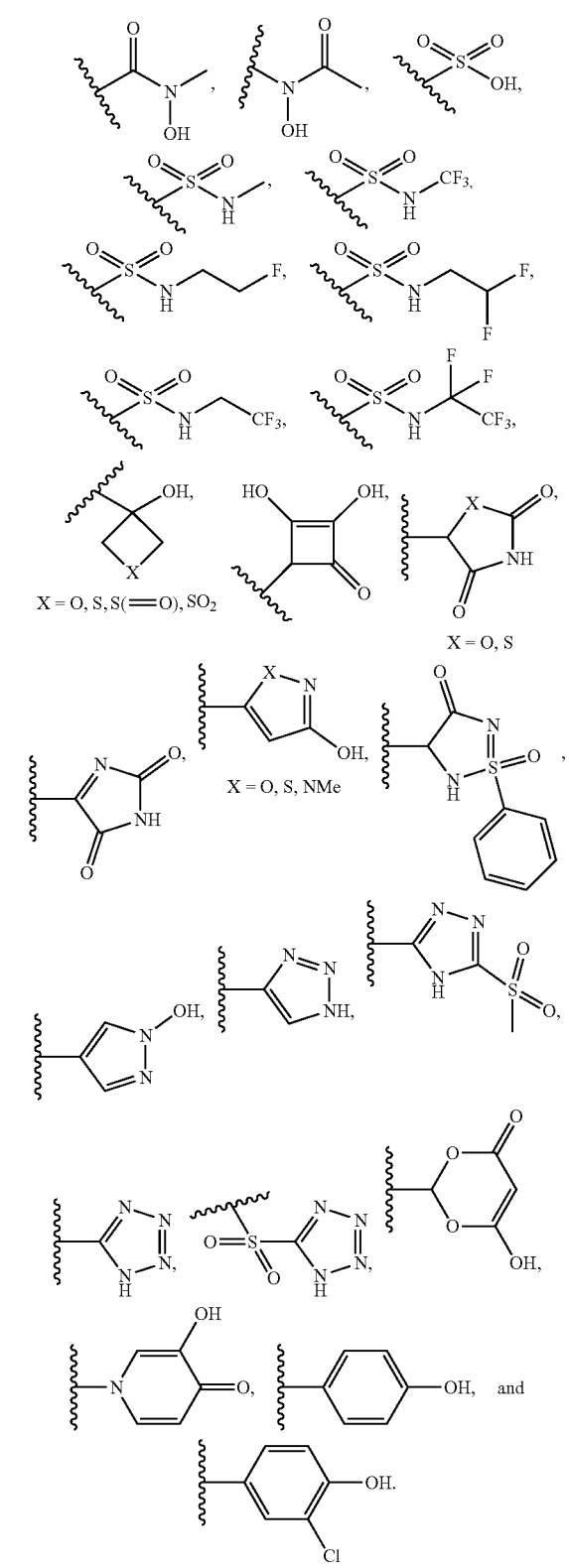

In some embodiments of Formulas I or Ia, $R^1$ is selected from the group consisting of —O($C_{1-6}$ alkylene)$_p R^{22}$, wherein $R^{22}$ is selected from the group consisting of —CO$_2$H, —C(=O)NHOH, —C(=O)CH$_2$OH, —C(=O)CH$_2$SH, —C(=O)NH—CN, In some embodiments of Formulas I or Ia, $R^1$ is selected from the group consisting of —($C_{1-6}$ alkylene)$_p$(carbocyclylene)$R^{22}$, wherein $R^{22}$ is selected from the group consisting of —CO$_2$H, —C(=O)NHOH, —C(=O)CH$_2$OH, —C(=O)CH$_2$SH, —C(=O)NH—CN,

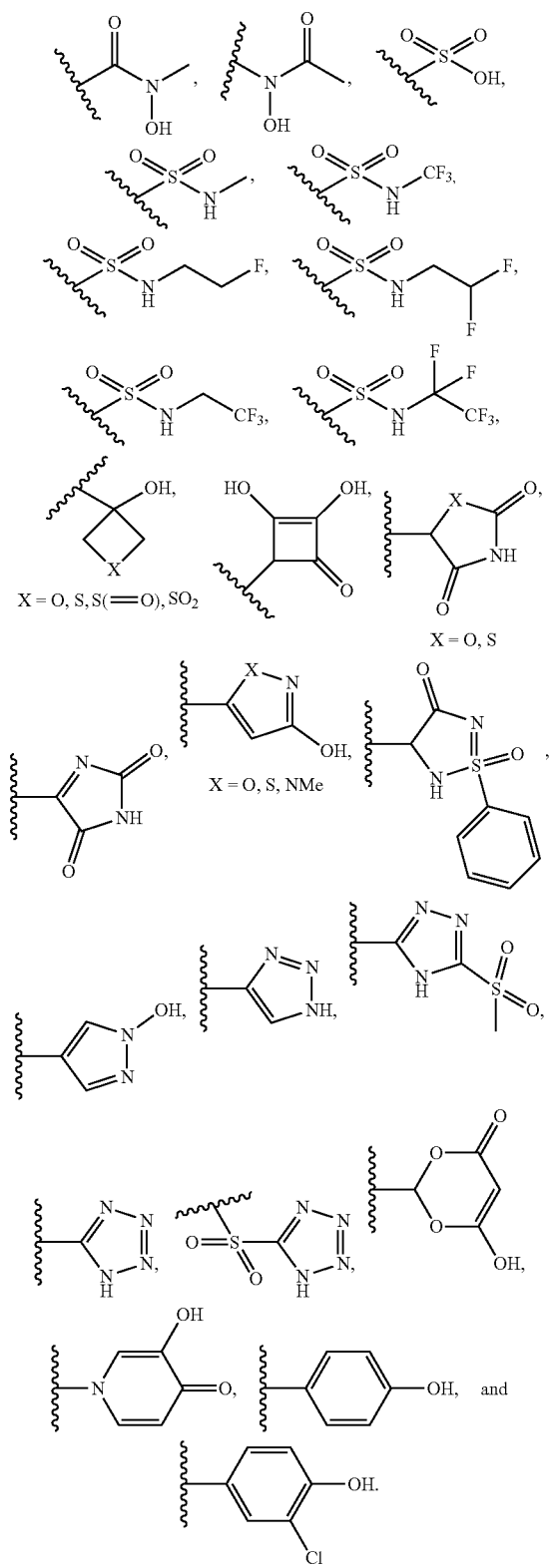

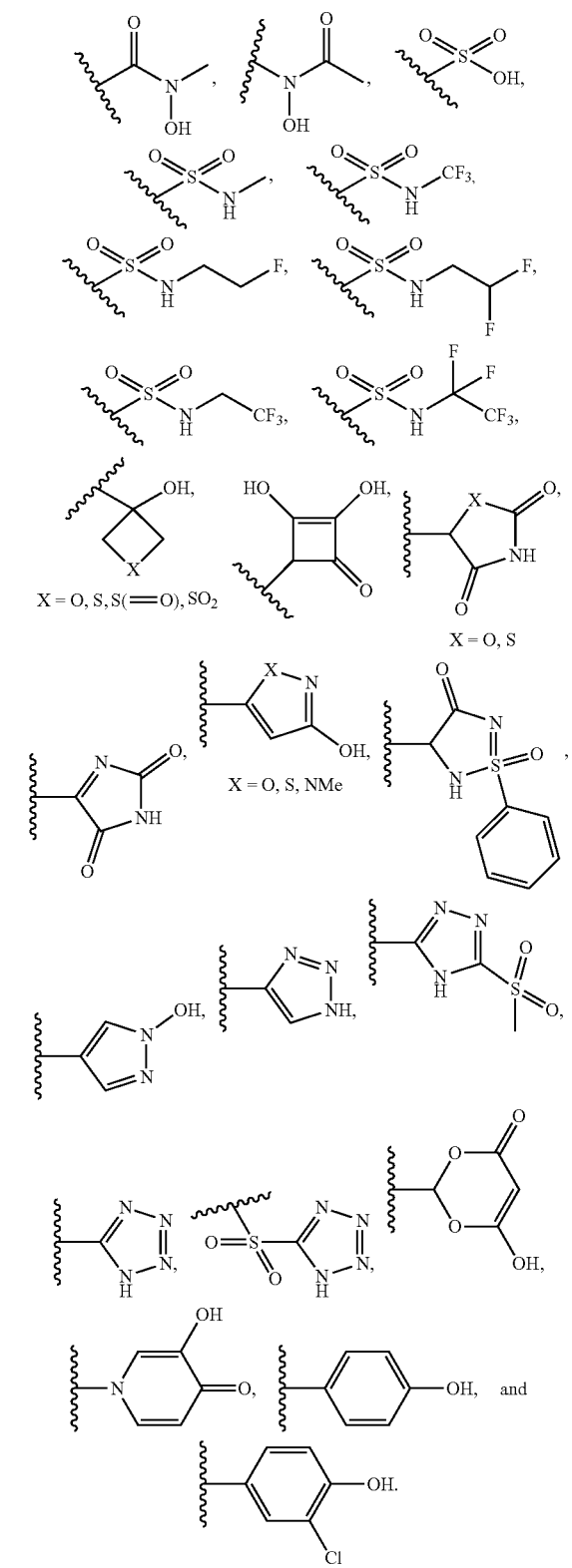

In some embodiments of Formulas I or Ia, $R^1$ is selected from the group consisting of —O($C_{1-6}$ alkylene)$_p$(carbocyclylene)$R^{22}$, wherein $R^{22}$ is selected from the group consisting of —$CO_2H$, —C(=O)NHOH, —C(=O)$CH_2$OH, —C(=O)$CH_2$SH, —C(=O)NH—CN, In some embodiments of Formulas I or Ia, $R^2$ is selected from the group consisting of halide (e.g., F, Cl, Br, I), Me, OMe, CN, —NHMe, —($C_{1-4}$ alkylene)OH; wherein —($C_{1-4}$ alkylene) of —($C_{1-4}$ alkylene)OH is optionally substituted with one or more OH.

In some embodiments of Formulas I or Ia, $R^2$ is selected from the group consisting of halide, Me, OMe, CN, $-SO_2R^{10}$, $-N(R^4)_2$, $-(C_{1-4}$ alkylene$)_p$OH; wherein $-(C_{1-4}$ alkylene) of $-(C_{1-4}$ alkylene$)_p$OH is optionally substituted with one or more OH.

In some embodiments of Formulas I or Ia, an adjacent $R^1$ and $R^2$ are taken together with the atoms to which they are attached to form a ring which is selected from the group consisting of

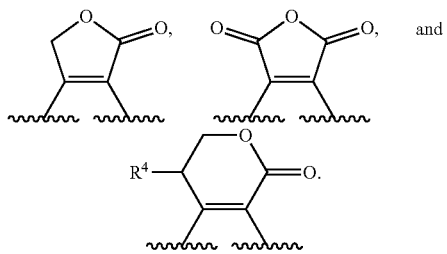

In some embodiments of Formulas I or Ia, $R^3$ is selected from the group consisting of unsubstituted $-(C_{1-9}$ alkyl) (e.g., $C_{1-8}$, $C_{1-7}$, $C_{1-6}$, $C_{1-5}$, $C_{1-4}$, $C_{1-3}$, $C_{1-2}$, $C_1$), unsubstituted $-(C_{2-9}$ alkenyl) (e.g., $C_{2-8}$, $C_{2-7}$, $C_{2-6}$, $C_{2-5}$, $C_{2-4}$, $C_{2-3}$, $C_2$), unsubstituted $-(C_{2-9}$ alkynyl) (e.g., $C_{2-8}$, $C_{2-7}$, $C_{2-6}$, $C_{2-5}$, $C_{2-4}$, $C_{2-3}$, $C_2$), unsubstituted $-(C_{1-9}$ haloalkyl) (e.g., $C_{1-8}$, $C_{1-7}$, $C_{1-6}$, $C_{1-5}$, $C_{1-4}$, $C_{1-3}$, $C_{1-2}$, $C_1$), $-(C_{1-4}$ alkylene)$OR^{21}$, and $-(C_{1-4}$ alkylene$)_p$carbocyclyl optionally substituted with one or more halides (e.g., F, Cl, Br, I); wherein each $-(C_{1-4}$ alkylene) is, independently, optionally substituted with one or more halides (e.g., F, Cl, Br, I).

In some embodiments of Formulas I or Ia, each $R^4$ is selected from the group consisting of halide (e.g., F, Cl, Br, I), unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-$OH, $-N(R^{23})_2$, $-$CN, and $-$OMe.

In some embodiments of Formulas I or Ia, each $R^5$ is selected from the group consisting of halide (e.g., F, Cl, Br, I), unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-$OH, $-N(R^{23})_2$, $-$CN, and $-$OMe.

In some embodiments of Formulas I or Ia, each $R^6$ is selected from the group consisting of halide (e.g., F, Cl, Br, I), unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-$OH, $-N(R^{23})_2$, $-$CN, and $-$OMe.

In some embodiments of Formulas I or Ia, each $R^7$ is selected from the group consisting of halide (e.g., F, Cl, Br, I), unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-$OH, $-N(R^{23})_2$, $-$CN, and $-$OMe.

In some embodiments of Formulas I or Ia, $R^8$ is selected from the group consisting of H, unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-(C_{1-3}$ alkylene$)_p$carbocyclyl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), $-(C_{1-3}$ alkylene$)_p$heterocyclyl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), $-(C_{1-3}$ alkylene$)_p$aryl optionally substituted with one of more halides and/or unsubstituted $-(C_{1-6}$ alkyl) (e.g., $C_{1-5}$, $C_{1-4}$, $C_{1-3}$, $C_{1-2}$, $C_1$), and $-(C_{1-3}$ alkylene$)_p$heteroaryl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$); wherein each $-(C_{1-4}$ alkylene) is, independently, optionally substituted with one or more halides (e.g., F, Cl, Br, I).

In some embodiments of Formulas I or Ia, $R^9$ is selected from the group consisting of unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-(C_{1-3}$ alkylene$)_p$carbocyclyl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), $-(C_{1-3}$ alkylene$)_p$heterocyclyl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), $-(C_{1-3}$ alkylene$)_p$aryl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), and $-(C_{1-3}$ alkylene$)_p$heteroaryl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$); wherein each $-(C_{1-4}$ alkylene) is, independently, optionally substituted with one or more halides (e.g., F, Cl, Br, I).

In some embodiments of Formulas I or Ia, $R^{10}$ is selected from the group consisting of unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-(C_{1-3}$ alkylene$)_p$carbocyclyl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), $-(C_{1-3}$ alkylene$)_p$heterocyclyl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), $-(C_{1-3}$ alkylene$)_p$aryl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$), and $-(C_{1-3}$ alkylene$)_p$heteroaryl optionally substituted with one of more halides (e.g., F, Cl, Br, I) and/or unsubstituted $-(C_{1-6}$ alkyl) (e.g., $C_{1-5}$, $C_{1-4}$, $C_{1-3}$, $C_{1-2}$, $C_1$); wherein each $-(C_{1-4}$ alkylene) is, independently, optionally substituted with one or more halides (e.g., F, Cl, Br, I).

In some embodiments of Formulas I or Ia, each $R^{11}$ is selected from the group consisting of H, unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), and unsubstituted $-(C_{1-6}$ haloalkyl) (e.g., $C_{1-5}$, $C_{1-4}$, $C_{1-3}$, $C_{1-2}$, $C_1$).

In some embodiments of Formulas I or Ia, $R^{12}$ is selected from the group consisting of unsubstituted $-(C_{1-6}$ alkyl) (e.g., $C_{1-5}$, $C_{1-4}$, $C_{1-3}$, $C_{1-2}$, $C_1$), unsubstituted $-(C_{2-6}$ alkenyl) (e.g., $C_{2-5}$, $C_{2-4}$, $C_{2-3}$, $C_2$), unsubstituted $-(C_{2-6}$ alkynyl) (e.g., $C_{2-5}$, $C_{2-4}$, $C_{2-3}$, $C_2$), unsubstituted $-(C_{1-6}$ haloalkyl) (e.g., $C_{1-5}$, $C_{1-4}$, $C_{1-3}$, $C_{1-2}$, $C_1$), $-(C_{1-3}$ alkylene$)_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$
Kanamoto et al., "Role of apoptosis signal-regulating kinase in regulation of the c-Jun N-Terminal kinase pathway and apoptosis in sympathetic neurons," Mol. Cell Biol., 20(1): 196-204, 2000.
Kawasaki et al., "Activation and involvement of p38 mitogen-activated protein kinase in glutamate-induced apoptosis in rat cerebellar granule cells," J. Biol. Chem., 272(30): 18518-18521, 1997.
Kim et al., "A conserved p38 MAP kinase pathway in Caenorhabclitis elegans innate immunity," Science, 297 (5581): 623-626, 2002.
Kuan et al., "The Jnk1 and Jnk2 protein kinases are required for regional specific apoptosis during early brain development," Neuron, 22(4): 667-676, 1999. alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —(Cl-3 alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, Cl); wherein each —($C_{1-4}$ alkylene) is, independently, optionally substituted with one or more halides (e.g., F, Cl, Br, I).

In some embodiments of Formulas I or Ia, each $R^{13}$ is selected from the group consisting of H, unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, each $R^{14}$ is selected from the group consisting of H, unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, each $R^{15}$ is selected from the group consisting of H, unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, $R^{16}$ is selected from the group consisting of unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, each $R^{17}$ is selected from the group consisting of H, unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, $R^{18}$ is selected from the group consisting of unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$ heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, each $R^{19}$ is selected from the group consisting of H, unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$ heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, $R^{20}$ is selected from the group consisting of H, unsubstituted —($C_{1-6}$ alkyl) (e.g., $C_{1-5}$, $C_{1-4}$, $C_{1-3}$, $C_{1-2}$, $C_1$), unsubstituted —($C_{2-6}$ alkenyl) (e.g., $C_{2-5}$, $C_{2-4}$, $C_{2-3}$, $C_2$), unsubstituted —($C_{2-6}$ alkynyl) (e.g., $C_{2-5}$, $C_{2-4}$, $C_{2-3}$, $C_2$), unsubstituted —($C_{1-6}$ haloalkyl) (e.g., $C_{1-5}$, $C_{1-4}$, $C_{1-3}$, $C_{1-2}$, $C_1$), —($C_{1-3}$ alkylene)$_p$carbocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$heterocyclyl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), —($C_{1-3}$ alkylene)$_p$aryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$), and —($C_{1-3}$ alkylene)$_p$heteroaryl optionally substituted with one of more halides (e.g., F, Cl, Br, I) and/or unsubstituted —($C_{1-6}$ alkyl) (e.g., $C_{1-5}$, $C_{1-4}$, $C_{1-3}$, $C_{1-2}$, $C_1$); wherein each —($C_{1-4}$ alkylene) is, independently, optionally substituted with one or more halides (e.g., F, Cl, Br, I).

In some embodiments of Formulas I or Ia, $R^{20}$ is selected from the group consisting of H and unsubstituted —($C_{1-6}$ alkyl) (e.g., $C_{1-5}$, $C_{1-4}$, $C_{1-3}$, $C_{1-2}$, $C_1$).

In some embodiments of Formulas I or Ia, $R^{20}$ is selected from the group consisting of H and Me.

In some embodiments of Formulas I or Ia, $R^{21}$ is selected from the group consisting of H, unsubstituted —($C_{1-5}$ alkyl) (e.g., $C_{1-4}$, $C_{1-3}$, $C_{1-2}$, $C_1$), unsubstituted —($C_{2-5}$ alkenyl) (e.g., $C_{2-4}$, $C_{2-3}$, $C_2$), unsubstituted —($C_{2-5}$ alkynyl) (e.g., $C_{2-4}$, $C_{2-3}$, $C_2$), and unsubstituted —($C_{1-5}$ haloalkyl) (e.g., $C_{1-4}$, $C_{1-3}$, $C_{1-2}$, $C_1$).

In some embodiments of Formulas I or Ia, $R^{22}$ is selected from the group consisting of —$CO_2H$, —C(=O)NHOH, —C(=O)$CH_2$OH, —C(=O)$CH_2$SH, —C(=O)NH—CN,

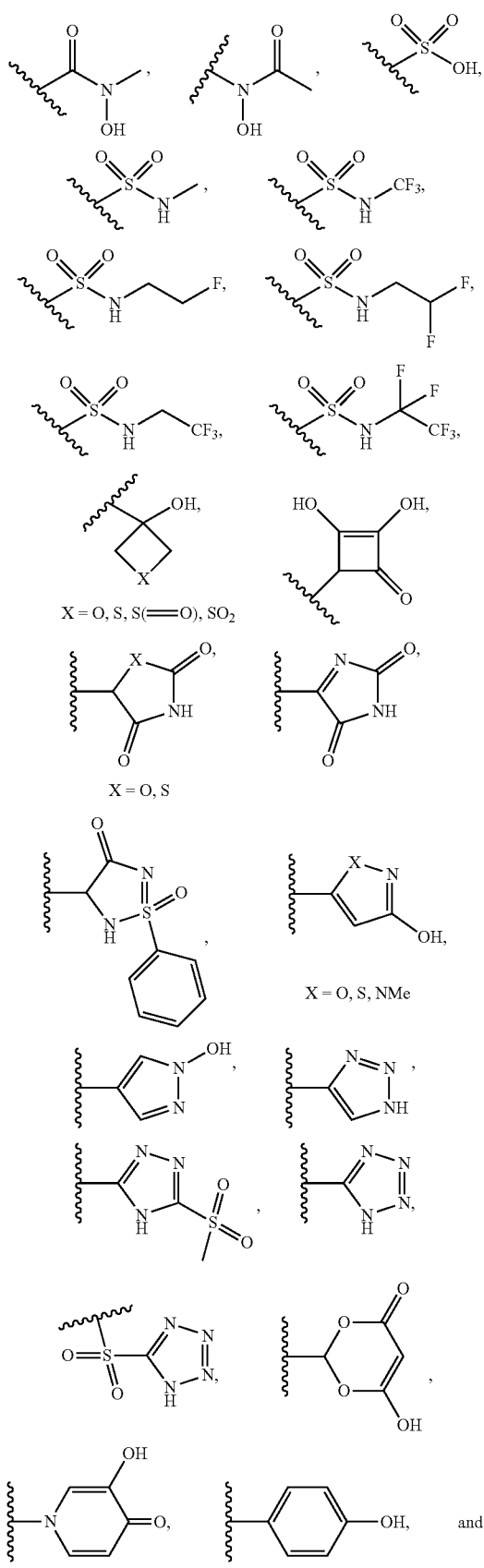

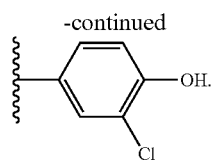

In some embodiments of Formulas I or Ia, each n is independently 0 to 5.

In some embodiments of Formulas I or Ia, each p is independently 0 or 1.

In some embodiments of Formulas I or Ia, each —($C_{1-4}$ alkylene) is —($C_{1-3}$ alkylene).

In some embodiments of Formulas I or Ia, each —($C_{1-4}$ alkylene) is —($C_{1-2}$ alkylene).

In some embodiments of Formulas I or Ia, each —($C_{1-4}$ alkylene) is —($C_1$ alkylene).

In some embodiments of Formulas I or Ia, each —($C_{1-4}$ alkylene) is —$CH_2$—.

In some embodiments of Formulas I or Ia, each —($C_{1-4}$ alkylene) is optionally substituted with halide (e.g., F, Cl, Br, I).

In some embodiments of Formulas I or Ia, each —($C_{1-4}$ alkylene) is optionally substituted with F.

In some embodiments of Formulas I or Ia, each -(carbocyclylene)- is cyclopropylene.

In some embodiments of Formulas I or Ia, each -(carbocyclylene)- is cyclobutylene.

In some embodiments of Formulas I or Ia, each -(carbocyclylene)- is cyclopentylene.

In some embodiments of Formulas I or Ia, each -(carbocyclylene)- is cyclohexylene.

In some embodiments of Formulas I or Ia, each -(carbocyclylene)- is optionally substituted with halide (e.g., F, Cl, Br, I).

In some embodiments of Formulas I or Ia, each -(carbocyclylene)- is optionally substituted with F.

In some embodiments of Formulas I or Ia, n is 0, 1, 2, 3, 4, or 5; in some embodiments of Formulas I or Ia, n is 0, 1, 2, 3, or 4; in some embodiments of Formulas I or Ia, n is 1, 2, 3, 4, or 5; in some embodiments of Formulas I or Ia, n is 1, 2, 3, or 4; in some embodiments of Formulas I or Ia, n is 2, 3, 4, or 5; in some embodiments of Formulas I or Ia, n is 2, 3, or 4; in some embodiments of Formulas I or Ia, n is 3, 4, or 5; in some embodiments of Formulas I or Ia, n is 3 or 4; in some embodiments of Formulas I or Ia, n is 0, 1, 2, or 3; in some embodiments of Formulas I or Ia, n is 1, 2, or 3; in some embodiments of Formulas I or Ia, n is 0, 1 or 2; in some embodiments of Formulas I or Ia, n is 1 or 2; in some embodiments of Formulas I or Ia, n is 0; in some embodiments of Formulas I or Ia, n is 1; in some embodiments of Formulas I or Ia, n is 2; in some embodiments of Formulas I or Ia, n is 3; in some embodiments of Formulas I or Ia, n is 4; in some embodiments of Formulas I or Ia, n is 5.

In some embodiments of Formulas I or Ia, each p is 0 or 1; in some embodiments of Formula I, p is 0; in some embodiments of Formula I, p is 1.

In some embodiments of Formula I, Ring A is -aryl.

In some embodiments of Formula I, Ring A is phenyl.

In some embodiments of Formulas I or Ia, $R^1$ is selected from the group consisting of —($C_{1-6}$ alkylene)$_p$$CO_2$H and a carbocyclic acid bioisostere as define herein.

In some embodiments of Formulas I or Ia, $R^1$ is selected from the group consisting of —O($C_{1-6}$ alkylene)$_p$$CO_2$H and a carbocyclic acid bioisostere as define herein.

In some embodiments of Formulas I or Ia, $R^1$ is selected from the group consisting of —($C_{1-6}$ alkylene)$_p$$CO_2$H, —O($C_{1-6}$ alkylene)$_p$$CO_2$H, and tetrazole.

In some embodiments of Formulas I or Ia, $R^1$ is selected from the group consisting of —($C_{1-6}$ alkylene)$_p$$CO_2$H and tetrazole.

In some embodiments of Formulas I or Ia, $R^1$ is selected from the group consisting of —O($C_{1-6}$ alkylene)$_p$$CO_2$H and tetrazole.

In some embodiments of Formulas I or Ia, $R^1$ is —($C_{1-6}$ alkylene)$CO_2$H.

In some embodiments of Formulas I or Ia, $R^1$ is —($C_{1-5}$ alkylene)$CO_2$H.

In some embodiments of Formulas I or Ia, $R^1$ is —($C_{1-4}$ alkylene)$CO_2$H.

In some embodiments of Formulas I or Ia, $R^1$ is —($C_{1-3}$ alkylene)$CO_2$H.

In some embodiments of Formulas I or Ia, $R^1$ is —($C_{1-2}$ alkylene)$CO_2$H.

In some embodiments of Formulas I or Ia, $R^1$ is —($CH_2$)$CO_2$H.

In some embodiments of Formulas I or Ia, $R^1$ is —(CHMe)$CO_2$H.

In some embodiments of Formulas I or Ia, $R^1$ is —($CMe_2$)$CO_2$H.

In some embodiments of Formulas I or Ia, $R^1$ is

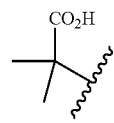

In some embodiments of Formulas I or Ia, $R^1$ is

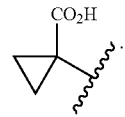

In some embodiments of Formulas I or Ia, $R^1$ is —$CO_2$H.

In some embodiments of Formulas I or Ia, $R^1$ is tetrazole.

In some embodiments of Formulas I or Ia, $R^1$ is —O($C_{1-6}$ alkylene)$CO_2$H.

In some embodiments of Formulas I or Ia, $R^1$ is —O($C_{1-5}$ alkylene)$CO_2$H.

In some embodiments of Formulas I or Ia, $R^1$ is —O($C_{1-4}$ alkylene)$CO_2$H.

In some embodiments of Formulas I or Ia, $R^1$ is —O($C_{1-3}$ alkylene)$CO_2$H.

In some embodiments of Formulas I or Ia, $R^1$ is —O($C_{1-2}$ alkylene)$CO_2$H.

In some embodiments of Formulas I or Ia, $R^1$ is —O($CH_2$)$CO_2$H.

In some embodiments of Formulas I or Ia, $R^1$ is —O(CHMe)$CO_2$H.

In some embodiments of Formulas I or Ia, $R^1$ is —O($CMe_2$)$CO_2$H.

In some embodiments of Formulas I or Ia, R¹ is

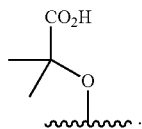

In some embodiments of Formulas I or Ia, R¹ is

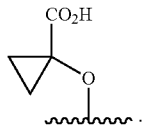

In some embodiments of Formulas I or Ia, R¹ is

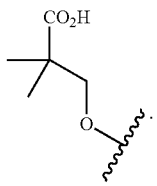 [SMILES: *OCC(C)(C)C(=O)O]

In some embodiments of Formulas I or Ia, R¹ is

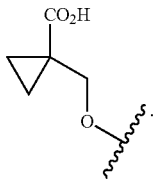 [SMILES: *OCC1(C(=O)O)CC1]

In some embodiments of Formulas I or Ia, R¹ is —(C$_{1-6}$ alkylene)CO$_2$Me.
In some embodiments of Formulas I or Ia, R¹ is —(C$_{1-5}$ alkylene)CO$_2$Me.
In some embodiments of Formulas I or Ia, R¹ is —(C$_{1-4}$ alkylene)CO$_2$Me.
In some embodiments of Formulas I or Ia, R¹ is —(C$_{1-3}$H)CM alkylene)CO$_2$Me.
In some embodiments of Formulas I or Ia, R¹ is —(CHM$_2$ alkylene)CO$_2$Me.
In some embodiments of Formulas I or Ia, R¹ is —(CH$_2$)CO$_2$Me.
In some embodiments of Formulas I or a, R is —(CHMe)CO$_2$Me.
In some embodiments of Formulas I or Ia, R¹ is —(CMe$_2$)CO$_2$Me.
In some embodiments of Formulas I or Ia, R¹ is

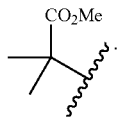

In some embodiments of Formulas I or Ia, R¹ is

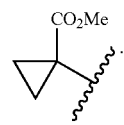

In some embodiments of Formulas I or Ia, R¹ is —CO$_2$Me.
In some embodiments of Formulas I or Ia, R¹⁰ is unsubstituted —(C$_{1-3}$ alkyl).
In some embodiments of Formulas I or Ia, each R¹⁴ is selected from the group consisting of H and unsubstituted —(C$_{1-3}$ alkyl).

Illustrative compounds of Formula I are shown in Table 1.

TABLE 1

| | |
|---|---|
| ![Compound 1] | 1 |
| ![Compound 2] | 2 |
| ![Compound 3] | 3 |

TABLE 1-continued
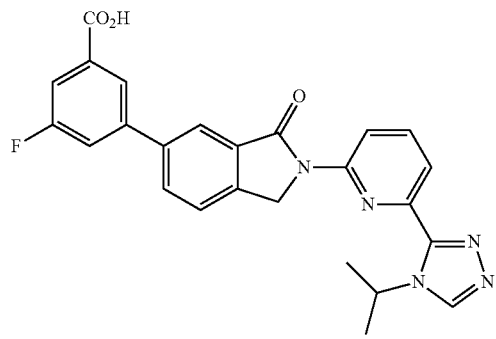 [SMILES: CC(C)n1cnnc1-c1cccc(N2Cc3ccc(-c4cc(F)cc(C(=O)O)c4)cc3C2=O)n1] 4
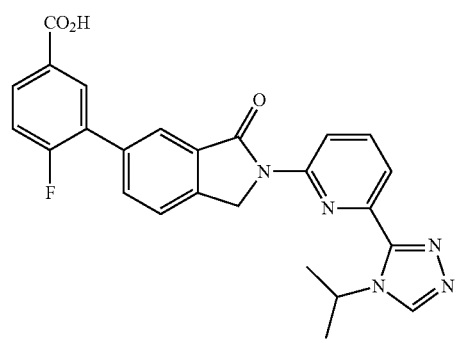 5
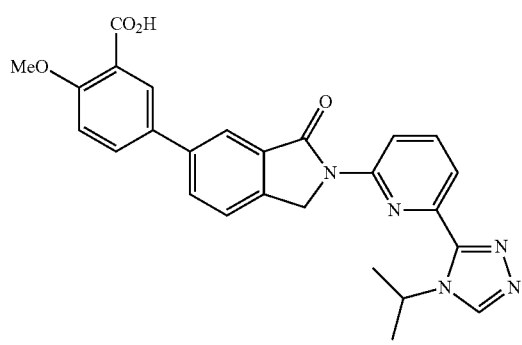 6
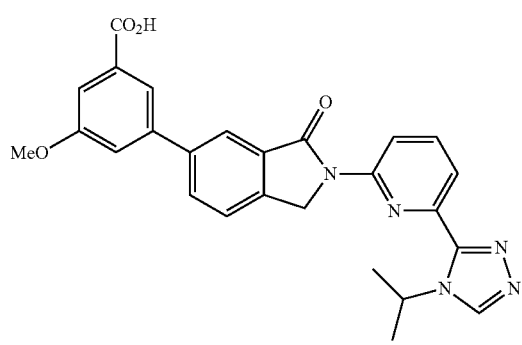 [SMILES: COc1cc(C(=O)O)cc(-c2ccc3c(c2)C(=O)N(c2cccc(-c4nncn4C(C)C)n2)C3)c1] 7
TABLE 1-continued
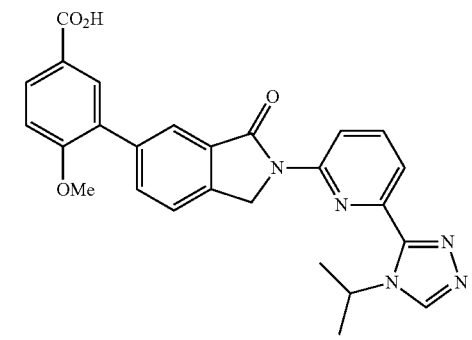 [SMILES: COc1ccc(C(=O)O)cc1-c1ccc2c(c1)C(=O)N(c1cccc(-c3nncn3C(C)C)n1)C2] 8

TABLE 1-continued
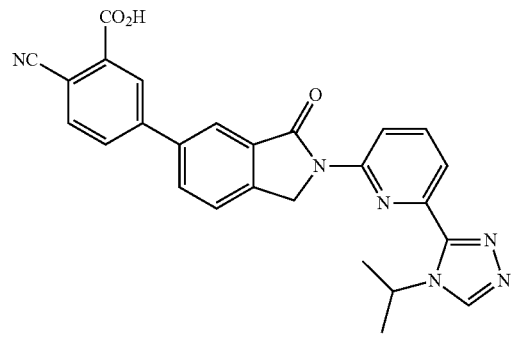 [SMILES: CC(C)n1cnnc1-c1cccc(N2Cc3ccc(-c4ccc(C#N)c(C(=O)O)c4)cc3C2=O)n1] 12
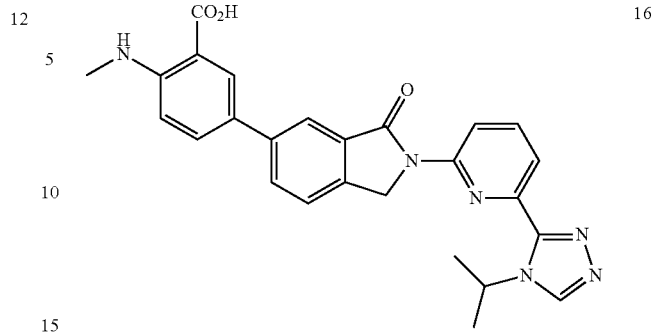 16
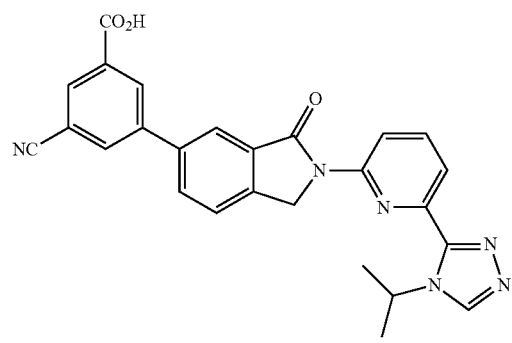 [SMILES: CC(C)n1cnnc1-c1cccc(N2Cc3ccc(-c4cc(C#N)cc(C(=O)O)c4)cc3C2=O)n1] 13
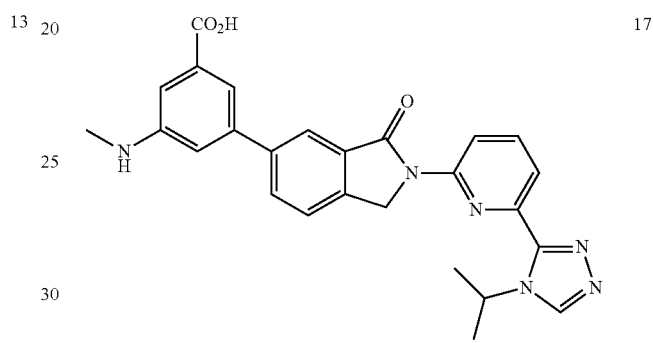 17
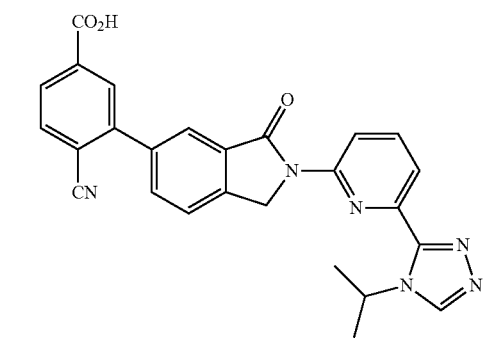 [SMILES: CC(C)n1cnnc1-c1cccc(N2Cc3ccc(-c4cc(C(=O)O)ccc4C#N)cc3C2=O)n1] 14
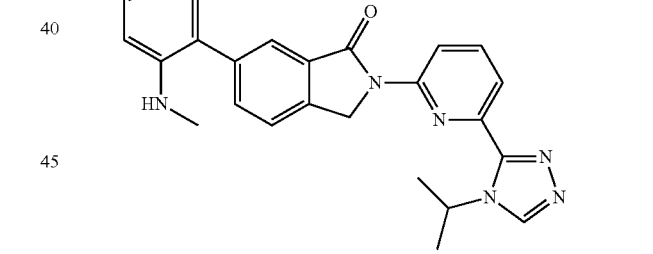 18
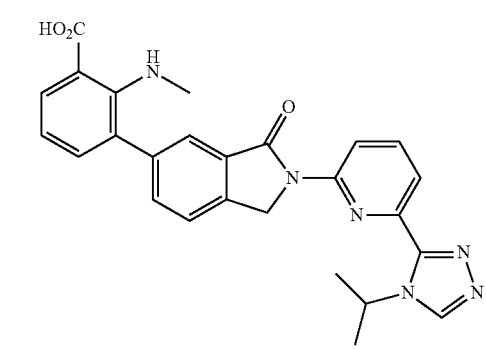 [SMILES: CNc1c(C(=O)O)cccc1-c1ccc2c(c1)C(=O)N(c1cccc(-c3nncn3C(C)C)n1)C2] 15
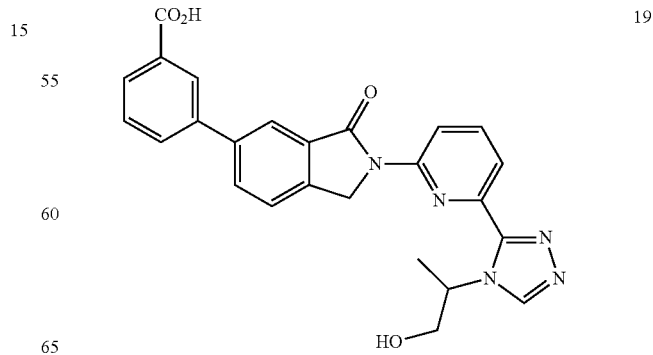 19

TABLE 1-continued
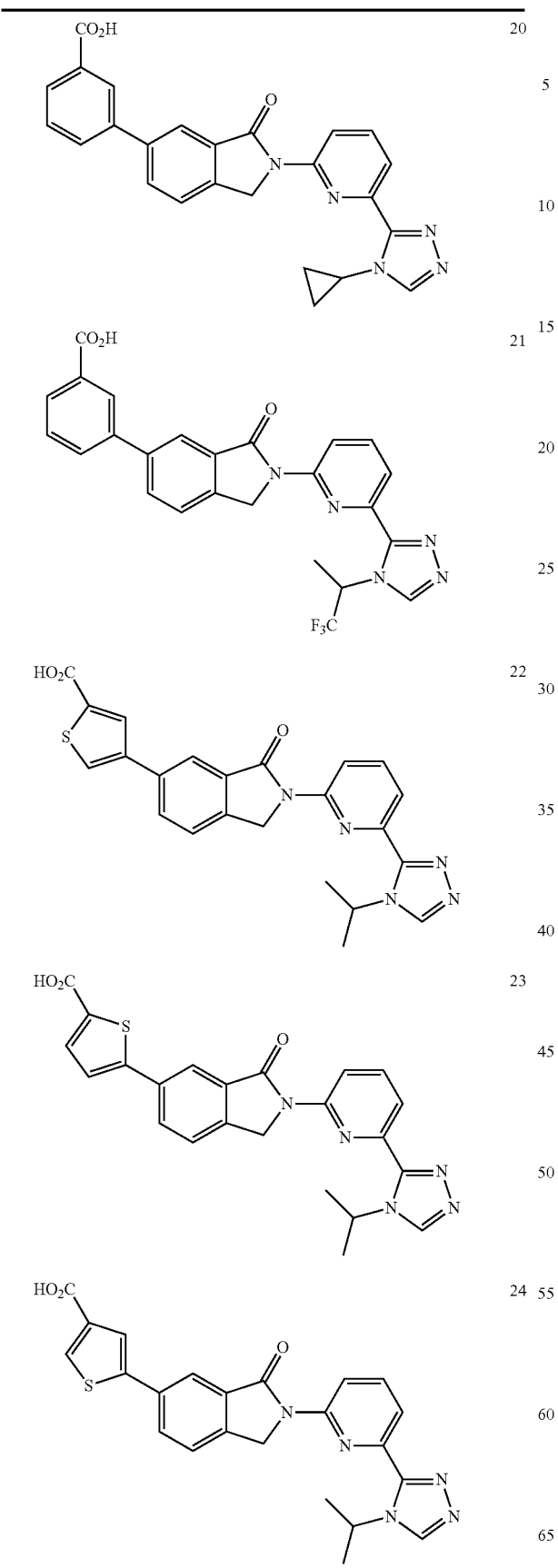
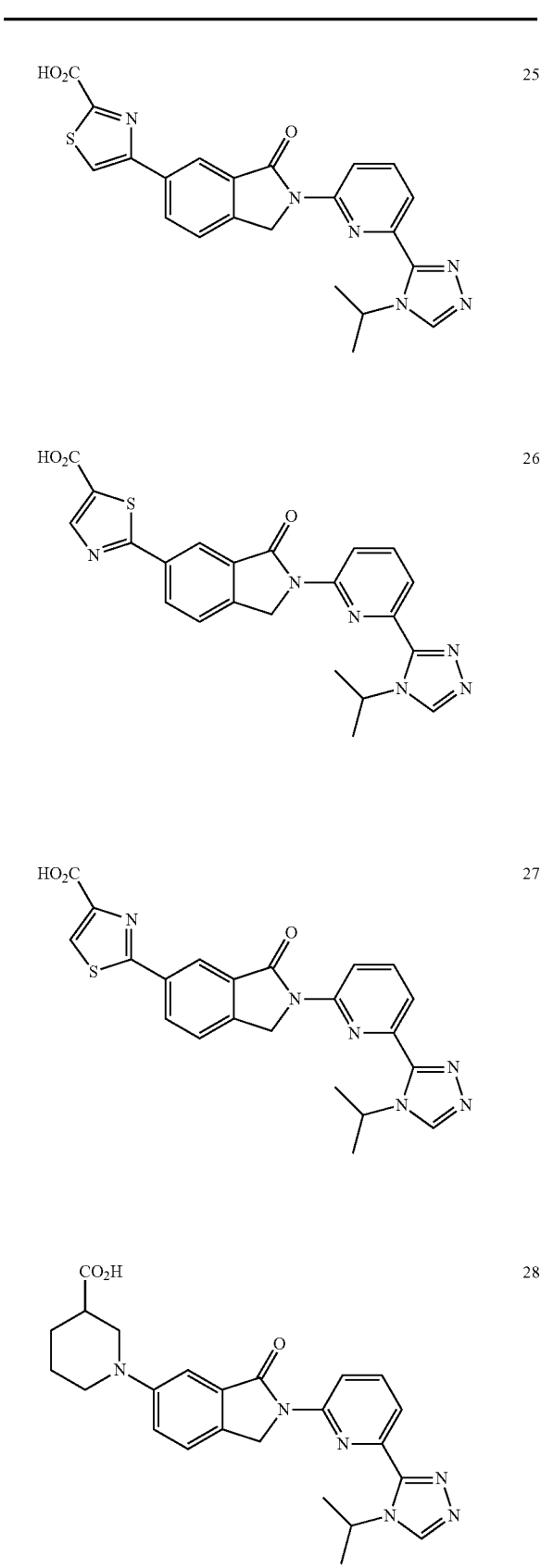

TABLE 1-continued
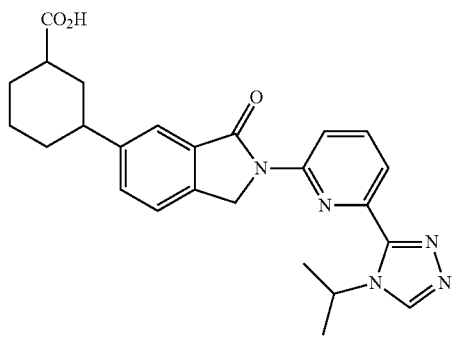 [SMILES: CC(C)n1cnnc1-c1cccc(N2Cc3ccc(C4CCCC(C(=O)O)C4)cc3C2=O)n1] 29
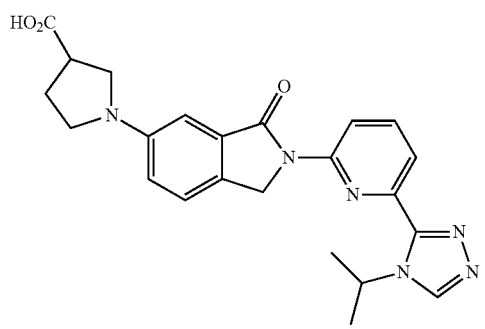 30
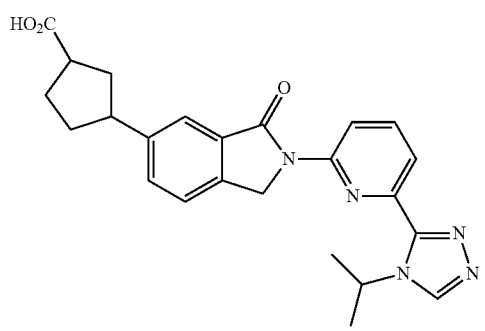 [SMILES: CC(C)n1cnnc1-c1cccc(N2Cc3ccc(C4CCC(C(=O)O)C4)cc3C2=O)n1] 31
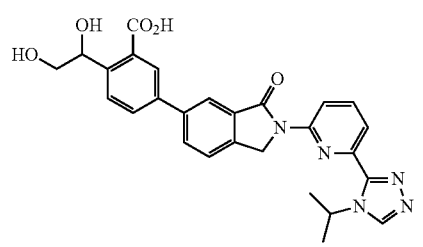 [SMILES: CC(C)n1cnnc1-c1cccc(N2Cc3ccc(-c4ccc(C(O)CO)c(C(=O)O)c4)cc3C2=O)n1] 32
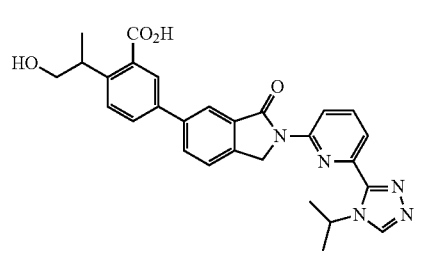 [SMILES: CC(CO)c1ccc(-c2ccc3c(c2)C(=O)N(c2cccc(-c4nncn4C(C)C)n2)C3)cc1C(=O)O] 33
TABLE 1-continued
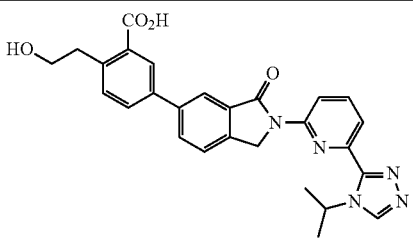 34
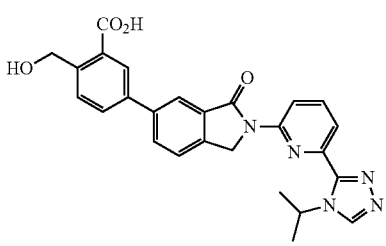 [SMILES: CC(C)n1cnnc1-c1cccc(N2Cc3ccc(-c4ccc(CO)c(C(=O)O)c4)cc3C2=O)n1] 35
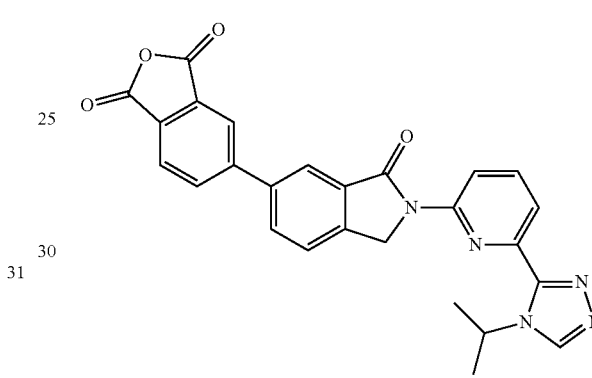 36
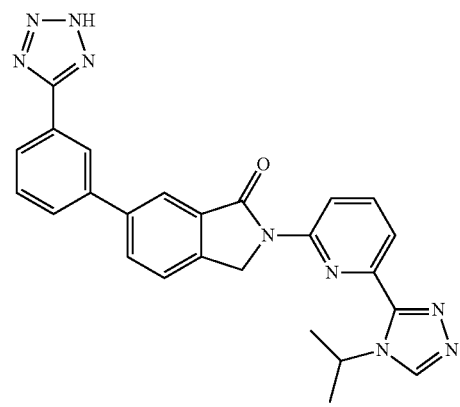 [SMILES: CC(C)n1cnnc1-c1cccc(N2Cc3ccc(-c4cccc(-c5nn[nH]n5)c4)cc3C2=O)n1] 37
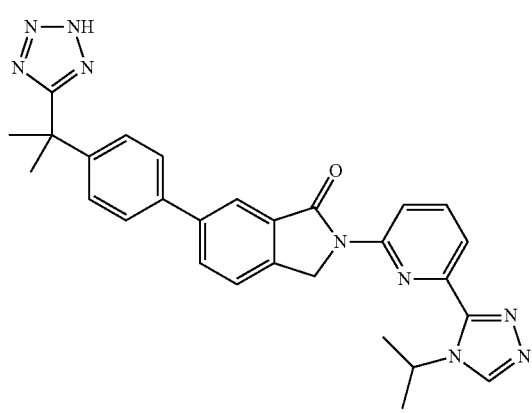 [SMILES: CC(C)n1cnnc1-c1cccc(N2Cc3ccc(-c4ccc(C(C)(C)c5nn[nH]n5)cc4)cc3C2=O)n1] 38

TABLE 1-continued
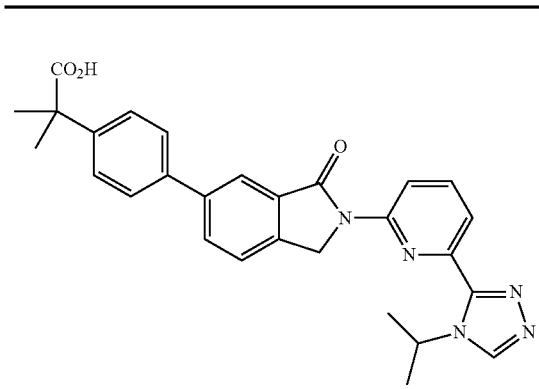
39
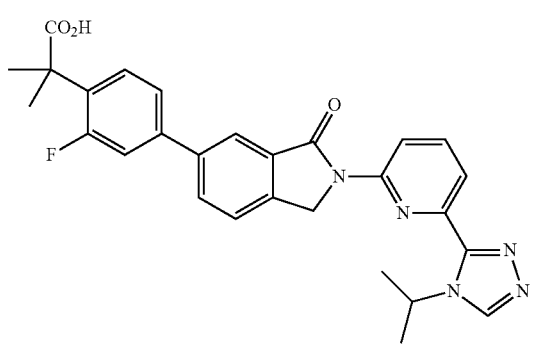 [SMILES: CC(C)n1cnnc1-c1cccc(N2Cc3ccc(-c4ccc(C(C)(C)C(=O)O)c(F)c4)cc3C2=O)n1]
40
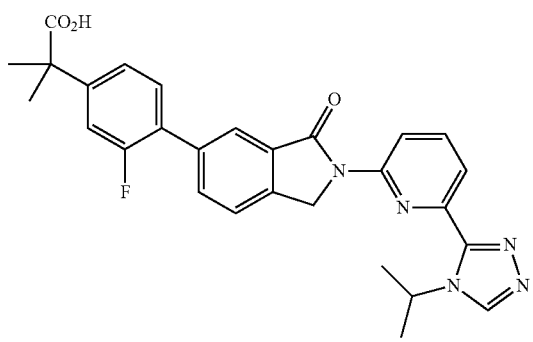 [SMILES: CC(C)n1cnnc1-c1cccc(N2Cc3ccc(-c4ccc(C(C)(C)C(=O)O)cc4F)cc3C2=O)n1]
41
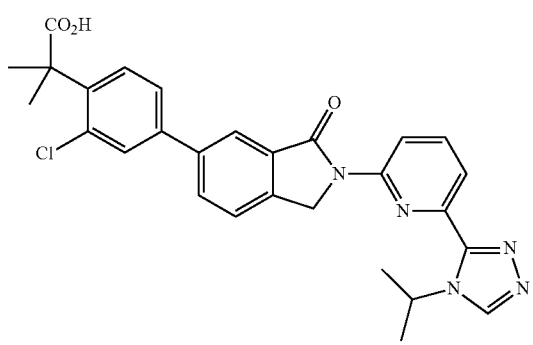 [SMILES: CC(C)n1cnnc1-c1cccc(N2Cc3ccc(-c4ccc(C(C)(C)C(=O)O)c(Cl)c4)cc3C2=O)n1]
42
TABLE 1-continued
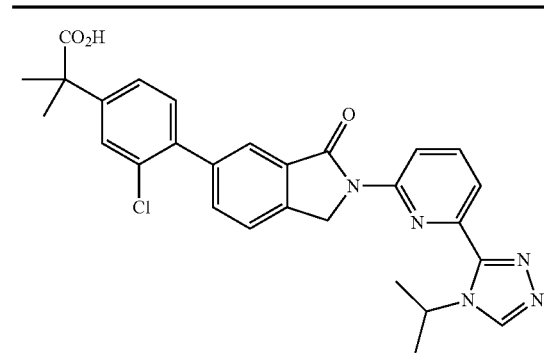
43
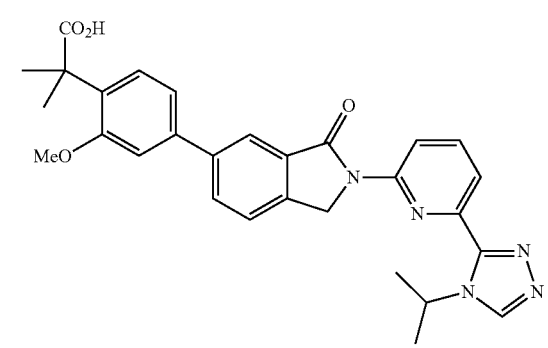 [SMILES: COc1cc(-c2ccc3c(c2)C(=O)N(c2cccc(-c4nncn4C(C)C)n2)C3)ccc1C(C)(C)C(=O)O]
44
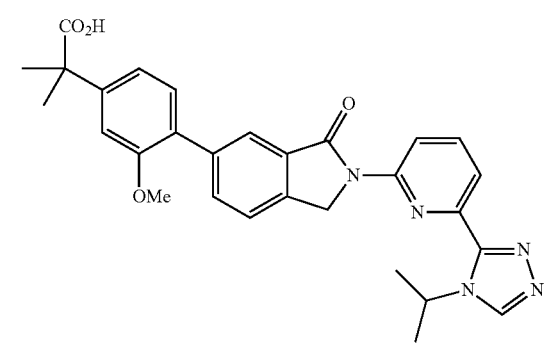
45
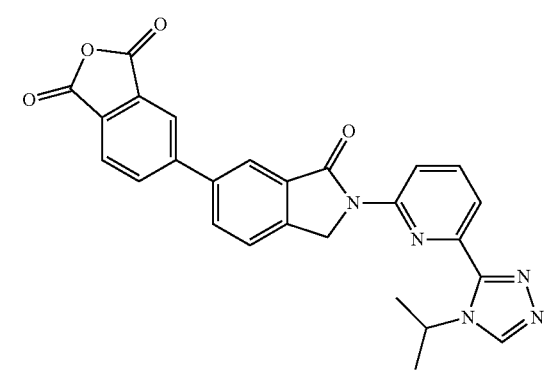 [SMILES: CC(C)n1cnnc1-c1cccc(N2Cc3ccc(-c4ccc5c(c4)C(=O)OC5=O)cc3C2=O)n1]
46

TABLE 1-continued
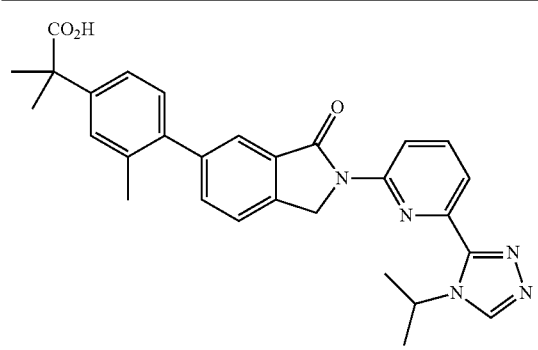
47
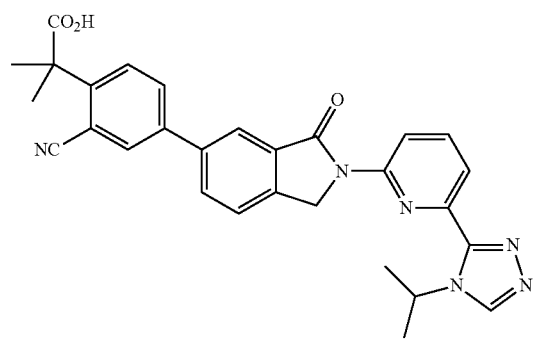
48
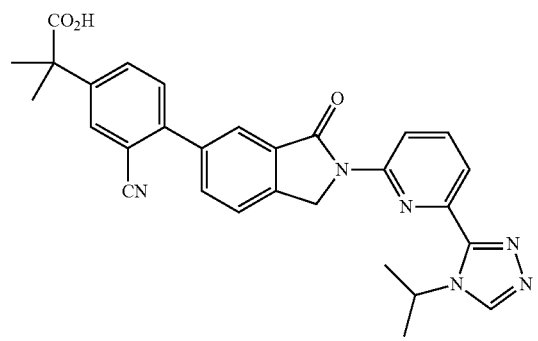 [SMILES: CC(C)n1cnnc1-c1cccc(N2Cc3ccc(-c4ccc(C(C)(C)C(=O)O)cc4C#N)cc3C2=O)n1]
49
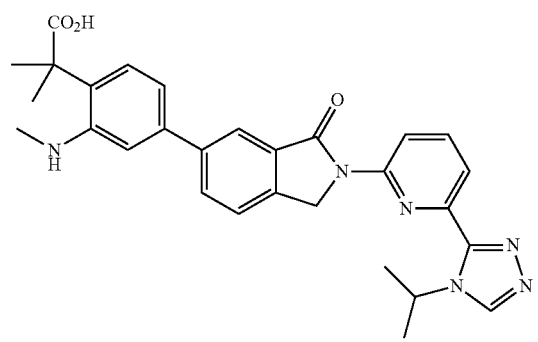 [SMILES: CNc1cc(-c2ccc3c(c2)C(=O)N(c2cccc(-c4nncn4C(C)C)n2)C3)ccc1C(C)(C)C(=O)O]
50
TABLE 1-continued
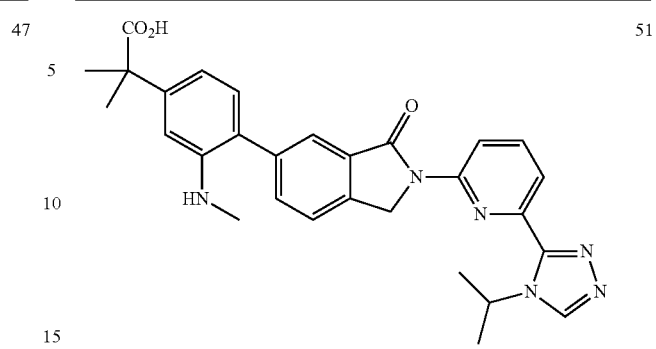
51
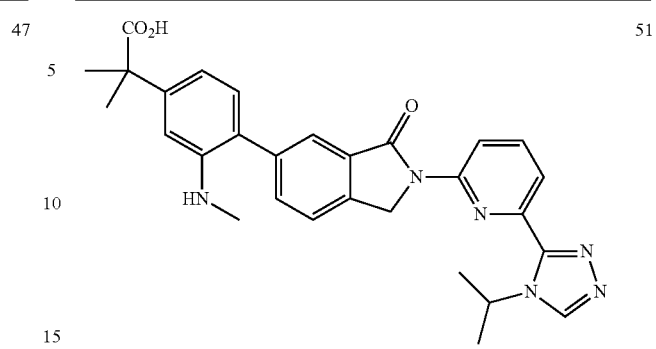
52
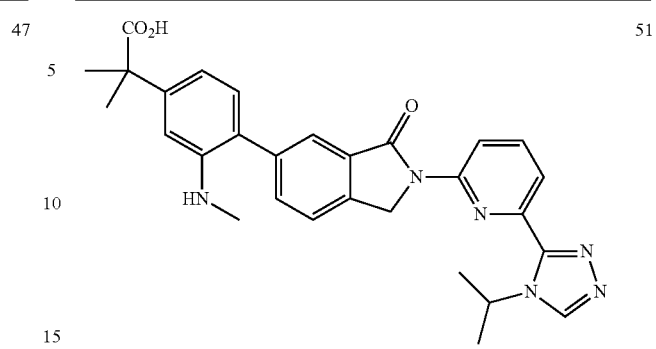
53
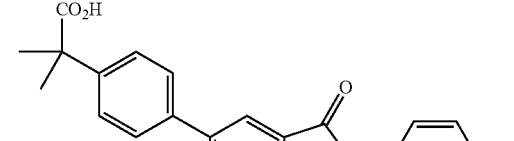
54

TABLE 1-continued
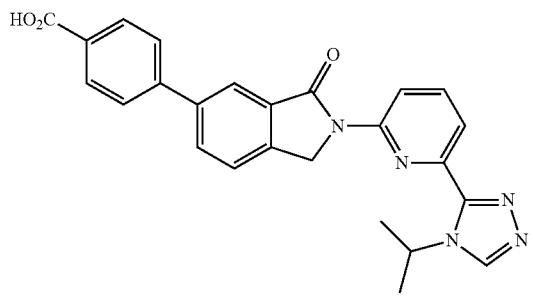 [SMILES: CC(C)n1cnnc1-c1cccc(N2Cc3ccc(-c4ccc(C(=O)O)cc4)cc3C2=O)n1] 55
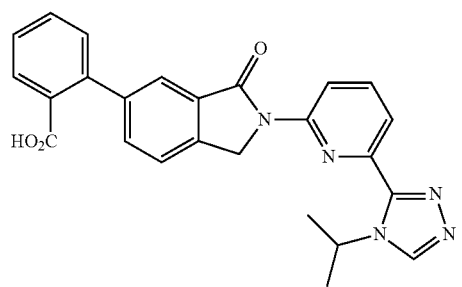 [SMILES: CC(C)n1cnnc1-c1cccc(N2Cc3ccc(-c4ccccc4C(=O)O)cc3C2=O)n1] 56
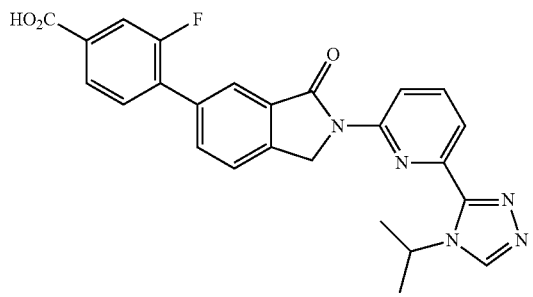 [SMILES: CC(C)n1cnnc1-c1cccc(N2Cc3ccc(-c4ccc(C(=O)O)cc4F)cc3C2=O)n1] 57
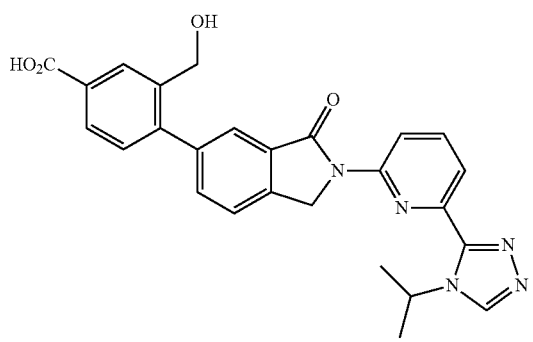 [SMILES: CC(C)n1cnnc1-c1cccc(N2Cc3ccc(-c4ccc(C(=O)O)cc4CO)cc3C2=O)n1] 58
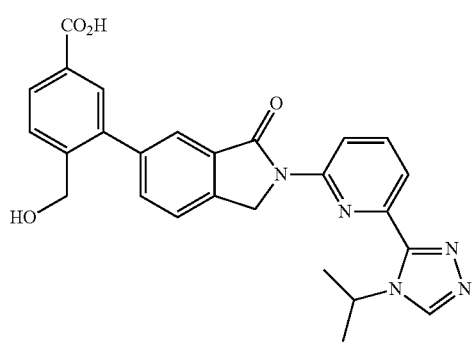 [SMILES: CC(C)n1cnnc1-c1cccc(N2Cc3ccc(-c4cc(C(=O)O)ccc4CO)cc3C2=O)n1] 59
TABLE 1-continued
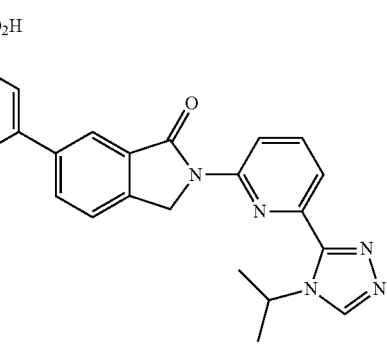 60
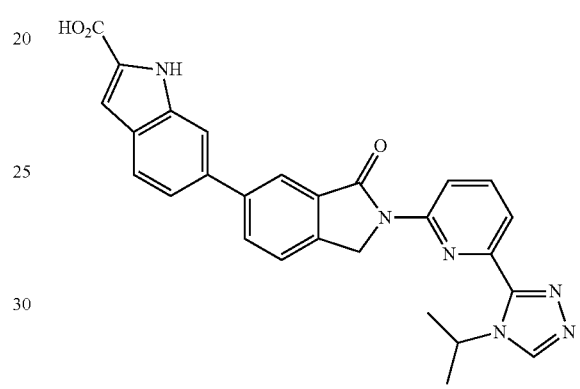 61
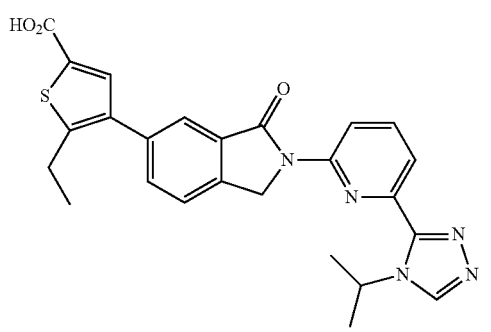 [SMILES: CCc1sc(C(=O)O)cc1-c1ccc2c(c1)C(=O)N(c1cccc(-c3nncn3C(C)C)n1)C2] 62
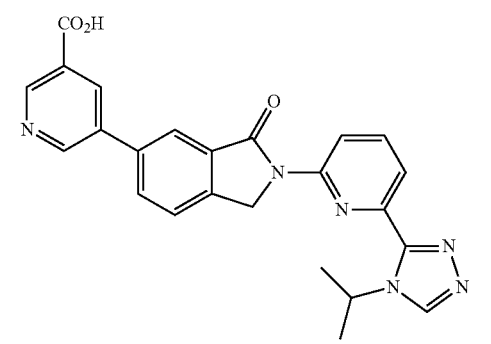 [SMILES: CC(C)n1cnnc1-c1cccc(N2Cc3ccc(-c4cncc(C(=O)O)c4)cc3C2=O)n1] 63

TABLE 1-continued
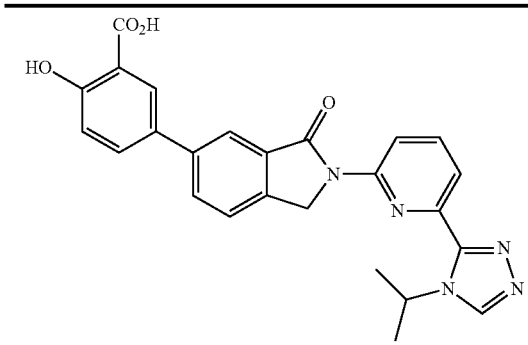
64
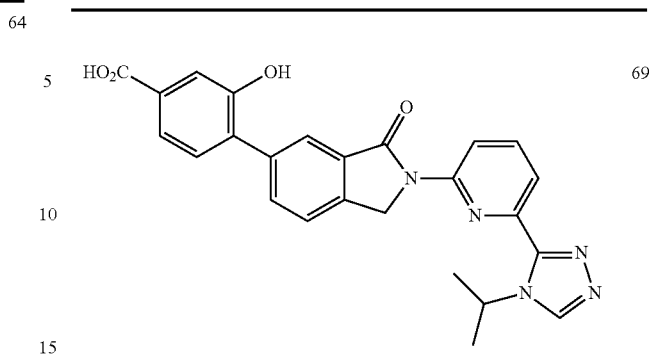
69
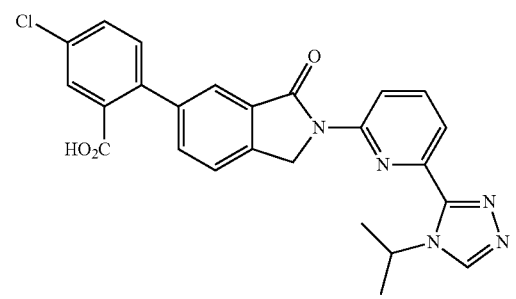 [SMILES: CC(C)n1cnnc1-c1cccc(N2Cc3ccc(-c4ccc(Cl)cc4C(=O)O)cc3C2=O)n1]
65
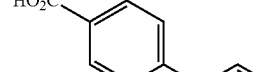
70
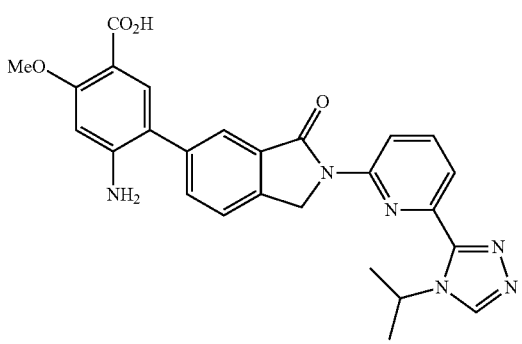 [SMILES: COc1cc(N)c(-c2ccc3c(c2)C(=O)N(c2cccc(-c4nncn4C(C)C)n2)C3)cc1C(=O)O]
66
71
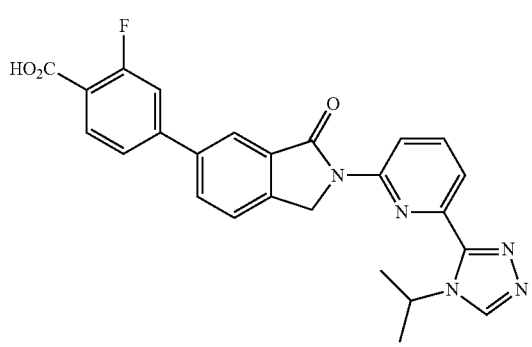 [SMILES: CC(C)n1cnnc1-c1cccc(N2Cc3ccc(-c4ccc(C(=O)O)c(F)c4)cc3C2=O)n1]
67
72
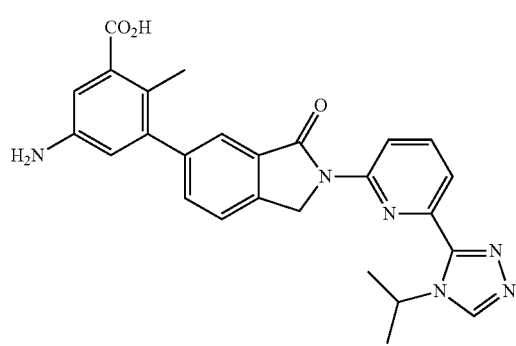 [SMILES: Cc1c(C(=O)O)cc(N)cc1-c1ccc2c(c1)C(=O)N(c1cccc(-c3nncn3C(C)C)n1)C2]
68
73

TABLE 1-continued
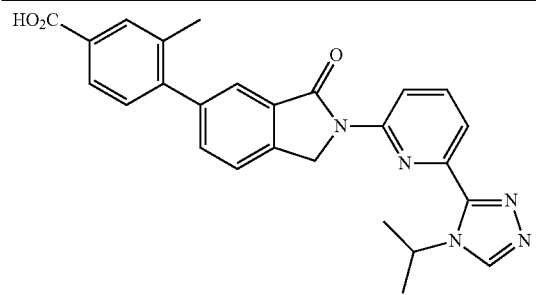 74
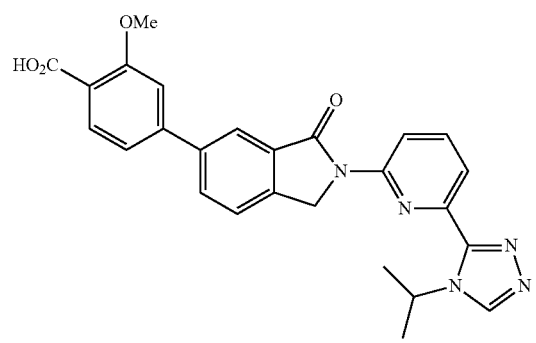 [SMILES: COc1cc(-c2ccc3c(c2)C(=O)N(c2cccc(-c4nncn4C(C)C)n2)C3)ccc1C(=O)O] 75
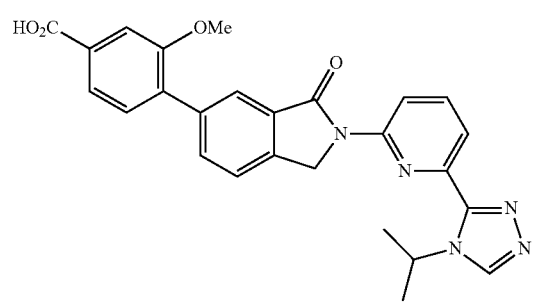 [SMILES: COc1cc(C(=O)O)ccc1-c1ccc2c(c1)C(=O)N(c1cccc(-c3nncn3C(C)C)n1)C2] 76
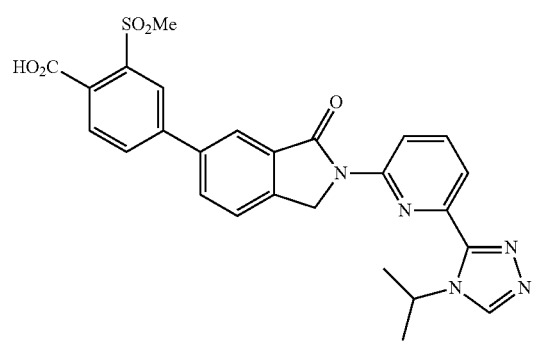 [SMILES: CC(C)n1cnnc1-c1cccc(N2Cc3ccc(-c4ccc(C(=O)O)c(S(C)(=O)=O)c4)cc3C2=O)n1] 77
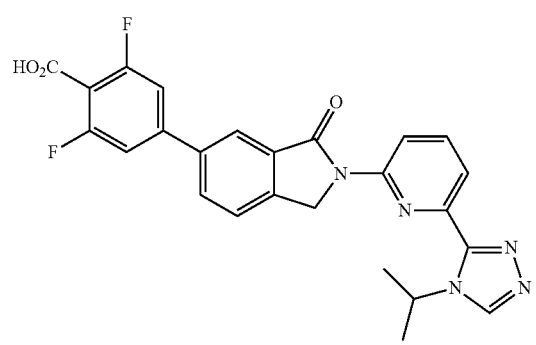 [SMILES: CC(C)n1cnnc1-c1cccc(N2Cc3ccc(-c4cc(F)c(C(=O)O)c(F)c4)cc3C2=O)n1] 78
TABLE 1-continued
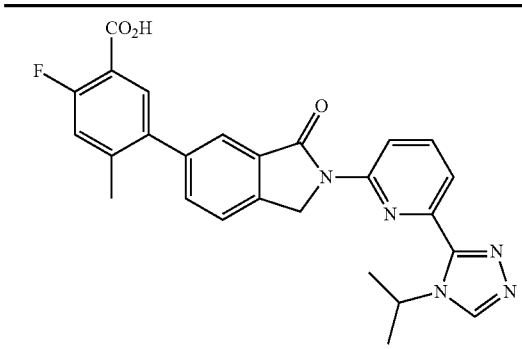 79
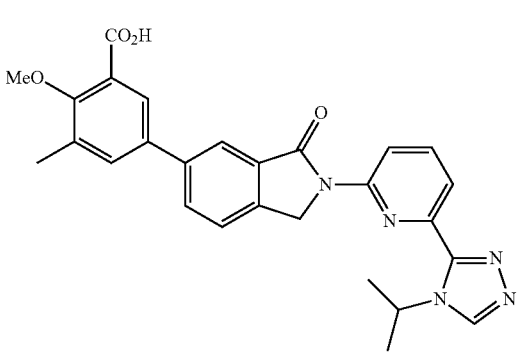 [SMILES: COc1c(C)cc(-c2ccc3c(c2)C(=O)N(c2cccc(-c4nncn4C(C)C)n2)C3)cc1C(=O)O] 80
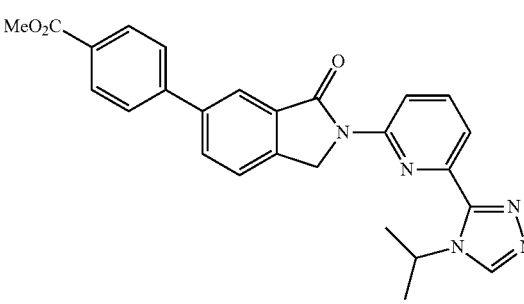 81
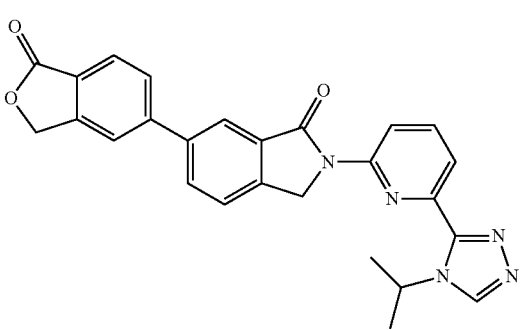 [SMILES: CC(C)n1cnnc1-c1cccc(N2Cc3ccc(-c4ccc5c(c4)COC5=O)cc3C2=O)n1] 82
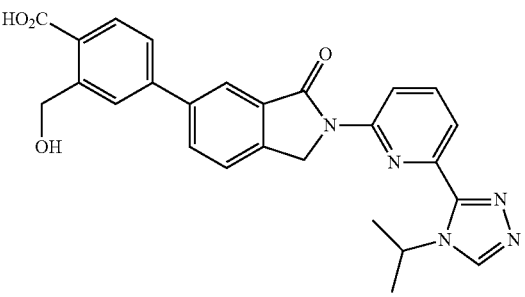 [SMILES: CC(C)n1cnnc1-c1cccc(N2Cc3ccc(-c4ccc(C(=O)O)c(CO)c4)cc3C2=O)n1] 83

TABLE 1-continued
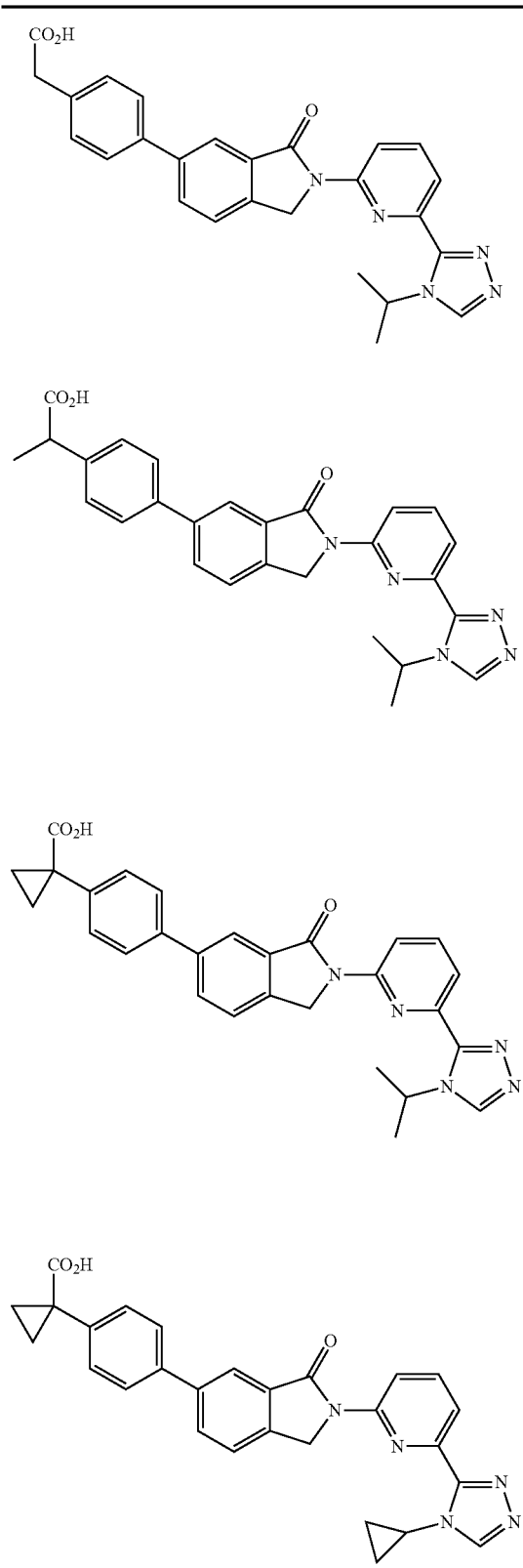
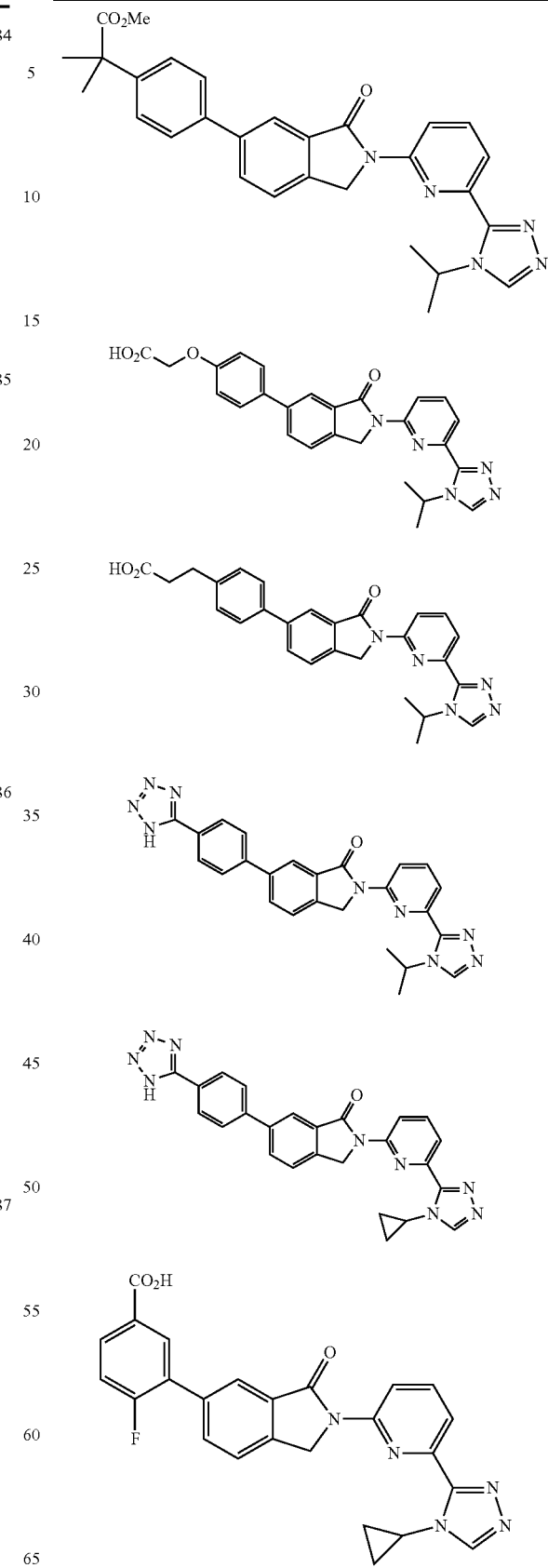

TABLE 1-continued
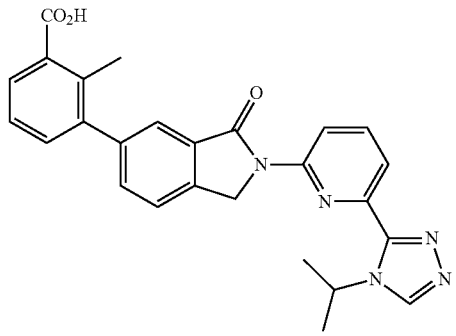 94
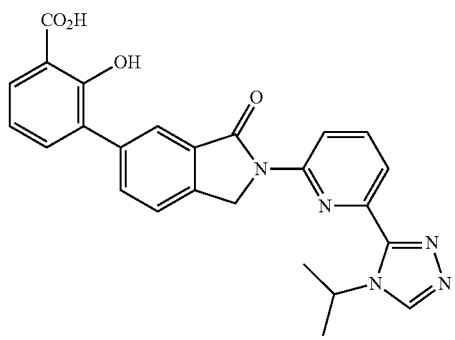 [SMILES: CC(C)n1cnnc1-c1cccc(N2Cc3ccc(-c4cccc(C(=O)O)c4O)cc3C2=O)n1] 95
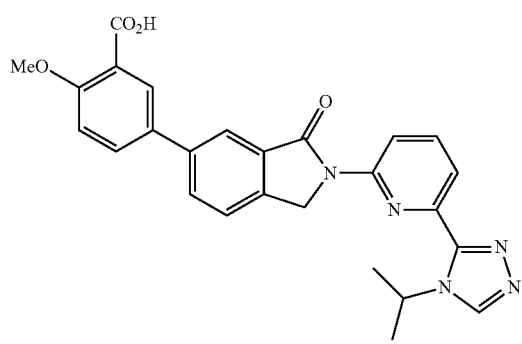 [SMILES: COc1ccc(-c2ccc3c(c2)C(=O)N(c2cccc(-c4nncn4C(C)C)n2)C3)cc1C(=O)O] 96
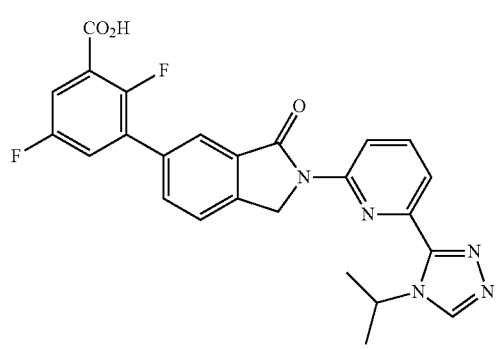 [SMILES: CC(C)n1cnnc1-c1cccc(N2Cc3ccc(-c4cc(F)cc(C(=O)O)c4F)cc3C2=O)n1] 97
TABLE 1-continued
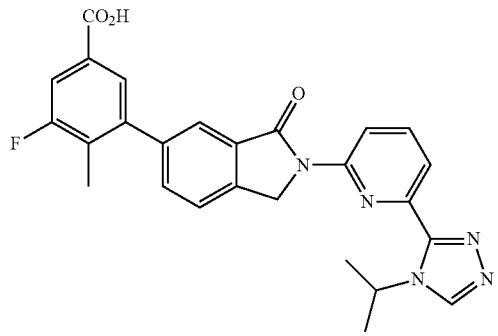 [SMILES: Cc1c(F)cc(C(=O)O)cc1-c1ccc2c(c1)C(=O)N(c1cccc(-c3nncn3C(C)C)n1)C2] 98
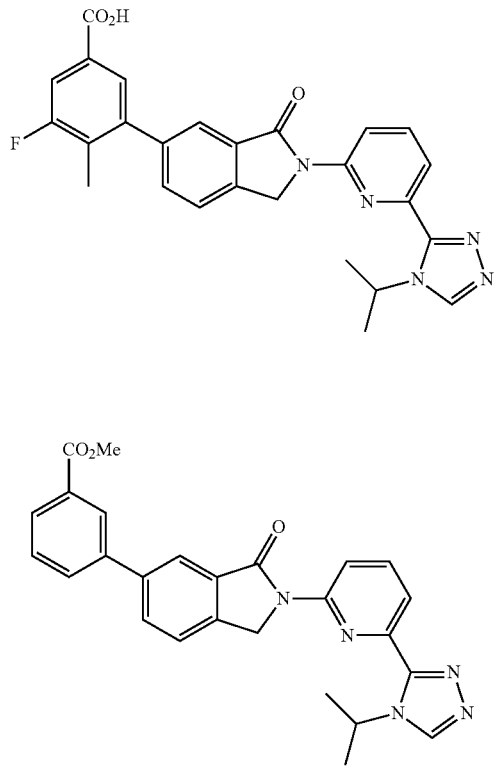 99
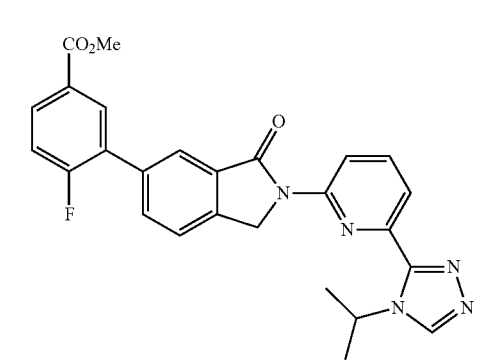 [SMILES: COC(=O)c1ccc(F)c(-c2ccc3c(c2)C(=O)N(c2cccc(-c4nncn4C(C)C)n2)C3)c1] 100
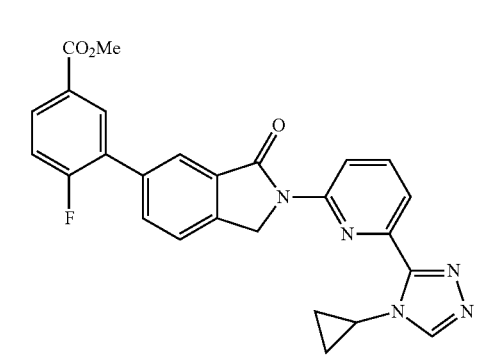 [SMILES: COC(=O)c1ccc(F)c(-c2ccc3c(c2)C(=O)N(c2cccc(-c4nncn4C4CC4)n2)C3)c1] 101

TABLE 1-continued
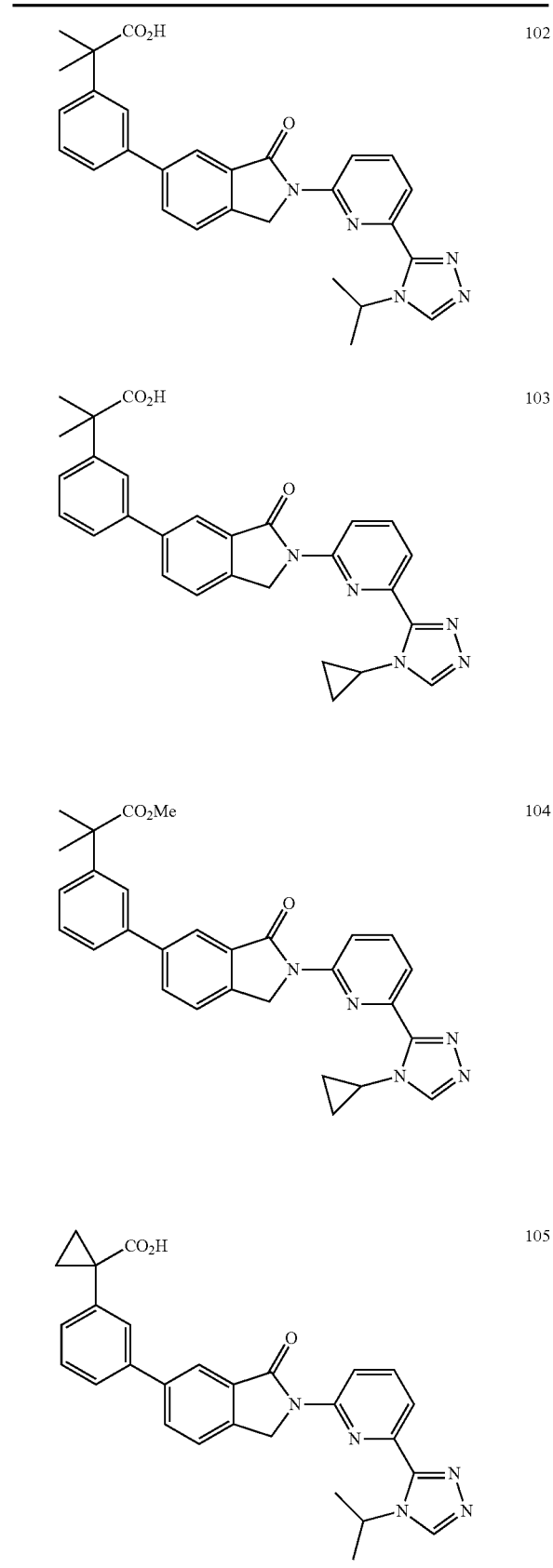
TABLE 1-continued
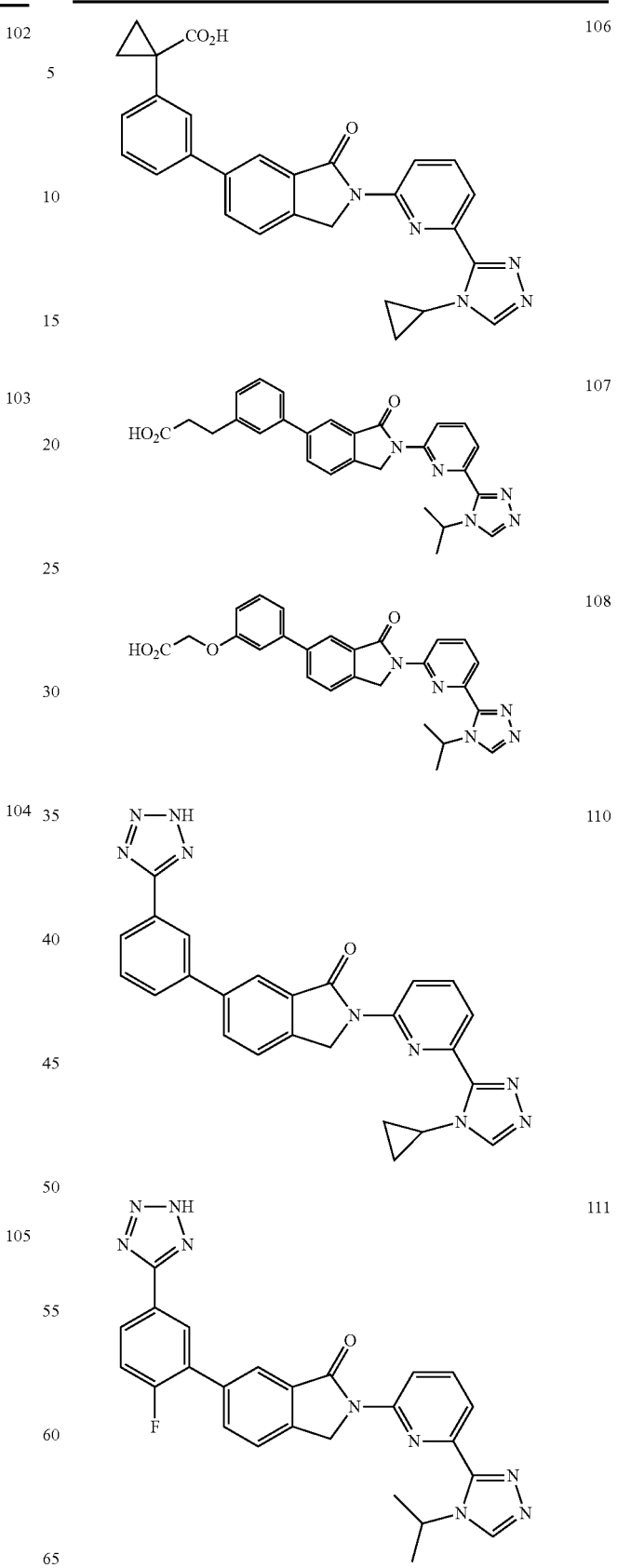

TABLE 1-continued
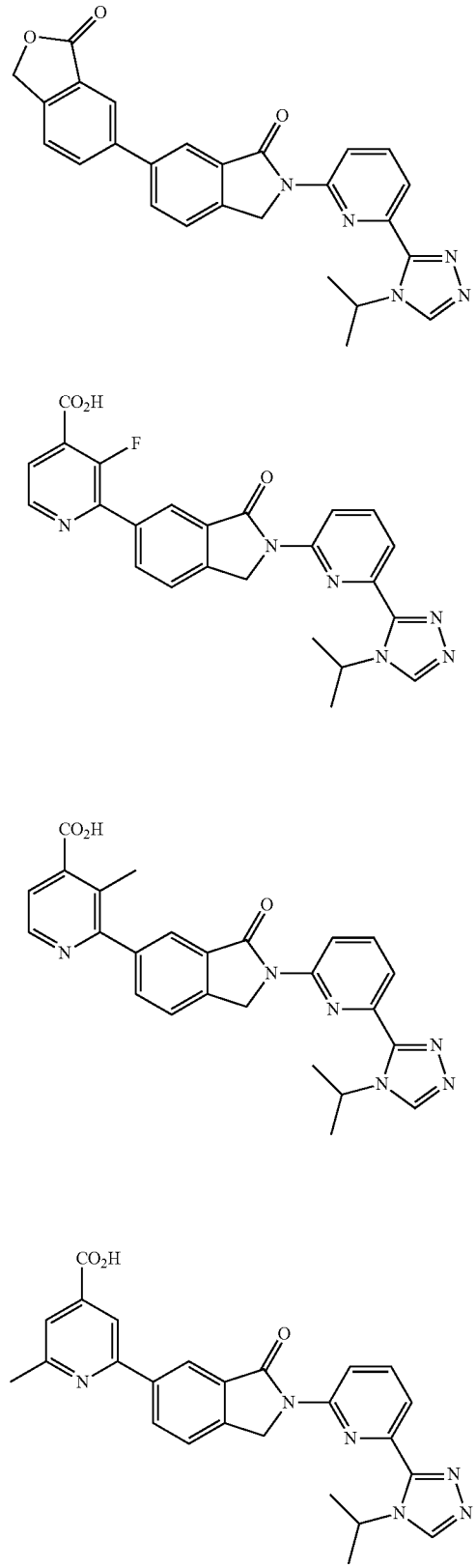
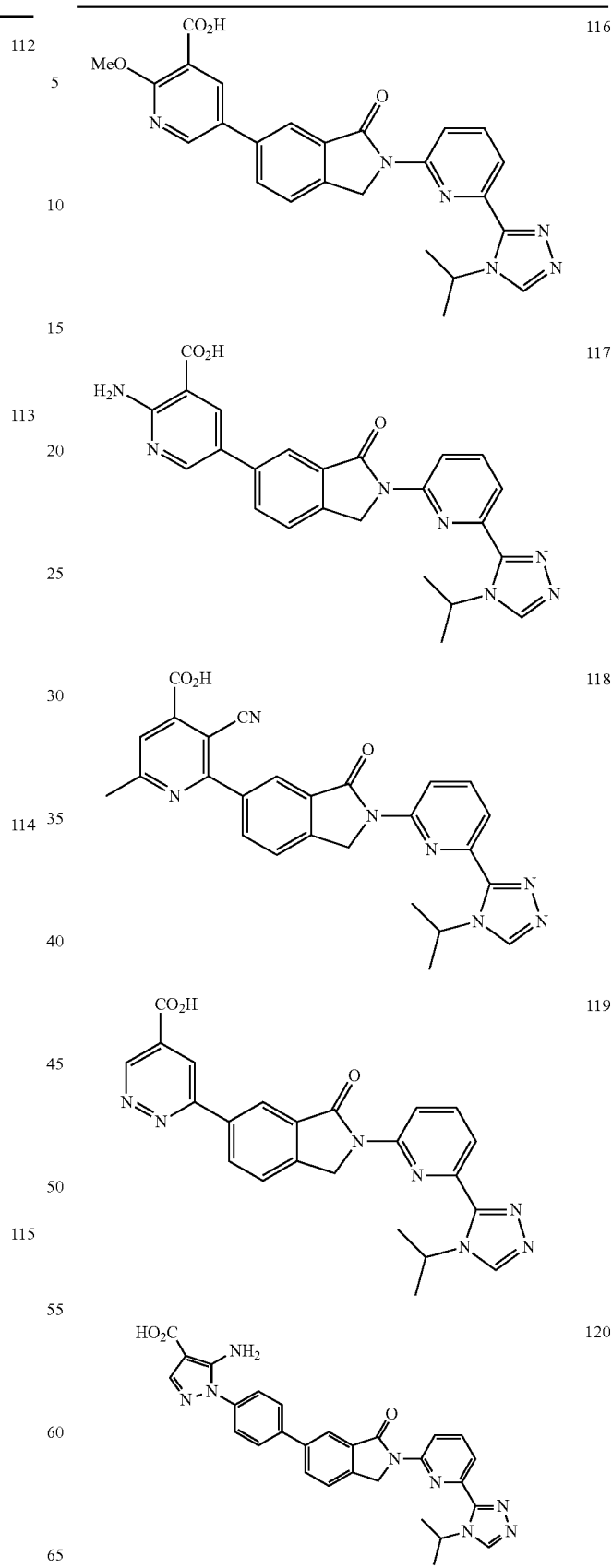

TABLE 1-continued
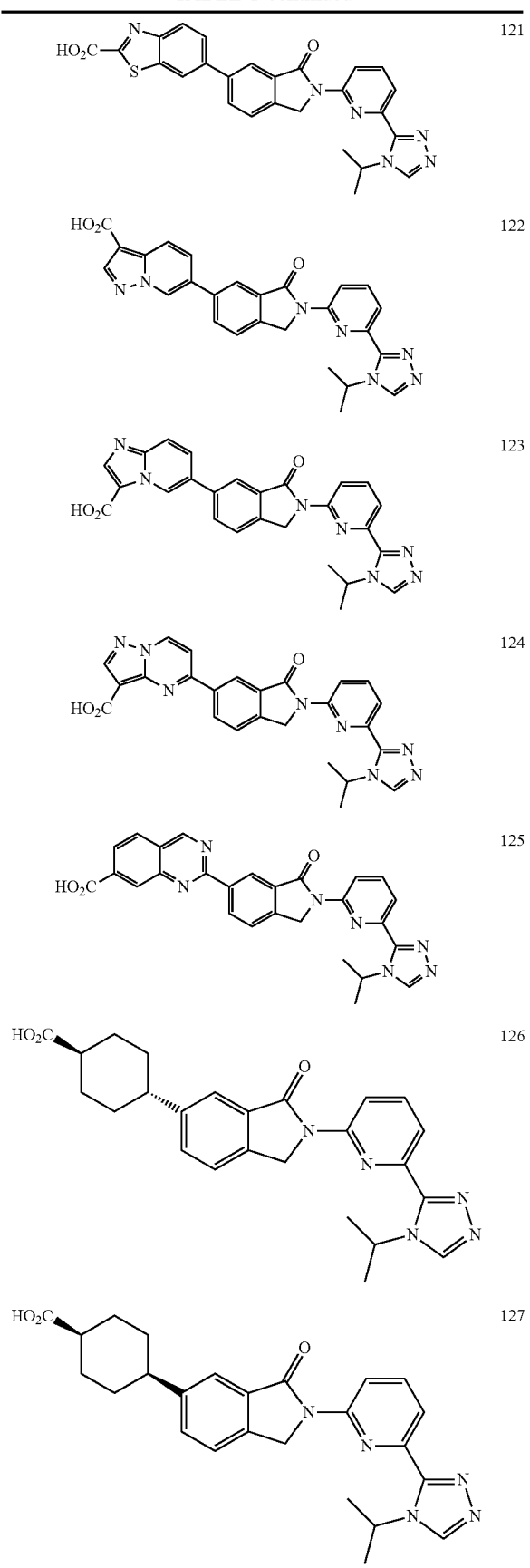

TABLE 1-continued

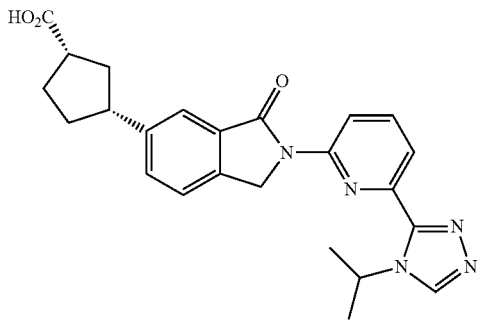 [SMILES: CC(C)n1cnnc1-c1cccc(N2Cc3ccc([C@@H]4CC[C@H](C(=O)O)C4)cc3C2=O)n1]

133

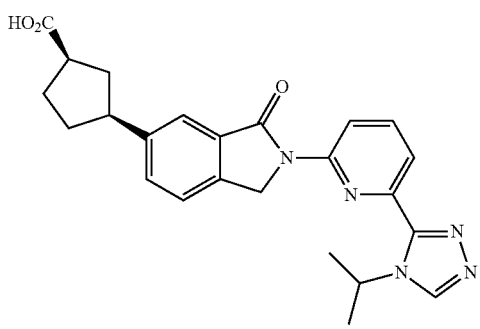 [SMILES: CC(C)n1cnnc1-c1cccc(N2Cc3ccc([C@H]4CC[C@@H](C(=O)O)C4)cc3C2=O)n1]

134

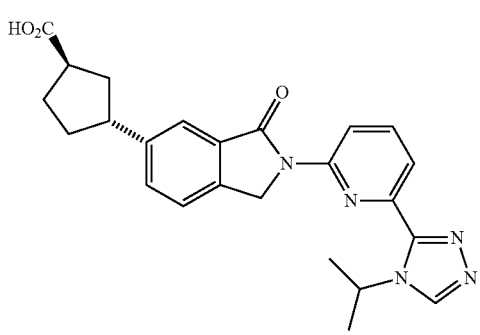 [SMILES: CC(C)n1cnnc1-c1cccc(N2Cc3ccc([C@@H]4CC[C@@H](C(=O)O)C4)cc3C2=O)n1]

135

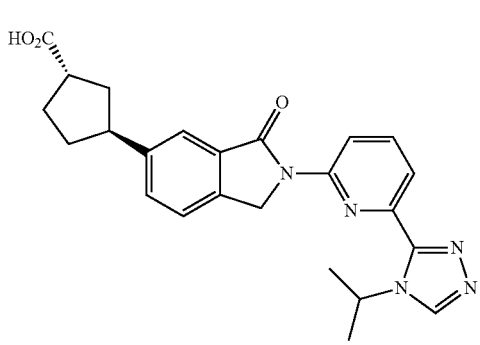 [SMILES: CC(C)n1cnnc1-c1cccc(N2Cc3ccc([C@H]4CC[C@H](C(=O)O)C4)cc3C2=O)n1]

136

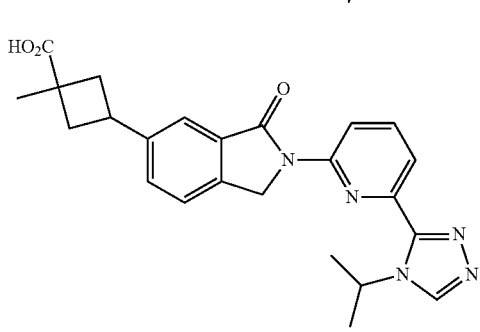

137

TABLE 1-continued

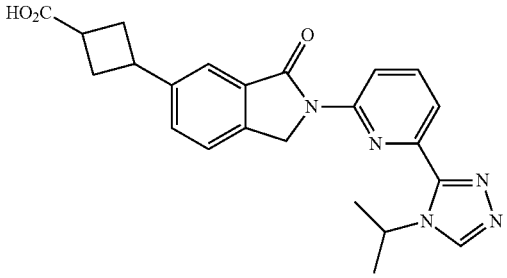 [SMILES: CC(C)n1cnnc1-c1cccc(N2Cc3ccc(C4CC(C(=O)O)C4)cc3C2=O)n1]

138

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable and could be higher if the composition is a solid or suspension, which could be subsequently diluted to the above percentages.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 µm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with one or more of cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes.

Methods of Treatment

The compounds and compositions provided herein can be used as inhibitors and/or modulators of apoptosis signal-regulating kinase 1 (ASK1), and thus can be used to treat a variety of disorders and diseases in which aberrant ASK1 activity is implicated, such as in cytokine responses, cell differentiation, and inflammatory and innate immune responses. Accordingly, the compounds and compositions provided herein can be used to treat cardiovascular diseases, inflammatory disorders (acute or chronic), autoimmune diseases, destructive bone disorders, fibrotic diseases/disorders such as alcoholic steatohepatitis; non-alcoholic fatty liver disease (NAFLD); non-alcoholic steatohepatitis (NASH), neurodegenerative disorders, and metabolic diseases such as diabetes.

Non-limiting examples of cardiovascular diseases which can be treated with the compounds and compositions provided herein include coronary artery diseases (CAD) such as acute coronary syndrome, angina pectoris (stable and unstable), myocardial infarction (commonly known as a heart attack), congestive heart failure or any type of heart failure, stroke, heart failure, pulmonary heart disease, pulmonary hypertension and pulmonary embolism, cardiac dysrhythmias, cardiac valves related conditions, endocarditis, inflammatory cardiomegaly, myocarditis, eosinophilic myocarditis, hypertensive heart disease, reinfarction, rheumatic heart disease, cardiomyopathy, heart arrhythmia, congenital heart disease, valvular heart disease, carditis, aortic aneurysms, peripheral artery disease, thromboembolic disease, venous thrombosis, cardiac death, from arrhythmia or any other heart related reason; rejection of a transplanted heart; conditions that lead to heart failure including myocardial infarction, angina, arrhythmias, valvular diseases, atrial and/or ventricular septal defects; conditions that cause atrial and or ventricular wall volume overload, including systemic arterial hypertension, cerebrovascular disease, renal artery stenosis, aortic aneurysm, conditions which have similar clinical symptoms as heart failure and as states that cause atrial and or ventricular pressure-overload, where the differential diagnosis between these conditions to the latter is of clinical importance including breathing difficulty and/or hypoxia due to pulmonary disease, anemia or anxiety.

Non-limiting examples of fibrotic diseases which can be treated with the compounds and compositions provided herein include skin fibrosis; scleroderma; progressive systemic fibrosis; lung fibrosis; muscle fibrosis; kidney fibrosis; intestinal fibrosis; glomerulosclerosis; glomerulonephritis; hypertrophic scar formation; uterine fibrosis; renal fibrosis; cirrhosis of the liver, liver fibrosis; adhesions; chronic obstructive pulmonary disease; fibrosis following myocardial infarction; pulmonary fibrosis; fibrosis and scarring associated with diffuse/interstitial lung disease; central nervous system fibrosis; fibrosis associated with proliferative vitreoretinopathy (PVR); restenosis; endometriosis; ischemic disease, and radiation fibrosis.

In some embodiments, the fibrosis is liver fibrosis associated with a disease such as hepatitis B; hepatitis C; parasitic liver diseases; posttransplant bacterial, viral and fungal infections; alcoholic liver disease (ALD) including alcoholic steatohepatitis; non-alcoholic fatty liver disease (NAFLD); non-alcoholic steatohepatitis (NASH); liver diseases induced by methotrexate, isoniazid, oxyphenistatin, methyldopa, chlorpromazine, tolbutamide, or amiodarone; autoimmune hepatitis; sarcoidosis; Wilson's disease; hemochromatosis; Gaucher's disease; types III, IV, VI, IX and X glycogen storage diseases; a1-antitrypsin deficiency; Zellweger syndrome; tyrosinemia; fructosemia; galactosemia; vascular derangement associated with Budd-Chiari syndrome, veno-occlusive disease, or portal vein thrombosis; or congenital hepatic fibrosis.

In some embodiments, the disease/disorder is non-alcoholic steatohepatitis (NASH).

In some embodiments, the disease/disorder is non-alcoholic fatty liver disease (NAFLD).

In some embodiments, the disease/disorder is alcoholic steatohepatitis.

In some embodiments, the fibrosis is intestinal fibrosis associated with a disease such as Crohn's disease, ulcerative colitis, post-radiation colitis, or microscopic colitis.

In some embodiments, the fibrosis is renal fibrosis associated with a disease such as diabetic nephropathy, hypertensive nephrosclerosis, chronic glomerulonephritis, chronic transplant glomerulopathy, chronic interstitial nephritis, or polycystic kidney disease.

The compounds and compositions provided herein have been found to possess immunomodulatory activities and are expected to control the innate and adaptive immune system (e.g. macrophages, microglia, dendritic cells, B and T cells) and suppress pro-inflammatory cytokine release (e.g. TNF, IL-6, IL-1, IFN-γ) which is well known to be involved in inflammatory disorders in a wide variety of disease areas. Therefore compounds and compositions provided herein can used to treat inflammation associated with disorders and diseases including but not limited to eye disorders, joint pain, arthritis (rheumatoid, osteo, psoriatic gout), cancers (colon, breast, lung, pancreas, and others), gastrointestinal disorders (ulcerative colitis and inflammatory bowel diseases), pulmonary disorders (chronic obstructive pulmonary disorder and asthma), allergies, skin disorders (atopic dermatitis and psoriasis), diabetes, pancreatitis, tendonitis, hepatitis, heart disease, myocarditis, stroke, lupus, and neurological disorders such as multiple sclerosis, Parkinson's and dementia including Alzheimer's disease.

Non-limiting examples of autoimmune diseases which can be treated with the compounds and compositions provided herein include includes myocarditis, postmyocardial infarction syndrome, postpericardiotomy syndrome, subacute bacterial endocarditis, anti-glomerular basement membrane nephritis, interstitial cystitis, lupus nephritis, autoimmune hepatitis, primary biliary cholangitis, primary sclerosing cholangitis, antisynthetase syndrome, alopecia areata, autoimmune angioedema, autoimmune progesterone dermatitis, autoimmune urticaria, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen planus, lichen sclerosus, linear IgA disease, morphea, pemphigus vulgaris, pityriasis lichenoides et varioliformis acuta (Mucha-Habermann disease), psoriasis, systemic scleroderma, vitiligo, Addison's disease, autoimmune polyendocrine syndrome (APS) type 1, autoimmune polyendocrine syndrome (APS) type 2, autoimmune polyendocrine syndrome (APS) type 3, autoimmune pancreatitis, diabetes mellitus type 1, autoimmune thyroiditis, Ord's thyroiditis, Graves' disease, autoimmune Oophoritis, endometriosis, autoimmune orchitis, Sjogren's syndrome, autoimmune enteropathy, Coeliac disease, Crohn's disease, microscopic colitis, ulcerative colitis, antiphospholipid syndrome, aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, Evans syndrome, pernicious anemia, pure red cell aplasia, thrombocytopenia, adiposis dolorosa, adult-onset Still's disease, Ankylosing Spondylitis, CREST syndrome, drug-induced lupus, eosinophilic fasciitis, Felty syndrome, IgG4-related disease, juvenile arthritis, Lyme disease (chronic), mixed connective tissue disease (MCTD), palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus (SLE), undifferentiated connective tissue disease (UCTD), dermatomyositis, fibromyalgia, inclusion body myositis, myositis, myasthenia gravis, neuromyotonia, paraneoplastic cerebellar degeneration, polymyositis, acute disseminated encephalomyelitis (ADEM), acute motor axonal neuropathy, anti-N-Methyl-D-Aspartate (Anti-NMDA) Receptor Encephalitis, Balo concentric sclerosis, Bickerstaffs encephalitis, chronic inflammatory demyelinating polyneuropathy, Guillain-Barré syndrome, Hashimoto's encephalopathy, idiopathic inflammatory demyelinating diseases, Lambert-Eaton myasthenic syndrome, multiple sclerosis, pattern II, Oshtoran syndrome, pediatric autoimmune neuropsychiatric disorder associated with *Streptococcus* (PANDAS), progressive inflammatory neuropathy, stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease, Meniere's disease, Behçet's disease, eosinophilic granulomatosis with polyangiitis (EGPA), giant cell arteritis, granulomatosis with polyangiitis (GPA), IgA vasculitis (IgAV), Kawasaki's disease, leukocytoclastic vasculitis, lupus vasculitis, rheumatoid vasculitis, microscopic polyangiitis (MPA), polyarteritis nodosa (PAN), polymyalgia rheumatica, urticarial vasculitis, and vasculitis.

Non-limiting examples of destructive bone disorders which can be treated with the compounds and compositions provided herein include metastatic bone disease, destructive bone lesions in primary amyloidosis, destructive bone disease caused by tertiary syphilis, destructive bone lesions caused by metastatic cancer, myeloma bone disease, and osteomyelitis.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's disease, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjogren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

Non-limiting examples of metabolic diseases which can be treated with the compounds and compositions provided herein include obesity, hyperthyroidism, hypothyroidism, diabetes, dyslipidemia, hypolipidemia, galactosemia, phenylketonuria, glycogen storage diseases, lactose intolerance, galactosemia, fructose malabsorption, hereditary fructose intolerance (HFI), hyperinsulinemic hypoglycemia, maturity onset diabetes of the young type II, glucose-6-phosphate isomerase deficiency, Tarui's Disease, aldolase A deficiency, triosephosphate isomerase deficiency (TPID), phosphoglycerate kinase deficiency, muscle phosphoglycerate mutase deficiency, enolase deficiency, pyruvate kinase deficiency, Baker-Winegrad disease, von Gierke's disease, Kostmann's disease, Dursun syndrome, CDG syndrome type It, Andersen's disease, Adult polyglucosan body disease (APBD), Hers disease, McArdle's disease, Forbes disease, Cori disease, Pompe's disease, alkaptonuria, aspartylglucosaminuria, methylmalonic acidemia, maple syrup urine disease, homocystinuria, tyrosinemia, trimethylaminuria, Hartnup disease, biotinidase deficiency, ornithine carbamoyltransferase deficiency, carbamoyl-phosphate synthase I deficiency disease, citrullinemia, hyperargininemia, hyperhomocysteinemia, hypermethioninemia, hyperlysinemias, honketotic hyperglycinemia, propionic acidemia, hyperprolinemia, carbamoyl phosphate synthetase I deficiency, methylmalonic acidemia, propionic acidemia, isovaleric acidemia, very long-chain acyl-coenzyme A dehydrogenase deficiency (VLCAD), long-chain 3-hydroxyacyl-coenzyme A dehydrogenase deficiency (LCHAD), medium-chain acyl-coenzyme A dehydrogenase deficiency (MCAD), short-chain acyl-coenzyme A dehydrogenase deficiency (SCAD), 3-hydroxyacyl-coenzyme A dehydrogenase deficiency (HADH), 2,4 dienoyl-CoA reductase deficiency, 3-hydroxy-3-methylglutaryl-CoA lyase deficiency, malonyl-CoA decarboxylase deficiency, primary carnitine deficiency, carnitine-acylcarnitine translocase deficiency, carnitine palmitoyltransferase I deficiency (CPT-I), carnitine palmitoyltransferase II deficiency (CPT-II), Wolman disease, cholesteryl ester storage disease, Gaucher disease, Niemann-Pick disease, Fabry disease, Farber's disease, gangliosidoses, Krabbe disease, metachromatic leukodystrophy, Lesch-Nyhan syndrome (LNS), acute intermittent porphyria, 18,20-desmolase (P450scc) deficiency, 3β-hydroxysteroid dehydrogenase type 2 deficiency, combined 17α-hydroxylase/17,20-lyase deficiency, isolated 17,20-lyase deficiency, 21-hydroxylase deficiency, 11β-hydroxylase type 1 deficiency, 11β-hydroxylase type 2 deficiency, 18-hydroxylase deficiency, 18-hydroxylase overactivity, 17β-hydroxysteroid dehydrogenase deficiency, 5α-reductase type 2 deficiency, aromatase deficiency, Kearns-Sayre syndrome, mitochondrial encephalomyopathy, lactic acidosis, and stroke-like syndrome, myoclonic epilepsy and ragged-red fibers, chronic progressive external ophthalmoplegia, Zellweger syndrome, Hunter syndrome, Salla disease, and Hurler disease.

In some embodiments, a compound of Formula (I) inhibits ASK1.

Evaluation of Biological Activity

The biological activity of the compounds described herein can be tested using any suitable assay known to those of skill in the art, see, e.g., biochemical direct phosphorylation of target protein, pseudosubstrate or peptide using radioactive ATP, or consumption of ATP/generation of ADP, or phosphorylation of downstream target proteins in cell-based systems using radioactive ATP or target phospho-specific antibodies To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described, and claimed herein. The reader will recognize that the skilled artisan, armed with the present disclosure, and skill in the art is able to prepare and use the disclosure without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* 7$^{th}$ Ed., John Wiley & Sons (2013), Carey and Sundberg, *Advanced Organic Chemistry* 5$^{th}$ Ed., Springer (2007), *Comprehensive Organic Transformations: A Guide to Functional Group Transformations,* 2$^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts *Greene's Protective Groups in Organic Synthesis,* 5th Ed., John Wiley & Sons (2014), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1$H) nuclear magnetic resonance spectra (NMR) were measured in the indicated solvents on a Bruker NMR spectrometer (Avance TM DRX500, 500 MHz for $^1$H) or Varian NMR spectrometer (Unity Plus 400, 400 MHz for ¹H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
CDCl₃=deuterated chloroform
DMF=N,N-dimethylformamide
DMF-DMA=N,N-dimethylformamide dimethyl acetal
DMSO-d₆=deuterated dimethylsulfoxide
ESIMS=electron spray mass spectrometry
IPA=isopropyl amine
LC/MS=Liquid chromatography-mass spectrometry
MeCN=acetonitrile
NMR=nuclear magnetic resonance
ON=overnight
Pd₂(dba)₃=tris(dibenzylideneacetone)dipalladium(0)
Pd(dppf)Cl₂=1,1'-bis(diphenylphosphino)ferrocene-palladium(II)dichloride
PhMe=toluene
PTSA=para-toluene sulfonic acid
Rt=retention time
XantPhos=4,5-bis(diphenylphosphino)-9,9-dimethylxanthene The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Intermediate isoindolin-1-one halide (VIII) can be prepared as depicted in Scheme 1.

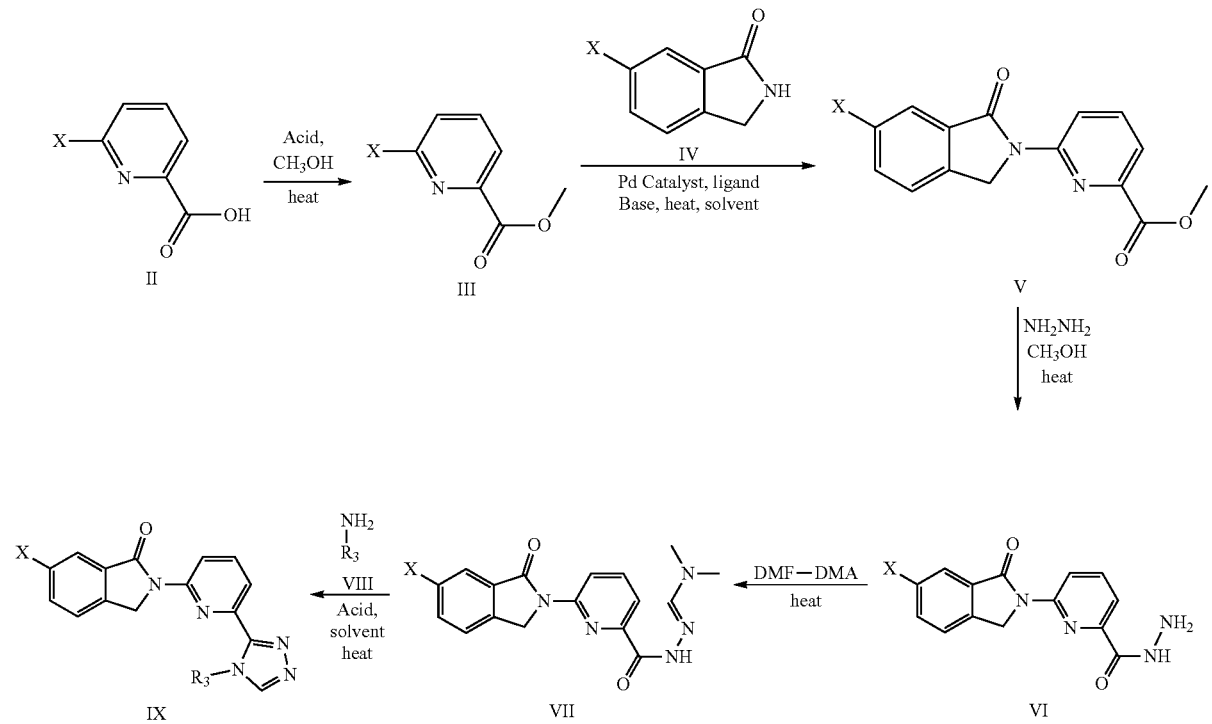

Scheme 1 shows a general method for preparing isoindolin-1-one halide or pseudohalide (IX) depicted in Scheme 1. According to the method, carboxylic acid starting material (II) was heated in methanol with acid (e.g. HCl or H₂SO₄) to give ester intermediate (III) which is then reacted with isoindolin-1-one intermediate (IV) in the presence of a palladium catalyst (e.g., Pd(PPh₃)₄, (PPh₃)₂PdCl₂, Pd(dppf)Cl₂ etc.), an optional ligand (e.g. 2-dicyclohexylphosphino) biphenyl, XantPhos), a base (e.g. KF, Na₂CO₃, NaHCO₃, Cs₂CO₃), and one or more solvents (e.g. dioxane, DCM, DMF, H₂O etc.) at elevated temperature (e.g., 90-145° C.) to give intermediate (V). Treatment of V with excess hydrazine hydrate in MeOH with heating (e.g., at about 60° C.) gives compound VI. Treatment of VI with DMF-DMA with heating (e.g., at about 80° C.) gives compound VII. Treatment of VII with appropriately-substituted amines (R₃—NH₂) (VIII) with acid (e.g., HOAc, PTSA) in solvent (e.g., MeCN, PhMe) at elevated temperature (e.g., 45-120° C.) gives isoindolin-1-one halide or pseudohalide (IX).

Compounds of Formula I of the present disclosure can be prepared as depicted in Scheme 2.

Scheme 2

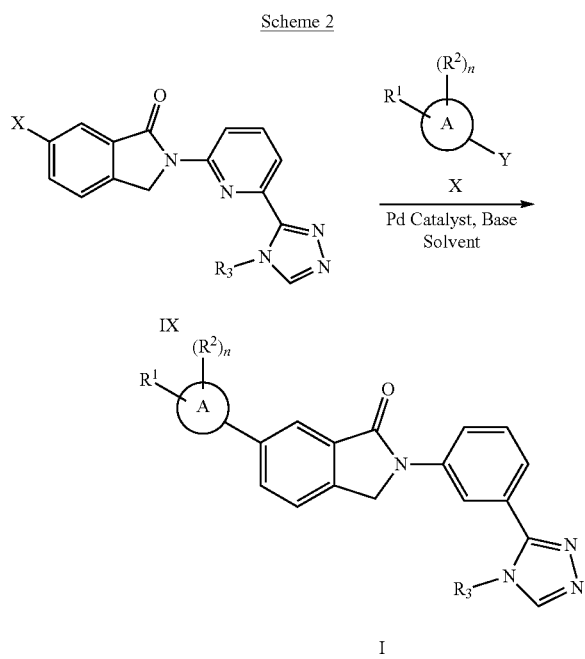

Scheme 2 shows a general method for preparing isoindolin-1-one derivatives (I) by reacting an isoindolin-1-one halide or pseudohalide (IX) with a boronic acid or ester (X) under Suzuki conditions. As shown in Scheme 2, the isoindolin-1-one halide or pseudohalide (IX) (e.g. X is Br, Cl, I or triflate) may be reacted with a boronic acid or ester (X e.g. Y is —B(OR*)$_2$, where each R* is H or C$_{1-4}$ alkyl or each R* together forms a C$_{1-8}$ alkanediyl such as 2,3-dimethylbutan-2,3-diyl) in the presence of palladium catalyst (e.g., Pd(PPh$_3$)$_4$, (PPh$_3$)$_2$PdCl$_2$, Pd(dppf)Cl$_2$ etc.), a base (e.g. KF, Na$_2$CO$_3$, NaHCO$_3$, Cs$_2$CO$_3$) and one or more solvents (e.g. dioxane, DCM, DMF, H$_2$O etc.) at elevated temperature (e.g., 90-145° C.). The method depicted in Scheme 2 may be varied as desired. For example, the halide or pseudohalide (IX) may be reacted with a boronic acid or boronic ester (X) and the resulting intermediate (not shown) further elaborated via, for example, alkylation, acylation, hydrolysis, oxidation, reduction, amidation, sulfonation, alkylation, alkylenation, and the like, to give the desired isoindolin-1-one derivatives (I).

Illustrative Compound Examples

Preparation of intermediate 2-bromo-6-(4-isopropyl-4H-1,2,4-triazol-3-yl)pyridine (XV) is depicted below in Scheme 3.

Scheme 3

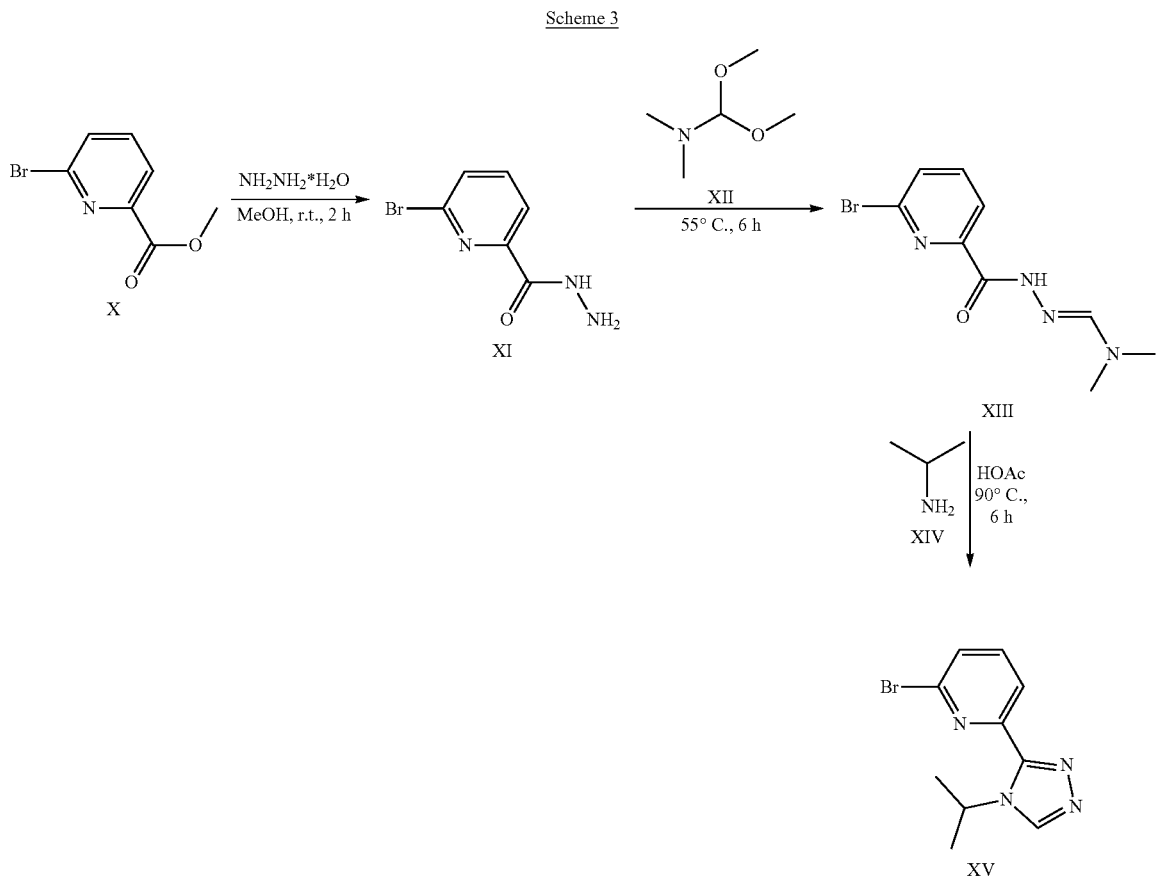

Step 1

To a solution of methyl 6-bromopicolinate (X) (5 g, 23.1 mmol) in MeOH (100 mL) was added hydrazine hydrate (11.57 g, 231 mmol) at room temperature and the reaction was stirred for 2 h. The reaction mixture was concentrated under reduced pressure to give 6-bromopicolinohydrazide (XI) (4.41 g, 20.4 mmol, 88.4% yield) which was used in the next step without further purification.

Step 2

A solution of 6-bromopicolinohydrazide (XI) (4.41 g, 20.4 mmol) in DMF-DMA (XII) (25 g, 21.0 mmol) was heated to 55° C. for 6 h. After cooling, the reaction mixture was concentrated under reduced pressure. The obtained residue was stirred with MTBE (100 mL) and filtered to give (E)-N'-(6-bromopicolinoyl)-N,N-dimethylformohydrazonamide (XIII) (2.62 g, 9.66 mmol, 47.4% yield) which was used in the next step without further purification.

Step 3

To a solution of (E)-N'-(6-bromopicolinoyl)-N,N-dimethylformohydrazonamide (XIII) (2.62 g, 9.66 mmol, 1.0 eq.) in glacial acetic acid (70 mL) was added isopropylamine (XIV) (1.7 g, 29 mmol, 3.0 eq) at room temperature. The reaction was stirred at 90° C. for 6 h. The reaction mixture was cooled to room temperature and the solvent was removed under reduced pressure. The residue was purified by column chromatography (100% EtOAc to wash out impurities followed by 100% THF) to give 2-bromo-6-(4-isopropyl-4H-1,2,4-triazol-3-yl)pyridine (XV) (1.0 g, 3.74 mmol, 38.8% yield, 92% purity). $^1$H NMR (DMSO-d$_6$, 400 MHz) δ ppm 1.52 (m, 6H), 5.23 (m, 1H), 7.48 (m, 1H), 7.73 (m, 1H), 8.05 (m, 1H), 8.69 (s, 1H), 8.94 (s, 1H). ESIMS) found for $C_{10}H_{11}BrN_4$ m/z 267.0; 269.0 (M+H).

Example 1

Preparation of aromatic carbocyclic acid derivatives (XXIII), is depicted below in Scheme 4.

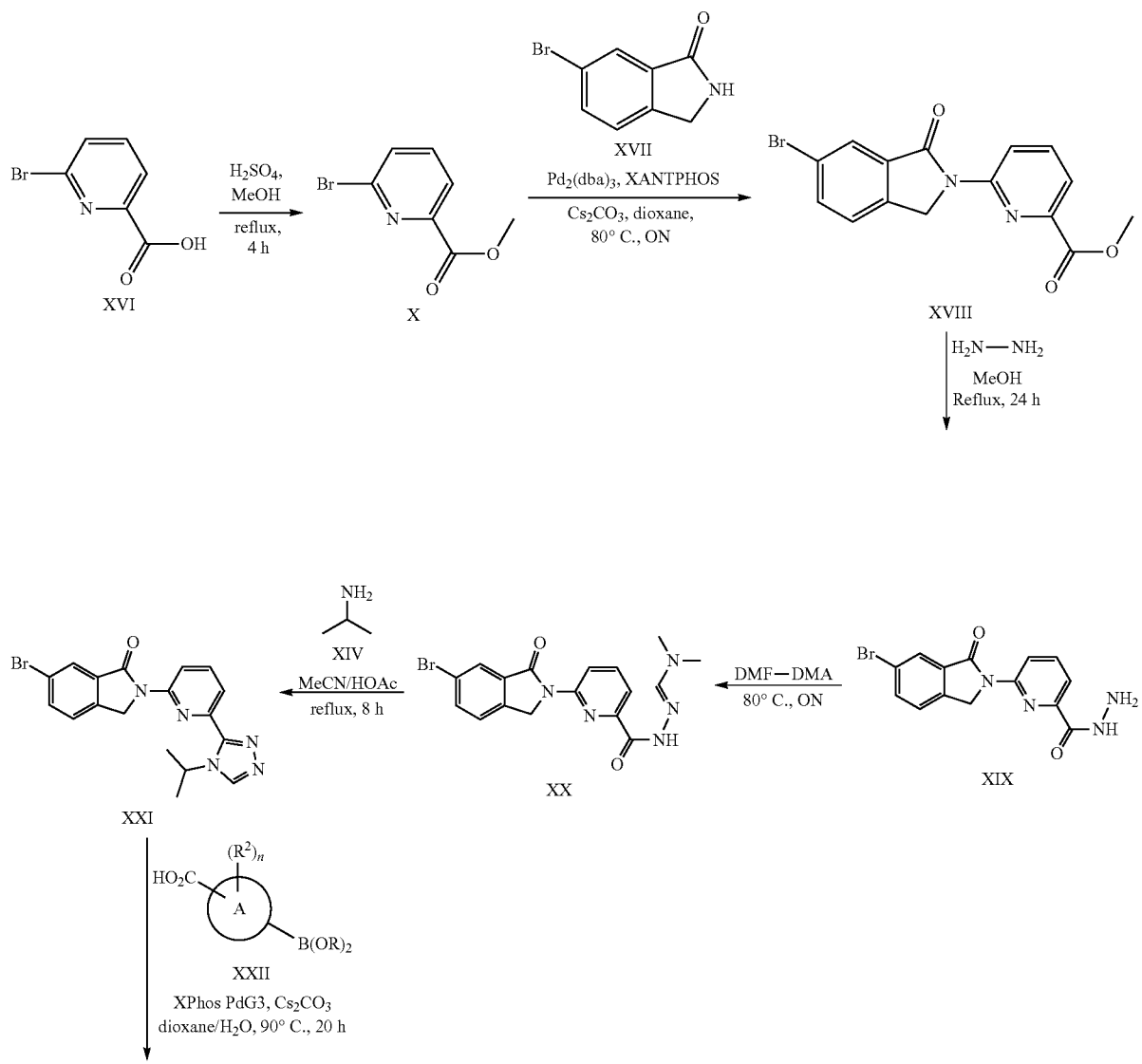

Scheme 4

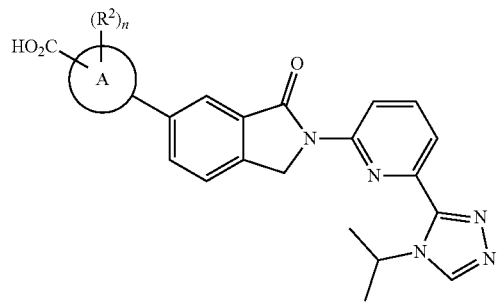

XXIII

Step 1

A solution of 6-bromopyridine-2-carboxylic acid (XVI) (20 g, 0.1 mol, 1 eq) in methanol (600 mL) containing conc. $H_2SO_4$ (10 mL) was heated at reflux for 4 hr. The reaction mixture was cooled to ~0° C. and conc. ammonia was added (pH=9). The resulting solution was evaporated to give a white residue. This white solid was partitioned between brine and dichloromethane (200/400 mL). The phases were separated, and the organic phase was washed with water, dried over $Na_2SO_4$, and concentrated to dryness to give methyl 6-bromopicolinate (X) as white solid (20.2 g, 94.5%). The crude ester was used without further purification. $^1$H NMR (500 MHz, $CDCl_3$) δ 4.28 (s, 3H), 8.50 (m, 2H), 8.92 (m, 1H).

Step 2

$Pd_2(dba)_3$ (350 mg, 0.38 mmol), XantPhos (540 mg, 0.93 mmol), cesium carbonate (9 g, 27.8 mmol, 2 eq), 6-bromo-isoindolin-1-one (XVII) (2.94 g, 14 mmol, 1 eq) and methyl 6-bromopicolinate (X) (3 g, 14 mmol, 1 eq) were combined in dioxane (100 mL). The mixture was degassed with nitrogen, sealed and heated at 80° C. for overnight. The reaction mixture was poured into water (100 mL). A precipitate formed was filtered and the filtrate was extracted with EtOAc (3*50 mL). The organic extracts were combined and concentrated. The resulting solid was triturated in IPA to give methyl 6-(6-bromo-1-oxoisoindolin-2-yl)picolinate (XVIII) as a solid (3.5 g, 73% yield). $^1$HNMR (400 MHz, DMSO-$d_6$) δ 3.90 (s, 3H), 5.12 (m, 2H), 7.73 (m, 1H), 7.85 (m, 1H), 7.95 (m, 2H), 8.10 (m, 1H), 8.70 (m, 1H).

Step 3

To a suspension of 6-(6-bromo-1-oxoisoindolin-2-yl)picolinate (XVIII) (1.5 g, 4.32 mmol, 1 eq) in MeOH (50 mL) was added hydrazine hydrate (0.5 mL, 0.1 mol, 23 eq) at 25° C. The reaction mixture was then heated at reflux for 24 h. The reaction was concentrated in vacuo and the resulting solid was triturated in IPA to give 6-(6-bromo-1-oxoisoindolin-2-yl)picolinohydrazide (XIX) (1.25 g, 83.9% yield). The crude product was used without further purification. $^1$HNMR (400 MHz, DMSO-$d_6$) δ 1.16 (m, 1H), 4.61 (m, 2H), 5.25 (m, 2H), 7.65 (m, 1H), 7.76 (m, 1H), 7.93 (m, 1H), 8.06 (m, 1H), 8.57 (m, 1H), 9.88 (m, 1H).

Step 4

6-(6-Bromo-1-oxoisoindolin-2-yl)picolinohydrazide (XIX) (1.25 g, 3.6 mmol, 1 eq) was dissolved in DMF-DMA (30 mL, 0.22 mol) and heated to 80° C. overnight. The reaction mixture was concentrated in vacuo then mixed with diethyl ether and the obtained solid was collected by filtration, rinsed with diethyl ether then dried in the vacuum to give (E)-N'-(6-(6-bromo-1-oxoisoindolin-2-yl)picolinoyl)-N,N-dimethylformohydrazonamide (XX) (1.1 g, 76% yield) as a white solid. $^1$HNMR (400 MHz, DMSO-$d_6$) δ 2.88 (s, 6H), 5.29 (m, 2H), 8.01 (m, 6H), 8.57 (m, 1H), 10.55 (m, 1H).

Step 5

(E)-N'-(6-(6-bromo-1-oxoisoindolin-2-yl)picolinoyl)-N,N-dimethylformohydrazonamide (XX) (1.1 g, 2.73 mmol, 1 eq) and propan-2-amine (XIV) (10 eq) were dissolved in MeCN/HOAc (60 mL/15 mL). The mixture was heated to reflux for 8 h. The reaction mixture was concentrated in vacuo and the resulting solid was triturated in water, filtered off and dried to give 6-bromo-2-(6-(4-isopropyl-4H-1,2,4-triazol-3-yl)pyridin-2-yl)isoindolin-1-one (XXI) (710 mg, 65% yield) as a white solid. $^1$HNMR (400 MHz, DMSO-$d_6$) δ 1.56 (m, 6H), 5.13 (m, 2H), 5.51 (m, 1H), 7.71 (m, 1H), 7.91 (m, 3H), 8.07 (m, 1H), 8.59 (m, 1H), 8.86 (m, 1H).

Step 6

A solution of 6-bromo-2-(6-(4-isopropyl-4H-1,2,4-triazol-3-yl)pyridin-2-yl)isoindolin-1-one (XXI) (100.0 mg, 0.252 mmol), the corresponding aryl boronic acid or aryl boronate (XXII) (0.323 mmol, 1.3 eq) and cesium carbonate (246 mg, 0.756 mmol, 3 eq) were mixed in 8-ml vial. Dioxane (4 mL) and water (1 mL) were then added. The vial was flushed with argon then XPhos Pd G3 (20.0 mg, 0.024 mmol, 0.1 eq) was added and the vial was sealed. The obtained mixture was stirred at 90° C. for 20 hours then cooled to room temperature and concentrated in vacuo. The residue was dissolved (or suspended) in MeOH (6 mL) followed by addition of lithium hydroxide monohydrate (53 mg, 1.26 mmol, 5 eq). The obtained mixture was stirred at room temperature for 3 days then quenched with TFA (213 μl, 2.75 mmol, 11 eq) and evaporated in vacuo. The residue was shaken on ultrasonic bath with water and MTBE. The solid precipitate formed was collected by filtration, dried and purified by HPLC (column: Waters SunFire C18, 5 μm, 19×100 mm; mobile phase: water-acetonitrile 30 mL/min) to provide the desired product (XXIII).

Example 2

Preparation of carbocyclic acid derivatives (XXIII), is depicted below in Scheme 5.

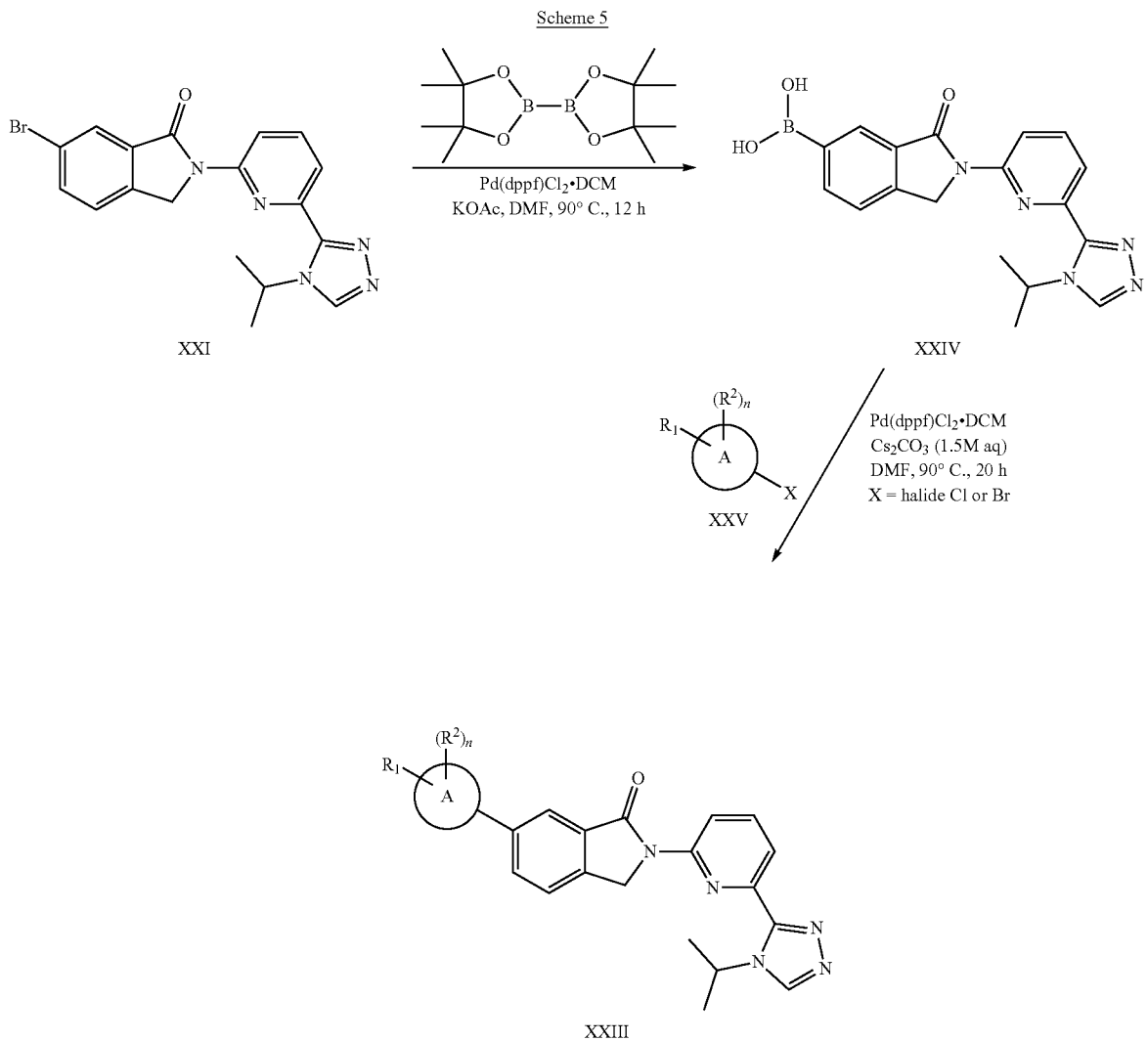

Step 1

To a solution of 6-bromo-2-(6-(4-isopropyl-4H-1,2,4-triazol-3-yl)pyridin-2-yl) isoindolin-1-one (XXI) (1.00 g, 2.51 mmol, 1.00 eq) and 4,4,4',4',5,5,5',5'-octamethyl-2,2'-bi(1,3,2-dioxaborolane) (765 mg, 3.01 mmol, 1.20 eq) in DMF (10.0 mL) was added Pd(dppf)Cl$_2$-DCM (184 mg, 25 μmol, 0.100 eq) and KOAc (739 mg, 7.53 mmol, 3.00 eq). The mixture was stirred at 90° C. for 12 hrs under N$_2$. After such time the mixture was concentrated in vacuum. The crude product was purified by reversed-phase HPLC (0.1% FA condition) to afford (2-(6-(4-isopropyl-4H-1,2,4-triazol-3-yl)pyridin-2-yl)-3-oxoisoindolin-5-yl)boronic acid (XXIV) (550 mg, 1.29 mmol, 51% yield, 85.0% purity) as a gray solid. $^1$HNMR (400 MHz, DMSO-d$_6$) δ 8.93 (s, 1H), 8.66 (m, 1H), 8.32 (m, 2H), 8.10 (m, 1H), 7.91 (m, 1H), 7.71 (m, 1H), 5.53 (m, 1H), 5.19 (m, 2H), 1.57 (m, 6H); ESIMS found for C$_{18}$H$_{18}$BN$_5$O$_3$ m/z 354.1 (M+H); Rt 0.646 min.

Step 2

To a solution of (2-(6-(4-isopropyl-4H-1,2,4-triazol-3-yl)pyridin-2-yl)-3-oxoisoindolin-5-yl)boronic acid (XXIV) (40.8 mg, 112 μmol, 1.00 eq) in DMF (1.00 mL) were added aryl halide or heteroaryl halide (XXV) (47.0 mg, 168 μmol, 1.20 eq), Pd(dppf)Cl$_2$-DCM (8.22 mg, 11.2 μmol, 0.100 eq) and Cs$_2$CO$_3$ (1.50 M, 224 uL, 3.00 eq). The mixture was stirred at 90° C. for 2 hrs. The mixture was filtered through a Celite pad and washed with DCM (20.0 mL) and MeOH (20.0 mL), concentrated to dryness, purified via prep-HPLC (Waters XBridge C18, 5 μm, 25×150 mm; mobile phase: water (10 mM NH$_4$HCO$_3$)-acetonitrile 30 mL/min 5%-35% over 10 min) and lyophilized to provide the desired product (XXIII).

Example 3

Preparation of 3-(2-(6-(4-isopropyl-4H-1,2,4-triazol-3-yl)pyridin-2-yl)-3-oxoisoindolin-5-yl)benzoic acid (1), is depicted below in Scheme 6.

Scheme 6

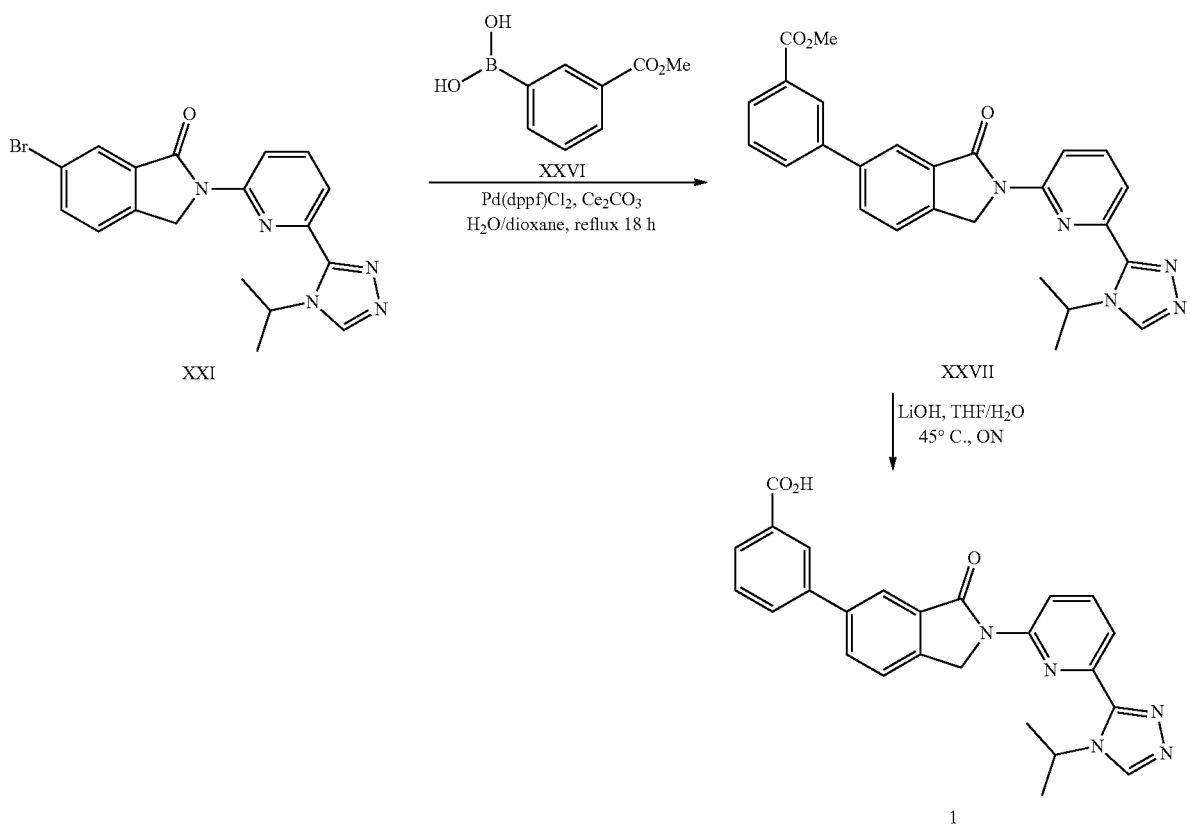

Step 1

To a suspension of 6-bromo-2-(6-(4-isopropyl-4H-1,2,4-triazol-3-yl)pyridin-2-yl)isoindolin-1-one (XXI) (155 mg, 0.4 mmol, 1 eq) and 5% cesium carbonate (200 mg) in water/dioxane (20 mL), flushed with nitrogen for 15 minutes. The 3-methoxycarbonylphenyl boronic acid (XXVI) (70 mg, 0.4 mmol, 1 eq) was added, followed by catalyst Pd(dppf)Cl$_2$*DCM (40 mg, 0.049 mmol, 0.12 eq). The solution was heated to reflux (105° C.) under nitrogen, for 18 h. The reaction mixture was concentrated in vacuo. Obtained residue was subjected to flash-chromatography in system MeOH/EtOAc 1:1 to give 120 mg (66.3% yield) of crude methyl 3-(2-(6-(4-isopropyl-4H-1,2,4-triazol-3-yl)pyridin-2-yl)-3-oxoisoindolin-5-yl)benzoate (XXVII) which was used in next step without further purification. $^1$HNMR (500 MHz, DMSO-d$_6$) δ 1.59 (m, 6H), 3.91 (m, 3H), 5.21 (m, 2H), 5.53 (m, 1H), 7.47 (m, 2H), 7.67 (m, 2H), 7.93 (m, 2H), 8.09 (m, 3H), 8.65 (m, 1H), 8.91 (m, 1H).

Step 2

To a solution of methyl 3-(2-(6-(4-isopropyl-4H-1,2,4-triazol-3-yl)pyridin-2-yl)-3-oxoisoindolin-5-yl)benzoate (XXVII) (120 mg, 0.26 mmol, 1 eq) in THF (10 ml) and H$_2$O (2 ml), was added LiOH.H$_2$O (100 mg, 2.38 mmol, 9 eq). The reaction mixture was stirred overnight at 45° C. The THF was evaporated under reduced pressure, 50 ml of water was added, and the resulting mixture was acidified with 1 M aqueous NaHSO$_4$ (pH=3) and extracted with EtOAc (3*50 mL). The organic extracts were combined and concentrated. The crude product was purified by HPLC to afford 3-(2-(6-(4-isopropyl-4H-1,2,4-triazol-3-yl)pyridin-2-yl)-3-oxoisoindolin-5-yl)benzoic acid (1) (17 mg, 11.8% yield) as a white solid. $^1$HNMR (400 MHz, DMSO-d$_6$) δ 1.59 (m, 6H), 5.22 (s, 2H), 5.53 (m, 1H), 7.64 (m, 1H), 7.89 (m, 1H), 7.93 (m, 1H), 7.98 (m, 1H), 8.09 (m, 4H), 8.26 (m, 1H), 8.65 (m, 1H), 8.94 (m, 1H), 13.17 (s, 1H). LCMS(ESIMS) found for C$_{25}$H$_{21}$N$_5$O$_3$ m/z 440.2 (M+1); Rt=1.24 min.

Example 4

Preparation of 2-(4-(2-(6-(4-isopropyl-4H-1,2,4-triazol-3-yl)pyridin-2-yl)-3-oxoisoindolin-5-yl)phenyl)-2-methyl-propanoic acid (39), is depicted below in Scheme 7.

Scheme 7

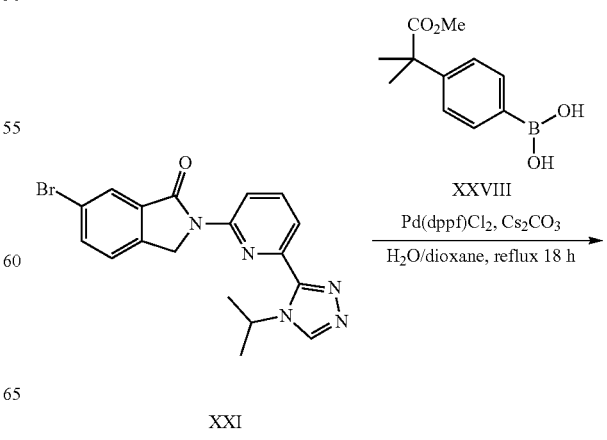

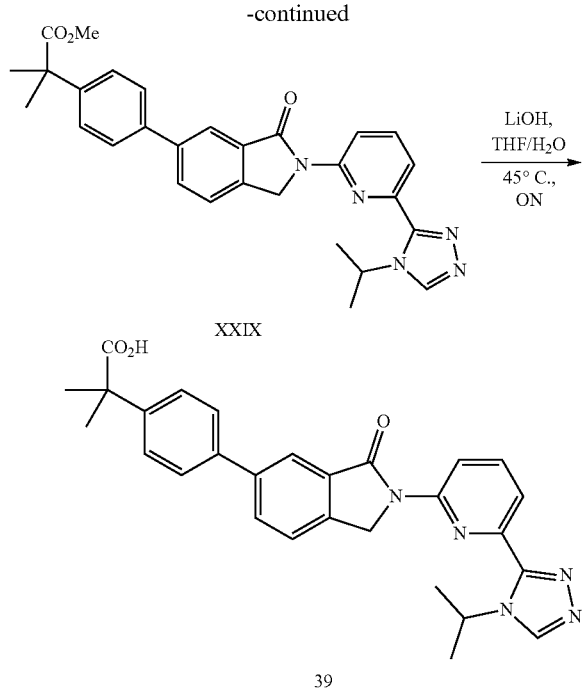

Step 1

To a suspension of 6-bromo-2-(6-(4-isopropyl-4H-1,2,4-triazol-3-yl)pyridin-2-yl)isoindolin-1-one (XXI) (155 mg, 0.4 mmol, 1 eq) and 5% cesium carbonate (200 mg) in water/dioxane (20 mL), flushed with nitrogen for 15 minutes. The (3-(4-methoxy-2-methyl-4-oxobutan-2-yl)phenyl) boronic acid (XXVIII) (130 mg, 0.4 mmol, 1 eq) was added, followed by catalyst Pd(dppf)Cl$_2$*DCM (40 mg, 0.049 mmol, 0.12 eq). The solution was heated to reflux (105° C.) under nitrogen, for 18 h. The reaction mixture was concentrated in vacuo. Obtained residue was subjected to flash-chromatography in system MeOH/EtOAc 1:1 to give 120 mg (66.3% yield) of methyl 2-(4-(2-(6-(4-isopropyl-4H-1,2,4-triazol-3-yl)pyridin-2-yl)-3-oxoisoindolin-5-yl)phenyl)-2-methylpropanoate (XXIX) which was used in next step without further purification. $^1$HNMR (400 MHz, DMSO-d$_6$) δ 1.55 (m, 13H), 3.62 (m, 3H), 5.19 (m, 2H), 5.52 (m, 1H), 7.42 (m, 2H), 7.74 (m, 2H), 7.83 (m, 1H), 7.91 (m, 1H), 8.05 (m, 4H), 8.65 (m, 1H), 8.94 (m, 1H).

Step 2

To a solution of methyl 2-(4-(2-(6-(4-isopropyl-4H-1,2,4-triazol-3-yl)pyridin-2-yl)-3-oxoisoindolin-5-yl)phenyl)-2-methylpropanoate (XXIX) (95 mg, 0.19 mmol, 1 eq) in THF (10 ml) and H$_2$O (2 ml), was added LiOH.H$_2$O (100 mg, 2.38 mmol, 10 eq). The reaction mixture was stirred overnight at 45° C. The THF was evaporated under reduced pressure, 50 ml of water was added, and the mixture was acidified with 1 M aqueous NaHSO$_4$ (pH=3), extracted with EtOAc (3.50 mL). The organic extracts were combined and concentrated. The crude product was purified by HPLC to afford 2-(4-(2-(6-(4-isopropyl-4H-1,2,4-triazol-3-yl)pyridin-2-yl)-3-oxoisoindolin-5-yl)phenyl)-2-methylpropanoic acid (63) (24 mg, 26.4% yield) as a white solid. $^1$HNMR (400 MHz, DMSO-d$_6$) δ 1.52 (m, 6H), 1.59 (m, 6H), 5.19 (s, 2H), 5.53 (m, 1H), 7.47 (m, 2H), 7.80 (m, 2H), 7.82 (m, 1H), 7.92 (m, 1H), 8.05 (m, 3H), 8.65 (m, 1H), 8.94 (s, 1H), 12.42 (s, 2H). LCMS(ESIMS) found for C$_{28}$H$_{27}$N$_5$O$_3$ m/z 482.2 (M+1); Rt=1.37 min.

Example 5

Preparation of 2-(4-(2-(6-(4-cyclopropyl-4H-1,2,4-triazol-3-yl)pyridin-2-yl)-3-oxoisoindolin-5-yl)phenyl)-2-methylpropanoic acid (53) and methyl 2-(4-(2-(6-(4-cyclopropyl-4H-1,2,4-triazol-3-yl)pyridin-2-yl)-3-oxoisoindolin-5-yl)phenyl)-2-methylpropanoate (132) are depicted below in Scheme 8.

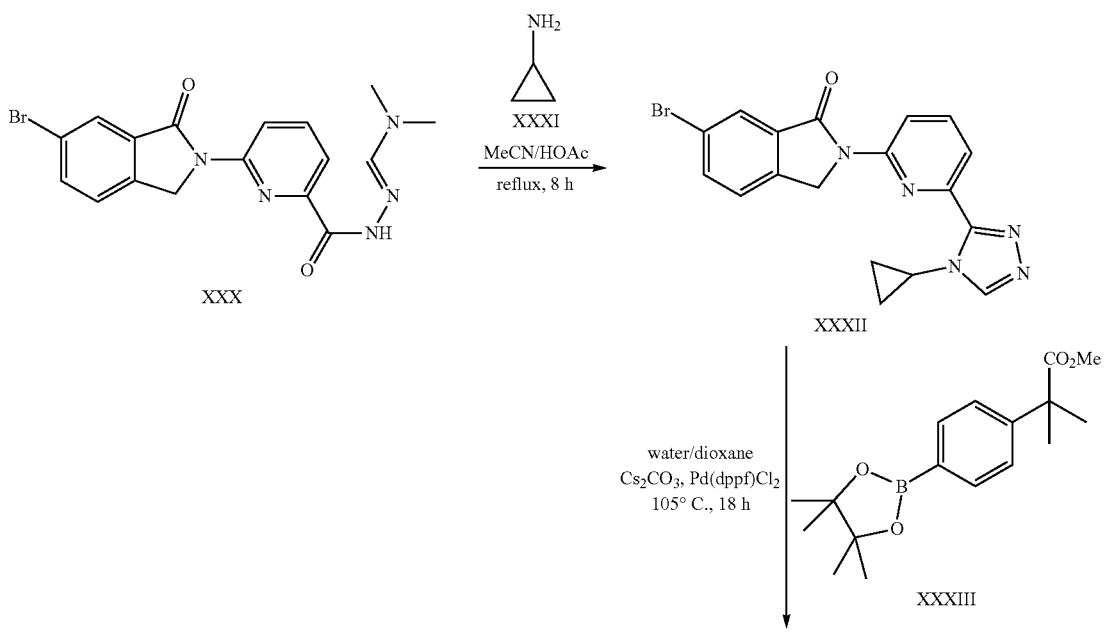

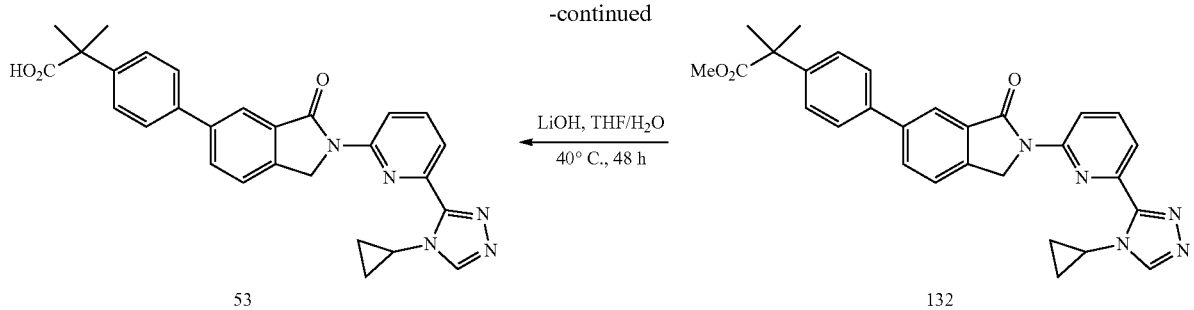

Step 1

(E)-N'-(6-(6-bromo-1-oxoisoindolin-2-yl)picolinoyl)-N,N-dimethylformohydrazonamide (XXI) (4.7 g, 12 mmol) and cyclopropylamine (XXXI) (3.43 g, 60 mmol) were dissolved in acetonitrile/acetic acid (80 mL/30 mL). The mixture was heated to reflux for 36 h before the mixture was concentrated in vacuo and the residue purified via flash chromatography (SiO$_2$, gradient CHCl$_3$/CH$_3$OH) to afford 6-bromo-2-(6-(4-cyclopropyl-4H-1,2,4-triazol-3-yl)pyridin-2-yl)isoindolin-1-one (XXXII) (1.1 g, 23% yield, 75% purity) as a yellow solid. The product was used in the next step without additional purification.

Step 2

To a suspension of compound 6-bromo-2-(6-(4-cyclopropyl-4H-1,2,4-triazol-3-yl)pyridin-2-yl)isoindolin-1-one (XXXII) (500 mg, approx. 1 mmol, 75% purity) and cesium carbonate (700 mg) in water/dioxane (1/10, 44 mL), flushed with argon gas for 5 minutes, was added methyl 2-methyl-2-(4-(4,4,5,5-tetramethyl-1,3,2-dioxaborolan-2-yl)phenyl)propanoate (XXXIII) (330 mg, 1.1 mmol), followed by Pd(dppf)Cl$_2$DCM (100 mg). The solution was heated at 105° C. for 18 h. The cooled reaction mixture was filtered through pad of SiO$_2$, washed with dioxane (100 mL) and concentrated in vacuum to give methyl 2-(4-(2-(6-(4-cyclopropyl-4H-1,2,4-triazol-3-yl)pyridin-2-yl)-3-oxoisoindolin-5-yl)phenyl)-2-methylpropanoate 132 (330 mg, 67% yield, 65% purity) which was used without further purification

Step 3

To a solution of methyl 2-(4-(2-(6-(4-cyclopropyl-4H-1,2,4-triazol-3-yl)pyridin-2-yl)-3-oxoisoindolin-5-yl)phenyl)-2-methylpropanoate 132 (330 mg, 65% purity) in a mixture of MeOH (30 mL), THF (3 mL) and H$_2$O (6 mL), was added LiOH (200 mg). The reaction mixture was stirred for 48 h at 40° C. The solvent was evaporated, 70 mL of water was added, and the mixture acidified with 1M NaHSO$_4$ (aq.) to pH=3. The precipitate that was formed was filtered off, dried and purified by prep-HPLC. Compound 2-(4-(2-(6-(4-cyclopropyl-4H-1,2,4-triazol-3-yl)pyridin-2-yl)-3-oxoisoindolin-5-yl)phenyl)-2-methylpropanoic acid 53 (41 mg, 0.085 mmol, 8% yield) was obtained as a white solid. $^1$H NMR (DMSO-d$_6$, 400 MHz) δ ppm 0.98 (m, 2H), 1.13 (m, 2H), 1.53 (s, 6H), 4.13 (m, 1H), 5.22 (s, 2H), 7.48 (m, 2H), 7.76 (m, 2H), 7.81 (m, 1H), 7.89 (m, 1H), 8.03 (m, 1H), 8.06 (s, 1H), 8.09 (m, 1H), 8.67 (m, 1H), 8.72 (s, 1H), 12.40 (s, 1H). ESIMS found for C$_{28}$H$_{25}$N$_5$O$_3$ m/z 480.2 (M+1).

Example 6

Preparation of trans-4-(2-(6-(4-Isopropyl-4H-1,2,4-triazol-3-yl)pyridin-2-yl)-3-oxoisoindolin-5-yl)cyclohexane-1-carboxylic acid 126 and cis-4-(2-(6-(4-Isopropyl-4H-1,2,4-triazol-3-yl)pyridin-2-yl)-3-oxoisoindolin-5-yl)cyclohexane-1-carboxylic acid 127 is depicted below in Scheme 9.

Scheme 9

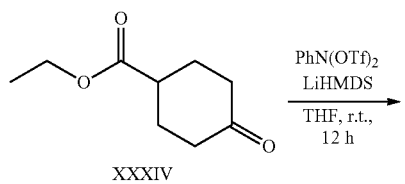

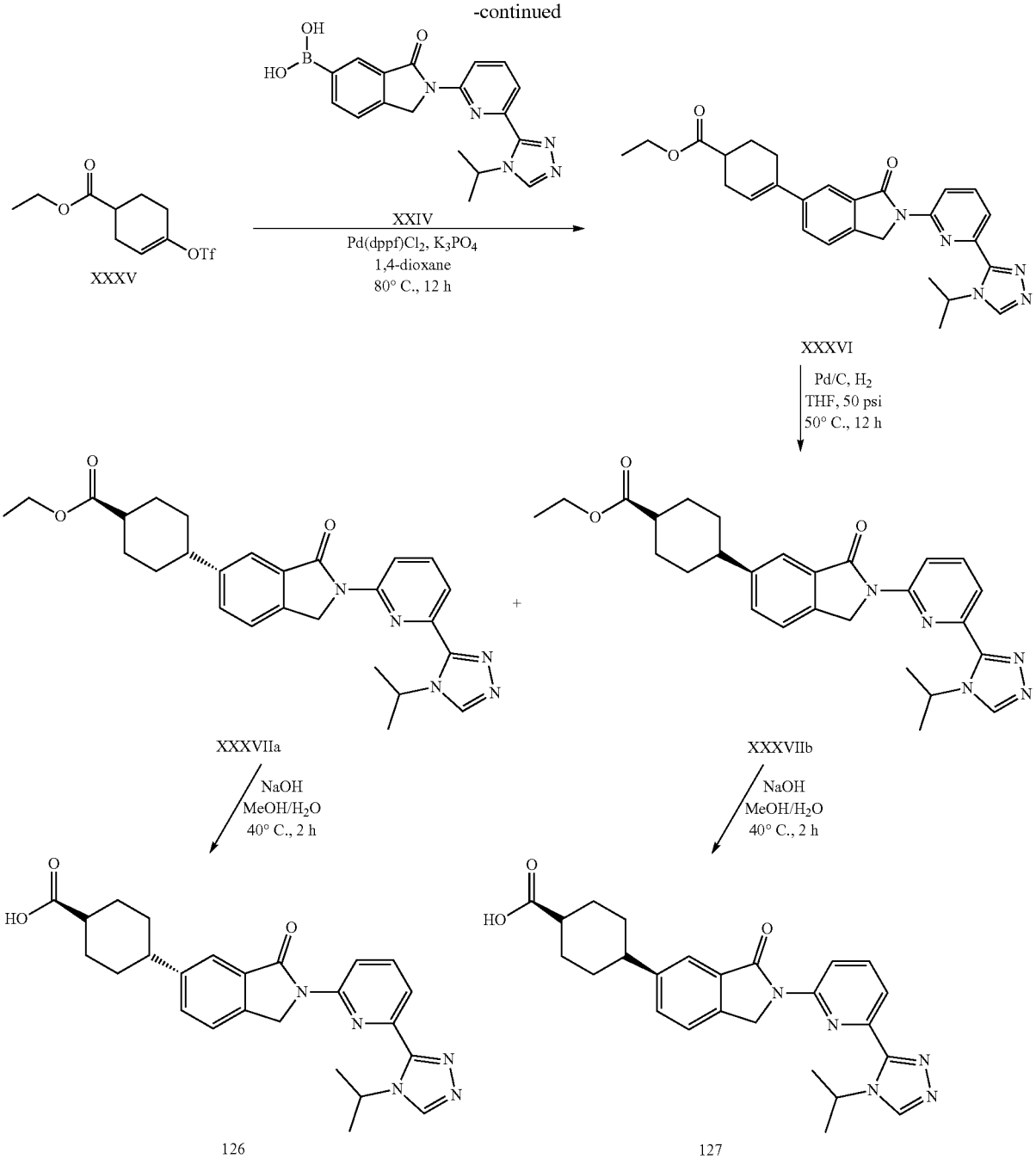

Step 1

To a solution of ethyl 4-oxocyclohexanecarboxylate (XXXIV) (5.00 g, 29.4 mmol, 4.67 mL, 1.00 eq) in THF (116 mL) was added LiHMDS (1 M, 30.8 mL, 1.05 eq) at −78° C. After 1 h a solution of 1,1,1-trifluoro-N-phenyl-N-(trifluoro methyl sulfonyl) methanesulfonamide (11.0 g, 30.8 mmol, 1.05 eq) in THF (16.0 mL) was added and 0.5 h after completed addition the cool bath was removed, and the reaction allowed to warm to ambient temperature and stirred for 12 h. After such time water (20 mL) was added and mixture extracted with ethyl acetate (20 mL×3). The combined organic phases were washed with brine (30.0 mL), dried over anhydrous $Na_2SO_4$, filtered and concentrated in vacuum. The residue was purified by column chromatography ($SiO_2$, Petroleum ether/EtOAc (1:0 to 5:1). Ethyl 4-((((trifluoromethyl)sulfonyl)oxy)cyclohex-3-enecarboxylate (XXXV) (4.00 g, 11.9 mmol, 40.5% yield) was obtained as a colorless oil. $^1H$ NMR ($CDCl_3$, 400 MHz) δ ppm 1.27 (m, 3H), 1.93 (m, 1H), 2.15 (m, 1H), 2.45 (m, 4H), 2.61 (m, 1H), 4.17 (m, 2H), 5.79 (m, 1H).

Step 2

To a solution of ethyl 4-((((trifluoromethyl)sulfonyl)oxy)cyclohex-3-enecarboxylate (XXXV) (500 mg, 1.65 mmol, 1.00 eq) and [2-[6-(4-isopropyl-1,2,4-triazol-3-yl)-2-pyridyl]-3-oxo-isoindolin-5-yl]boronic acid (XXIV) (600 mg, 1.65 mmol, 1.00 eq) in dioxane (10.0 mL) was added $K_3PO_4$ (702 mg, 3.31 mmol, 2.00 eq) and Pd(dppf)Cl$_2$ (121 mg, 165 μmol, 0.100 eq) and the mixture stirred at 80° C. for 12 hrs under N$_2$. The reaction mixture was poured into H$_2$O (15.0 mL) and extracted with ethyl acetate (15 mL×3). The organic phase was washed with brine (35.0 mL), dried over anhydrous Na$_2$SO$_4$ and concentrated in vacuum. The residue was purified by column chromatography (SiO$_2$, Petroleum ether/EtOAc (1:1 to 0:1) to return ethyl 4-(2-(6-(4-isopropyl-4H-1,2,4-triazol-3-yl)pyridin-2-yl)-3-oxoisoindolin-5-yl)cyclohex-3-enecarboxylate (XXXVI) (250 mg, 355 μmol, 21.5% yield) as a yellow solid $^1$H NMR (DMSO-d$_6$, 400 MHz) δ ppm 1.23 (m, 3H), 1.58 (m, 8H), 1.76 (m, 1H), 2.13 (m, 1H), 2.42 (br s, 2H), 2.62 (m, 1H), 4.13 (m, 2H), 5.15 (m, 2H), 5.53 (m, 1H), 6.32 (br s, 1H), 7.70 (m, 1H), 7.81 (m, 2H), 7.92 (m, 1H), 8.08 (m, 1H), 8.65 (m, 1H), 8.94 (m, 1H); ESIMS found for C$_{27}$H$_{29}$N$_5$O$_3$ m/z: 472.2 [M+H]; Rt 1.002 min.

Step 3

To a solution of ethyl 4-(2-(6-(4-isopropyl-4H-1,2,4-triazol-3-yl)pyridin-2-yl)-3-oxoisoindolin-5-yl)cyclohex-3-enecarboxylate (XXXVI) (250 mg, 530 μmol, 1.00 eq) in THF (10.0 mL) was added 10% Pd/C (25.0 mg) and the mixture stirred vigorously at 50° C. for 12 h under H$_2$ (50 psi). The reaction mixture was filtered, and the filtrate was concentrated in vacuum. The residue was purified and stereoisomer separated with prep-HPLC (column: Water Xbridge C18 150 mm×25 mm×5 μm; [water (water/10 mM NH$_4$HCO$_3$)-MeCN]; B %: 38%-68%, 10 min) and lyophilized to return trans-ethyl 4-(2-(6-(4-isopropyl-4H-1,2,4-triazol-3-yl)pyridin-2-yl)-3-oxoisoindolin-5-yl)cyclohexanecarboxylate (XXXVIIa) as a white solid (20.0 mg, 38.0 μmol, 7.17% yield)$^1$H NMR (CDCl$_3$, 400 MHz) δ ppm 1.28 (m, 3H), 1.55 (m, 3H), 1.63 (m, 6H), 1.69 (br s, 1H), 2.03 (m, 2H), 2.15 (m, 2H), 2.39 (m, 1H), 2.67 (m, 1H), 4.16 (m, 2H), 5.01 (s, 2H), 5.61 (m, 1H), 7.49 (s, 2H), 7.81 (s, 1H), 7.94 (m, 1H), 8.05 (m, 1H), 8.40 (s, 1H), 8.74 (m, 1H); and cis-ethyl 4-(2-(6-(4-isopropyl-4H-1,2,4-triazol-3-yl)pyridin-2-yl)-3-oxoisoindolin-5-yl) cyclohexanecarboxylate (XXXVIIb) (50.0 mg, 95.0 μmol, 17.9% yield) as a white solid $^1$H NMR (CDCl$_3$, 400 MHz) δ ppm 1.29 (m, 3H), 1.62 (m, 6H), 1.75 (m, 6H), 2.28 (m, 2H), 2.70 (m, 2H), 4.20 (m, 2H), 4.99 (s, 2H), 5.60 (m, 1H), 7.48 (m, 2H), 7.78 (s, 1H), 7.90 (m, 1H), 8.03 (m, 1H), 8.39 (s, 1H), 8.72 (m, 1H).

Step 4

To a solution of trans-ethyl 4-(2-(6-(4-isopropyl-4H-1,2,4-triazol-3-yl) pyridin-2-yl)-3-oxoisoindolin-5-yl)cyclohexanecarboxylate (XXXVIIa) (20.0 mg, 42.2 μmol, 1.00 eq) in MeOH (0.40 mL) and H$_2$O (0.10 mL) was added NaOH (5.07 mg, 126.7 μmol, 3.00 eq), the mixture was stirred at 40° C. for 2 h. The reaction mixture was adjusted to pH=7 with HCl (4N, 0.1 mL), then filtered and the filter cake was dried in vacuum. Trans-4-(2-(6-(4-isopropyl-4H-1,2,4-triazol-3-yl)pyridin-2-yl)-3-oxoisoindolin-5-yl)cyclohexanecarboxylic acid 126 (7.56 mg, 16.5 mol, 39.0% yield) was obtained as an off-white solid $^1$H NMR (DMSO-d$_6$, 400 MHz) δ ppm 1.52 (m, 10H), 1.87 (m, 2H), 2.01 (m, 2H), 2.30 (m, 1H), 2.67 (m, 1H), 5.10 (s, 2H), 5.51 (m, 1H), 7.64 (m, 3H), 7.90 (m, 1H), 8.07 (m, 1H), 8.63 (m, 1H), 9.02 (s, 1H); ESIMS found for C$_{25}$H$_{27}$N$_5$O$_3$ m/z: 446.2 [M+H]; Rt 0.873 min.

Example 7

Preparation of 1-(2-(6-(4-isopropyl-4H-1,2,4-triazol-3-yl) pyridin-2-yl)-3-oxoisoindolin-5-yl)piperidine-4-carboxylic acid (128) is depicted below in Scheme 10.

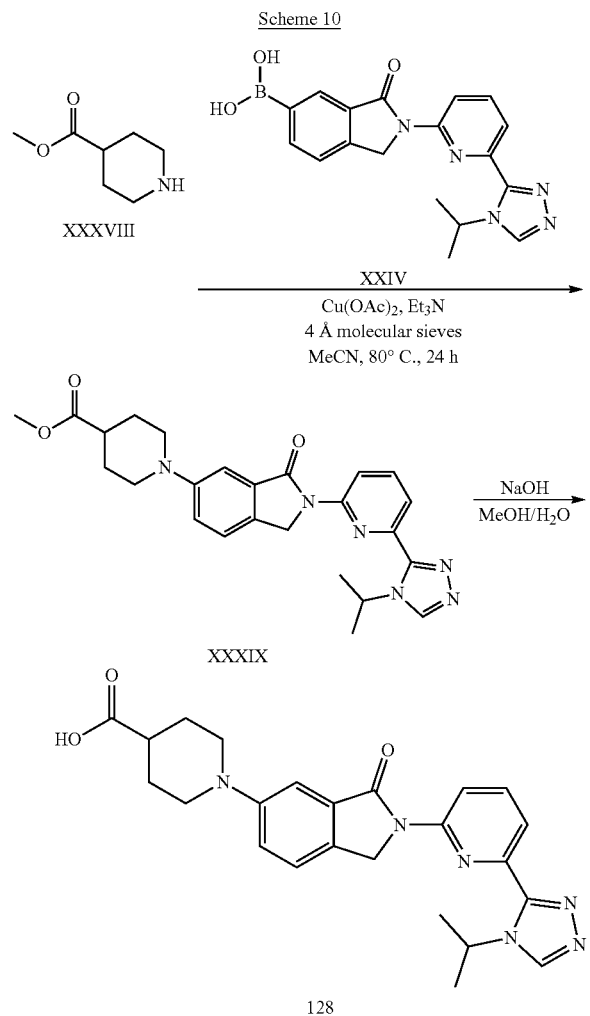

Scheme 10

Step 1

A solution of methyl piperidine-4-carboxylate (XXXVIII) (158 mg, 1.10 mmol, 2.00 eq), (2-(6-(4-isopropyl-4H-1,2,4-triazol-3-yl)pyridin-2-yl)-3-oxoisoindolin-5-yl)boronic acid (XXIV) (200 mg, 550 μmol, 1.00 eq), Cu(OAc)$_2$ (100 mg, 550 μmol, 1.00 eq), Et$_3$N (111 mg, 1.10 mmol, 153 μL, 2.00 eq) and powdered activated 4 Å molecular sieves (100 mg) in MeCN (5.00 mL) was stirred at 80° C. in a sealed tube for 24 hrs. The mixture was filtered through a Celite® pad and washed with DCM (30.0 mL×2), the filtrate was concentrated, and the residue purified by silica gel chromatography (hexanes:EtOAc 30:1 to 5:1) to give methyl 1-(2-(6-(4-isopropyl-4H-1,2,4-triazol-3-yl)pyridin-2-yl)-3-oxoisoindolin-5-yl)piperidine-4-carboxylate (XXXIX) (600 mg, crude) as yellow oil. ESIMS found for C$_{25}$H$_{28}$N$_6$O$_3$ m/z 461.2 (M+1). Rt 0.732 min.

Step 2

To a solution of methyl 1-(2-(6-(4-isopropyl-4H-1,2,4-triazol-3-yl) pyridin-2-yl)-3-oxoisoindolin-5-yl)piperidine-4-carboxylate (XXXIX) (150 mg, 325 μmol, 1.00 eq) in MeOH (3.00 mL) and H$_2$O (0.500 mL) was added NaOH (39.1 mg, 977 μmol, 3.00 eq). The mixture was stirred at 20° C. for 4 h. The mixture was concentrated in vacuo to remove MeOH and diluted with water (10 mL). The mixture was acidized by 1N.aq. HCl to pH=6, solid was formed, filtered and the filter cake was washed with water (20 mL) to give crude product. The crude product was purified by Prep-HPLC (column: Phenomenex luna C18 250 mm×50 mm×10 μm; [water (0.1% TFA)-MeCN]; B %: 15%-45%, 9 min) and lyophilized. 1-(2-(6-(4-isopropyl-4H-1,2,4-triazol-3-yl)pyridin-2-yl)-3-oxoisoindolin-5-yl) piperidine-4-carboxylic acid 128 (7.14 mg, 0.016 mmol, 5% yield) as yellow solid. $^1$H NMR (DMSO-$d_6$, 400 MHz) δ ppm 1.56 (m, 6H), 1.68 (m, 2H), 1.94 (m, 2H), 2.42 (m, 1H), 2.87 (m, 2H), 3.74 (m, 2H), 5.07 (m, 2H), 5.55 (m, 1H), 7.27 (m, 1H), 7.43-7.37 (m, 1H), 7.57 (m, 1H), 7.90 (m, 1H), 8.07 (m, 1H), 8.64 (m, 1H), 9.00 (m, 1H); ESIMS found for $C_{24}H_{26}N_6O_3$ m/z: 447.3 [M+H]; Rt 0.803 min.

The following compounds were prepared in accordance with the procedures described in the above Examples 1-7.

2

2-Fluoro-3-(2-(6-(4-isopropyl-4H-1,2,4-triazol-3-yl)pyridin-2-yl)-3-oxoisoindolin-5-yl) Benzoic Acid 2

White solid (36.42 mg, 79.61 μmol, 32% yield). $^1$H NMR (DMSO-$d_6$, 400 MHz) δ ppm 1.59 (m, 6H), 5.24 (s, 2H), 5.54 (m, 1H), 7.41 (m, 1H), 7.87 (m, 6H), 8.10 (m, 1H), 8.66 (m, 1H), 8.94 (s, 1H); ESIMS found for $C_{25}H_{20}FN_5O_3$ m/z: 458.3 [M+H]; Rt 0.714 min.

3

2-Fluoro-5-(2-(6-(4-isopropyl-4H-1,2,4-triazol-3-yl)pyridin-2-yl)-3-oxoisoindolin-5-yl)benzoic Acid 3

White solid (27.1 mg, 0.06 mmol, 24% yield). $^1$H NMR (DMSO-$d_6$, 400 MHz) δ ppm 1.55 (m, 6H), 5.20 (s, 2H), 5.53 (m, 1H), 7.44 (m, 1H), 7.84 (m, 1H), 7.92 (m, 1H), 8.05 (m, 4H), 8.16 (m, 1H), 8.64 (m, 1H), 8.94 (s, 1H), 13.39 (bs, 1H); ESIMS found for $C_{25}H_{20}FN_5O_3$ m/z 458.2 [M+H]$^+$; 456.2 [M−H]$^−$.

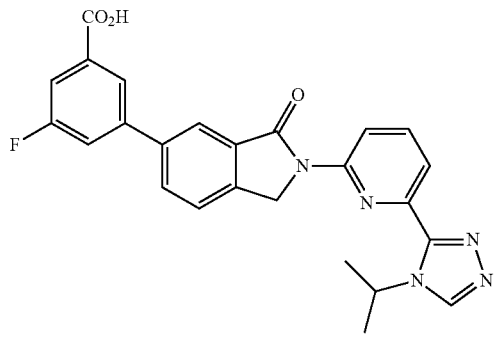

4

3-Fluoro-5-(2-(6-(4-isopropyl-4H-1,2,4-triazol-3-yl)pyridin-2-yl)-3-oxoisoindolin-5-yl)benzoic Acid 4

Light tan solid (10.3 mg, 0.023 mmol, 9% yield). ESIMS found for $C_{25}H_{20}FN_5O_3$ m/z: 458.2 [M+H]$^+$; 456.2 [M−H]$^−$.

5

4-Fluoro-3-(2-(6-(4-isopropyl-4H-1,2,4-triazol-3-yl)pyridin-2-yl)-3-oxoisoindolin-5-yl)benzoic Acid 5

Brown solid (26.6 mg, 56.6 μmol, 45% yield). $^1$H NMR (DMSO-$d_6$, 400 MHz) δ ppm 1.59 (m, 6H), 5.24 (s, 2H), 5.55 (m, 1H), 7.51 (m, 1H), 7.93 (m, 3H), 8.00 (s, 1H), 8.04 (m, 1H), 8.12 (m, 2H), 8.67 (m, 1H), 9.00 (s, 1H); ESIMS found for $C_{25}H_{20}FN_5O_3$ m/z: 458.2 [M+H]; Rt 0.902 min.

8

3-(2-(6-(4-Isopropyl-4H-1,2,4-triazol-3-yl)pyridin-2-yl)-3-oxoisoindolin-5-yl)-4-methoxybenzoic Acid 8

Off white solid (62.8 mg, 129 μmol, 52% yield). $^1$H NMR (DMSO-d$_6$, 400 MHz) δ ppm 1.60 (m, 6H), 3.89 (s, 3H), 5.22 (s, 2H), 5.55 (m, 1H), 7.28 (m, 1H), 7.84 (m, 2H), 7.93 (m, 3H), 8.01 (m, 1H), 8.10 (m, 1H), 8.67 (m, 1H), 8.98 (s, 1H); ESIMS found for $C_{26}H_{23}N_5O_4$ m/z: 470.1 [M+H]; Rt 0.874 min.

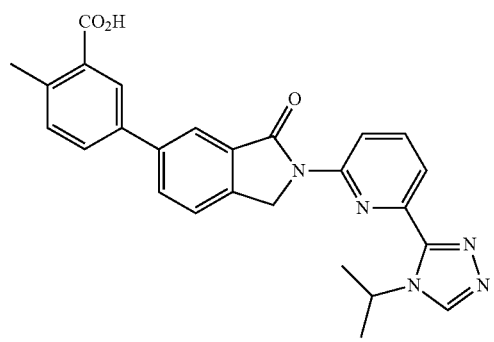

9

5-(2-(6-(4-Isopropyl-4H-1,2,4-triazol-3-yl)pyridin-2-yl)-3-oxoisoindolin-5-yl)-2-methylbenzoic acid 9

Light tan solid (37.1 mg, 0.082 mmol, 33% yield). ESIMS found for $C_{26}H_{23}N_5O_3$ m/z: 454.0 [M+H]$^+$; 452.0 [M−H]$^−$.

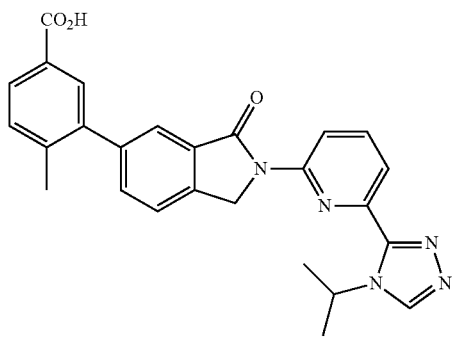

11

3-(2-(6-(4-Isopropyl-4H-1,2,4-triazol-3-yl)pyridin-2-yl)-3-oxoisoindolin-5-yl)-4-methylbenzoic Acid 11

White solid (28.7 mg, 0.06 mmol, 25% yield). $^1$H NMR (DMSO-d$_6$, 400 MHz) δ ppm 1.56 (m, 6H), 2.32 (s, 3H), 5.25 (s, 2H), 5.55 (m, 1H), 7.49 (m, 1H), 7.76 (m, 1H), 7.77 (s, 1H), 7.81 (s, 1H), 7.84 (m, 1H), 7.89 (m, 1H), 7.93 (m, 1H), 8.09 (m, 1H), 8.64 (m, 1H), 8.94 (s, 1H), 12.97 (bs, 1H); ESIMS found for $C_{26}H_{23}N_5O_3$ m/z: 454.2 [M+H]$^+$; 452.2 [M−H]$^−$.

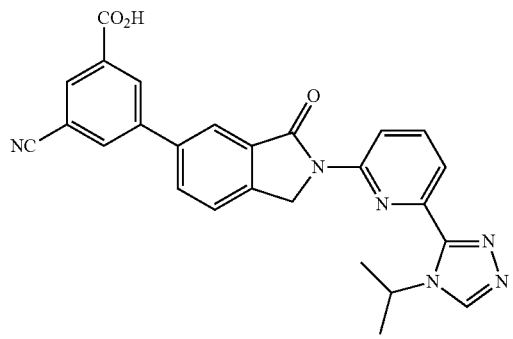

13

3-Cyano-5-(2-(6-(4-isopropyl-4H-1,2,4-triazol-3-yl)pyridin-2-yl)-3-oxoisoindolin-5-yl) benzoic Acid 13

Gray solid (28.5 mg, 49.8 μmol, 44% yield). $^1$H NMR (DMSO-d$_6$, 400 MHz) δ ppm 1.59 (m, 6H), 5.24 (s, 2H), 5.55 (m, 1H), 7.92 (m, 2H), 8.11 (m, 1H), 8.18 (m, 1H), 8.24 (m, 1H), 8.32 (m, 1H), 8.53 (m, 1H), 8.61 (m, 1H), 8.68 (m, 1H), 8.96 (s, 1H); ESIMS found for $C_{26}H_{20}N_6O_3$ m/z: 465.2 [M+H]; Rt 0.894 min.

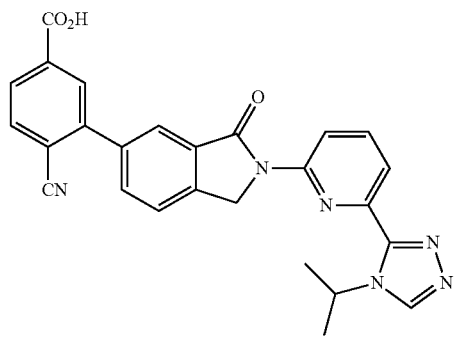

14

4-Cyano-3-(2-(6-(4-isopropyl-4H-1,2,4-triazol-3-yl)pyridin-2-yl)-3-oxoisoindolin-5-yl) Benzoic Acid 14

White solid (12.5 mg, 25.8 μmol, 23% yield). $^1$H NMR (DMSO-d$_6$, 400 MHz) δ ppm 1.59 (m, 6H), 5.28 (s, 2H), 5.55 (m, 1H), 7.97 (m, 3H), 8.12 (m, 5H), 8.66 (m, 1H), 8.96 (m, 1H); ESIMS found for $C_{26}H_{20}N_6O_3$ m/z: 465.1 [M+H]; Rt 0.874 min.

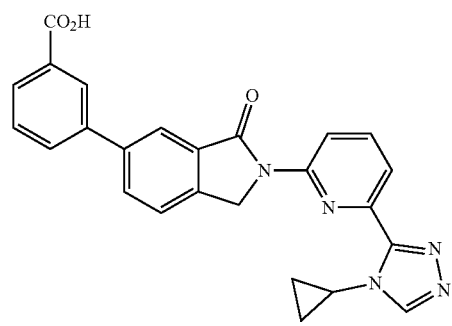

20

3-(2-(6-(4-Cyclopropyl-4H-1,2,4-triazol-3-yl)pyridin-2-yl)-3-oxoisoindolin-5-yl)benzoic Acid 20

White solid (26.3 mg, 58.9 μmol, 39% yield). $^1$H NMR (DMSO-$d_6$, 400 MHz) δ ppm 0.98 (m, 2H), 1.14 (m, 2H), 4.13 (m, 1H), 5.25 (s, 2H), 7.46 (s, 1H), 7.78 (m, 1H), 7.84 (m, 1H), 7.91 (m, 2H), 8.04 (m, 2H), 8.10 (m, 1H), 8.23 (s, 1H), 8.70 (m, 1H), 8.73 (s, 1H); ESIMS found for $C_{25}H_{19}N_5O_3$ m/z: 438.4 [M+H]; Rt 0.716 min.

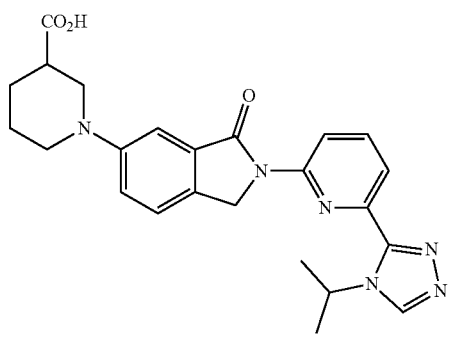

1-(2-(6-(4-Isopropyl-4H-1,2,4-triazol-3-yl)pyridin-2-yl)-3-oxoisoindolin-5-yl)piperidine-3-carboxylic Acid 28

Light tan solid (28.6 mg, 0.06 mmol, 24% yield). $^1$H NMR (DMSO-$d_6$, 400 MHz) δ ppm 1.59 (m, 8H), 1.76 (m, 1H), 1.92 (m, 1H), 2.59 (m, 1H), 2.91 (m, 1H), 3.07 (m, 1H), 3.55 (m, 1H), 3.72 (m, 1H), 5.05 (s, 2H), 5.52 (m, 1H), 7.27 (m, 1H), 7.39 (m, 1H), 7.57 (m, 1H), 7.90 (m, 1H), 8.08 (m, 1H), 8.65 (m, 1H), 9.05 (m, 1H); ESIMS found for $C_{24}H_{26}N_6O_3$ m/z: 447.2 [M+H]; Rt 0.696 min.

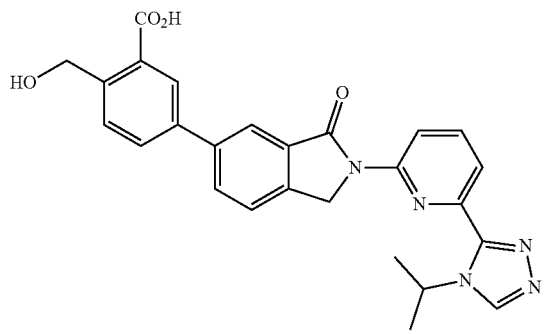

2-(Hydroxymethyl)-5-(2-(6-(4-isopropyl-4H-1,2,4-triazol-3-yl)pyridin-2-yl)-3-oxoisoindolin-5-yl)benzoic Acid 35

Light tan solid (28.6 mg, 0.06 mmol, 24% yield). $^1$H NMR (DMSO-$d_6$, 400 MHz) δ ppm 1.59 (m, 6H), 4.85 (s, 2H), 5.23 (s, 2H), 5.56 (m, 1H), 7.79 (m, 1H), 7.86 (m, 1H), 7.96 (m, 2H), 8.10 (m, 3H), 8.18 (m, 1H), 8.68 (m, 1H), 8.94 (s, 1H); ESIMS found for $C_{26}H_{23}N_5O_4$ m/z: 470.4 [M+H]; Rt 0.736 min.

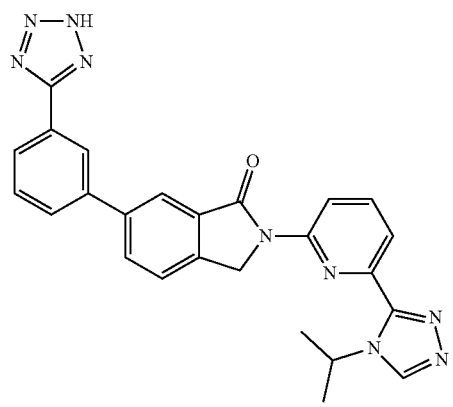

6-(3-(2H-Tetrazol-5-yl)phenyl)-2-(6-(4-isopropyl-4H-1,2,4-triazol-3-yl)pyridin-2-yl)isoindolin-1-one 37

Light tan solid (28.6 mg, 0.06 mmol, 24% yield). $^1$H NMR (DMSO-$d_6$, 400 MHz) δ ppm 1.60 (m, 6H), 5.26 (s, 2H), 5.56 (m, 1H), 7.73 (m, 1H), 7.94 (m, 2H), 8.01 (m, 1H), 8.13 (m, 3H), 8.21 (s, 1H), 8.46 (s, 1H), 8.70 (m, 1H), 8.96 (s, 1H); ESIMS found for $C_{26}H_{21}N_9O$ m/z: 464.2 [M+H]; Rt 0.882 min.

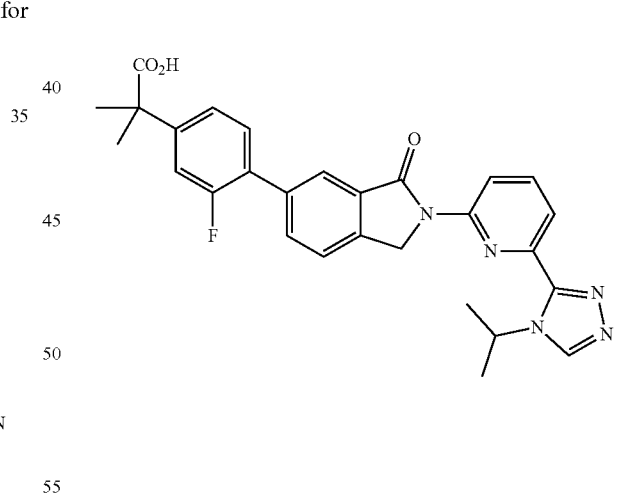

2-(3-Fluoro-4-(2-(6-(4-isopropyl-4H-1,2,4-triazol-3-yl)pyridin-2-yl)-3-oxoisoindolin-5-yl)phenyl)-2-methylpropanoic Acid 41

White solid (41 mg, 80.6 μmol, 49% yield). $^1$H NMR (DMSO-$d_6$, 400 MHz) δ ppm 1.51 (s, 6H), 1.59 (m, 6H), 5.22 (s, 2H), 5.54 (m, 1H), 7.31 (m, 2H), 7.60 (m, 1H), 7.86 (m, 1H), 7.94 (m, 3H), 8.10 (m, 1H), 8.66 (m, 1H), 8.94 (s, 1H); ESIMS found for $C_{28}H_{26}FN_5O_3$ m/z: 500.4 [M+H]; Rt 0.801 min.

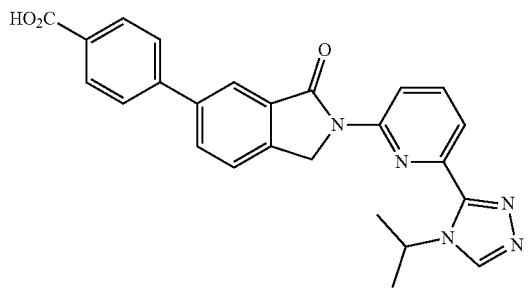

4-(2-(6-(4-Isopropyl-4H-1,2,4-triazol-3-yl)pyridin-2-yl)-3-oxoisoindolin-5-yl)benzoic Acid 55

Light tan solid (6.2 mg, 0.014 mmol, 6% yield). ESIMS found for $C_{25}H_{21}N_5O_3$ m/z: 440.2 [M+H]$^+$.

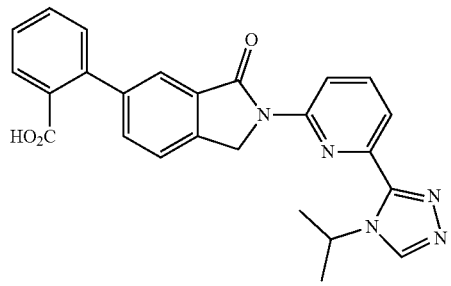

2-(2-(6-(4-Isopropyl-4H-1,2,4-triazol-3-yl)pyridin-2-yl)-3-oxoisoindolin-5-yl)benzoic Acid 56

Light tan solid (16.5 mg, 0.04 mmol, 15% yield). $^1$H NMR (DMSO-d$_6$, 400 MHz) δ ppm 1.55 (m, 6H), 5.24 (s, 2H), 5.53 (m, 1H), 7.46 (m, 1H), 7.58 (m, 1H), 7.63 (m, 1H), 7.68 (m, 1H), 7.73 (s, 1H), 7.78 (m, 1H), 7.82 (m, 1H), 7.93 (m, 1H), 8.08 (m, 1H), 8.64 (m, 1H), 8.94 (s, 1H), 12.91 (bs, 1H); ESIMS found for $C_{25}H_{21}N_5O_3$ m/z: 440.2 [M+H]$^+$; 438.2 [M−H]$^−$.

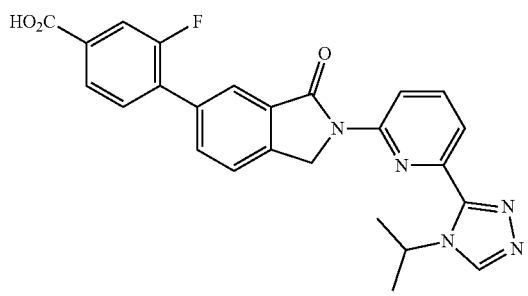

3-Fluoro-4-(2-(6-(4-isopropyl-4H-1,2,4-triazol-3-yl)pyridin-2-yl)-3-oxoisoindolin-5-yl)benzoic Acid 57

White solid (9.4 mg, 0.02 mmol, 8% yield). $^1$H NMR (DMSO-d$_6$, 400 MHz) δ ppm 1.49 (m, 6H), 5.19 (s, 2H), 5.56 (m, 1H), 8.00 (m, 8H), 8.66 (m, 1H), 8.93 (s, 1H), 13.38 (bs, 1H); ESIMS found for $C_{25}H_{20}FN_5O_3$ m/z: 458.2 [M+H]$^+$; 456.0 [M−H]$^−$.

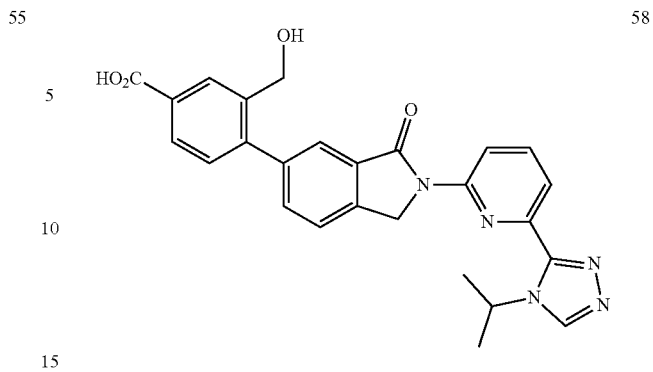

3-(Hydroxymethyl)-4-(2-(6-(4-isopropyl-4H-1,2,4-triazol-3-yl)pyridin-2-yl)-3-oxoisoindolin-5-yl)benzoic Acid 58

White solid (11.3 mg, 0.024 mmol, 10% yield). ESIMS found for $C_{26}H_{23}N_5O_4$ m/z: 470.2 [M+H]$^+$; 468.2 [M−H]$^−$.

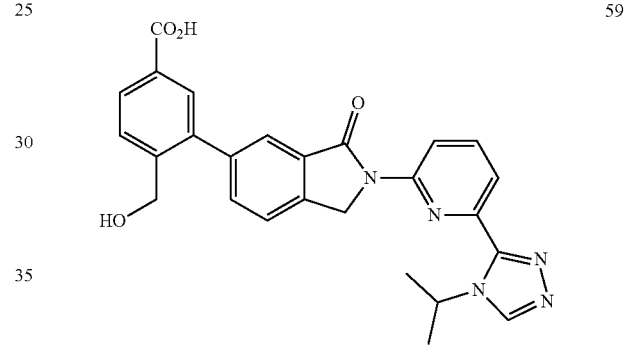

4-(Hydroxymethyl)-3-(2-(6-(4-isopropyl-4H-1,2,4-triazol-3-yl)pyridin-2-yl)-3-oxoisoindolin-5-yl)benzoic Acid 59

Light tan solid (17.6 mg, 0.037 mmol, 15% yield). $^1$H NMR (DMSO-d$_6$, 400 MHz) δ ppm 1.54 (m, 6H), 4.46 (s, 2H), 5.24 (s, 2H), 5.40 (s, 1H), 5.55 (m, 1H), 7.75 (m, 2H), 7.83 (m, 3H), 7.93 (m, 1H), 8.00 (m, 1H), 8.09 (m, 1H), 8.66 (m, 1H), 8.94 (s, 1H), 13.04 (bs, 1H); ESIMS found for $C_{26}H_{23}N_5O_4$ m/z: 470.2 [M+H]$^+$; 468.2 [M−H]$^−$.

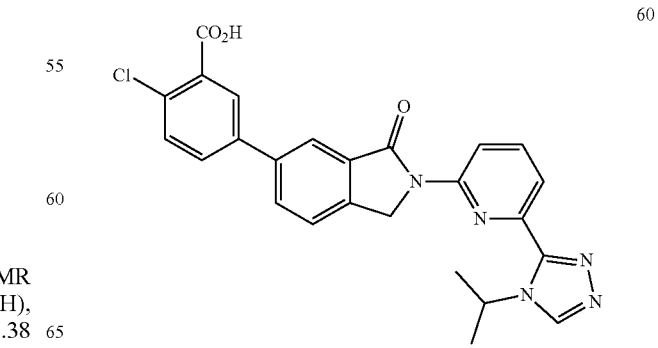

2-Chloro-5-(2-(6-(4-isopropyl-4H-1,2,4-triazol-3-yl)pyridin-2-yl)-3-oxoisoindolin-5-yl)benzoic Acid 60

Light tan solid (26.0 mg, 0.055 mmol, 22% yield). $^1$H NMR (DMSO-d$_6$, 400 MHz) δ ppm 1.54 (m, 6H), 5.19 (s, 2H), 5.54 (m, 1H), 7.64 (m, 1H), 7.84 (m, 1H), 7.94 (m, 2H), 8.07 (m, 3H), 8.13 (s, 1H), 8.64 (m, 1H), 8.94 (s, 1H), 13.63 (bs, 1H); ESIMS found for C$_{25}$H$_{20}$ClN$_5$O$_3$ m/z: 474.2 [M+H]$^+$; 472.2 [M−H]$^-$.

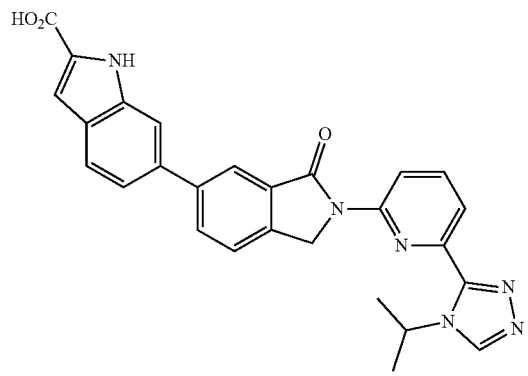

6-(2-(6-(4-Isopropyl-4H-1,2,4-triazol-3-yl)pyridin-2-yl)-3-oxoisoindolin-5-yl)-1H-indole-2-carboxylic Acid 61

Light tan solid (28.6 mg, 0.06 mmol, 24% yield). $^1$H NMR (DMSO-d$_6$, 400 MHz) δ ppm 1.59 (m, 6H), 5.20 (s, 2H), 5.55 (m, 1H), 7.11 (m, 1H), 7.46 (m, 1H), 7.72 (m, 3H), 8.06 (m, 4H), 8.77 (m, 1H), 9.05 (s, 1H), 11.89 (s, 1H); ESIMS found for C$_{27}$H$_{22}$N$_6$O$_3$ m/z: 479.0 [M+H]$^+$; 477.0 [M−H]$^-$.

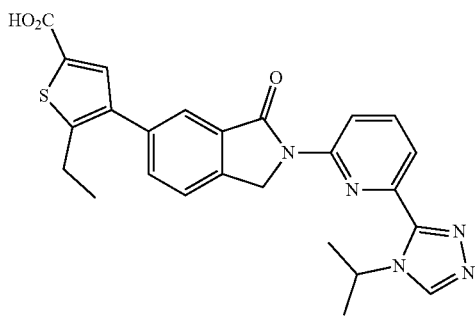

5-Ethyl-4-(2-(6-(4-isopropyl-4H-1,2,4-triazol-3-yl)pyridin-2-yl)-3-oxoisoindolin-5-yl)thiophene-2-carboxylic Acid 62

Light tan solid (30.0 mg, 0.063 mmol, 25% yield). ESIMS found for C$_{25}$H$_{23}$N$_5$O$_3$S m/z: 474.0 [M+H]$^+$; 472.0 [M−H]$^-$.

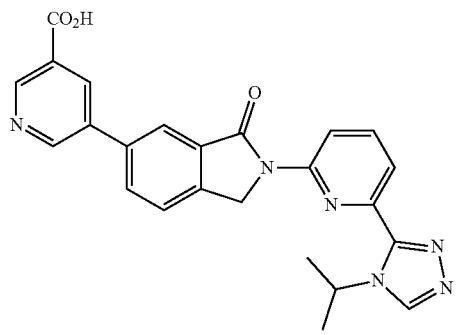

5-(2-(6-(4-Isopropyl-4H-1,2,4-triazol-3-yl)pyridin-2-yl)-3-oxoisoindolin-5-yl)nicotinic Acid 63

Light tan solid (12.6 mg, 0.029 mmol, 11% yield). ESIMS found for C$_{24}$H$_{20}$N$_6$O$_3$S m/z: 441.2 [M+H]$^+$.

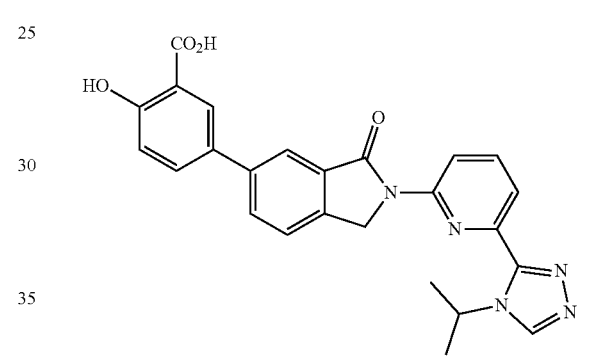

2-Hydroxy-5-(2-(6-(4-isopropyl-4H-1,2,4-triazol-3-yl)pyridin-2-yl)-3-oxoisoindolin-5-yl)benzoic Acid 64

Light tan solid (22.4 mg, 0.049 mmol, 20% yield). ESIMS found for C$_{25}$H$_{21}$N$_5$O$_4$ m/z: 456.2 [M+H]$^+$; 454.0 [M−H]$^-$.

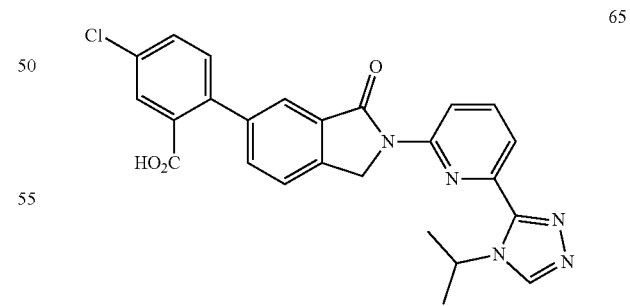

5-Chloro-2-(2-(6-(4-isopropyl-4H-1,2,4-triazol-3-yl)pyridin-2-yl)-3-oxoisoindolin-5-yl)benzoic Acid 65

Light tan solid (16.8 mg, 0.035 mmol, 14% yield). ESIMS found for C$_{25}$H$_{20}$ClN$_5$O$_3$ m/z: 474.0 [M+H]$^+$; 471.9 [M−H]$^-$.

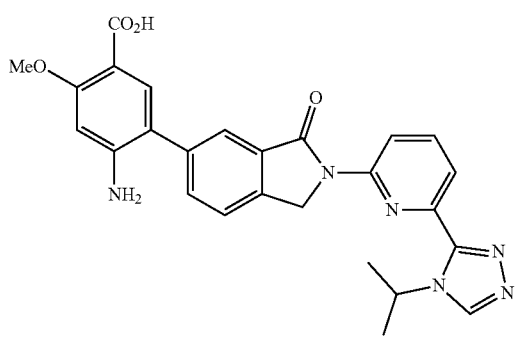

4-Amino-5-(2-(6-(4-isopropyl-4H-1,2,4-triazol-3-yl)pyridin-2-yl)-3-oxoisoindolin-5-yl)-2-methoxybenzoic Acid 66

Light tan solid (17.9 mg, 0.037 mmol, 15% yield). ESIMS found for $C_{26}H_{24}N_6O_4$ m/z: 485.2 [M+H]$^+$; 483.0 [M−H]$^-$.

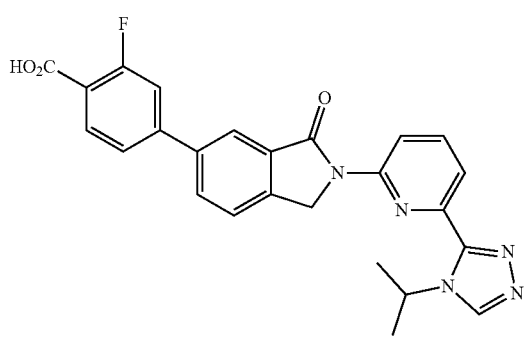

2-Fluoro-4-(2-(6-(4-isopropyl-4H-1,2,4-triazol-3-yl)pyridin-2-yl)-3-oxoisoindolin-5-yl)benzoic Acid 67

Light tan solid (2.1 mg, 0.005 mmol, 2% yield). ESIMS found for $C_{25}H_{20}FN_5O_3$ m/z: 458.2 [M+H]$^+$; 456.2 [M−H]$^-$.

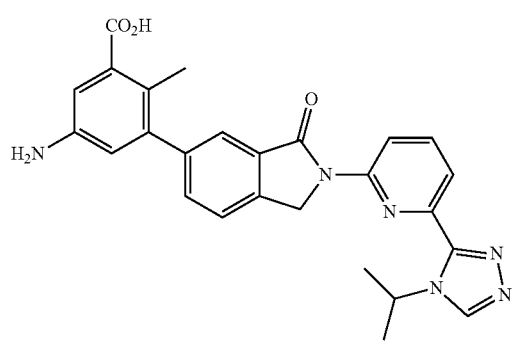

5-Amino-3-(2-(6-(4-isopropyl-4H-1,2,4-triazol-3-yl)pyridin-2-yl)-3-oxoisoindolin-5-yl)-2-methylbenzoic Acid 68

Light tan solid (10.2 mg, 0.022 mmol, 9% yield). ESIMS found for $C_{26}H_{24}N_6O_3$ m/z: 469.0 [M+H]$^+$; 467.0 [M−H]$^-$.

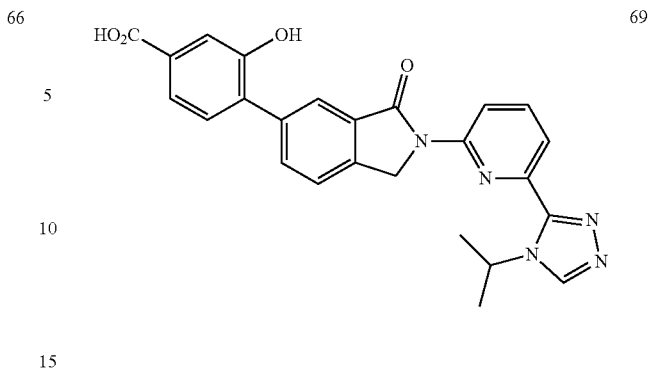

3-Hydroxy-4-(2-(6-(4-isopropyl-4H-1,2,4-triazol-3-yl)pyridin-2-yl)-3-oxoisoindolin-5-yl)benzoic Acid 69

Light tan solid (5.2 mg, 0.011 mmol, 5% yield). ESIMS found for $C_{25}H_{21}N_5O_4$ m/z: 456.0 [M+H]$^+$; 454.0 [M−H]$^-$.

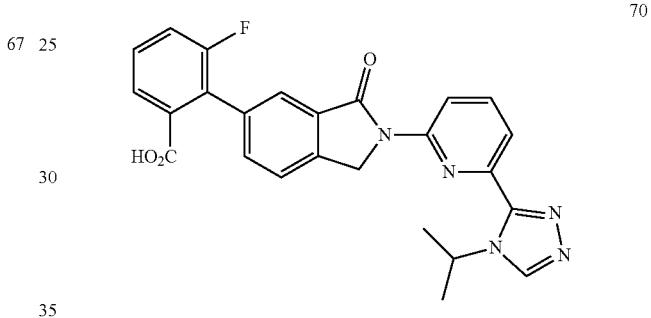

3-Fluoro-2-(2-(6-(4-isopropyl-4H-1,2,4-triazol-3-yl)pyridin-2-yl)-3-oxoisoindolin-5-yl)benzoic Acid 70

Light tan solid (5.2 mg, 0.011 mmol, 5% yield). ESIMS found for $C_{25}H_{20}FN_5O_3$ m/z: 458.2 [M+H]$^+$; 456.0 [M−H]$^-$.

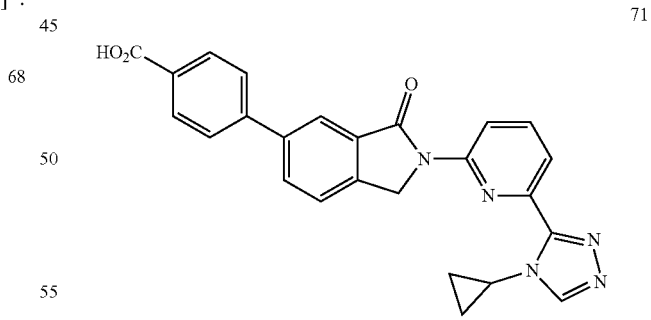

4-(2-(6-(4-Cyclopropyl-4H-1,2,4-triazol-3-yl)pyridin-2-yl)-3-oxoisoindolin-5-yl)benzoic Acid 71

White solid (21.3 mg, 47.6 μmol, 32% yield). $^1$H NMR (DMSO-d$_6$, 400 MHz) δ ppm 1.00 (m, 2H), 1.15 (m, 2H), 4.13 (m, 1H), 5.25 (s, 2H), 7.86 (m, 1H), 7.92 (m, 3H), 8.05 (s, 2H), 8.15-8.08 (m, 3H), 8.69 (m, 1H), 8.73 (s, 1H); ESIMS found for $C_{25}H_{19}N_5O_3$ m/z: 438.4 [M+H]; Rt 0.695 min.

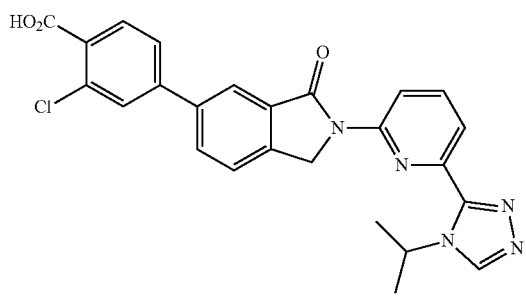

2-Chloro-4-(2-(6-(4-isopropyl-4H-1,2,4-triazol-3-yl)pyridin-2-yl)-3-oxoisoindolin-5-yl)benzoic Acid 72

White solid (73.9 mg, 148 μmol, 59% yield). $^1$H NMR (DMSO-$d_6$, 400 MHz) δ ppm 1.59 (m, 6H), 5.22 (s, 2H), 5.55 (m, 1H), 7.50 (m, 1H), 7.63 (m, 1H), 7.70 (m, 1H), 7.84 (m, 1H), 7.93 (m, 1H), 8.09 (m, 3H), 8.68 (m, 1H), 8.94 (s, 1H); ESIMS found for $C_{25}H_{20}ClN_5O_3$ m/z: 474.3 [M+H]; Rt 0.708 min.

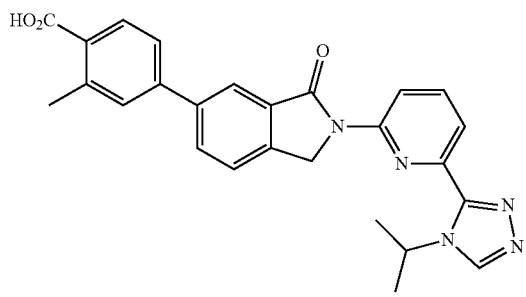

4-(2-(6-(4-isopropyl-4H-1,2,4-triazol-3-yl)pyridin-2-yl)-3-oxoisoindolin-5-yl)-2-methyl 73

White solid (2.35 mg, 4.21 μmol, 4% yield). $^1$H NMR (DMSO-$d_6$, 400 MHz) δ ppm 1.60 (m, 6H), 2.64 (s, 3H), 5.24 (s, 2H), 5.56 (m, 1H), 7.72 (m, 1H), 7.78 (s, 1H), 7.88 (m, 1H), 7.96 (m, 2H), 8.13 (m, 3H), 8.68 (m, 1H), 8.95 (s, 1H); ESIMS found for $C_{26}H_{23}N_5O_3$ m/z: 454.1 [M+H]; Rt 0.915 min.

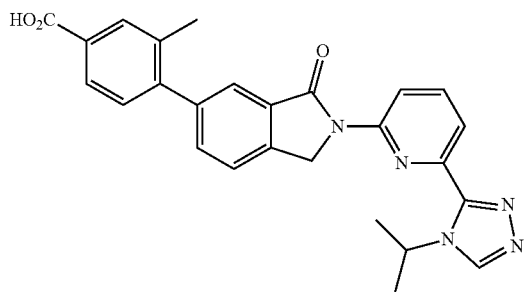

4-(2-(6-(4-Isopropyl-4H-1,2,4-triazol-3-yl)pyridin-2-yl)-3-oxoisoindolin-5-yl)-3-methylbenzoic Acid 74

White solid (7.67 mg, 16.2 μmol, 6% yield). $^1$H NMR (DMSO-$d_6$, 400 MHz) δ ppm 1.59 (m, 6H), 2.32 (s, 3H), 5.24 (s, 2H), 5.53 (m, 1H), 7.41 (m, 1H), 7.77 (m, 2H), 7.86 (m, 2H), 7.93 (m, 2H), 8.10 (s, 1H), 8.65 (m, 1H), 8.95 (s, 1H); ESIMS found for $C_{26}H_{23}N_5O_3$ m/z: 454.1 [M+H]; Rt 0.897 min.

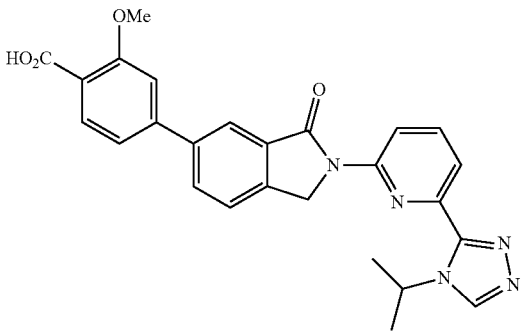

4-(2-(6-(4-Isopropyl-4H-1,2,4-triazol-3-yl)pyridin-2-yl)-3-oxoisoindolin-5-yl)-2-methoxybenzoic Acid 75

White solid (42 mg, 0.089 mmol, 8% yield). $^1$H NMR (DMSO-$d_6$, 400 MHz) δ ppm 1.59 (m, 6H), 3.97 (s, 3H), 5.22 (s, 2H), 5.55 (m, 1H), 7.40 (m, 1H), 7.46 (s, 1H), 7.77 (m, 1H), 7.86 (m, 1H), 7.93 (m, 1H), 8.10 (m, 2H), 8.17 (s, 1H), 8.67 (m, 1H), 8.94 (s, 1H), 12.65 (br.s, 1H); ESIMS found for $C_{26}H_{23}N_5O_4$ m/z: 470.2 [M+H].

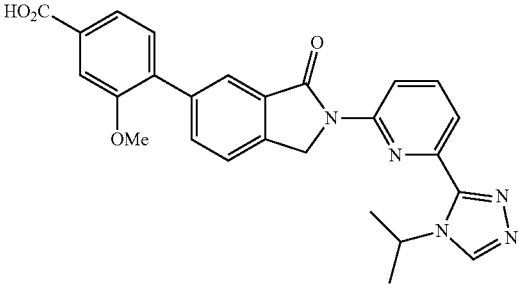

4-(2-(6-(4-Isopropyl-4H-1,2,4-triazol-3-yl)pyridin-2-yl)-3-oxoisoindolin-5-yl)-3-methoxybenzoic Acid 75

Brown solid (19.1 mg, 37.6 μmol, 15% yield). $^1$H NMR (DMSO-$d_6$, 400 MHz) δ ppm 1.60 (m, 6H), 3.88 (s, 3H), 5.23 (s, 2H), 5.55 (m, 1H), 7.54 (m, 2H), 7.66 (m, 2H), 7.88 (m, 4H), 8.10 (m, 1H), 8.68 (m, 1H), 9.01 (s, 1H); ESIMS found for $C_{26}H_{23}N_5O_4$ m/z: 470.2 [M+H]; Rt 0.883 min.

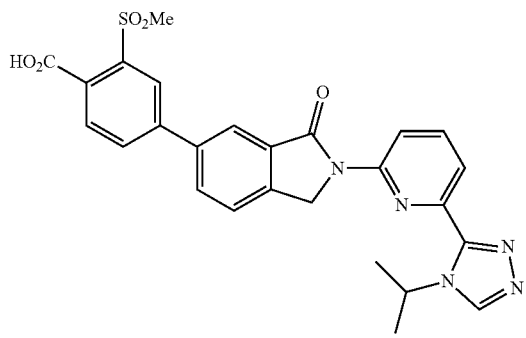

4-(2-(6-(4-Isopropyl-4H-1,2,4-triazol-3-yl)pyridin-2-yl)-3-oxoisoindolin-5-yl)-2-(methylsulfonyl)benzoic Acid 77

Gray solid (9.42 mg, 0.117 mmol, 15% yield). $^1$H NMR (DMSO-d$_6$, 400 MHz) δ ppm 1.59 (m, 6H), 3.48 (s, 3H), 5.26 (s, 2H), 5.55 (m, 1H), 7.86 (m, 1H), 7.94 (m, 2H), 8.14 (m, 2H), 8.23 (m, 2H), 8.31 (m, 1H), 8.68 (m, 1H), 8.94 (s, 1H); ESIMS found for C$_{26}$H$_{23}$N$_5$O$_5$S m/z: 518.2 [M+H]; Rt 0.854 min.

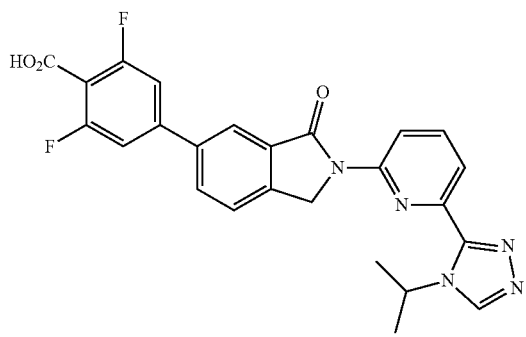

2,6-Difluoro-4-(2-(6-(4-isopropyl-4H-1,2,4-triazol-3-yl)pyridin-2-yl)-3-oxoisoindolin-5-yl) Benzoic Acid 78

White solid (3.41 mg, 7.03 μmol, 3% yield). $^1$H NMR (DMSO-d$_6$, 400 MHz) δ ppm 1.59 (m, 6H), 5.22 (s, 2H), 5.54 (m, 1H), 7.66 (m, 2H), 7.91 (m, 2H), 8.23-8.06 (m, 3H), 8.67 (m, 1H), 8.94 (s, 1H); ESIMS found for C$_{25}$H$_{19}$F$_2$N$_5$O$_3$ m/z: 476.3 [M+H]; Rt 0.708 min.

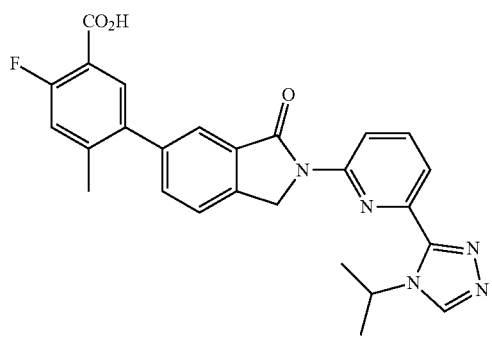

2-Fluoro-5-(2-(6-(4-isopropyl-4H-1,2,4-triazol-3-yl)pyridin-2-yl)-3-oxoisoindolin-5-yl)-4-methylbenzoic Acid 79

Off-white solid (34.55 mg, 72.41 μmol, 53% yield). $^1$H NMR (DMSO-d$_6$, 400 MHz) δ ppm 1.60 (m, 6H), 2.32 (s, 3H), 5.25 (s, 2H), 5.55 (m, 1H), 7.36 (m, 1H), 7.75 (m, 2H), 7.79 (s, 1H), 7.85 (m, 1H), 7.94 (m, 1H), 8.11 (m, 1H), 8.67 (m, 1H), 9.00 (m, 1H); ESIMS found for C$_{26}$H$_{22}$FN$_5$O$_3$ m/z: 472.3 [M+H]; Rt 0.907 min.

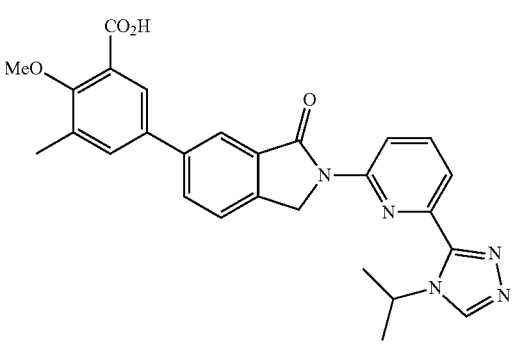

5-(2-(6-(4-Isopropyl-4H-1,2,4-triazol-3-yl)pyridin-2-yl)-3-oxoisoindolin-5-yl)-2-methoxy-3-methylbenzoic Acid 80

Off-white solid (16.5 mg, 32.7 μmol, 24% yield). $^1$H NMR (DMSO-d$_6$, 400 MHz) δ ppm 1.58 (m, 6H), 2.35 (s, 3H), 3.79 (s, 3H), 5.21 (s, 2H), 5.55 (m, 1H), 7.84 (m, 3H), 7.92 (m, 1H), 8.06 (m, 3H), 8.66 (m, 1H), 8.94 (s, 1H); ESIMS found for C$_{27}$H$_{25}$N$_5$O$_4$ m/z: 484.3 [M+H]; Rt 0.914 min.

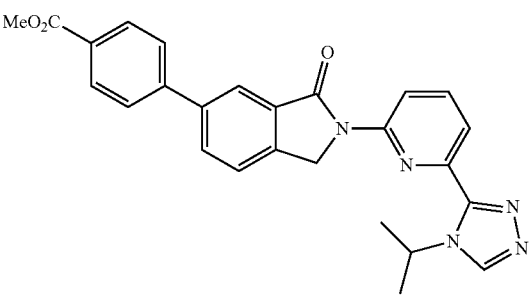

Methyl 4-(2-(6-(4-isopropyl-4H-1,2,4-triazol-3-yl)pyridin-2-yl)-3-oxoisoindolin-5-yl)benzoate 81

White solid (26.0 mg, 56.8 μmol, 71% yield). $^1$H NMR (DMSO-d$_6$, 400 MHz) δ ppm 1.61 (m, 6H), 3.90 (s, 3H), 5.24 (s, 2H), 5.58 (m, 1H), 7.94 (m, 4H), 8.12 (m, 5H), 8.72 (m, 1H), 9.32 (s, 1H); ESIMS found for C$_{26}$H$_{23}$N$_5$O$_3$ m/z: 454.4 [M+H]; Rt 0.966 min.

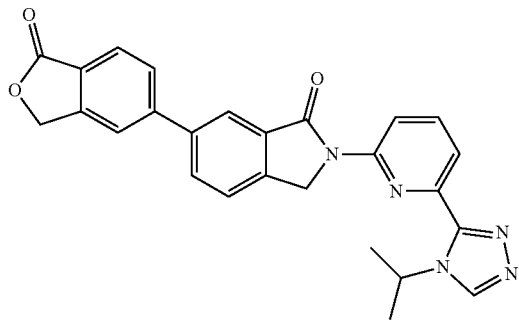

2-(6-(4-Isopropyl-4H-1,2,4-triazol-3-yl)pyridin-2-yl)-6-(1-oxo-1,3-dihydroisobenzofuran-5-yl)isoindolin-1-one 82

White solid (6.18 mg, 13.5 μmol, 5% yield). $^1$H NMR (DMSO-d$_6$, 400 MHz) δ ppm 1.59 (m, 6H), 5.25 (s, 2H), 5.50 (s, 2H), 5.55 (m, 1H), 7.95 (m, 3H), 8.02 (m, 1H), 8.14 (m, 4H), 8.67 (m, 1H), 8.94 (s, 1H); ESIMS found for $C_{26}H_{21}N_5O_3$ m/z: 452.2 [M+H]; Rt 0.891 min.

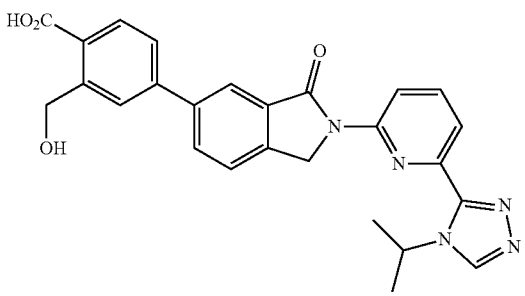

2-(Hydroxymethyl)-4-(2-(6-(4-isopropyl-4H-1,2,4-triazol-3-yl)pyridin-2-yl)-3-oxoisoindolin-5-yl)benzoic Acid 83

White solid (30.1 mg, 63.5 μmol, 46% yield). $^1$H NMR (DMSO-d$_6$, 400 MHz) δ ppm 1.59 (m, 6H), 4.76 (s, 2H), 5.23 (s, 2H), 5.54 (m, 1H), 7.70 (m, 1H), 7.87 (m, 2H), 7.93 (m, 2H), 8.10 (m, 3H), 8.68 (m, 1H), 8.95 (s, 1H); ESIMS found for $C_{26}H_{23}N_5O_4$ m/z: 470.3 [M+H]; Rt 0.693 min.

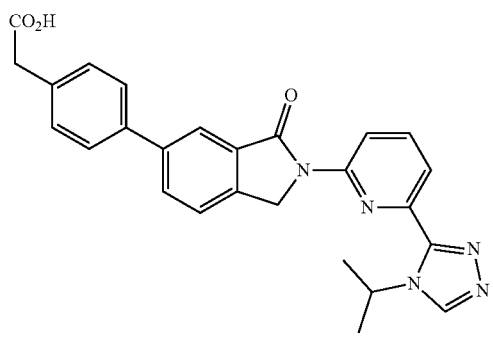

2-(4-(2-(6-(4-Isopropy-4H-1,2,4-triazol-3-yl)pyridin-2-yl)-3-oxoisoindolin-5-yl)phenyl)acetic Acid 84

White solid (25 mg, 0.055 mmol, 7% yield). $^1$H NMR (DMSO-d$_6$, 400 MHz) δ ppm 1.59 (m, 6H), 3.65 (s, 2H), 5.21 (s, 2H), 5.54 (m, 1H), 7.40 (m, 2H), 7.74 (m, 2H), 7.84 (m, 1H), 7.93 (m, 1H), 8.05 (m, 2H), 8.10 (m, 1H), 8.67 (m, 1H), 8.94 (s, 1H), 12.35 (brs, 1H); ESIMS found for $C_{26}H_{23}N_5O_3$ m/z: 454.2 [M+H].

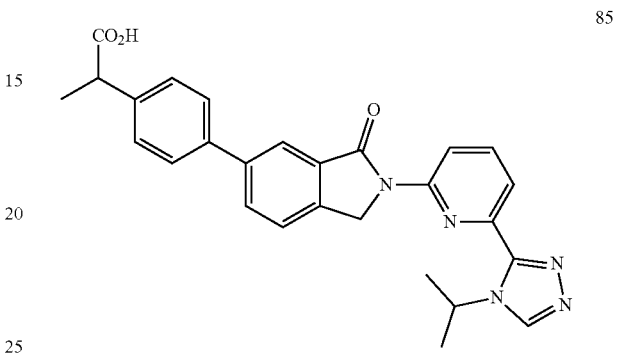

2-(4-(2-(6-(4-Isopropyl-4H-1,2,4-triazol-3-yl)pyridin-2-yl)-3-oxoisoindolin-5-yl)phenyl)propanoic Acid 85

White solid (85 mg, 181 mmol, 24% yield). $^1$H NMR (DMSO-d$_6$, 400 MHz) δ ppm 1.59 (m, 6H), 3.76 (m, 1H), 5.20 (s, 2H), 5.54 (m, 1H), 7.42 (m, 2H), 7.75 (m 2H), 7.83 (m, 1H), 7.93 (m, 1H), 8.04 (m, 2H), 8.09 (m, 1H), 8.67 (m, 1H), 8.94 (s, 1H), 12.37 (s, 1H); ESIMS found for $C_{27}H_{25}N_5O_3$ m/z: 468.2 [M+H].

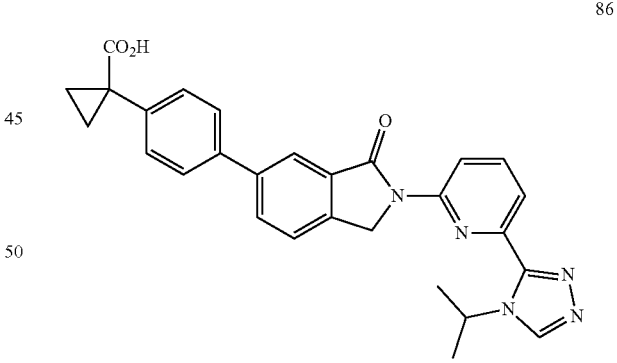

1-(4-(2-(6-(4-Isopropyl-4H-1,2,4-triazol-3-yl)pyridin-2-yl)-3-oxoisoindolin-5-yl)phenyl)cyclopropane-1-carboxylic Acid 86

White solid (31 mg, 0.064 mmol, 7% yield). $^1$H NMR (DMSO-d$_6$, 400 MHz) δ ppm 1.21 (m, 2H), 1.49 (m, 2H), 1.58 (m, 6H), 5.21 (s, 2H), 5.54 (m, 1H), 7.46 (m, 2H), 7.71 (m, 2H), 7.83 (m, 1H), 7.93 (m, 1H), 8.04 (m, 2H), 8.10 (m, 1H), 8.67 (m, 1H), 8.94 (s, 1H), 12.37 (s, 1H); ESIMS found for $C_{25}H_{25}N_5O_3$ m/z: 480.2 [M+H].

87

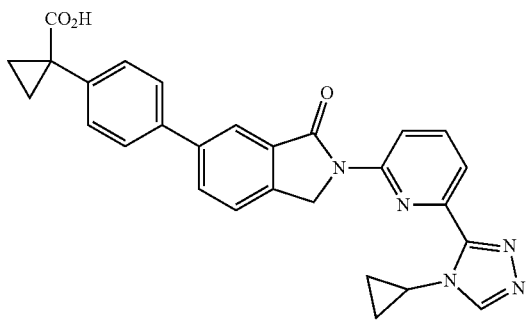

1-(4-(2-(6-(4-Cyclopropyl-4H-1,2,4-triazol-3-yl)pyridin-2-yl)-3-oxoisoindolin-5-yl)phenyl)cyclopropane-1-carboxylic Acid 87

White solid (35 mg, 0.073 mmol, 11% yield). $^1$H NMR (DMSO-d$_6$, 400 MHz) δ ppm 0.99 (m, 2H), 1.13 (m, 2H), 1.20 (m, 2H), 1.50 (m, 2H), 4.11 (m, 1H), 5.22 (s, 2H), 7.45 (m, 2H), 7.71 (m, 2H), 7.81 (m, 1H), 7.89 (m, 1H), 8.00 (m, 2H), 8.09 (m, 1H), 8.67 (m, 1H), 8.72 (s, 1H), 12.37 (s, 1H); ESIMS found for $C_{28}H_{23}N_5O_3$ m/z: 478.0 [M+H].

88

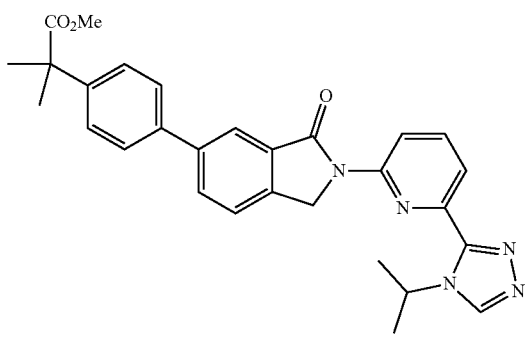

Methyl 2-(4-(2-(6-(4-isopropyl-4H-1,2,4-triazol-3-yl)pyridin-2-yl)-3-oxoisoindolin-5-yl)phenyl)-2-methylpropanoate 88

White solid (6.62 mg, 13.1 μmol, 10% yield). $^1$H NMR (DMSO-d$_6$, 400 MHz) δ ppm 1.57 (s, 6H), 1.59 (m, 6H), 3.63 (s, 3H), 5.22 (s, 2H), 5.53 (m, 1H), 7.46 (m, 2H), 7.78 (m, 2H), 7.86 (s, 1H), 7.94 (m, 1H), 8.07 (s, 3H), 8.68 (m, 1H), 8.94 (s, 1H); ESIMS found for $C_{29}H_{29}N_5O_3$ m/z: 496.5 [M+H]; Rt 1.019 min.

89

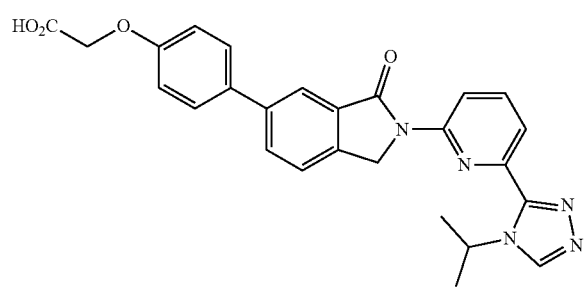

2-(4-(2-(6-(4-Isopropyl-4H-1,2,4-triazol-3-yl)pyridin-2-yl)-3-oxoisoindolin-5-yl)phenoxy) acetic Acid 89

White solid (22.9 mg, 46.6 μmol, 34% yield). $^1$H NMR (DMSO-d$_6$, 400 MHz) δ ppm 1.59 (m, 6H), 4.76 (s, 2H), 5.20 (s, 2H), 5.56 (m, 1H), 7.05 (m, 2H), 7.73 (m, 2H), 7.81 (m, 1H), 7.93 (m, 1H), 8.02 (s, 2H), 8.10 (s, 1H), 8.68 (m, 1H), 8.96 (s, 1H); ESIMS found for $C_{26}H_{23}N_5O_4$ m z: 470.2 [M+H]; Rt 0.885 min.

90

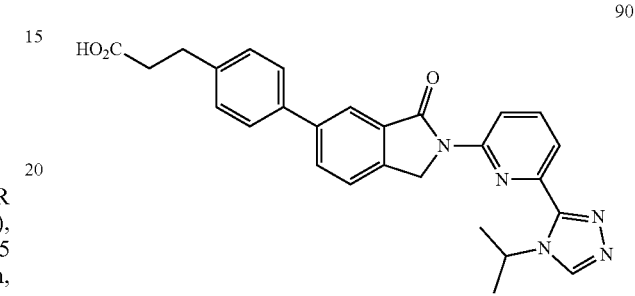

3-(4-(2-(6-(4-Isopropyl-4H-1,2,4-triazol-3-yl)pyridin-2-yl)-3-oxoisoindolin-5-yl)phenyl)propanoic Acid 90

White solid (2.54 mg, 4.67 μmol, 2% yield). $^1$H NMR (DMSO-d$_6$, 400 MHz) δ ppm 1.59 (m, 6H), 2.57 (br s, 2H), 2.88 (m, 2H), 5.20 (s, 2H), 5.54 (m, 1H), 7.37 (m, 2H), 7.69 (m, 2H), 7.82 (m, 1H), 7.93 (m, 1H), 8.07 (m, 3H), 8.67 (m, 1H), 8.94 (s, 1H); ESIMS found for $C_{27}H_{25}N_5O_3$ m/z: 468.3 [M+H]; Rt 0.732 min.

91

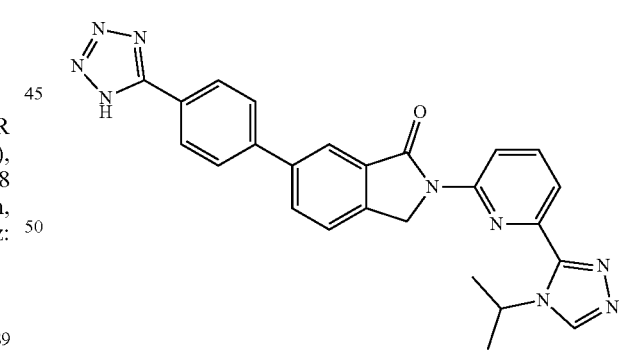

6-(4-(2H-Tetrazol-5-yl)phenyl)-2-(6-(4-isopropyl-4H-1,2,4-triazol-3-yl)pyridin-2-yl)isoindolin-1-one 91

White solid (50 mg, 103.56 μmol, 38% yield). $^1$HNMR (DMSO-d$_6$, 400 MHz) δ ppm 1.60 (m, 6H), 5.25 (s, 2H), 5.55 (m, 1H), 7.92 (m, 2H), 8.03 (m, 2H), 8.15 (m, 5H), 8.69 (m, 1H), 8.95 (s, 1H); ESIMS found for $C_{25}H_{21}N_9O$ m/z: 464.4 [M+H]; Rt 0.736 min.

92

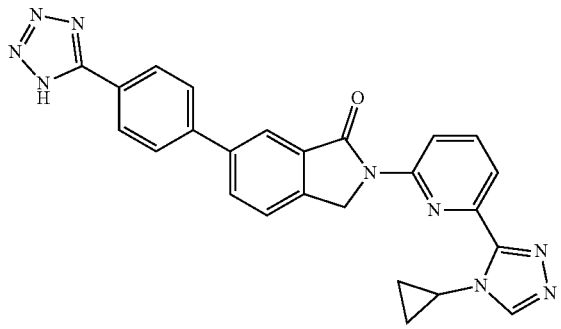

6-(4-(2H-Tetrazol-5-yl)phenyl)-2-(6-(4-cyclopropyl-4H-1,2,4-triazol-3-yl)pyridin-2-yl)isoindolin-1-one 92

White solid (50 mg, 103.56 µmol, 38% yield). $^1$HNMR (DMSO-d$_6$, 400 MHz) δ ppm 0.99 (m, 2H), 1.13 (m, 2H), 4.12 (m, 1H), 5.25 (s, 2H), 7.88 (m, 2H), 8.00 (m, 2H), 8.16 (m, 5H), 8.70 (m, 2H); ESIMS found for C$_{25}$H$_{19}$N$_9$O m/z: 462.4 [M+H]; Rt 0.724 min.

93

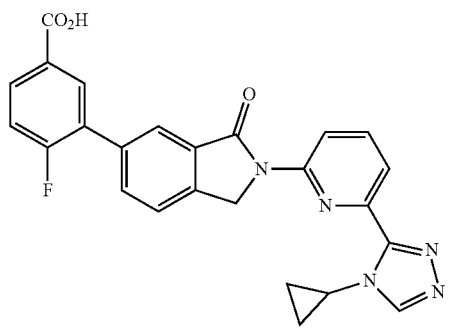

3-(2-(6-(4-Cyclopropyl-4H-1,2,4-triazol-3-yl)pyridin-2-yl)-3-oxoisoindolin-5-yl)-4-fluorobenzoic Acid 93

White solid (14.8 mg, 31.7 µmol, 25% yield). $^1$H NMR (DMSO-d$_6$, 400 MHz) δ ppm 1.00 (m, 2H), 1.15 (m, 2H), 4.13 (s, 1H), 5.27 (s, 2H), 7.52 (m, 1H), 7.88 (m, 1H), 7.91 (m, 1H), 7.96 (m, 1H), 8.01 (s, 1H), 8.06 (m, 1H), 8.11 (m, 1H), 8.14 (m, 1H), 8.68 (m, 1H), 8.74 (s, 1H); ESIMS found for C$_{25}$H$_{18}$FN$_5$O$_3$ m/z: 456.3 [M+H]; Rt 0.738 min.

94

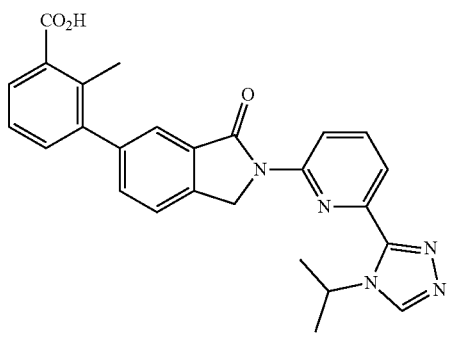

3-(2-(6-(4-Isopropyl-4H-1,2,4-triazol-3-yl)pyridin-2-yl)-3-oxoisoindolin-5-yl)-2-methylbenzoic Acid 94

Off-white solid (36.6 mg, 77.7 µmol, 31% yield). $^1$H NMR (DMSO-d$_6$, 400 MHz) δ ppm 1.68 (m, 6H), 2.51 (s, 3H), 5.14 (s, 2H), 5.65 (m, 1H), 7.37 (m, 1H), 7.45 (m, 1H), 7.63 (m, 2H), 7.95 (m, 2H), 8.07 (m, 2H), 8.49 (s, 1H), 8.79 (m, 1H); ESIMS found for C$_{26}$H$_{23}$N$_5$O$_3$ m/z: 454.1 [M+H]; Rt 0.882 min.

95

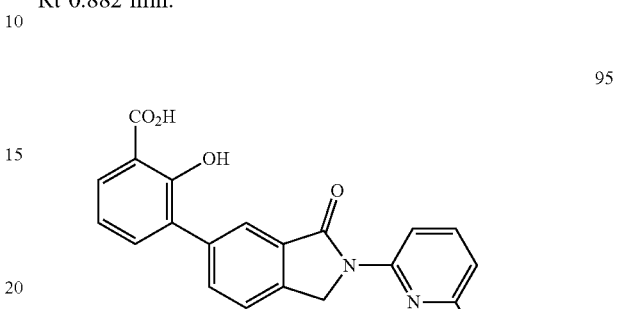

2-Hydroxy-3-(2-(6-(4-isopropyl-4H-1,2,4-triazol-3-yl)pyridin-2-yl)-3-oxoisoindolin-5-yl) benzoic Acid 95

Brown solid (15.1 mg, 28.5 µmol, 25% yield). $^1$H NMR (DMSO-d$_6$, 400 MHz) δ ppm 1.59 (m, 6H), 5.22 (s, 2H), 5.54 (m, 1H), 7.07 (m, 1H), 7.70 (m, 1H), 7.81 (m, 1H), 7.91 (m, 3H), 8.02 (s, 1H), 8.09 (m, 1H), 8.67 (m, 1H), 8.95 (s, 1H); ESIMS found for C$_{25}$H$_{21}$N$_5$O$_4$ m/z: 456.2 [M+H]; Rt 0.920 min.

96

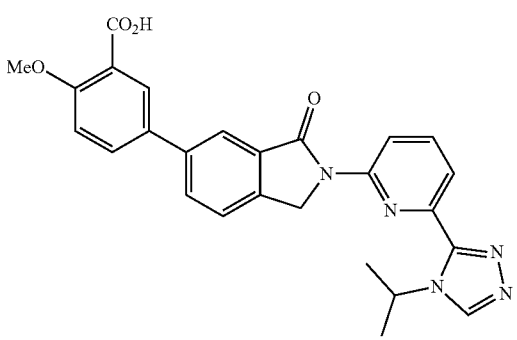

5-(2-(6-(4-Isopropyl-4H-1,2,4-triazol-3-yl)pyridin-2-yl)-3-oxoisoindolin-5-yl)-2-methoxybenzoic Acid 96

White solid (65 mg, 0.14 mmol, 14% yield). $^1$H NMR (DMSO-d$_6$, 400 MHz) δ ppm 1.59 (m, 6H), 3.88 (s, 3H), 5.19 (s, 2H), 5.54 (m, 1H), 7.25 (m, 1H), 7.81 (m, 1H), 7.94 (m, 2H), 8.01 (m, 3H), 8.09 (m, 1H), 8.66 (m, 1H), 8.94 (s, 1H), 12.75 (br s, 1H); ESIMS found for C$_{26}$H$_{23}$N$_5$O$_4$ m/z: 470.2 [M+H].

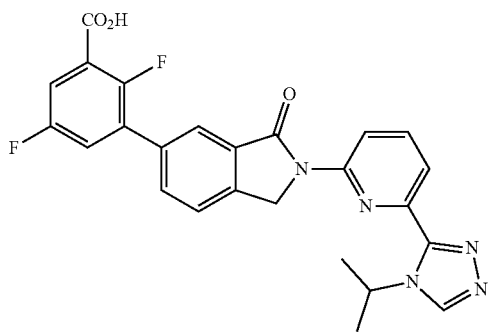

2,5-Difluoro-3-(2-(6-(4-isopropyl-4H-1,2,4-triazol-3-yl)pyridin-2-yl)-3-oxoisoindolin-5-yl) Benzoic Acid 97

White solid (7.41 mg, 14.5 μmol, 11% yield). $^1$H NMR (DMSO-d$_6$, 400 MHz) δ ppm 1.60 (m, 6H), 5.25 (s, 2H), 5.57 (m, 1H), 7.76 (m, 2H), 7.93 (m, 2H), 8.00 (m, 1H), 8.10 (m, 2H), 8.67 (m, 1H), 8.95 (s, 1H); ESIMS found for C$_{25}$H$_{19}$F$_2$N$_5$O$_3$ m/z: 476.0 [M+H]; Rt 0.897 min.

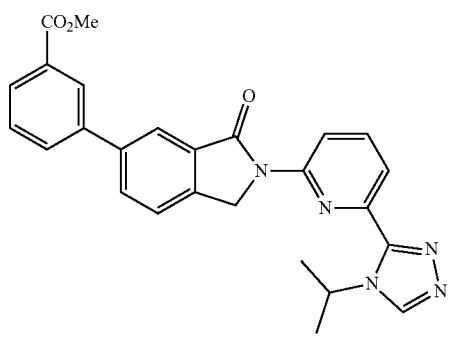

3-Fluoro-5-(2-(6-(4-isopropyl-4H-1,2,4-triazol-3-yl)pyridin-2-yl)-3-oxoisoindolin-5-yl)-4-methylbenzoic Acid 98

White solid (42.1 mg, 86.6 μmol, 35% yield). $^1$H NMR (DMSO-d$_6$, 400 MHz) δ ppm 1.58 (m, 6H), 2.22 (m, 3H), 5.24 (s, 2H), 5.53 (m, 1H), 7.68 (m, 2H), 7.76 (m, 1H), 7.81 (s, 1H), 7.86 (m, 1H), 7.92 (m, 1H), 8.09 (m, 1H), 8.65 (m, 1H), 8.94 (s, 1H); ESIMS found for C$_{26}$H$_{22}$FN$_5$O$_3$ m/z: 472.1 [M+H]; Rt 0.840 min.

Methyl 3-(2-(6-(4-isopropyl-4H-1,2,4-triazol-3-yl)pyridin-2-yl)-3-oxoisoindolin-5-yl)benzoate 99

White solid (19.0 mg, 40.6 μmol, 89% yield). $^1$H NMR (DMSO-d$_6$, 400 MHz) δ ppm 1.60 (m, 6H), 3.91 (s, 3H), 5.24 (s, 2H), 5.56 (m, 1H), 7.68 (m, 1H), 7.89 (m, 1H), 7.94 (m, 1H), 8.02 (m, 1H), 8.12 (m, 4H), 8.29 (s, 1H), 8.70 (m, 1H), 9.13 (s, 1H); ESIMS found for C$_{26}$H$_{23}$N$_5$O$_3$ m/z: 454.4 [M+H]; Rt 1.018 min.

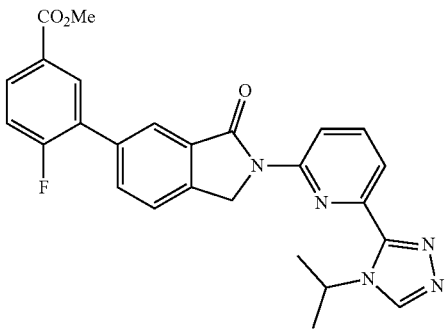

Methyl 4-fluoro-3-(2-(6-(4-isopropyl-4H-1,2,4-triazol-3-yl)pyridin-2-yl)-3-oxoisoindolin-5-yl)benzoate 100

White solid (9.63 mg, 19.4 μmol, 4% yield). $^1$H NMR (DMSO-d$_6$, 400 MHz) δ ppm 1.60 (m, 6H), 3.91 (s, 3H), 5.26 (s, 2H), 5.55 (m, 1H), 7.56 (m, 1H), 7.95 (m, 3H), 8.02 (s, 1H), 8.11 (m, 2H), 8.17 (m, 1H), 8.67 (m, 1H), 8.96 (s, 1H); ESIMS found for C$_{26}$H$_{22}$FN$_5$O$_3$ m/z: 472.3 [M+H]; Rt 1.030 min.

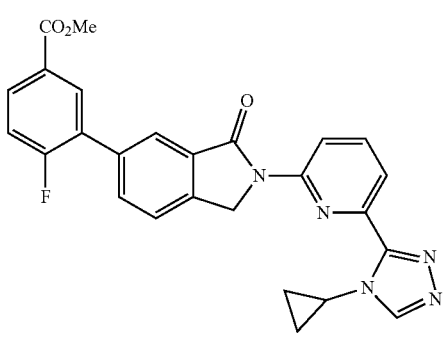

Methyl 3-(2-(6-(4-cyclopropyl-4H-1,2,4-triazol-3-yl)pyridin-2-yl)-3-oxoisoindolin-5-yl)-4-fluorobenzoate 101

White solid (17.0 mg, 34.7 μmol, 28% yield). $^1$H NMR (DMSO-d$_6$, 400 MHz) δ ppm 0.99 (m, 2H), 1.14 (m, 2H), 4.12 (m, 1H), 5.26 (s, 2H), 7.51 (m, 1H), 7.88 (m, 2H), 7.95 (m, 1H), 8.00 (s, 1H), 8.04 (m, 1H), 8.11 (m, 2H), 8.67 (m, 1H), 8.73 (s, 1H); ESIMS found for C$_{26}$H$_{20}$FN$_5$O$_3$ m/z: 456.1 [M+H]; Rt 0.800 min.

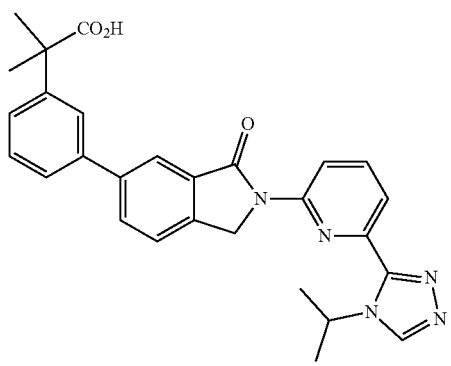

2-(3-(2-(6-(4-Isopropyl-4H-1,2,4-triazol-3-yl)pyridin-2-yl)-3-oxoisoindolin-5-yl)phenyl)-2-methylpropanoic Acid 102

White solid (58 mg, 0.12 mmol, 15% yield). $^1$H NMR (DMSO-d$_6$, 400 MHz) δ ppm 1.61 (m, 12H), 5.22 (s, 2H) 5.53 (m, 1H), 7.41 (m, 1H), 7.48 (m, 1H), 7.64 (m, 1H), 7.67 (s, 1H), 7.85 (m, 1H), 7.93 (m, 1H), 8.03 (m, 2H), 8.10 (m, 1H), 8.67 (m, 1H), 8.94 (s, 1H), 12.80 (br s, 1H); ESIMS found for C$_{28}$H$_{27}$N$_5$O$_3$ m/z: 482.0 [M+H].

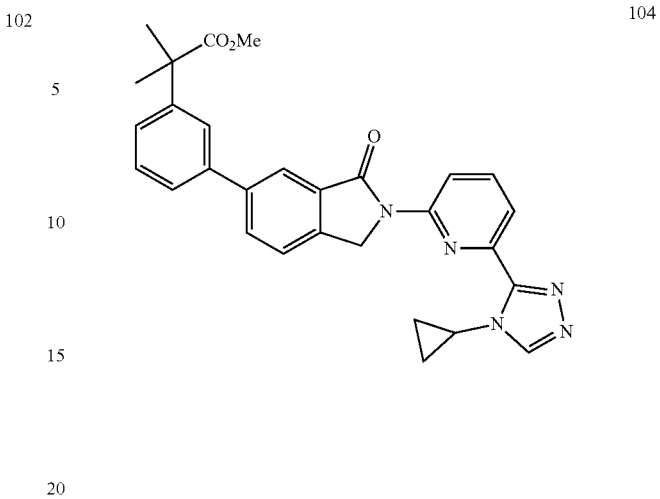

Methyl 2-(3-(2-(6-(4-cyclopropyl-4H-1,2,4-triazol-3-yl)pyridin-2-yl)-3-oxoisoindolin-5-yl)phenyl)-2-methylpropanoate 104

White solid (10.0 mg, 19.2 μmol, 31% yield). $^1$H NMR (DMSO-d$_6$, 400 MHz) δ ppm 1.01 (m, 2H), 1.14 (m, 2H), 1.60 (s, 6H), 3.62 (s, 3H), 4.10 (m, 1H), 5.24 (s, 2H), 7.35 (m, 1H), 7.49 (m, 1H), 7.64 (m, 2H), 7.83 (m, 1H), 7.90 (m, 1H), 8.03 (m, 2H), 8.11 (m, 1H), 8.69 (m, 1H), 8.83 (s, 1H); ESIMS found for C$_{2-9}$H$_{27}$N$_5$O$_3$ m/z: 494.2 [M+H]; Rt 0.996 min.

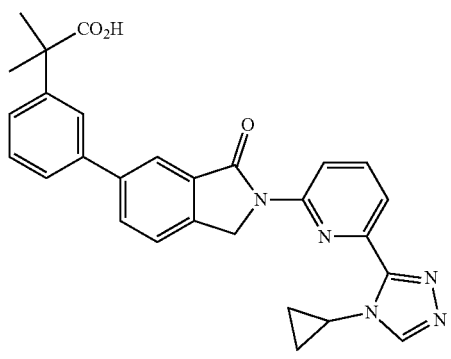

2-(3-(2-(6-(4-Cyclopropyl-4H-1,2,4-triazol-3-yl)pyridin-2-yl)-3-oxoisoindolin-5-yl)phenyl)-2-methylpropanoic Acid 103

White solid (10.0 mg, 20.4 μmol, 14.7% yield). $^1$H NMR (DMSO-d$_6$, 400 MHz) δ ppm 0.99 (m, 2H), 1.14 (m, 2H), 1.55 (s, 6H), 4.12 (m, 1H), 5.24 (s, 2H), 7.41 (m, 1H), 7.48 (m, 1H), 7.65 (m, 2H), 7.83 (m, 1H), 7.90 (m, 1H), 8.02 (m, 2H), 8.10 (m, 1H), 8.70 (m, 2H); ESIMS found for C$_{28}$H$_{25}$N$_5$O$_3$ m/z: 480.3 [M+H]; Rt 0.774 min.

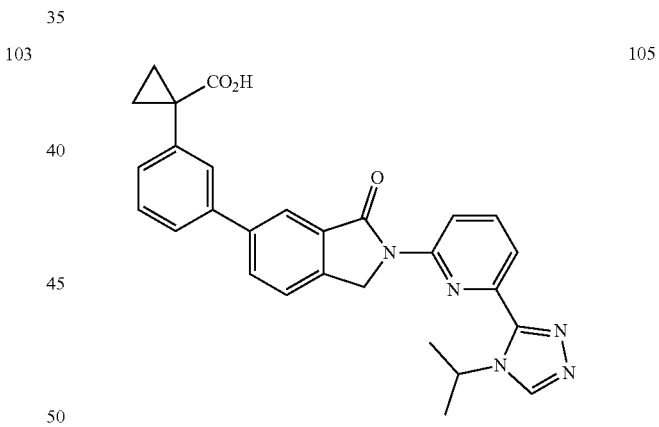

1-(3-(2-(6-(4-Isopropyl-4H-1,2,4-triazol-3-yl)pyridin-2-yl)-3-oxoisoindolin-5-yl)phenyl)cyclopropane-1-carboxylic Acid 105

Off-white solid (34 mg, 67.5 μmol, 36% yield). $^1$H NMR (DMSO-d$_6$, 400 MHz) δ ppm 1.22 (m, 2H), 1.48 (s, 2H), 1.60 (m, 6H), 5.23 (s, 2H), 5.56 (m, 1H), 7.44 (s, 2H), 7.64 (m, 1H), 7.71 (s, 1H), 7.85 (m, 1H), 7.94 (m, 1H), 8.07 (s, 3H), 8.68 (m, 1H), 8.94 (s, 1H); ESIMS found for C$_{28}$H$_{25}$N$_5$O$_3$ m/z: 480.2 [M+H]; Rt 0.923 min.

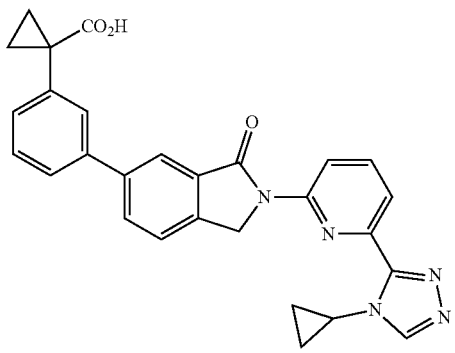

1-(3-(2-(6-(4-Cyclopropyl-4H-1,2,4-triazol-3-yl)pyridin-2-yl)-3-oxoisoindolin-5-yl)phenyl)cyclopropane-1-carboxylic Acid 106

White solid (24.1 mg, 48.5 μmol, 44% yield). $^1$H NMR (DMSO-d$_6$, 400 MHz) δ ppm 0.98 (m, 2H), 1.18 (m, 2H), 1.24 (m, 2H), 1.49 (m, 2H), 4.12 (m, 1H), 5.23 (s, 2H), 7.37 (m, 1H), 7.44 (m, 1H), 7.64 (m, 1H), 7.69 (s, 1H), 7.81 (m, 1H), 7.89 (m, 1H), 8.08 (m, 3H), 8.68 (m, 1H), 8.72 (s, 1H); ESIMS found for C$_{25}$H$_{23}$N$_5$O$_3$ m/z: 478.4 [M+H]; Rt 0.771 min.

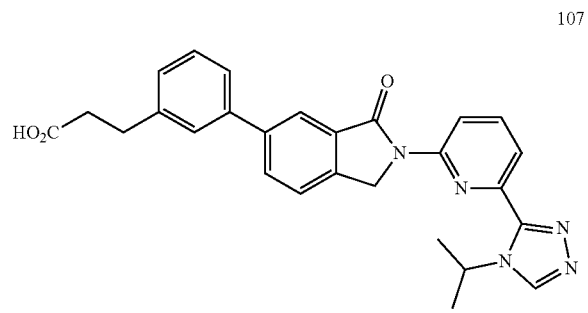 [SMILES: CC(C)n1cnnc1-c1cccc(N2Cc3ccc(-c4cccc(CCC(=O)O)c4)cc3C2=O)n1]

3-(3-(2-(6-(4-Isopropyl-4H-1,2,4-triazol-3-yl)pyridin-2-yl)-3-oxoisoindolin-5-yl)phenyl) Propanoic Acid 107

Off-white solid (8.23 mg, 15.7 μmol, 6% yield). $^1$H NMR (DMSO-d$_6$, 400 MHz) δ ppm 1.60 (m, 6H), 2.64 (m, 2H), 2.94 (m, 2H), 5.23 (s, 2H), 5.55 (m, 1H), 7.30 (m, 1H), 7.43 (m, 1H), 7.60 (m, 5H), 7.85 (m, 1H), 7.94 (m, 1H), 8.07 (m, 3H), 8.69 (m, 1H), 8.96 (s, 1H); ESIMS found for C$_{27}$H$_{25}$N$_5$O$_3$ m/z: 468.1 [M+H]; Rt 0.891 min.

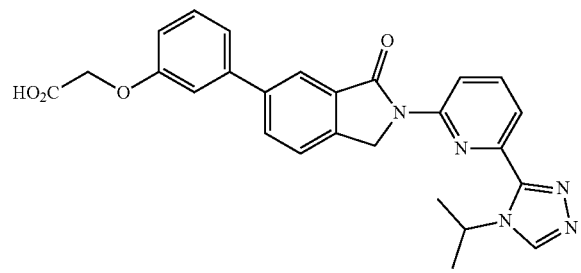

2-(3-(2-(6-(4-Isopropyl-4H-1,2,4-triazol-3-yl)pyridin-2-yl)-3-oxoisoindolin-5-yl)phenoxy) Acetic Acid 108

White solid (36.4 mg, 74.6 μmol, 54% yield). $^1$H NMR (DMSO-d$_6$, 400 MHz) δ ppm 1.60 (m, 6H), 4.83 (s, 2H), 5.22 (s, 2H), 5.55 (m, 1H), 6.99 (m, 1H), 7.28 (m, 1H), 7.41 (m, 2H), 7.85 (m, 1H), 7.95 (m, 1H), 8.09 (m, 3H), 8.69 (m, 1H), 9.00 (s, 1H); ESIMS found for C$_{26}$H$_{23}$N$_5$O$_4$ m/z: 470.2 [M+H]; Rt 0.894 min.

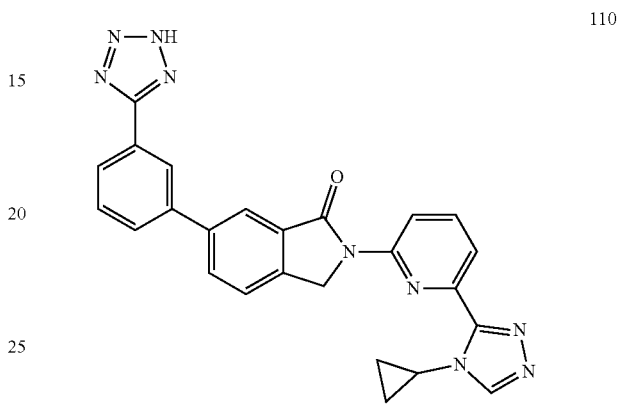

6-(3-(2H-Tetrazol-5-yl)phenyl)-2-(6-(4-cyclopropyl-4H-1,2,4-triazol-3-yl)pyridin-2-yl)isoindolin-1-one 110

White solid (50.3 mg, 103 μmol, 37% yield). $^1$H NMR (DMSO-d$_6$, 400 MHz) δ ppm 0.97 (m, 2H), 1.21-1.08 (m, 2H), 4.13 (m, 1H), 5.27 (s, 2H), 7.71 (m, 1H), 7.91 (m, 3H), 8.15 (m, 4H), 8.42 (m, 1H), 8.73 (m, 2H); ESIMS found for C$_{25}$H$_{19}$N$_9$O m/z: 462.4 [M+H]; Rt 0.735 min.

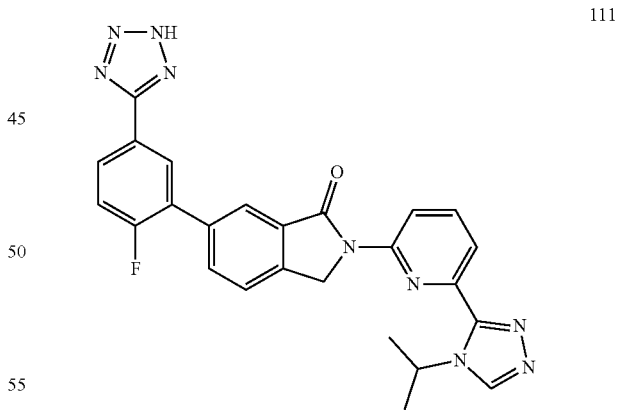

6-(2-Fluoro-5-(2H-tetrazol-5-yl)phenyl)-2-(6-(4-isopropyl-4H-1,2,4-triazol-3-yl)pyridin-2-yl)isoindolin-1-one 111

White solid (5.00 mg, 10.1 μmol, 7% yield). $^1$H NMR (DMSO-d$_6$, 400 MHz) δ ppm 1.60 (m, 6H), 5.27 (s, 2H), 5.56 (m, 1H), 7.58 (m, 1H), 7.94 (m, 2H), 8.02 (m, 1H), 8.11 (m, 3H), 8.28 (m, 1H), 8.68 (m, 1H), 8.95 (s, 1H); ESIMS found for C$_{25}$H$_{20}$FN$_9$O m/z: 482.4 [M+H]; Rt 0.746 min.

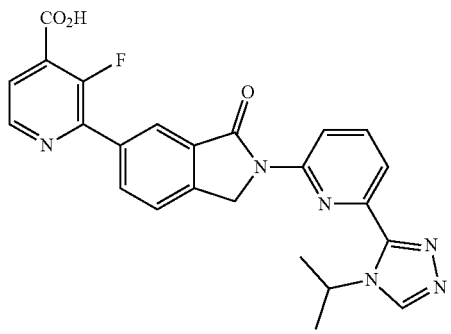

3-Fluoro-2-(2-(6-(4-isopropyl-4H-1,2,4-triazol-3-yl) 103yridine-2-yl)-3-oxoisoindolin-5-yl) Isonicotinic Acid 113

Off-white solid (10.1 mg, 21.6 μmol, 19% yield) as off-white solid. $^1$H NMR (DMSO-d$_6$, 400 MHz) δ ppm 1.59 (m, 6H), 3.99 (s, 3H), 5.22 (s, 2H), 5.60 (m, 1H), 7.86 (m, 1H), 7.93 (m, 1H), 8.11 (m, 3H), 8.45 (m, 1H), 8.67 (m, 1H), 8.79 (m, 1H), 8.94 (s, 1H), 13.20 (m, 1H); ESIMS found for $C_{24}H_{19}FN_6O_3$ m/z: 459.1 [M+H]; Rt 0.846 min.

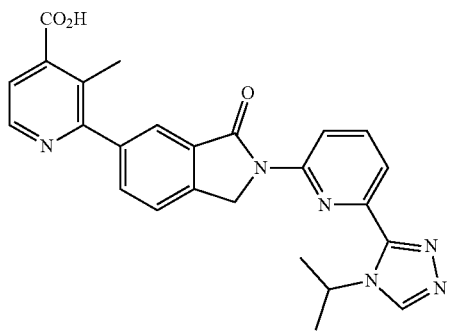

2-(2-(6-(4-Isopropyl-4H-1,2,4-triazol-3-yl)pyridin-2-yl)-3-oxoisoindolin-5-yl)-3-methylisonicotinic Acid 114

White solid (31.3 mg, 68.7 μmol, 61% yield). $^1$H NMR (DMSO-d$_6$, 400 MHz) δ ppm 1.60 (m, 6H), 2.45 (s, 3H), 5.26 (s, 2H), 5.56 (m, 1H), 7.66 (m, 1H), 7.91 (m, 4H), 8.11 (m, 1H), 8.67 (m, 2H), 9.02 (s, 1H); ESIMS found for $C_{25}H_{22}N_6O_3$ m/z: 455.2 [M+H]; Rt 0.765 min.

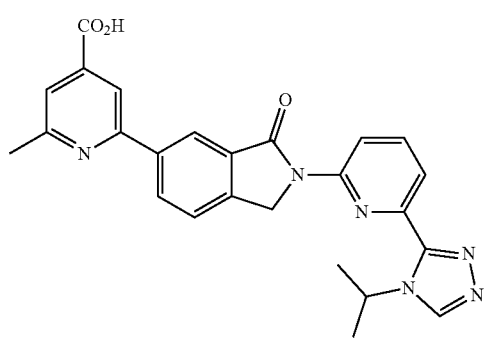

2-(2-(6-(4-Isopropyl-4H-1,2,4-triazol-3-yl)pyridin-2-yl)-3-oxoisoindolin-5-yl)-6-methylisonicotinic Acid 115

White solid (1.84 mg, 3.81 μmol, 3% yield). $^1$H NMR (DMSO-d$_6$, 400 MHz) δ ppm 1.60 (m, 6H), 2.68 (s, 3H), 5.25 (s, 2H), 5.56 (m, 1H), 7.73 (s, 1H), 7.92 (m, 2H), 8.13 (m, 1H), 8.25 (s, 1H), 8.52 (m, 2H), 8.70 (m, 1H), 8.99 (s, 1H); ESIMS found for $C_{25}H_{22}N_6O_3$ m/z: 455.1 [M+H]; Rt 0.852 min.

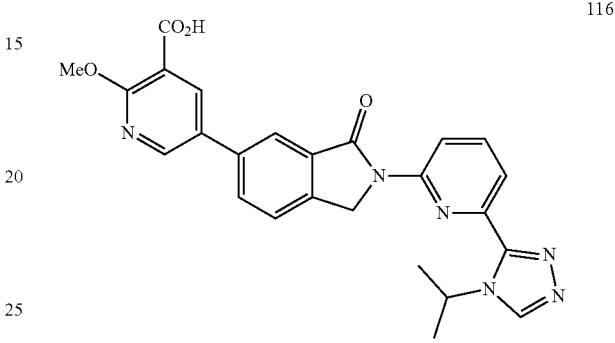

5-(2-(6-(4-Isopropyl-4H-1,2,4-triazol-3-yl)pyridine-2-yl)-3-oxoisoindolin-5-yl)-2-methoxynicotinic Acid 116

White solid (7.58 mg, 14.82 μmol, 11% yield). $^1$H NMR (DMSO-d$_6$, 400 MHz) δ ppm 1.59 (m, 6H), 3.99 (s, 3H), 5.22 (s, 2H), 5.60 (m, 1H), 7.86 (m, 1H), 7.93 (m, 1H), 8.11 (m, 3H), 8.45 (m, 1H), 8.67 (m, 1H), 8.79 (m, 1H), 8.94 (s, 1H), 13.20 (m, 1H); ESIMS found for $C_{25}H_{22}N_6O_4$ m/z: 471.2 [M+H]; Rt 0.864 min.

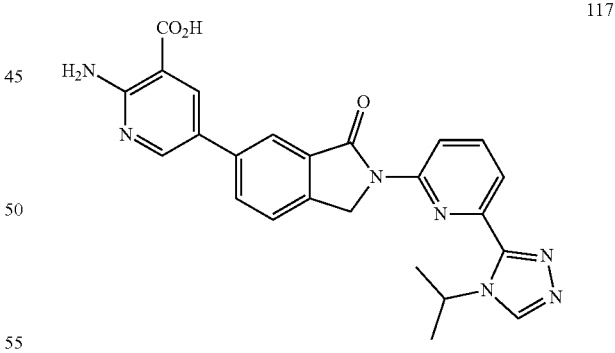

2-Amino-5-(2-(6-(4-isopropyl-4H-1,2,4-triazol-3-yl)pyridin-2-yl)-3-oxoisoindolin-5-yl) Nicotinic Acid 117

Brown solid (10.4 mg, 21.1 μmol, 19% yield). $^1$H NMR (DMSO-d$_6$, 400 MHz) δ ppm 1.59 (m, 6H), 5.20 (s, 2H), 5.54 (m, 1H), 7.82 (m, 1H), 7.93 (m, 1H), 8.02 (m, 2H), 8.10 (m, 1H), 8.42 (m, 1H), 8.68 (m, 2H), 8.96 (s, 1H); ESIMS found for $C_{24}H_{21}N_7O_3$ m/z: 456.2 [M+H]; Rt 0.780 min.

118

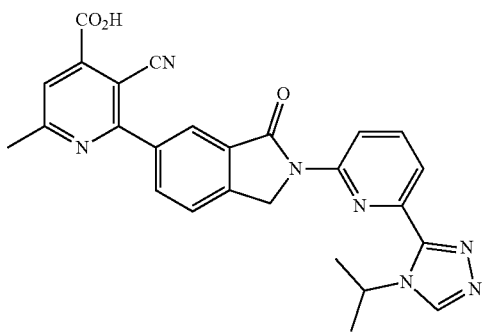

3-Cyano-2-(2-(6-(4-isopropyl-4H-1,2,4-triazol-3-yl)pyridin-2-yl)-3-oxoisoindolin-5-yl)-6-methylisonicotinic Acid 118

White solid (6.62 mg, 13.25 μmol, 10% yield). $^1$H NMR (DMSO-d$_6$, 400 MHz) δ ppm 1.59 (m, 6H), 2.63 (s, 3H), 5.28 (s, 2H), 5.55 (m, 1H), 7.65 (s, 1H), 7.92 (m, 2H), 8.10 (m, 2H), 8.18 (m, 1H), 8.67 (m, 1H), 8.94 (s, 1H); ESIMS found for C$_{26}$H$_{21}$N$_7$O$_3$ m/z: 480.2 [M+H]; Rt 0.843 min.

119

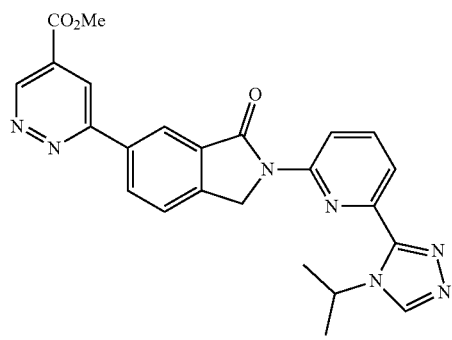

6-(2-(6-(4-Isopropyl-4H-1,2,4-triazol-3-yl)pyridin-2-yl)-3-oxoisoindolin-5-yl)pyridazine-4-carboxylic Acid 119

White solid (2.88 mg, 5.87 μmol, 4% yield). $^1$H NMR (DMSO-d$_6$, 400 MHz) δ ppm 1.60 (m, 6H), 5.29 (s, 2H), 5.56 (m, 1H), 7.96 (m, 2H), 8.11 (m, 1H), 8.50 (s, 1H), 8.60 (s, 2H), 8.69 (s, 1H), 8.95 (s, 1H), 9.50 (s, 1H); ESIMS found for C$_{23}$H$_{19}$N$_7$O$_3$ m/z: 442.2 [M+H]; Rt 0.814 min.

120

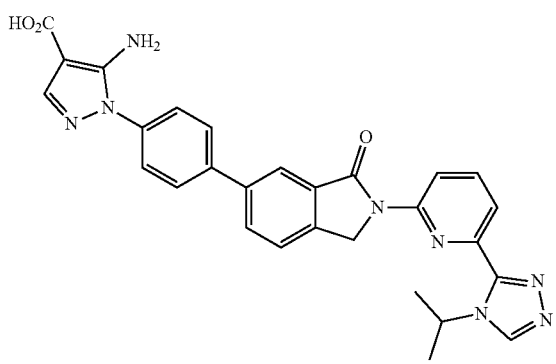

5-Amino-1-(4-(2-(6-(4-isopropyl-4H-1,2,4-triazol-3-yl)pyridin-2-yl)-3-oxoisoindolin-5-yl)phenyl)-1H-pyrazole-4-carboxylic Acid 120

Yellow solid (8.04 mg, 13.9 μmol, 7% yield). $^1$H NMR (DMSO-d$_6$, 400 MHz) δ ppm 1.60 (m, 6H), 5.24 (s, 2H), 5.55 (m, 1H), 6.39 (br s, 2H), 7.76-7.67 (m, 3H), 7.89 (m, 1H), 7.97 (m, 3H), 8.13 (m, 3H), 8.69 (m, 1H), 8.95 (s, 1H); ESIMS found for C$_{28}$H$_{24}$N$_5$O$_3$ m/z: 521.3 [M+H]; Rt 0.871 min.

121

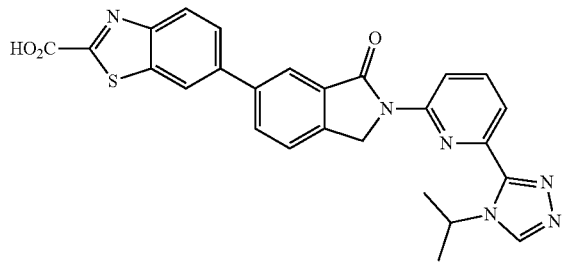

6-(2-(6-(4-Isopropyl-4H-1,2,4-triazol-3-yl)pyridin-2-yl)-3-oxoisoindolin-5-yl)benzo[d]thiazole-2-carboxylic Acid 121

Yellow solid (12.0 mg, 22.0 μmol, 16% yield). $^1$H NMR (DMSO-d$_6$, 400 MHz) δ ppm 1.59 (m, 6H), 5.24 (s, 2H), 5.55 (m, 1H), 7.88 (m, 1H), 7.95 (m, 2H), 8.14 (m, 4H), 8.55 (br s, 1H), 8.69 (m, 1H), 8.94 (s, 1H); ESIMS found for C$_{26}$H$_{20}$N$_6$O$_3$S m/z: 497.2 [M+H]; Rt 0.887 min.

122

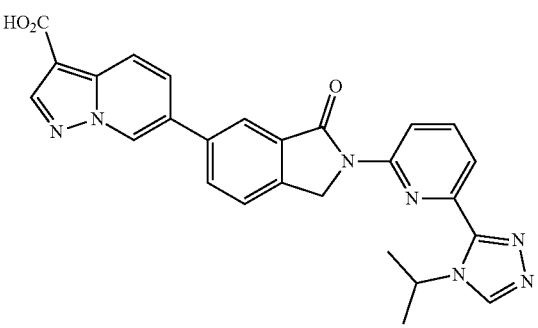

6-(2-(6-(4-Isopropyl-4H-1,2,4-triazol-3-yl)pyridin-2-yl)-3-oxoisoindolin-5-yl)pyrazolo[1,5-a]pyridine-3-carboxylic Acid 122

Brown solid (5.95 mg, 11.9 μmol, 9% yield). $^1$H NMR (DMSO-d$_6$, 400 MHz) δ ppm 1.59 (m, 6H), 5.24 (s, 2H), 5.55 (m, 1H), 7.92 (m, 2H), 8.10 (m, 2H), 8.19 (m, 2H), 8.26 (s, 1H), 8.47 (s, 1H), 8.68 (m, 1H), 8.96 (s, 1H), 9.38 (s, 1H); ESIMS found for C$_{26}$H$_{21}$N$_7$O$_3$ m/z: 480.4 [M+H]; Rt 0.866 min.

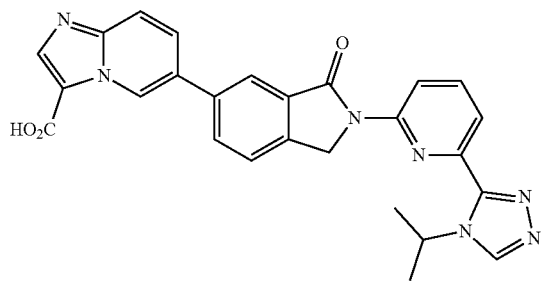

6-(2-(6-(4-Isopropyl-4H-1,2,4-triazol-3-yl)pyridin-2-yl)-3-oxoisoindolin-5-yl)imidazo[1,2-a]pyridine-3-carboxylic Acid 123

Off-white solid (18.96 mg, 39.54 μmol, 29% yield). $^1$H NMR (DMSO-$d_6$, 400 MHz) δ ppm 1.60 (m, 6H), 5.26 (s, 2H), 5.55 (m, 1H), 7.94 (m, 3H), 8.10 (m, 4H), 8.35 (m, 1H), 8.69 (m, 1H), 8.97 (m, 1H), 9.60 (s, 1H); ESIMS found for $C_{26}H_{21}N_7O_3$ m/z: 480.2 [M+H]; Rt 0.786

5-(2-(6-(4-Isopropyl-4H-1,2,4-triazol-3-yl)pyridin-2-yl)-3-oxoisoindolin-5-yl)pyrazolo[1,5-a]pyrimidine-3-carboxylic Acid 124

Off-white solid (1.61 mg, 3.17 μmol, 2% yield). $^1$H NMR (DMSO-$d_6$, 400 MHz) δ ppm 1.60 (m, 6H), 5.29 (s, 2H), 5.57 (m, 1H), 7.95 (m, 3H), 8.12 (m, 1H), 8.47 (br s, 1H), 8.69 (m, 2H), 8.77 (s, 1H), 8.95 (s, 1H), 9.25 (m, 1H); ESIMS found for $C_{25}H_{20}N_8O_3$ m/z: 481.2 [M+H]; Rt 0.834 min.

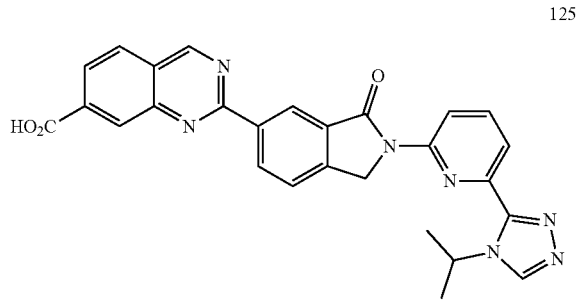 [SMILES: CC(C)n1cnnc1-c1cccc(N2Cc3ccc(-c4ncc5ccc(C(=O)O)cc5n4)cc3C2=O)n1]

2-(2-(6-(4-Isopropyl-4H-1,2,4-triazol-3-yl)pyridin-2-yl)-3-oxoisoindolin-5-yl)quinazoline-7-carboxylic Acid 125

White solid (3.48 mg, 7.03 μmol, 5% yield). $^1$H NMR (DMSO-$d_6$, 400 MHz) δ ppm 1.59 (m, 6H), 5.25 (s, 2H), 5.56 (m, 1H), 7.93 (m, 2H), 8.08 (m, 1H), 8.18 (m, 2H), 8.51 (s, 1H), 8.68 (m, 1H), 8.96 (m, 3H), 9.76 (m, 1H); ESIMS found for $C_{27}H_{21}N_7O_3$ m/z: 492.2 [M+H]; Rt 0.897 min.

cis-4-(2-(6-(4-Isopropyl-4H-1,2,4-triazol-3-yl)pyridin-2-yl)-3-oxoisoindolin-5-yl)cyclohexane-1-carboxylic Acid 127

White solid (24.6 mg, 50.4 μmol, 68.2% yield). $^1$H NMR (DMSO-$d_6$, 400 MHz) δ ppm 1.67 (m, 12H), 2.12 (m, 2H), 2.73 (m, 2H), 5.11 (s, 2H), 5.55 (m, 1H), 7.72-7.52 (m, 3H), 7.92 (m, 1H), 8.10 (m, 1H), 8.66 (m, 1H), 9.24 (s, 1H); ESIMS found for $C_{25}H_{27}N_5O_3$ m/z: 446.2 [M+H]; Rt 0.886 min.

2-(1-(2-(6-(4-Isopropyl-4H-1,2,4-triazol-3-yl)pyridin-2-yl)-3-oxoisoindolin-5-yl)piperidin-4-yl)acetic Acid 129

Off-white solid (34.5 mg, 71.3 μmol, 12% yield). $^1$H NMR (DMSO-$d_6$, 400 MHz) δ ppm 1.36 (m, 2H), 1.57 (m, 6H), 1.83 (m, 3H), 2.22 (m, 2H), 2.81 (m, 2H), 3.78 (m, 2H), 5.05 (s, 2H), 5.54 (m, 1H), 7.30 (br s, 1H), 7.40 (m, 1H), 7.57 (m, 1H), 7.91 (m, 1H), 8.08 (m, 1H), 8.65 (m, 1H), 8.98 (s, 1H); ESIMS found for $C_{25}H_{28}N_6O_3$ m/z: 461.3 [M+H]; Rt 0.771 min.

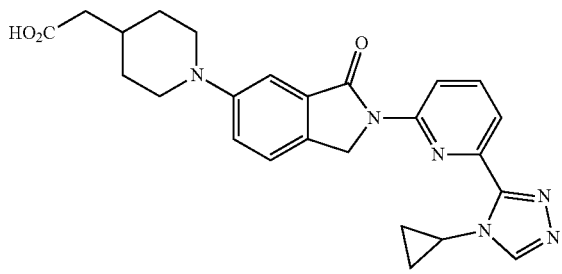

2-(1-(2-(6-(4-Cyclopropyl-4H-1,2,4-triazol-3-yl)
pyridin-2-yl)-3-oxoisoindolin-5-yl)piperidin-4-yl)
acetic Acid 130

Off-white solid (2 mg, 4.7 μmol, 1% yield). $^1$H NMR (DMSO-$d_6$, 400 MHz) δ ppm 0.96 (m, 2H), 1.11 (m, 2H), 1.28 (m, 2H), 1.81 (m, 3H), 2.15 (m, 2H), 2.74 (m, 2H), 3.76 (m, 2H), 4.08 (m, 1H), 5.04 (s, 2H), 7.22 (m, 1H), 7.34 (m, 1H), 7.51 (m, 1H), 7.85 (m, 1H), 8.05 (m, 1H), 8.63 (m, 1H), 8.69 (s, 1H); ESIMS found for $C_{25}H_{26}N_6O_3$ m/z: 459.3 [M+H]; Rt 0.698 min.

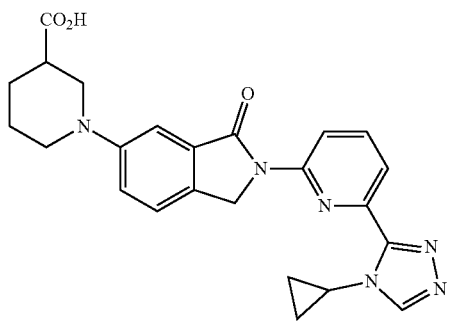

1-(2-(6-(4-Cyclopropyl-4H-1,2,4-triazol-3-yl)pyridin-2-yl)-3-oxoisoindolin-5-yl)piperidine-3-carboxylic Acid 131

Off-white solid (3.5 mg, 7.6 μmol, 7% yield). $^1$H NMR (DMSO-$d_6$, 400 MHz) δ ppm 0.95 (m, 2H), 1.10 (m, 2H), 1.58 (m, 2H), 1.75 (m, 1H), 1.94 (m, 1H), 2.88 (m, 1H), 3.04 (m, 1H), 3.56 (m, 1H), 3.73 (m, 1H), 4.08 (m, 1H), 5.06 (s, 2H), 7.23 (br s, 1H), 7.36 (m, 1H), 7.54 (m, 1H), 7.86 (m, 1H), 8.06 (m, 1H), 8.64 (m, 1H), 8.70 (s, 1H); ESIMS found for $C_{24}H_{24}N_6O_3$ m/z: 445.4 [M+H]; Rt 0.699 min.

Example 8

ASK1 Kinase Active Site Binding Assay

Compound binding to the ASK1 kinase active site was determined using the KINOMEscan Assay platform (DiscoverX, San Diego, Calif.). Briefly, ASK1-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 mL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR. Binding constants (Kds) were calculated with a standard dose-response curve using the Hill equation. The Hill Slope was set to −1. Curves were fitted using a non-linear least square fit with the Levenberg-Marquardt algorithm.

Table 2 shows the measured Kds for representative compounds of Formula I as described herein.

TABLE 2

| Compound | Kd (nM) | IC$_{50}$ (nM) |
|---|---|---|
| 1 | 0.75 | 5.2 |
| 39 | 0.86 | 3.3 |

Example 9

ASK1 Kinase Activity Inhibition Assay

Inhibition of ASK1 kinase activity was determined radiometrically using 33P substrate incorporation (Reaction Biology Corp., Malvern, Pa.). Briefly, recombinant human ASK1 protein, 20 μM substrate (myelin basic protein (MBP)), and compound (diluted from DMSO stock to give 1% final DMSO) were incubated in Base Reaction buffer (20 mM Hepes (pH 7.5), 10 mM MgCl2, 1 mM EGTA, 0.02% Brij35, 0.02 mg/mL BSA, 0.1 mM Na3VO4, 2 mM DTT, 1% DMSO) at room temperature for 20 minutes. The reaction was initiated by addition of 10 μM 33P-ATP (specific activity 10 μCi/4l). The reaction was then allowed to proceed for 2 hours at room temperature. Upon reaction termination, the mixture was spotted on P81 exchange paper and kinase activity by incorporation of 33P into MBP substrate was detected by filter-binding method.

Table 3 shows the measured activity for representative compounds of Formula I as described herein.

TABLE 3

| Compound | IC$_{50}$ (nM) |
|---|---|
| 1 | 5.2 |
| 2 | 4.3 |
| 3 | 4.9 |

TABLE 3-continued

| Compound | IC$_{50}$ (nM) |
|---|---|
| 4 | 6.7 |
| 5 | 0.3 |
| 8 | 10.7 |
| 9 | 5.6 |
| 11 | 5.9 |
| 13 | 1.6 |
| 14 | 15.6 |
| 20 | 5.3 |
| 28 | 11.2 |
| 35 | 4 |
| 37 | 2.8 |
| 39 | 3.3 |
| 41 | 4.7 |
| 53 | 2.6 |
| 55 | 5.4 |
| 56 | 42.2 |
| 57 | 5.8 |
| 58 | 5.1 |
| 59 | 5.3 |
| 60 | 5 |
| 61 | 5.1 |
| 62 | 6.8 |
| 63 | 5.1 |
| 64 | 7 |
| 65 | 34.4 |
| 66 | 8.9 |
| 67 | 5.4 |
| 68 | 12.4 |
| 69 | 6.6 |
| 70 | 160 |
| 71 | 4.3 |
| 72 | 4.7 |
| 73 | 14.3 |
| 74 | 5.7 |
| 75 | 5.6 |
| 76 | 8.2 |
| 77 | 2.8 |
| 78 | 4.6 |
| 79 | 4.6 |
| 80 | 5.2 |
| 81 | 14.9 |
| 82 | 3.2 |
| 83 | 6.2 |
| 84 | 4.3 |
| 85 | 3.6 |
| 86 | 1.83 |
| 87 | 2.5 |
| 88 | 4.9 |
| 89 | 4.9 |
| 90 | 4.4 |
| 91 | 7.9 |
| 92 | 5.52 |
| 93 | 12.4 |
| 94 | 6.9 |
| 95 | 3.4 |
| 96 | 4.9 |
| 97 | 4.7 |
| 98 | 4.9 |
| 99 | 6.37 |
| 100 | 6.57 |
| 101 | 3.28 |
| 102 | 0.7 |
| 103 | 12.5 |
| 104 | 46.6 |
| 105 | 7.3 |
| 106 | 8.4 |
| 107 | 5.2 |
| 108 | 5.2 |
| 110 | 5.44 |
| 111 | 6.4 |
| 113 | 1.6 |
| 114 | 2.1 |
| 115 | 6.5 |
| 116 | 4.6 |
| 117 | 1.9 |
| 118 | 67.1 |
| 119 | 5.2 |
| 120 | 8.2 |
| 121 | 4.1 |
| 122 | 3.9 |
| 123 | 3.5 |
| 124 | 8.3 |
| 125 | 7 |
| 126 | 13.4 |
| 127 | 14.6 |
| 128 | 6.16 |
| 129 | 6.6 |
| 130 | 19.2 |
| 131 | 21.7 |

Liver Selective Targeting of Compounds

Tissue concentrations of endogenous chemicals and nutrients are in large part regulated by membrane transporters through their substrate specificity and differential tissue distributions. These transporters also play a key role in the disposition of therapeutic agents thus affecting their efficacy and safety profile. The efficacy and safety profile of drugs are dictated by their target selectivity, pharmacokinetics, tissue distribution and free drug concentrations in targeted organs. Many efficacious compounds fail in development due to adverse responses derived from exposure in non-targeted organs. A transporter-mediated tissue-targeting strategy, where the structural features recognized by the transporters are incorporated into the therapeutic molecule design, is emerging as an effective approach in drug discovery.

The existence of these abundant and tissue specific transporters provides opportunities to explore liver-targeted drug design, utilizing the core structure recognition elements from their known substrates. We have taken the strategy of utilizing homing moieties for liver-targeting through interaction with the organic anion transporting polypeptides (OATP) transporters to achieve higher liver tissue exposure at a given dose relative to that of plasma or non-target tissues. The approach utilizes a strategy to design compounds with low passive permeability to minimize distribution into extra-hepatic tissues, while optimizing properties to drive OATP-mediated uptake for enhanced exposure of the target organ. The aim of this strategy is to mitigate potential non-liver mediated adverse events while maintaining and enhancing therapeutic effects. ASK1 inhibitors were designed using a set of complementary assays to guide the optimization of structure-activity-relationship (SAR). Compounds with low passive cell permeability were selected to minimize diffusion-mediated non-selective tissue disposition while cellular systems utilizing recombinantly overexpressed OATP transporters were utilized to identify transporter-mediated liver targeted compounds.

In summary, liver-targeted selective ASK1 enzyme inhibitors successfully designed by embedding the core structure recognition elements of OATP substrates. This approach has emerged as a practical strategy to enhance liver exposure over other organs for enhanced efficacy or improved therapeutic window.

Example 10

Transporter Mediated Cellular Uptake

To determine transporter mediated cellular uptake of compounds, HEK293 stably expressing either human OATP1B1 or human OATP1B3 transporter, or mock transfected cells were cultured at 37° C. in an atmosphere of 95:5 air:CO$_2$ DMEM/F12 medium containing 10% FBS, 100 unit/mL penicillin-G and 100 μg/mL streptomycin. Transporter expressing cell culture medium also contained 500 μg/mL G418 disulfate solution. Cells were plated onto 24-well poly-D-lysine coated culture plates at the density 5×105 cells/well 24 hours prior to uptake assay. Compound stock solutions were made at 1000× final concentration in 100% DMSO. Final compound solutions were prepared by diluting stock solutions into HBSS buffer (pH 7.4) On the day of the uptake assay cell culture media was removed and cells were washed twice with 300 μL of HBSS buffer (pH 7.4). Cellular uptake of compound into the cells was measured by adding 300 μL of final compound solutions in HBSS and incubating them at 37° C. for 0.5 minutes (OATP1B1) or 5 minutes (OATP1B3). Reactions were quenched by removing the buffer containing the TA and the cells were washed twice with 300 μL of HBSS buffer. Cells were lysed by adding 300 μL of MeOH:H$_2$O (2:1) and incubated for 20 minutes at 4° C. The amount of compound in the cell lysate was determined by LC-MS/MS. The amount of protein in each well was quantified using the BCA kit for protein determination and used to normalize compound uptake (Sigma-Aldrich, St Louis, Mo., USA).

Uptake of the probe substrate in control cells provided background activity values for all data points.

Incubation with probe substrate (solvent only) provided 100% activity values.

A reference positive control was used for each transporter

Table 4 shows whether the representative compounds of Formula I as described herein are substrates for either human OATP1B1 or human OATP1B3 transporters as compared against two positive controls and two literature inhibitors of ASK1.

TABLE 4

| Compound | OATP1B1 Uptake (Percent of no transporter control cell) | OATP1B3 Uptake (Percent of no transporter control cell) |
| --- | --- | --- |
| Estrone 3-sulphate (OATP1B1 positive control) | 685% | Not determined |
| Estradiol (OATP1B3 positive control) | Not determined | 490% |
| Compound #1 | 753% | 399% |
| Compound #39 | 175% | 316% |
| Compound #102 | 221% | 632% |
| ASK1 Inhibitor #1 | 62.9% | 86.0% |
| ASK1 Inhibitor #2 | 76.4% | 105% |

Structures of ASK1 Inhibitors #1 and 2.

ASK1 Inhibitor #1

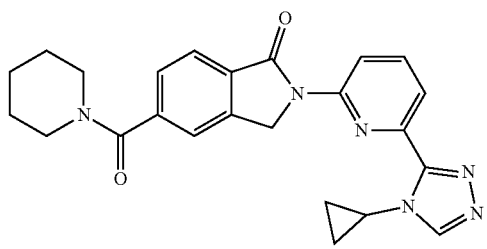

(US10150755)

ASK1 Inhibitor #2

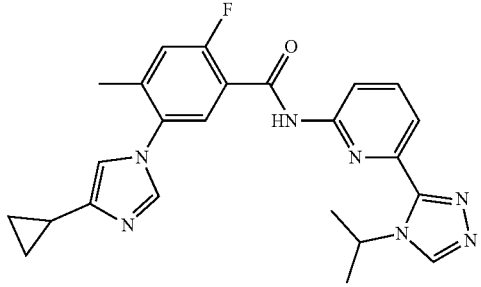

(WO2013112741)

What is claimed is:

1. A compound, or a pharmaceutically acceptable salt thereof, of Formula I:

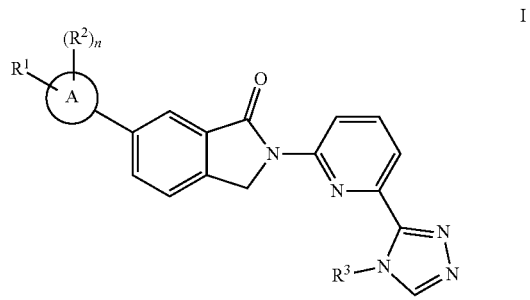

wherein:

Ring A is selected from the group consisting of aryl, heteroaryl, 5-6-membered heterocyclyl, and 4-6-membered carbocyclyl;

$R^1$ is selected from the group consisting of —(C$_{1-6}$ alkylene)$_p$CO$_2$R$^{20}$, —O(C$_{1-6}$ alkylene)$_p$CO$_2$R$^{20}$, —(C$_{1-6}$ alkylene)$_p$(carbocyclylene)CO$_2$R$^{20}$, —O(C$_{1-6}$ alkylene)$_p$(carbocyclylene)CO$_2$R$^{20}$, unsubstituted —(C$_{2-9}$ alkenyl), unsubstituted —(C$_{2-9}$ alkynyl), unsubstituted —(C$_{1-9}$ haloalkyl), —(C$_{1-6}$ alkylene)carbocyclyl optionally substituted with 1-10 R$^4$, —(C$_{1-6}$ alkylene)$_p$heterocyclyl optionally substituted with 1-10 R$^5$, —(C$_{1-6}$ alkylene)$_p$aryl optionally substituted with 1-5 R$^6$, —(C$_{1-6}$ alkylene)$_p$heteroaryl optionally substituted with 1-5 R$^7$, —(C$_{1-6}$ alkylene)$_p$OR$^8$, —(C$_{1-6}$ alkylene)$_p$SR$^8$, —(C$_{1-6}$ alkylene)$_p$S(=O)R$^9$, —(C$_{1-6}$ alkylene)$_p$SO$_2$R$^{10}$, —(C$_{1-6}$ alkylene)$_p$N(R$^{11}$)SO$_2$R$^{12}$, —(C$_{1-6}$ alkylene)$_p$SO$_2$N(R$^{13}$)$_2$, —(C$_{1-6}$ alkylene)$_p$N(R$^{14}$)$_2$, —(C$_{1-6}$ alkylene)$_p$N(R$^{11}$)C(=O)N(R$^{15}$)$_2$, —(C$_{1-6}$ alkylene)$_p$NR$^{11}$C(=O)OR$^{16}$, —(C$_{1-6}$ alkylene)$_p$C(=O)N(R$^{17}$)$_2$, —(C$_{1-6}$ alkylene)$_p$N(R$^{11}$)C(=O)R$^{18}$, and —(C$_{1-6}$ alkylene)$_p$OC(=O)N(R$^{19}$)$_2$; wherein each —(C$_{1-4}$ alkylene) is, independently, optionally substituted with one or more substituents as defined anywhere herein; wherein each (carbocyclylene) is, independently, optionally substituted with one or more substituents as defined anywhere herein; wherein each CO$_2$R$^{20}$ can be replaced with a carbocyclic acid bioisostere thereof;

$R^2$ is selected from the group consisting of halide, Me, OMe, CN, —SO$_2$R$^{10}$, —N(R$^{14}$)$_2$, —(C$_{1-4}$ alkylene)

$_p$OH; wherein —(C$_{1-4}$ alkylene) of —(C$_{1-4}$ alkylene)$_p$OH is optionally substituted with one or more OH;

alternatively, an adjacent R$^1$ and R$^2$ are taken together with the atoms to which they are attached to form a ring which is selected from the group consisting of

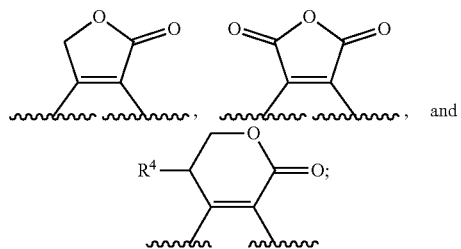

R$^3$ is selected from the group consisting of unsubstituted —(C$_{1-9}$ alkyl), unsubstituted —(C$_{2-9}$ alkenyl), unsubstituted —(C$_{2-9}$ alkynyl), unsubstituted —(C$_{1-9}$ haloalkyl), —(C$_{1-4}$ alkylene)OR$^{21}$, and —(C$_{1-4}$ alkylene)$_p$carbocyclyl optionally substituted with one or more halides; wherein each —(C$_{1-4}$ alkylene) is, independently, optionally substituted with one or more halides;

each R$^4$ is selected from the group consisting of halide, unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —OH, —N(R$^{23}$)$_2$, —CN, and —OMe;

each R$^5$ is selected from the group consisting of halide, unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —OH, —N(R$^{23}$)$_2$, —CN, and —OMe;

each R$^6$ is selected from the group consisting of halide, unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —OH, —N(R$^{23}$)$_2$, —CN, and —OMe;

each R$^7$ is selected from the group consisting of halide, unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —OH, —N(R$^{23}$)$_2$, —CN, and —OMe;

R$^8$ is selected from the group consisting of H, unsubstituted —(C$_{3-6}$ alkyl), unsubstituted —(C$_{2-6}$ alkenyl), unsubstituted —(C$_{2-6}$ alkynyl), unsubstituted —(C$_{1-6}$ haloalkyl), —(C$_{1-3}$ alkylene)$_p$carbocyclyl optionally substituted with one of more halides and/or unsubstituted —(C$_{1-6}$ alkyl), —(C$_{1-3}$ alkylene)$_p$heterocyclyl optionally substituted with one of more halides and/or unsubstituted —(C$_{1-6}$ alkyl), —(C$_{1-3}$ alkylene)$_p$aryl optionally substituted with one of more halides and/or unsubstituted —(C$_{1-6}$ alkyl), and —(C$_{1-3}$ alkylene)$_p$heteroaryl optionally substituted with one of more halides and/or unsubstituted —(C$_{1-6}$ alkyl); wherein each —(C$_{1-4}$ alkylene) is, independently, optionally substituted with one or more halides;

R$^9$ is selected from the group consisting of unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —(C$_{1-3}$ alkylene)$_p$carbocyclyl optionally substituted with one of more halides and/or unsubstituted —(C$_{1-6}$ alkyl), —(C$_{1-3}$ alkylene)$_p$heterocyclyl optionally substituted with one of more halides and/or unsubstituted —(C$_{1-6}$ alkyl), —(C$_{1-3}$ alkylene)$_p$aryl optionally substituted with one of more halides and/or unsubstituted —(C$_{1-6}$ alkyl), and —(C$_{1-3}$ alkylene)$_p$heteroaryl optionally substituted with one of more halides and/or unsubstituted —(C$_{1-6}$ alkyl); wherein each —(C$_{1-4}$ alkylene) is, independently, optionally substituted with one or more halides;

R$^{10}$ is selected from the group consisting of unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —(C$_{1-3}$ alkylene)$_p$carbocyclyl optionally substituted with one of more halides and/or unsubstituted —(C$_{1-6}$ alkyl), —(C$_{1-3}$ alkylene)$_p$heterocyclyl optionally substituted with one of more halides and/or unsubstituted —(C$_{1-6}$ alkyl), —(C$_{1-3}$ alkylene)$_p$aryl optionally substituted with one of more halides and/or unsubstituted —(C$_{1-6}$ alkyl), and —(C$_{1-3}$ alkylene)$_p$heteroaryl optionally substituted with one of more halides and/or unsubstituted —(C$_{1-6}$ alkyl); wherein each —(C$_{1-4}$ alkylene) is, independently, optionally substituted with one or more halides;

each R$^{11}$ is selected from the group consisting of H, unsubstituted —(C$_{1-6}$ alkyl), unsubstituted —(C$_{2-6}$ alkenyl), unsubstituted —(C$_{2-6}$ alkynyl), and unsubstituted —(C$_{1-6}$ haloalkyl);

R$^{12}$ is selected from the group consisting of unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —(C$_{1-3}$ alkylene)$_p$carbocyclyl optionally substituted with one of more halides and/or unsubstituted —(C$_{1-6}$ alkyl), —(C$_{1-3}$ alkylene)$_p$heterocyclyl optionally substituted with one of more halides and/or unsubstituted —(C$_{1-6}$ alkyl), —(C$_{1-3}$ alkylene)$_p$aryl optionally substituted with one of more halides and/or unsubstituted —(C$_{1-6}$ alkyl), and —(C$_{1-3}$ alkylene)$_p$heteroaryl optionally substituted with one of more halides and/or unsubstituted —(C$_{1-6}$ alkyl); wherein each —(C$_{1-4}$ alkylene) is, independently, optionally substituted with one or more halides;

each R$^{13}$ is selected from the group consisting of H, unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —(C$_{1-3}$ alkylene)$_p$carbocyclyl optionally substituted with one of more halides and/or unsubstituted —(C$_{1-6}$ alkyl), —(C$_{1-3}$ alkylene)$_p$heterocyclyl optionally substituted with one of more halides and/or unsubstituted —(C$_{1-6}$ alkyl), —(C$_{1-3}$ alkylene)$_p$aryl optionally substituted with one of more halides and/or unsubstituted —(C$_{1-6}$ alkyl), and —(C$_{1-3}$ alkylene)$_p$heteroaryl optionally substituted with one of more halides and/or unsubstituted —(C$_{1-6}$ alkyl); wherein each —(C$_{1-4}$ alkylene) is, independently, optionally substituted with one or more halides;

each R$^{14}$ is selected from the group consisting of H, unsubstituted —(C$_{1-6}$ alkyl), unsubstituted —(C$_{2-6}$ alkenyl), unsubstituted —(C$_{2-6}$ alkynyl), unsubstituted —(C$_{1-6}$ haloalkyl), —(C$_{1-3}$ alkylene)$_p$carbocyclyl optionally substituted with one of more halides and/or unsubstituted —(C$_{1-6}$ alkyl), —(C$_{1-3}$ alkylene)$_p$heterocyclyl optionally substituted with one of more halides and/or unsubstituted —(C$_{1-6}$ alkyl), —(C$_{1-3}$ alkylene)$_p$aryl optionally substituted with one of more halides and/or unsubstituted —(C$_{1-6}$ alkyl), and —(C$_{1-3}$ alkylene)$_p$heteroaryl optionally substituted with one of more halides and/or unsubstituted —(C$_{1-6}$ alkyl); wherein each —(C$_{1-4}$ alkylene) is, independently, optionally substituted with one or more halides;

each $R^{15}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{16}$ is selected from the group consisting of unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

each $R^{17}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{18}$ is selected from the group consisting of unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

each $R^{19}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one of more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{20}$ is selected from the group consisting of H, unsubstituted —$(C_{1-6}$ alkyl), unsubstituted —$(C_{2-6}$ alkenyl), unsubstituted —$(C_{2-6}$ alkynyl), unsubstituted —$(C_{1-6}$ haloalkyl), —$(C_{1-3}$ alkylene)$_p$carbocyclyl optionally substituted with one or more halides and/or unsubstituted —$(C_{1-6}$ alkyl), —$(C_{1-3}$ alkylene)$_p$heterocyclyl optionally substituted with one of more halides and/or unsubstituted —$(C_{1-6}$ alkyl), —$(C_{1-3}$ alkylene)$_p$aryl optionally substituted with one of more halides and/or unsubstituted —$(C_{1-6}$ alkyl), and —$(C_{1-3}$ alkylene)$_p$heteroaryl optionally substituted with one of more halides and/or unsubstituted —$(C_{1-6}$ alkyl); wherein each —$(C_{1-4}$ alkylene) is, independently, optionally substituted with one or more halides;

$R^{21}$ is selected from the group consisting of H, unsubstituted —$(C_{1-5}$ alkyl), unsubstituted —$(C_{2-5}$ alkenyl), unsubstituted —$(C_{2-5}$ alkynyl), and unsubstituted —$(C_{1-5}$ haloalkyl);

each n is independently 0 to 5; and each p is independently 0 or 1.

2. The compound of claim 1, wherein Ring A is phenyl.

3. A compound, or a pharmaceutically acceptable salt thereof, of Formula Ia:

Ia wherein:

$R^1$ is selected from the group consisting of —$(C_{1-6}$ alkylene)$_p$CO$_2$H, —O$(C_{1-6}$ alkylene)$_p$CO$_2$H, —$(C_{1-6}$ alkylene)$_p$(carbocyclylene)CO$_2$H, —O$(C_{1-6}$ alkylene)$_p$(carbocyclylene)CO$_2$H, and tetrazole; wherein each —$(C_{1-4}$ alkylene) is, independently, optionally substituted with one or more substituents as defined anywhere herein; wherein each (carbocyclylene) is, independently, optionally substituted with one or more substituents as defined anywhere herein;

$R^2$ is selected from the group consisting of halide, Me, OMe, CN, —SO$_2$R$^{10}$, —N(R$^{14}$)$_2$, —$(C_{1-4}$ alkylene)$_p$OH; wherein —$(C_{1-4}$ alkylene) of —$(C_{1-4}$ alkylene)$_p$OH is optionally substituted with one or more OH;

$R^3$ is selected from the group consisting of unsubstituted —$(C_{1-9}$ alkyl), unsubstituted —$(C_{1-9}$ haloalkyl), and -carbocyclyl optionally substituted with one or more halides;

$R^{10}$ is unsubstituted —$(C_{1-3}$ alkyl);

each $R^{14}$ is selected from the group consisting of H and unsubstituted —$(C_{1-3}$ alkyl);

each n is independently 0 to 5; and each p is independently 0 or 1.

4. The compound of claim 1, wherein $R^1$ is —$(C_{1-3}$ alkylene)CO$_2$H.

5. The compound of claim 3, wherein $R^1$ is —($C_{1-3}$ alkylene)$CO_2H$.

6. The compound of claim 4, wherein $R^1$ is —($CMe_2$)$CO_2H$.

7. The compound of claim 5, wherein $R^1$ is —($CMe_2$)$CO_2H$.

8. The compound of claim 1, wherein $R^1$ is —$CO_2H$.

9. The compound of claim 3, wherein $R^1$ is —$CO_2H$.

10. The compound of claim 1, wherein n is 0.

11. The compound of claim 3, wherein n is 0.

12. The compound of claim 1, wherein $R^3$ is unsubstituted —($C_{1-9}$ alkyl).

13. The compound of claim 12, wherein $R^3$ is unsubstituted —($C_{1-3}$ alkyl).

14. The compound of claim 13, wherein $R^3$ is isopropyl.

15. The compound of claim 3, wherein $R^3$ is isopropyl.

16. The compound of claim 1, wherein the compound of Formula I is selected from the group consisting of:

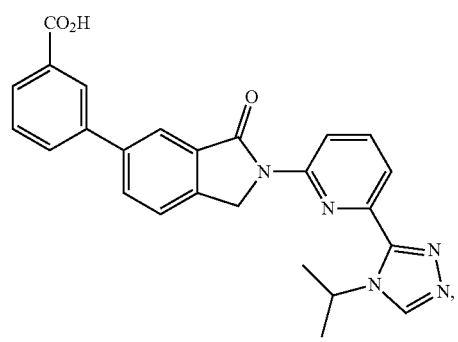

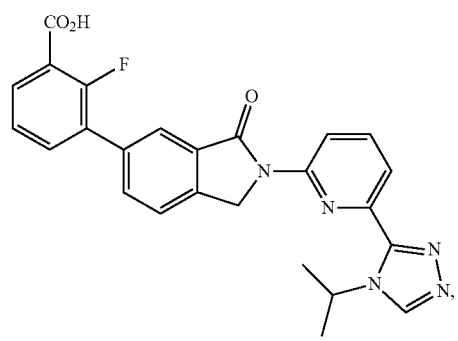

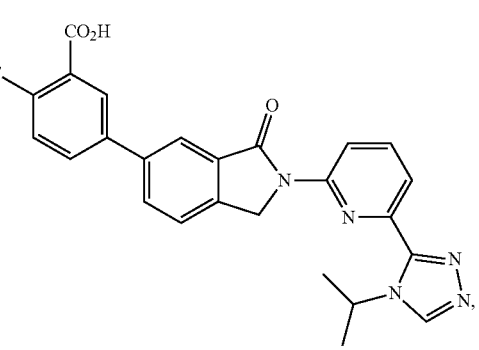

-continued

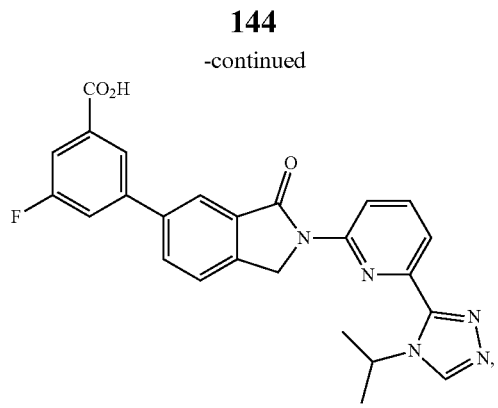

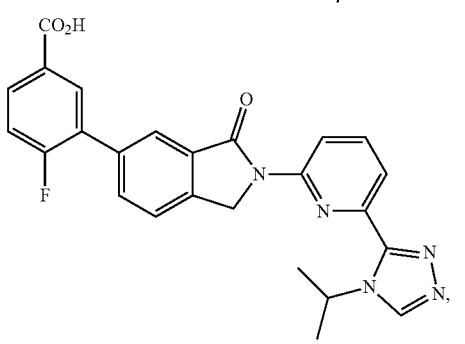

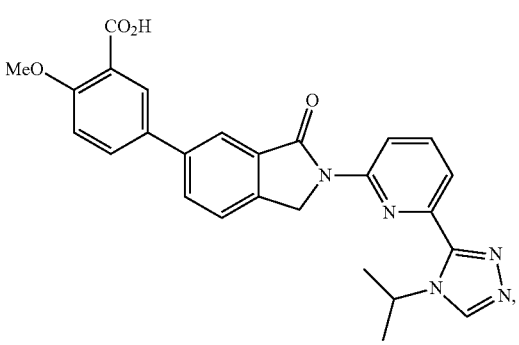

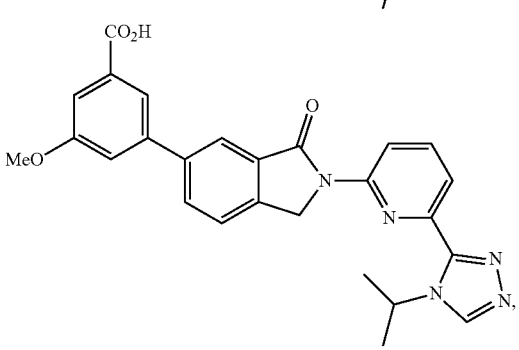

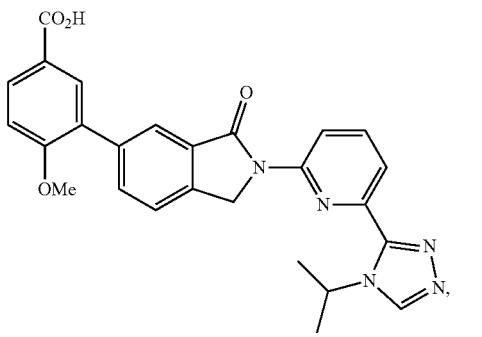

145
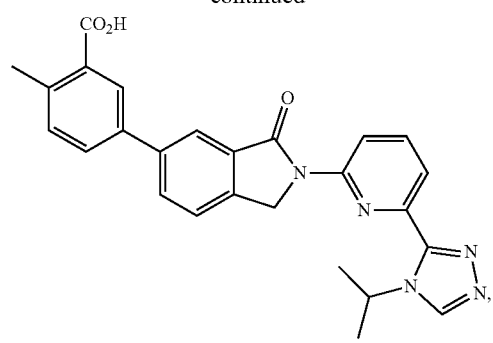
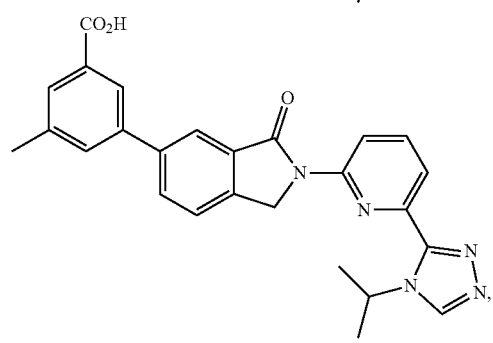
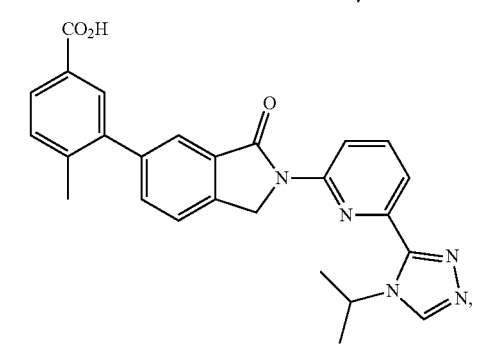
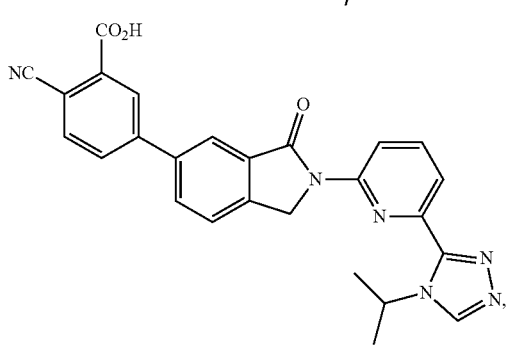
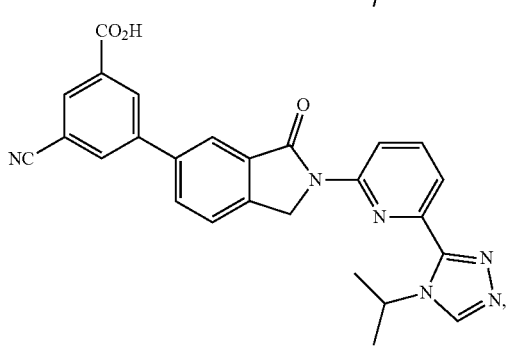
146
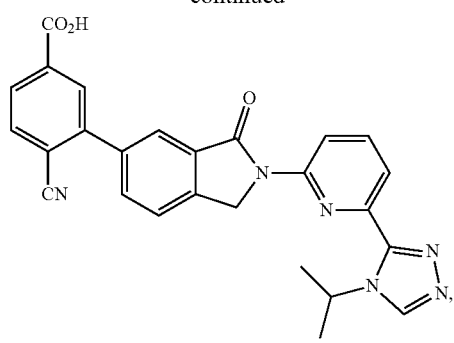
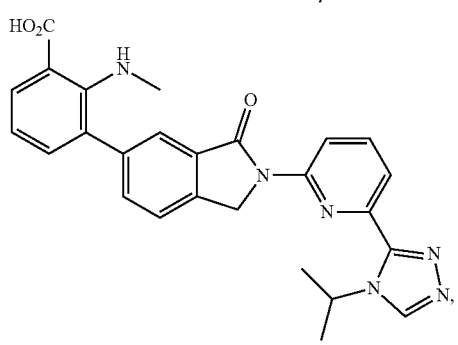
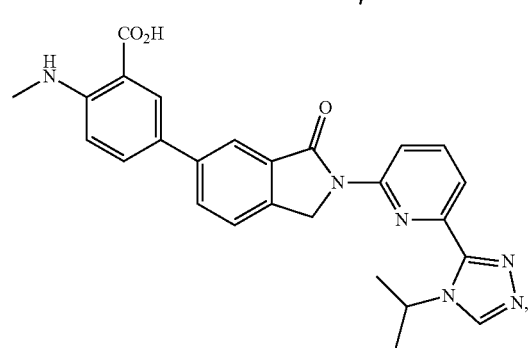
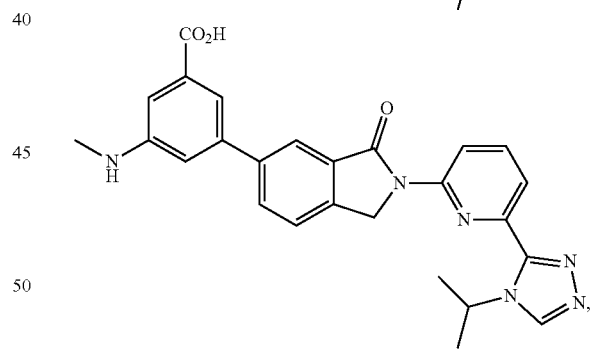
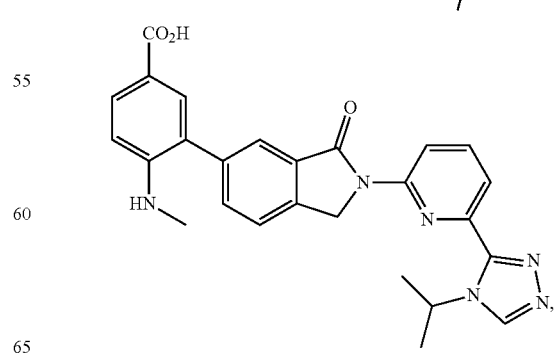

-continued
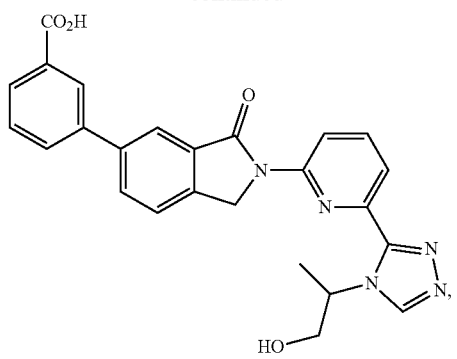
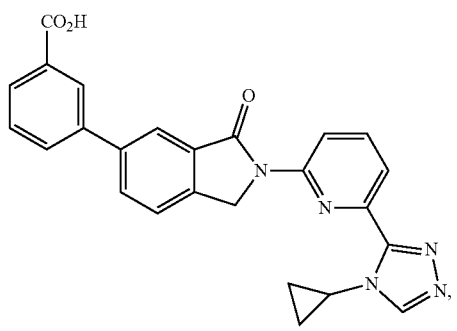
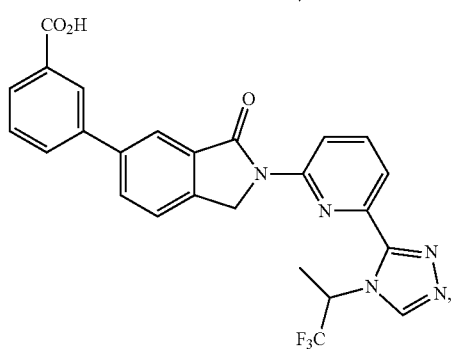
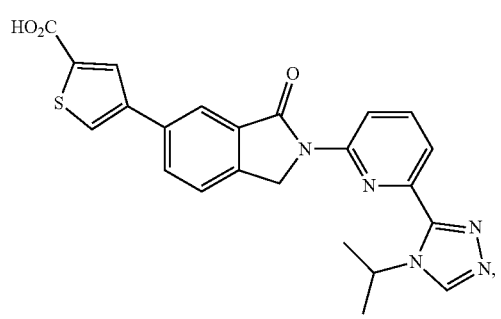
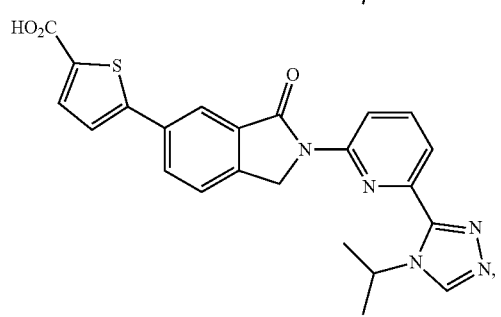
-continued
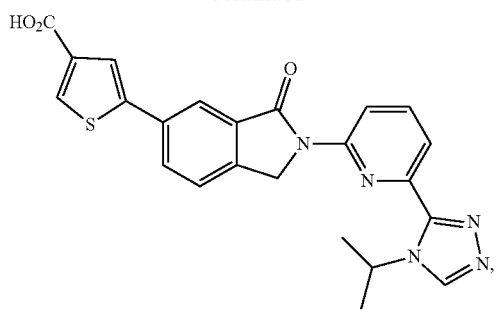
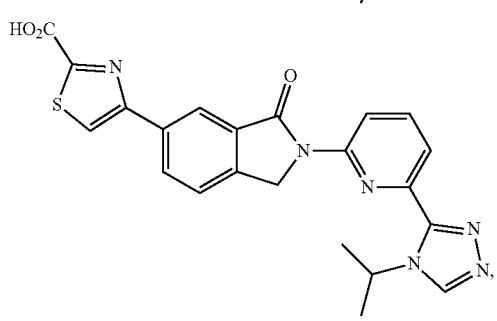
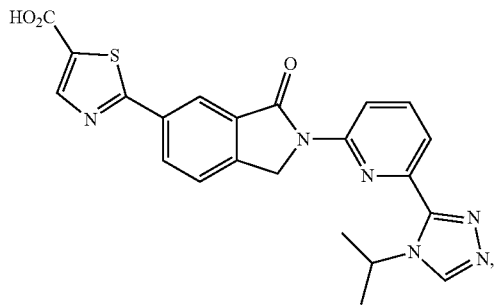
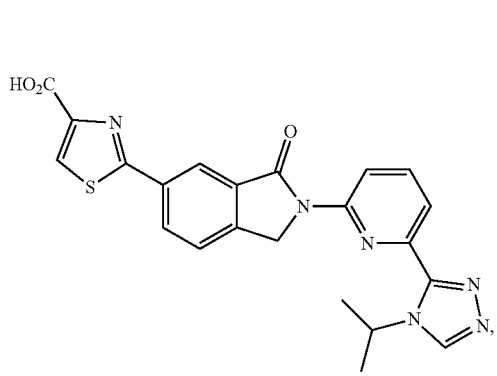
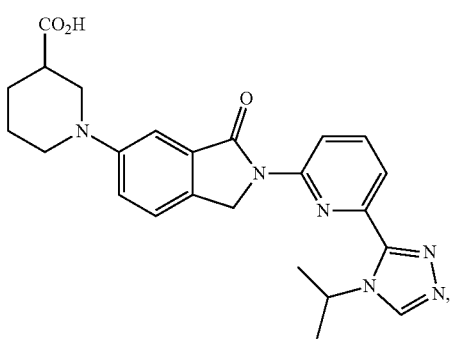

149
-continued
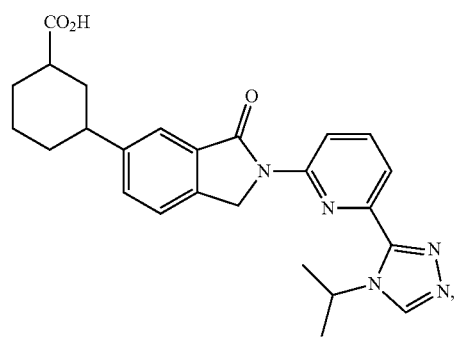
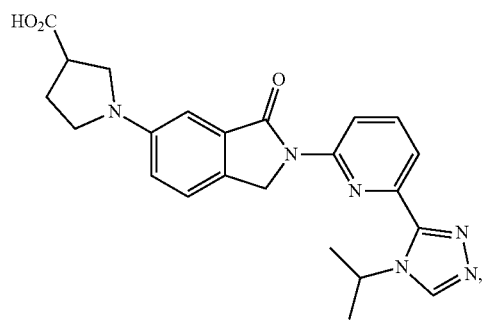
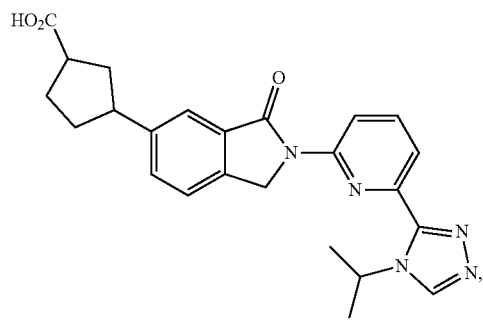
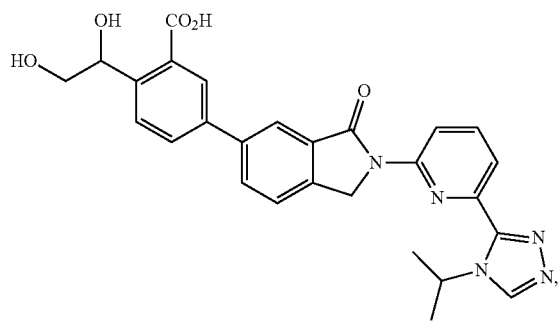
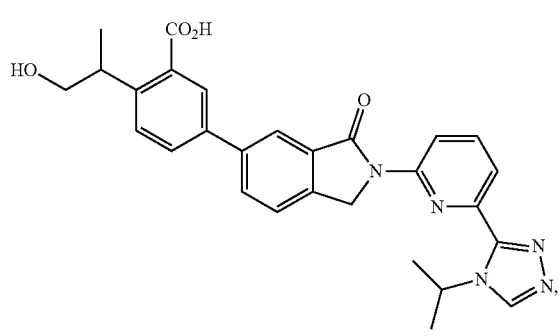
150
-continued
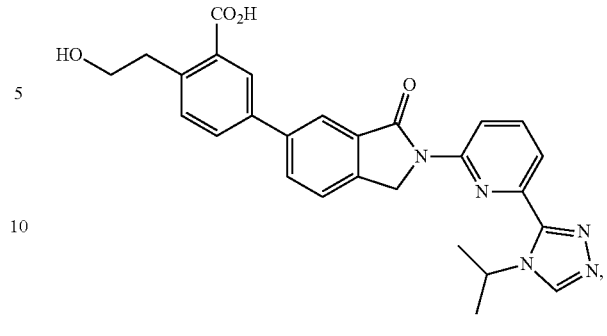
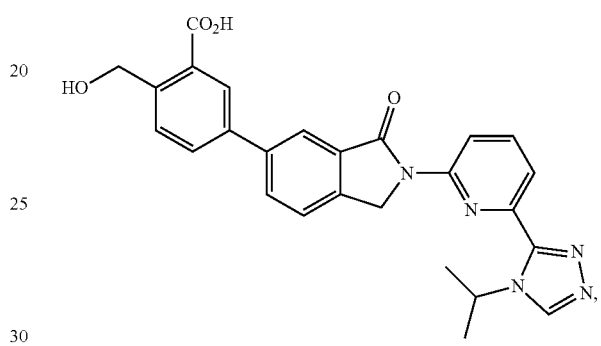
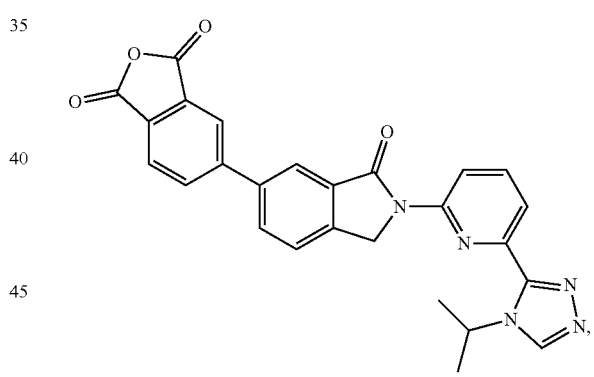
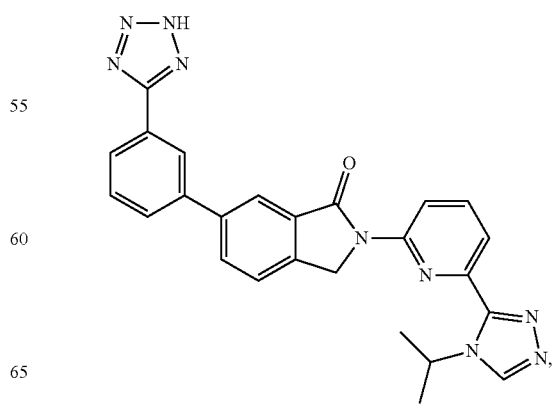

151 -continued
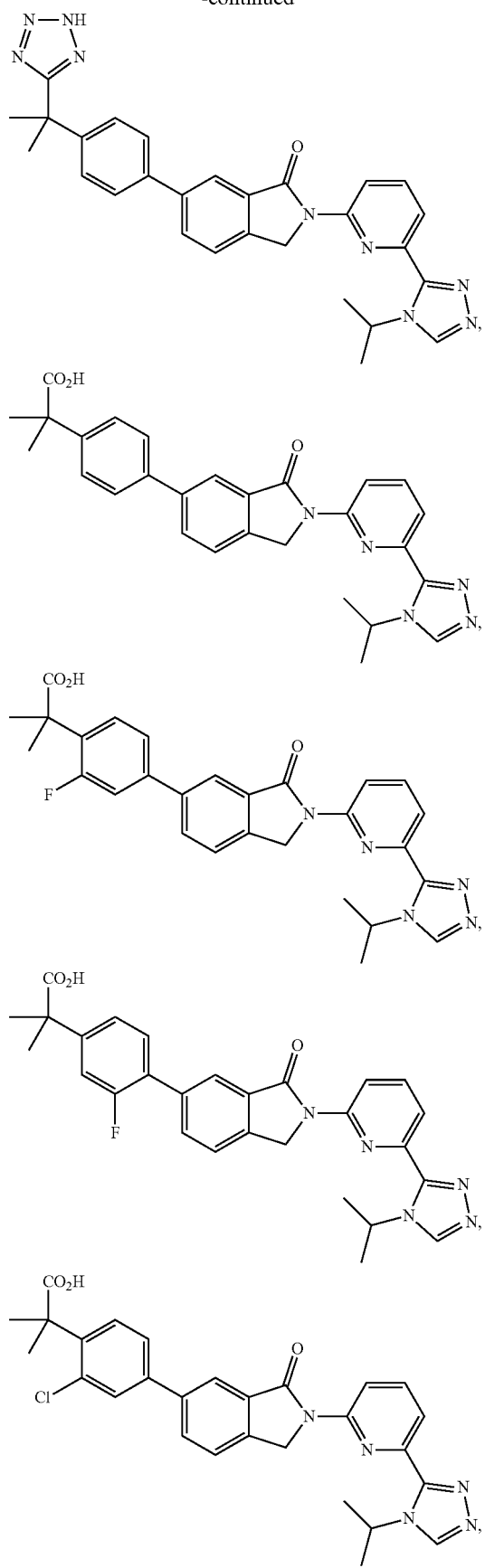
152 -continued
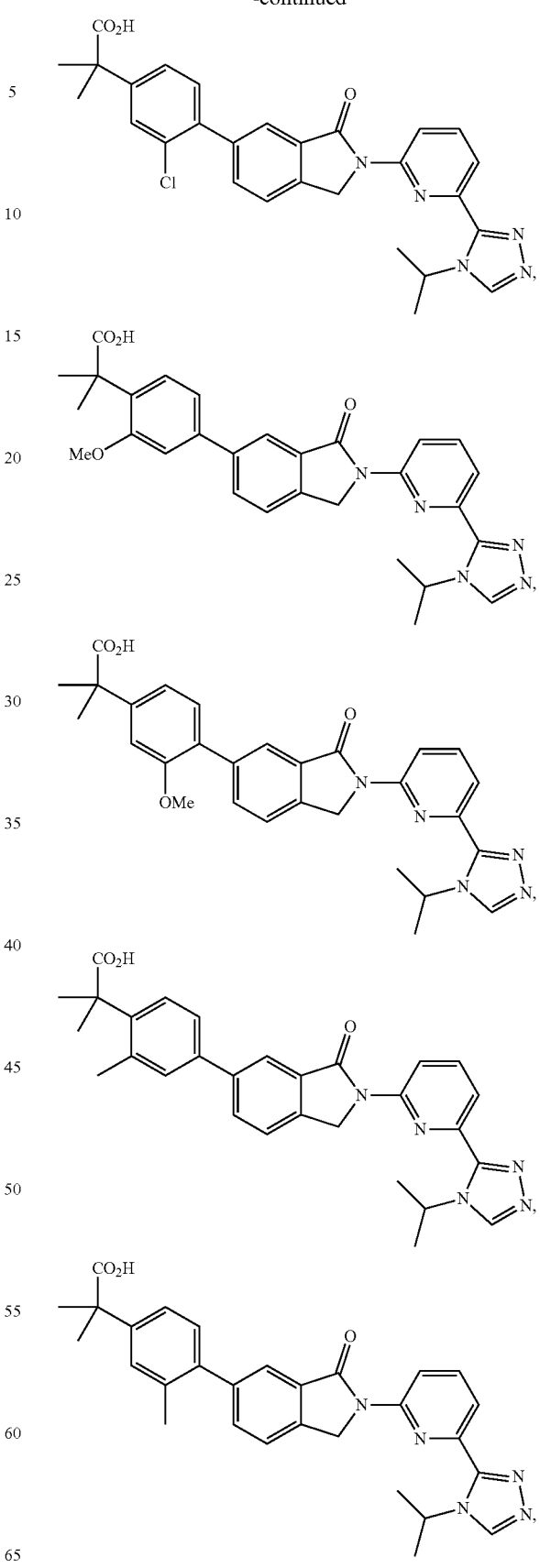

153
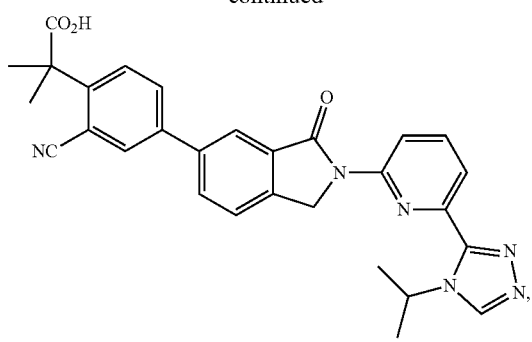
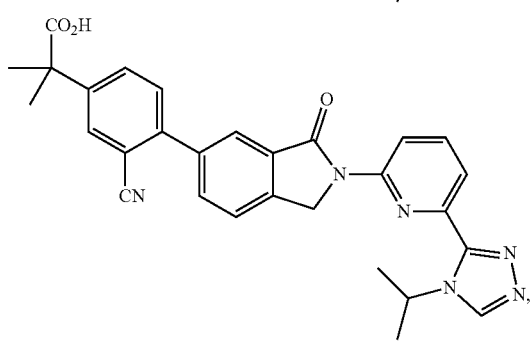
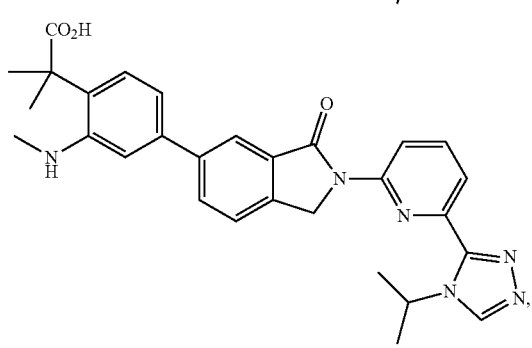
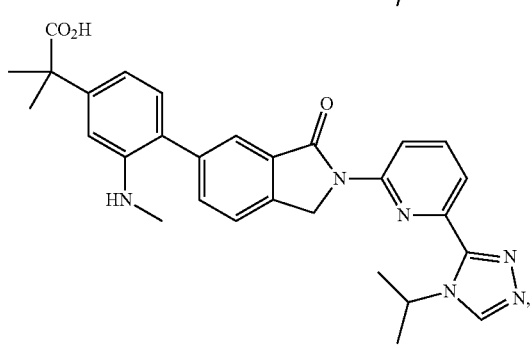
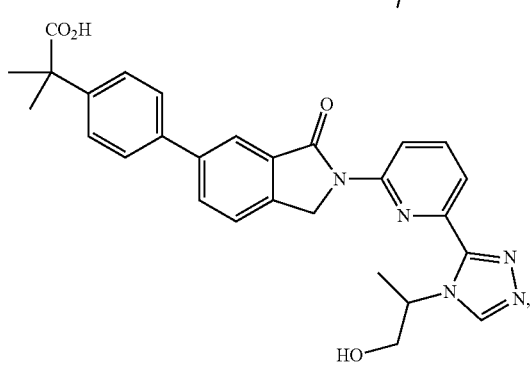
154
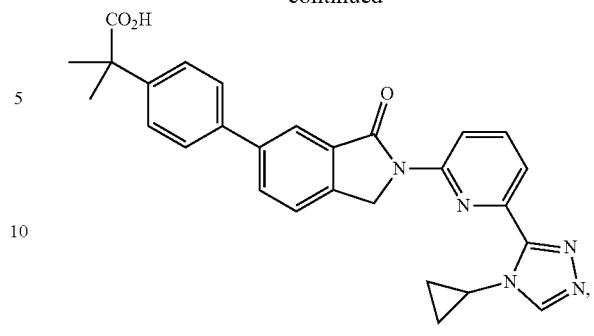
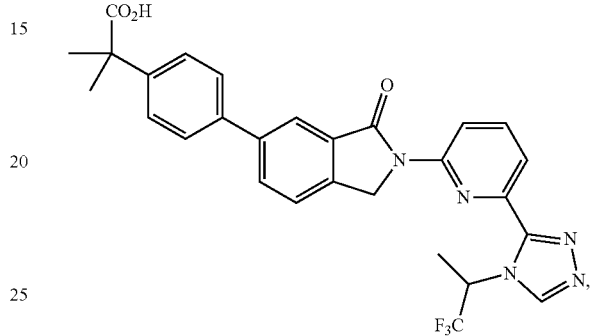
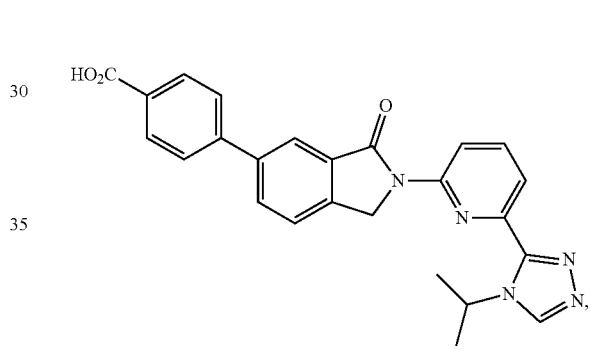
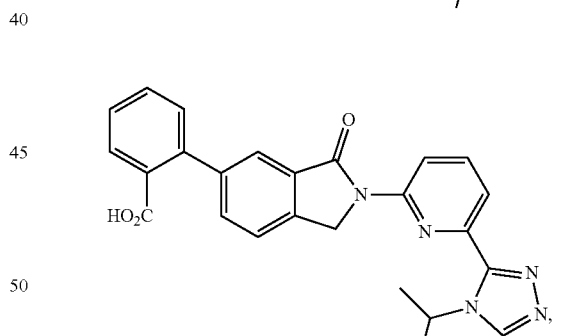
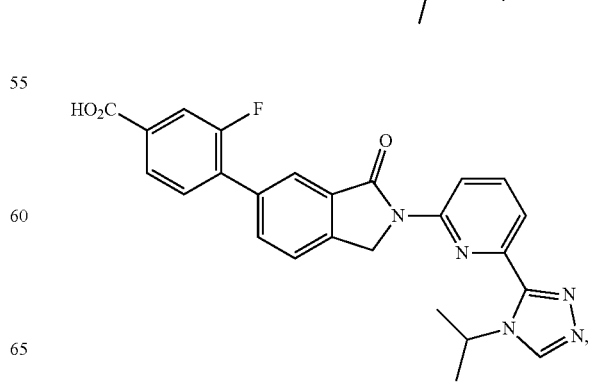

155
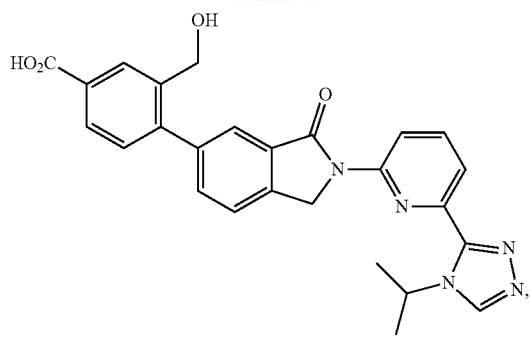
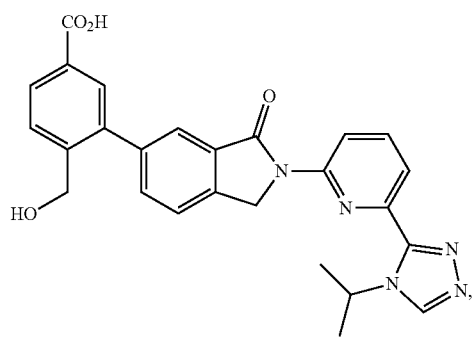
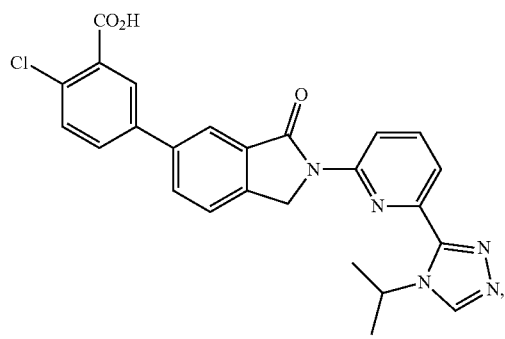
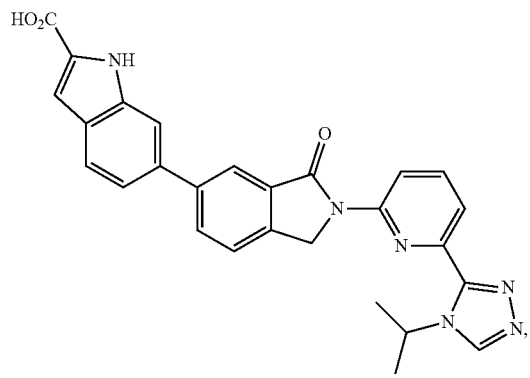
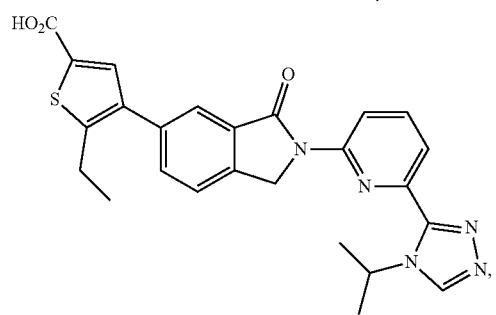
156
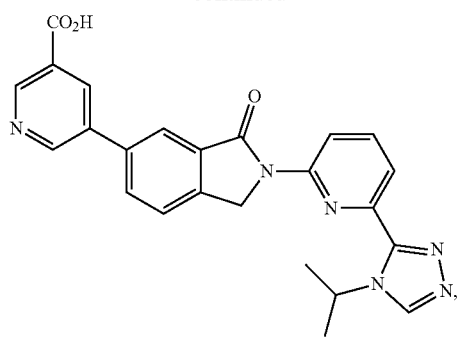
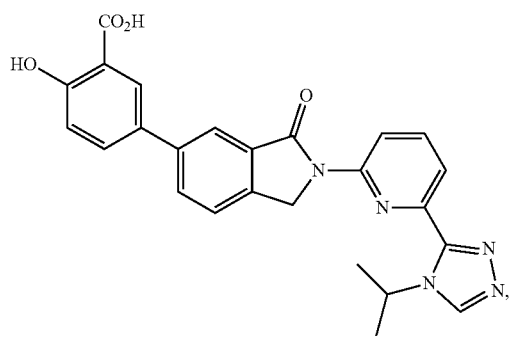
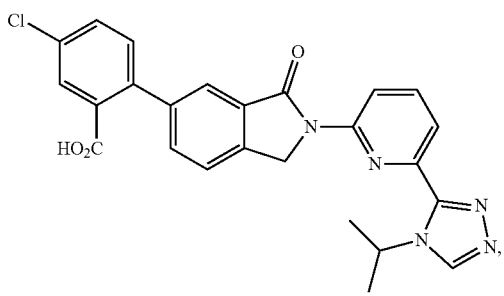
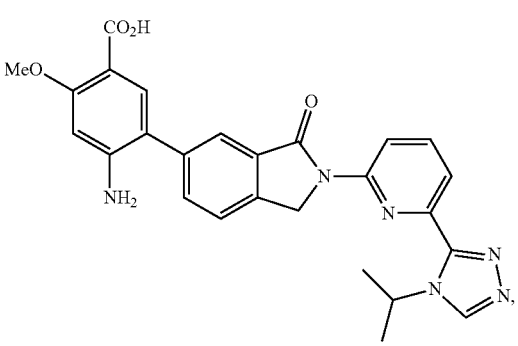
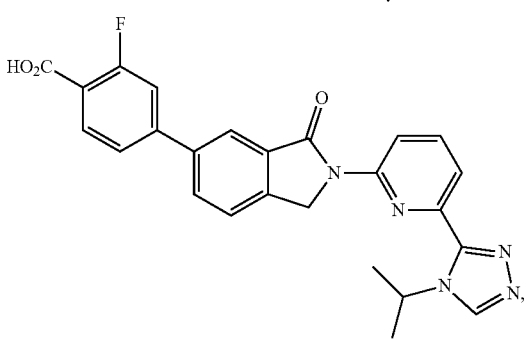

157
-continued
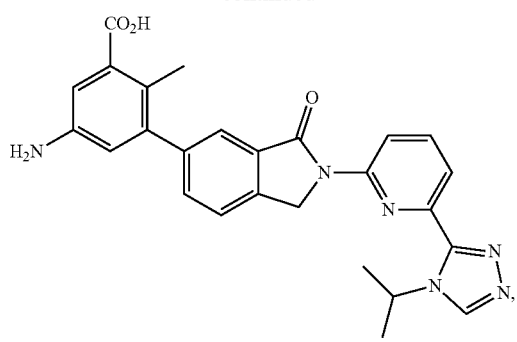
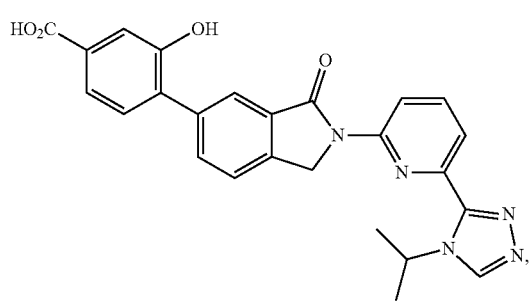
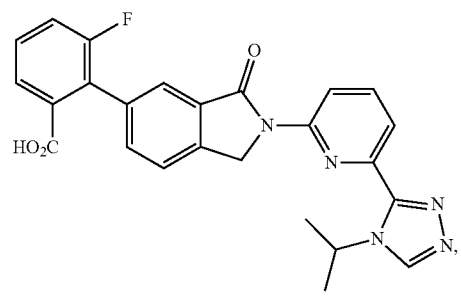
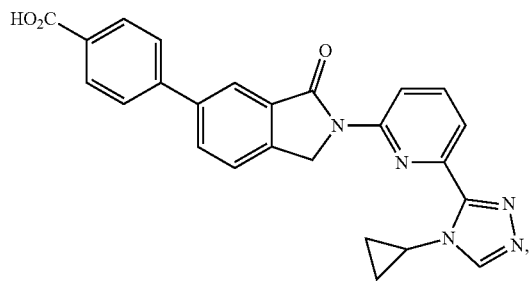
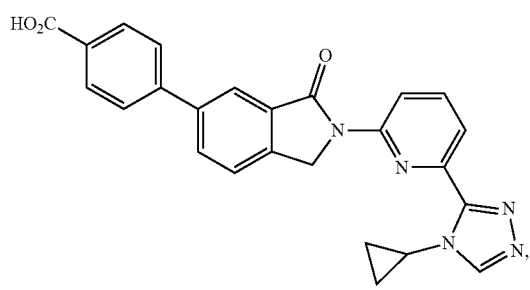
158
-continued
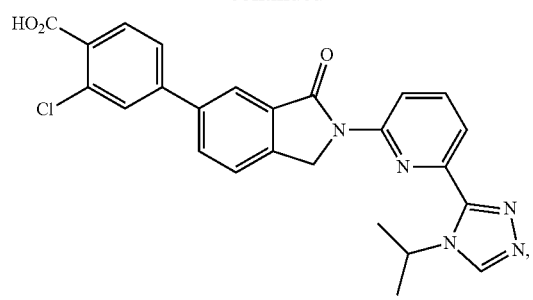
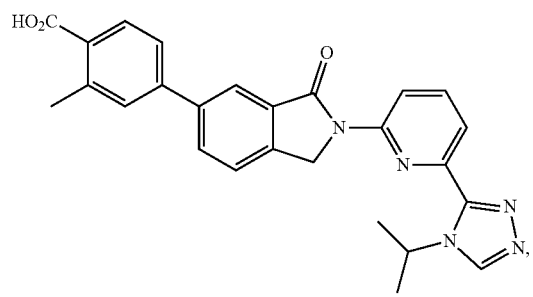
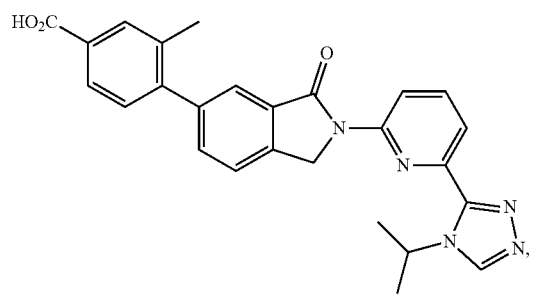
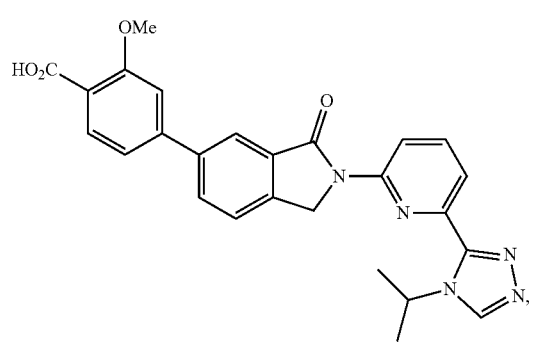
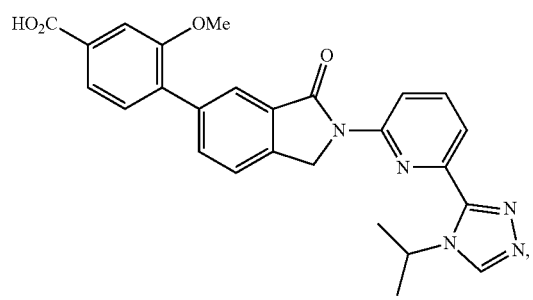

159
-continued
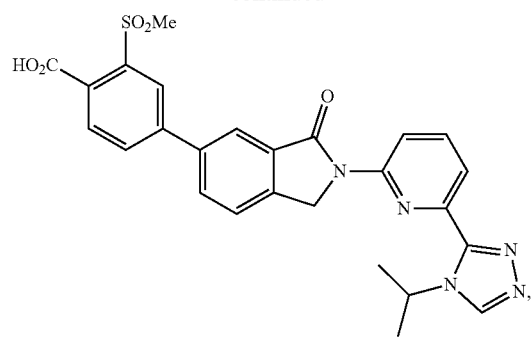
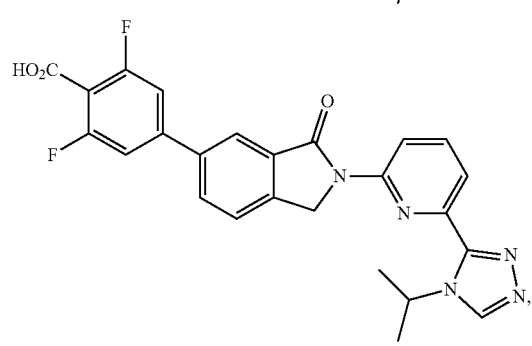
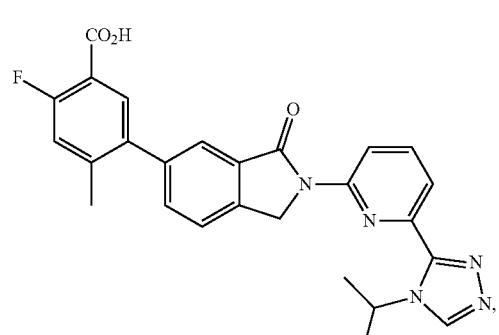
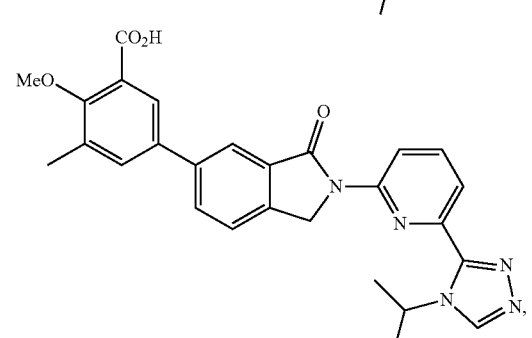
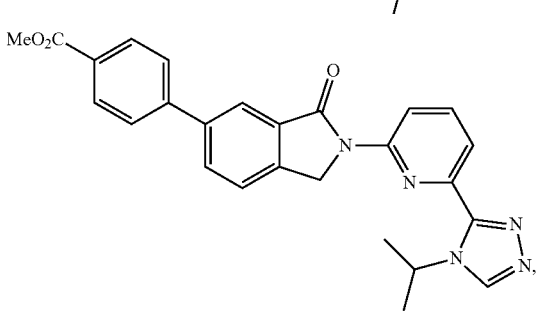
160
-continued
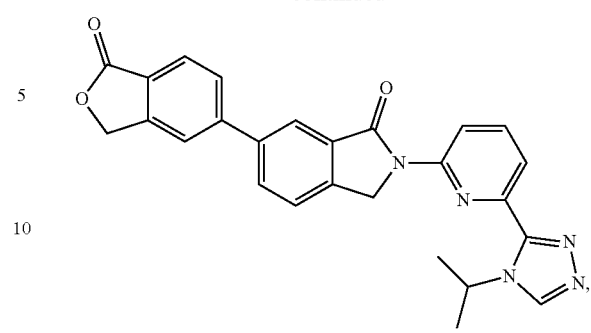
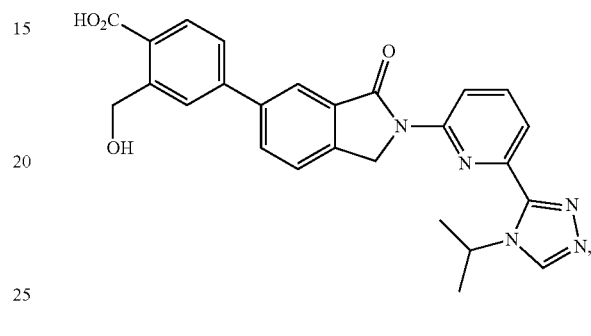
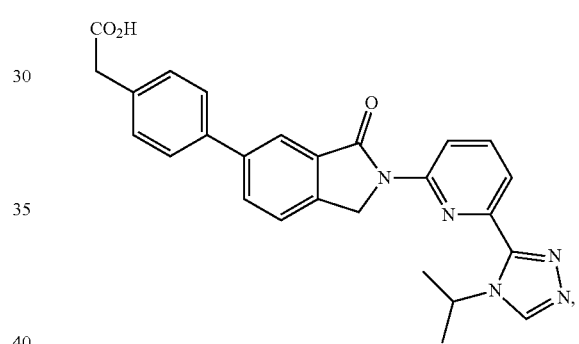
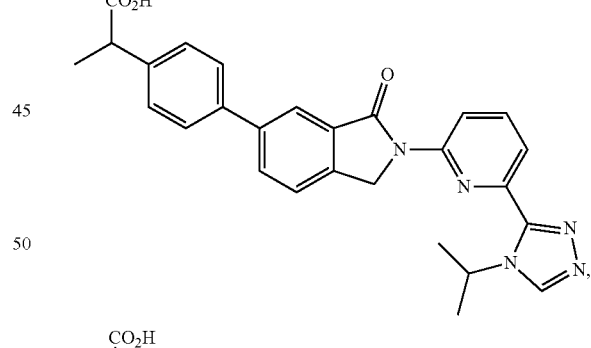
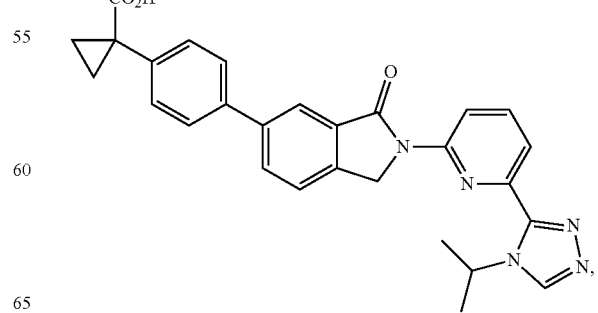

161
-continued
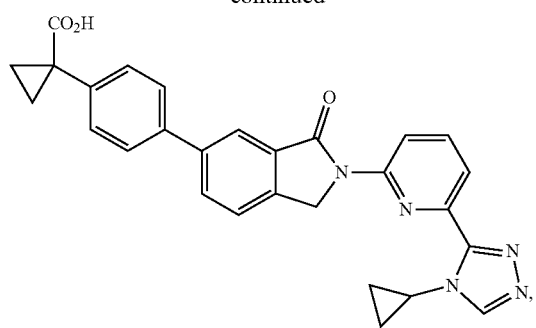
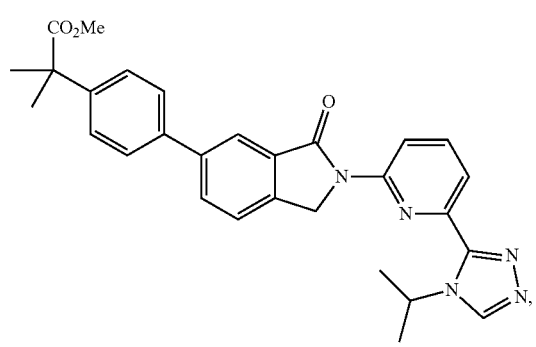
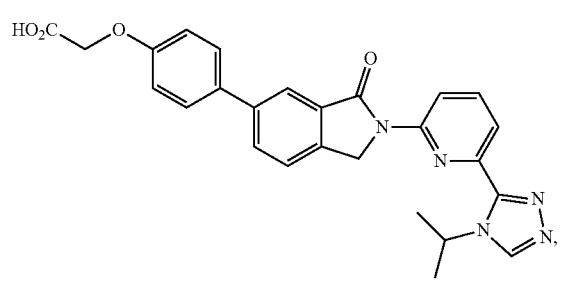
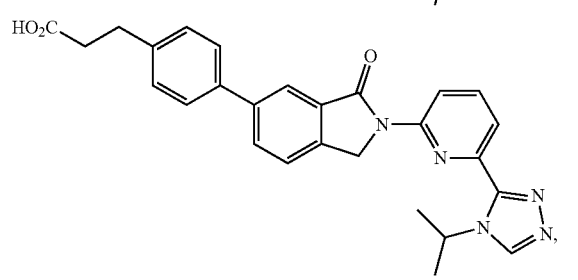
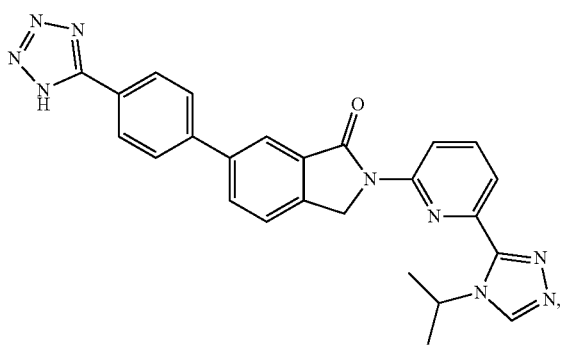
162
-continued
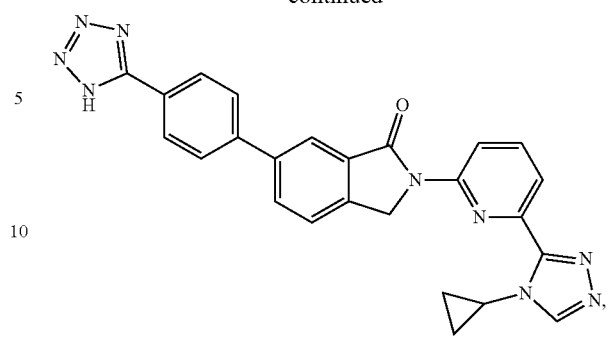
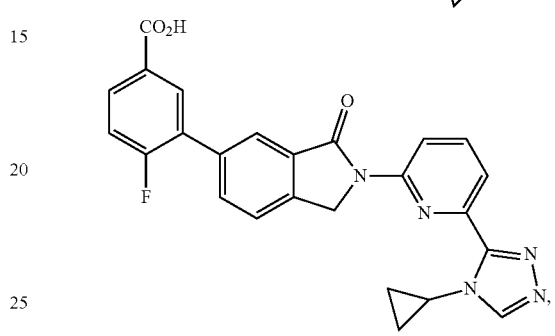
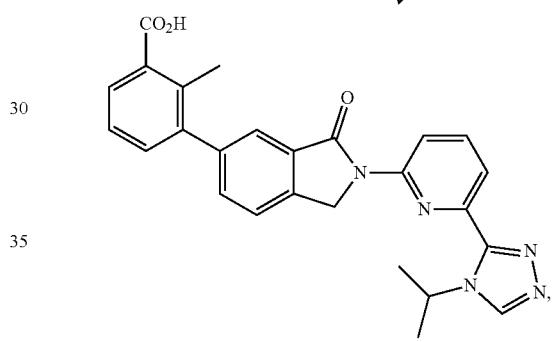
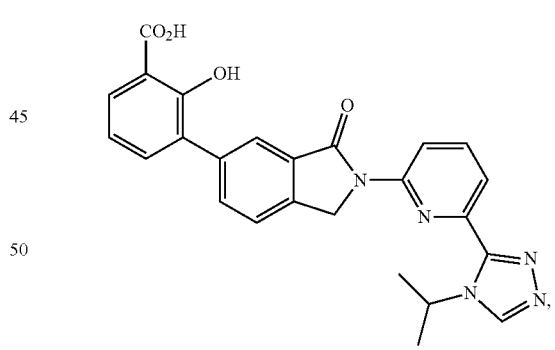
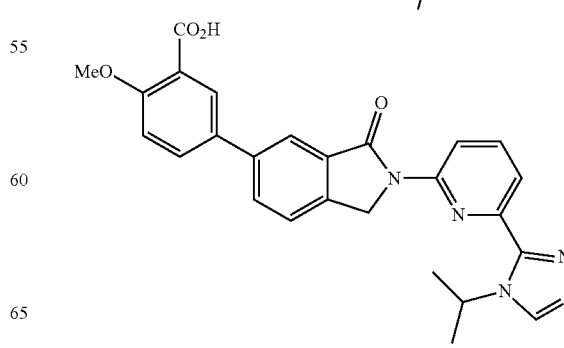

-continued
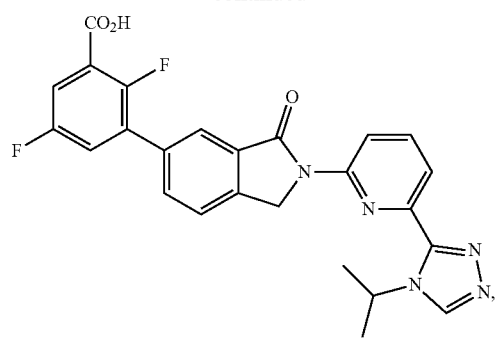
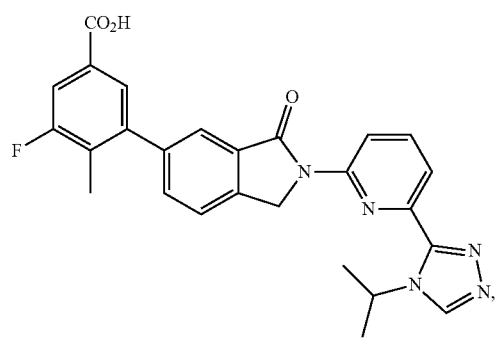
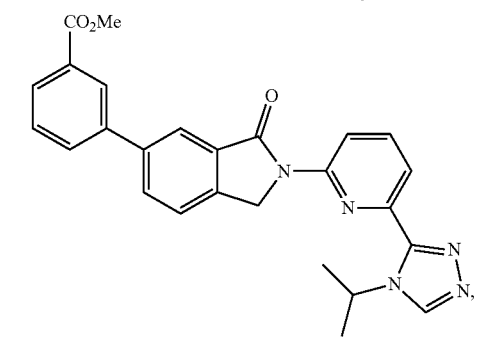
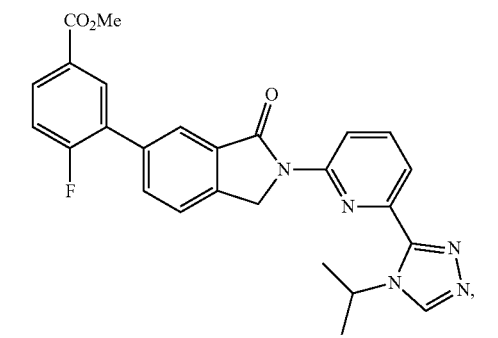
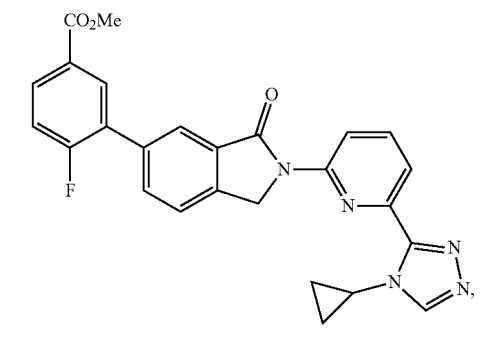
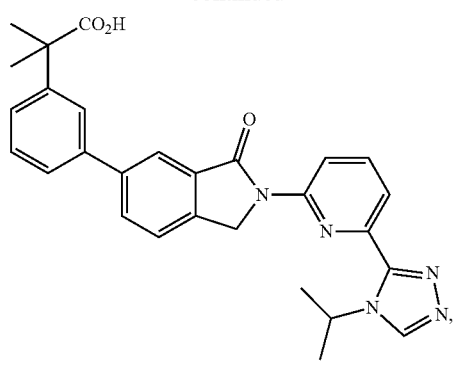
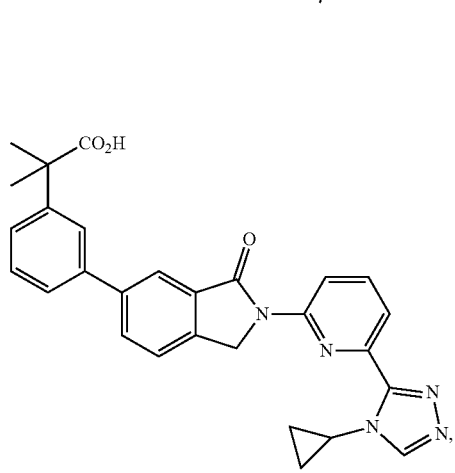
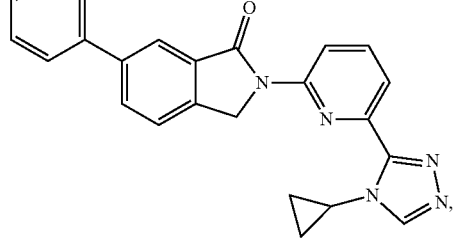
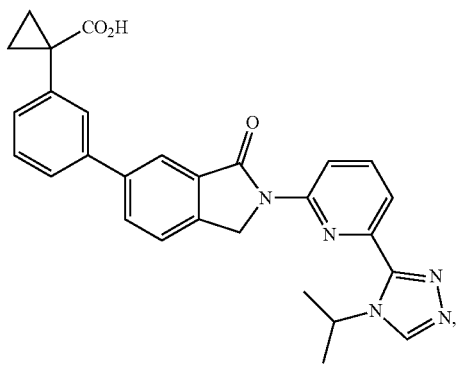

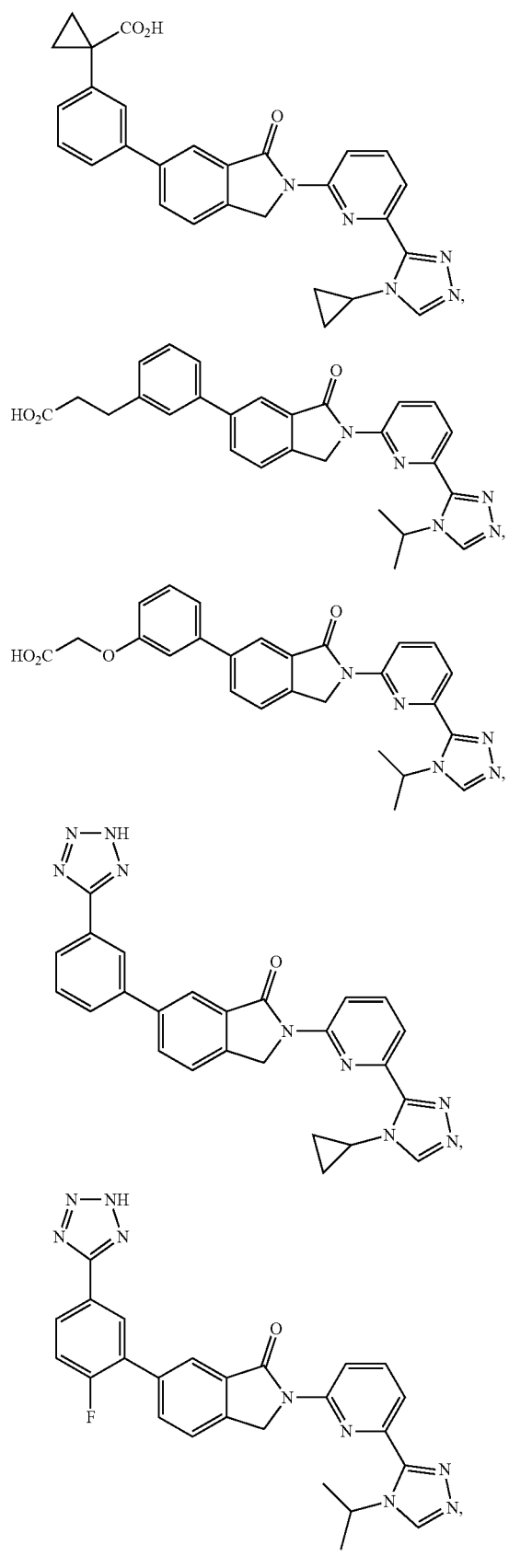
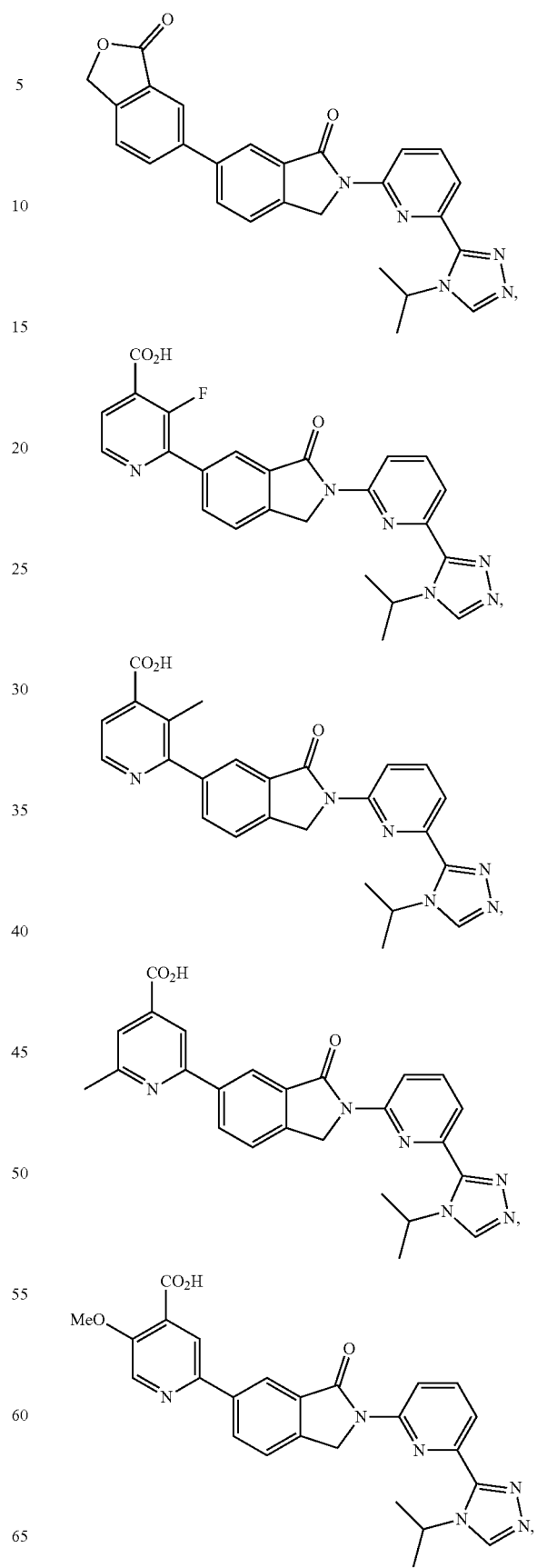

-continued
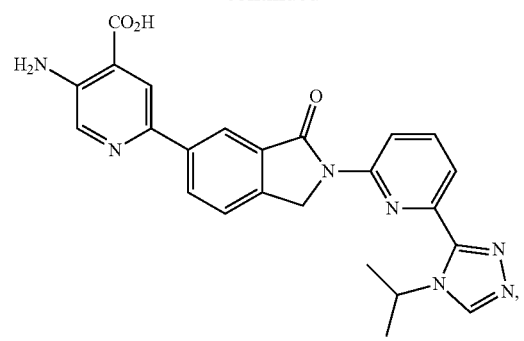
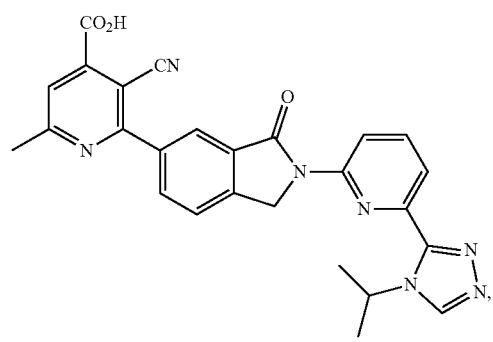
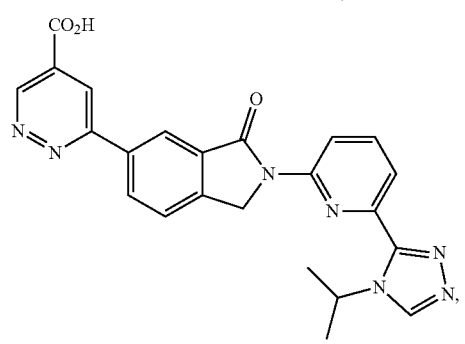
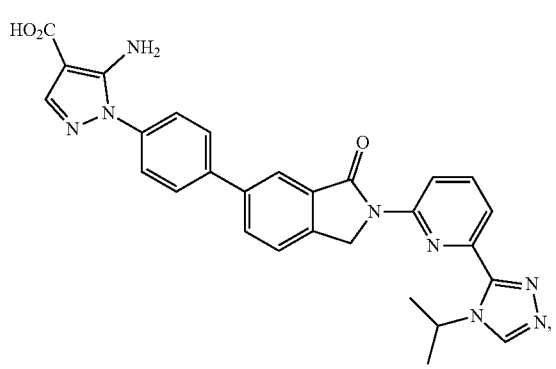
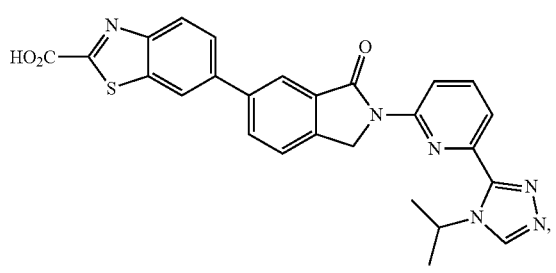
-continued
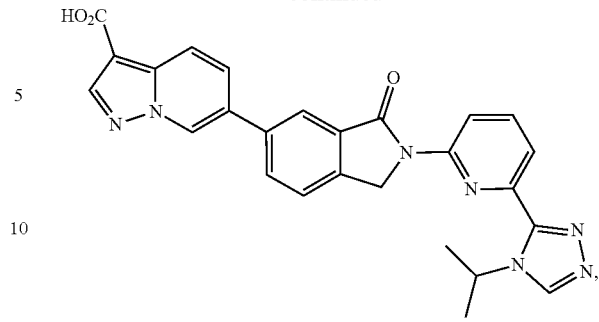
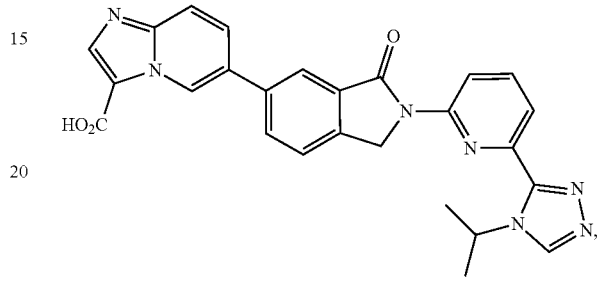
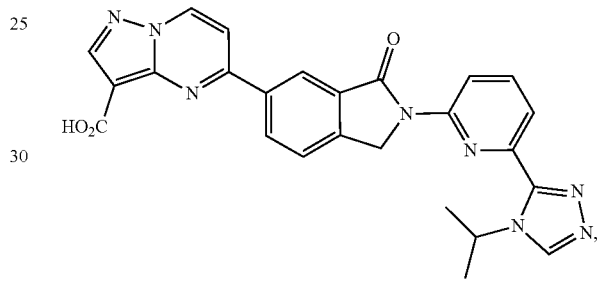
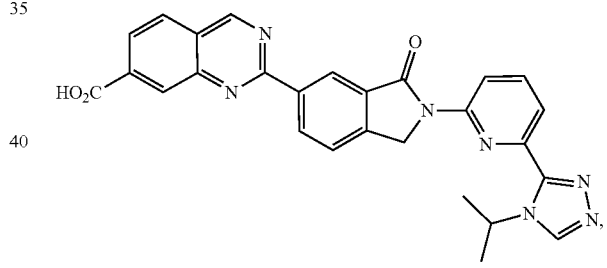
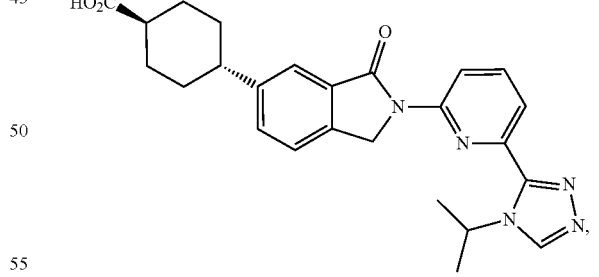
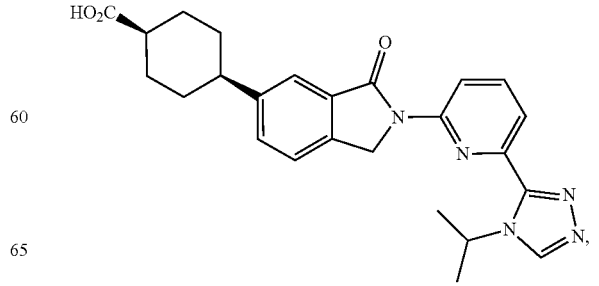

169
-continued
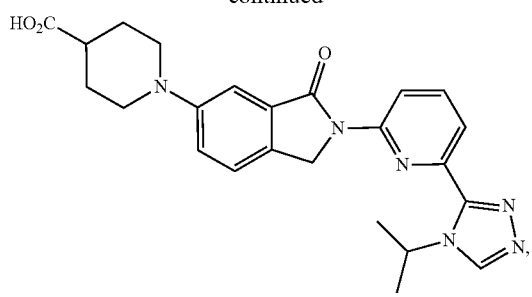
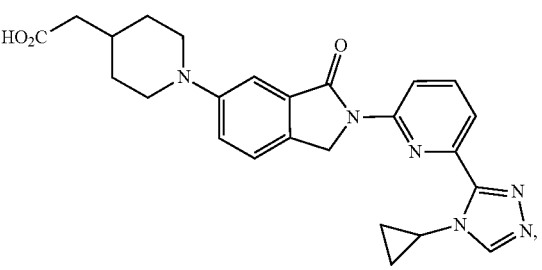
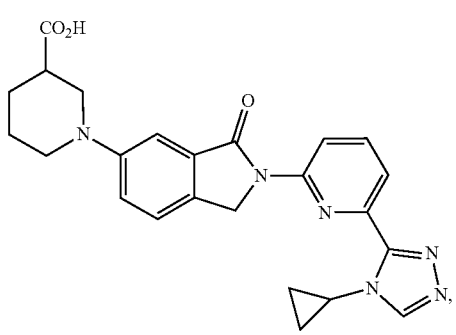
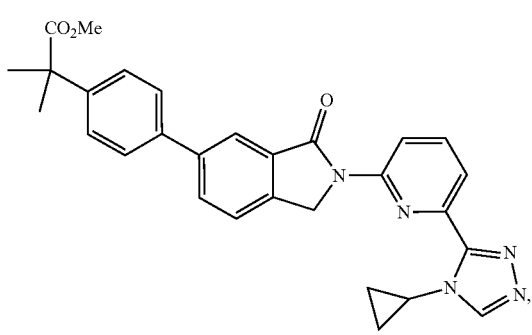
170
-continued
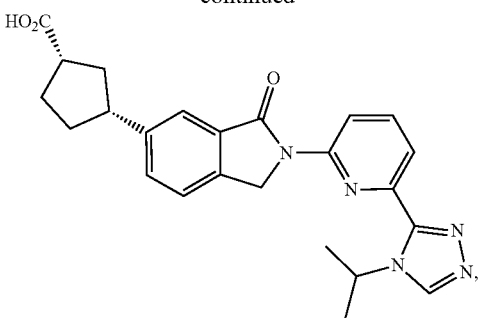
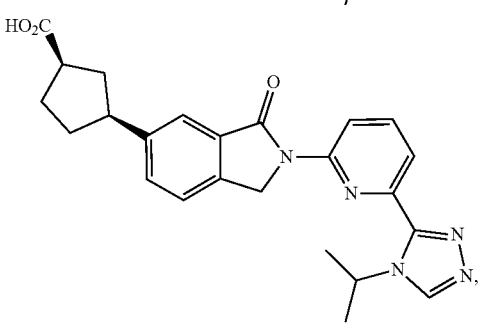
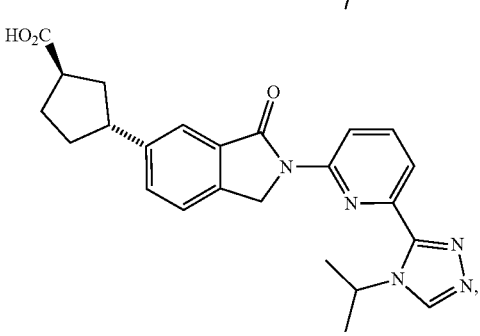
and

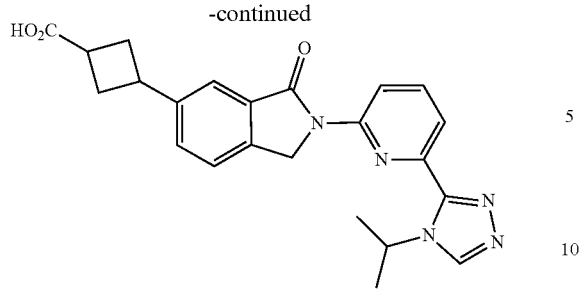

or a pharmaceutically acceptable salt thereof.

17. A pharmaceutical composition comprising a therapeutically effective amount of a compound of claim 1, or a pharmaceutically acceptable salt thereof, and a pharmaceutically acceptable excipient.

18. A pharmaceutical composition comprising a therapeutically effective amount of a compound of claim 3, or a pharmaceutically acceptable salt thereof, and a pharmaceutically acceptable excipient.

* * * * *